United States Patent
Hartman et al.

(10) Patent No.: US 10,538,519 B2
(45) Date of Patent: *Jan. 21, 2020

(54) DERIVATIVES AND METHODS OF TREATING HEPATITIS B INFECTIONS

(71) Applicant: Novira Therapeutics, Inc., Doylestown, PA (US)

(72) Inventors: George D. Hartman, Lansdale, PA (US); Scott Kuduk, Harleysville, PA (US)

(73) Assignee: NOVIRA THERAPEUTICS, INC., Doylestown, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/024,954

(22) Filed: Jul. 2, 2018

(65) Prior Publication Data

US 2019/0031653 A1 Jan. 31, 2019

Related U.S. Application Data

(63) Continuation of application No. 15/375,652, filed on Dec. 12, 2016, now Pat. No. 10,077,264, which is a continuation of application No. 14/984,654, filed on Dec. 30, 2015, now Pat. No. 9,550,779.

(60) Provisional application No. 62/163,150, filed on May 18, 2015, provisional application No. 62/097,835, filed on Dec. 30, 2014.

(51) Int. Cl.
| | |
|---|---|
| *C07D 471/04* | (2006.01) |
| *A61K 38/21* | (2006.01) |
| *A61K 39/29* | (2006.01) |
| *C12N 7/00* | (2006.01) |
| *A61K 31/437* | (2006.01) |
| *A61K 31/5377* | (2006.01) |
| *A61K 45/06* | (2006.01) |
| *A61K 31/4545* | (2006.01) |
| *A61P 31/12* | (2006.01) |
| *A61K 31/501* | (2006.01) |

(52) U.S. Cl.
CPC .......... *C07D 471/04* (2013.01); *A61K 31/437* (2013.01); *A61K 31/4545* (2013.01); *A61K 31/501* (2013.01); *A61K 31/5377* (2013.01); *A61K 38/212* (2013.01); *A61K 39/292* (2013.01); *A61K 45/06* (2013.01); *A61P 31/12* (2018.01); *C12N 7/00* (2013.01); *C12N 2730/10111* (2013.01); *C12N 2730/10134* (2013.01); *C12N 2730/10171* (2013.01)

(58) Field of Classification Search
None
See application file for complete search history.

(56) References Cited

U.S. PATENT DOCUMENTS

| | | |
|---|---|---|
| 4,500,525 A | 2/1985 | Winters et al. |
| 8,273,765 B2 | 9/2012 | Fancelli et al. |
| 8,288,425 B2 | 10/2012 | Edwards et al. |
| 9,242,981 B2 | 1/2016 | Shipps, Jr. et al. |
| 9,351,965 B2 | 5/2016 | Shipps, Jr. et al. |
| 9,518,057 B2 | 12/2016 | Hartman et al. |
| 9,527,845 B2 | 12/2016 | Hartman et al. |
| 9,550,779 B2 | 1/2017 | Hartman et al. |
| 2006/0014756 A1 | 1/2006 | Edwards et al. |
| 2006/0135508 A1 | 6/2006 | Villa et al. |
| 2014/0330009 A1 | 11/2014 | Bialy et al. |
| 2016/0046648 A1 | 2/2016 | Petrukhin et al. |
| 2016/0185778 A1 | 6/2016 | Hartman et al. |
| 2016/0185779 A1 | 6/2016 | Hartman et al. |

FOREIGN PATENT DOCUMENTS

| | | |
|---|---|---|
| WO | 2002/012242 A2 | 2/2002 |
| WO | 2002/014314 A2 | 2/2002 |
| WO | 2004/014374 A1 | 2/2004 |
| WO | 2008/005511 A2 | 1/2008 |
| WO | 2010/060854 A1 | 6/2010 |
| WO | 2012/036997 A1 | 3/2012 |
| WO | 2014/152013 A1 | 9/2014 |
| WO | 2016/109663 A2 | 7/2016 |
| WO | 2016/109684 A2 | 7/2016 |
| WO | 2016/109689 A2 | 7/2016 |
| WO | 2016/113273 A1 | 7/2016 |

OTHER PUBLICATIONS

Samala et al. (Sep. 12, 2013) "Development of 3-phenyl-4,5,6,7-tetrahydro-1H-pyrazolo[4,3-c]pyridine derivatives as novel Mycobacterium tuberculosis pantothenate synthetase inhibitors," Eur. J. Med. Chem. 9:356-364.
SciFinder Database. CAS Registration No. 895821-52-0. Chemical Abstract Services. American Chemical Society. [Last Accessed Jul. 25, 2016].
SciFinder Database. CAS Registration No. 895828-24-7. Chemical Abstract Services. American Chemical Society. [Last Accessed Jul. 25, 2016].
SciFinder Database. CAS Registration No. 895835-76-4. Chemical Abstract Services. American Chemical Society. [Last Accessed Jul. 25, 2016].
SciFinder Database. CAS Registration No. 895842-18-9. Chemical Abstract Services. American Chemical Society. [Last Accessed Jul. 25, 2016].
SciFinder Database. CAS Registration No. 899378-47-3. Chemical Abstract Services. American Chemical Society. [Last Accessed Jul. 25, 2016].
SciFinder Database. CAS Registration No. 903199-10-0. Chemical Abstract Services. American Chemical Society. [Last Accessed Jul. 25, 2016].
SciFinder Database. CAS Registration No. 903585-33-1. Chemical Abstract Services. American Chemical Society. [Last Accessed Jul. 25, 2016].

(Continued)

*Primary Examiner* — Heidi Reese
(74) *Attorney, Agent, or Firm* — Brian C. Trinque; Lathrop Gage LLP

(57) ABSTRACT

Provided herein are compounds useful for the treatment of HBV infection in a subject in need thereof, pharmaceutical compositions thereof, and methods of inhibiting, suppressing, or preventing HBV infection in the subject.

13 Claims, No Drawings

(56) References Cited

OTHER PUBLICATIONS

SciFinder Database. CAS Registration No. 903853-89-4. Chemical Abstract Services. American Chemical Society. [Last Accessed Jul. 25, 2016].
SciFinder Database. CAS Registration No. 903867-06-1. Chemical Abstract Services. American Chemical Society. [Last Accessed Jul. 25, 2016].
SciFinder Database. CAS Registration No. 903867-67-4. Chemical Abstract Services. American Chemical Society. [Last Accessed Jul. 25, 2016].
SciFinder Database. CAS Registration No. 906757-81-1. Chemical Abstract Services. American Chemical Society. [Last Accessed Jul. 25, 2016].
SciFinder Database. CAS Registration No. 906762-37-6. Chemical Abstract Services. American Chemical Society. [Last Accessed Jul. 25, 2016].
SciFinder Database. CAS Registration No. 1061115-87-4. Chemical Abstract Services. American Chemical Society. [Last Accessed Jul. 25, 2016].
SciFinder Database. CAS Registration No. 1067040-18-9. Chemical Abstract Services. American Chemical Society. [Last Accessed Jul. 25, 2016].
SciFinder Database. CAS Registration No. 1069950-13-5. Chemical Abstract Services. American Chemical Society. [Last Accessed Jul. 25, 2016].
SciFinder Database. CAS Registration No. 1070212-99-5. Chemical Abstract Services. American Chemical Society. [Last Accessed Jul. 25, 2016].
SciFinder Database. CAS Registration No. 1070291-29-0. Chemical Abstract Services. American Chemical Society. [Last Accessed Jul. 25, 2016].
SciFinder Database. CAS Registration No. 1087421-81-5. Chemical Abstract Services. American Chemical Society. [Last Accessed Jul. 25, 2016].
SciFinder Database. CAS Registration No. 1087511-95-2. Chemical Abstract Services. American Chemical Society. [Last Accessed Jul. 25, 2016].
SciFinder Database. CAS Registration No. 1087555-42-7. Chemical Abstract Services. American Chemical Society. [Last Accessed Jul. 25, 2016].
SciFinder Database. CAS Registration No. 1172227-82-5. Chemical Abstract Services. American Chemical Society. [Last Accessed Jul. 25, 2016].
SciFinder Database. CAS Registration No. 1172868-89-1. Chemical Abstract Services. American Chemical Society. [Last Accessed Jul. 25, 2016].
SciFinder Database. CAS Registration No. 1279839-42-7. Chemical Abstract Services. American Chemical Society. [Last Accessed Jul. 25, 2016].
SciFinder Database. CAS Registration No. 1279878-41-9. Chemical Abstract Services. American Chemical Society. [Last Accessed Jul. 25, 2016].
SciFinder Database. CAS Registration No. 1279879-10-5. Chemical Abstract Services. American Chemical Society. [Last Accessed Jul. 25, 2016].
SciFinder Database. CAS Registration No. 1279891-91-6. Chemical Abstract Services. American Chemical Society. [Last Accessed Jul. 25, 2016].
SciFinder Database. CAS Registration No. 1279891-93-8. Chemical Abstract Services. American Chemical Society. [Last Accessed Jul. 25, 2016].
SciFinder Database. CAS Registration No. 1331941-88-8. Chemical Abstract Services. American Chemical Society. [Last Accessed Jul. 25, 2016].
SciFinder Database. CAS Registration No. 1332163-49-1. Chemical Abstract Services. American Chemical Society. [Last Accessed Jul. 25, 2016].
SciFinder Database. CAS Registration No. 1332212-51-7. Chemical Abstract Services. American Chemical Society. [Last Accessed Jul. 25, 2016].
SciFinder Database. CAS Registration No. 1333648-57-9. Chemical Abstract Services. American Chemical Society. [Last Accessed Jul. 25, 2016].
SciFinder Database. CAS Registration No. 1333801-98-1. Chemical Abstract Services. American Chemical Society. [Last Accessed Jul. 25, 2016].
SciFinder Database. CAS Registration No. 1333912-79-0. Chemical Abstract Services. American Chemical Society. [Last Accessed Jul. 25, 2016].
SciFinder Database. CAS Registration No. 1340862-20-5. Chemical Abstract Services. American Chemical Society. [Last Accessed Jul. 25, 2016].
SciFinder Database. CAS Registration No. 1340896-72-1. Chemical Abstract Services. American Chemical Society. [Last Accessed Jul. 25, 2016].
SciFinder Database. CAS Registration No. 1341016-11-2. Chemical Abstract Services. American Chemical Society. [Last Accessed Jul. 25, 2016].
SciFinder Database. CAS Registration No. 1355539-18-2. Chemical Abstract Services. American Chemical Society. [Last Accessed Jul. 25, 2016].
SciFinder Database. CAS Registration No. 1355607-29-2. Chemical Abstract Services. American Chemical Society. [Last Accessed Jul. 25, 2016].
SciFinder Database. CAS Registration No. 1355640-11-7. Chemical Abstract Services. American Chemical Society. [Last Accessed Jul. 25, 2016].
SciFinder Database. CAS Registration No. 1355842-55-5. Chemical Abstract Services. American Chemical Society. [Last Accessed Jul. 25, 2016].
SciFinder Database. CAS Registration No. 1355890-97-9. Chemical Abstract Services. American Chemical Society. [Last Accessed Jul. 25, 2016].
SciFinder Database. CAS Registration No. 1360376-35-7. Chemical Abstract Services. American Chemical Society. [Last Accessed Jul. 25, 2016].
SciFinder Database. CAS Registration No. 1368359-39-0. Chemical Abstract Services. American Chemical Society. [Last Accessed Jul. 25, 2016].
SciFinder Database. CAS Registration No. 1369082-23-4. Chemical Abstract Services. American Chemical Society. [Last Accessed Jul. 25, 2016].
SciFinder Database. CAS Registration No. 1497548-79-4. Chemical Abstract Services. American Chemical Society. [Last Accessed Jul. 25, 2016].
SciFinder Database. CAS Registration No. 1497623-25-2. Chemical Abstract Services. American Chemical Society. [Last Accessed Jul. 25, 2016].
SciFinder Database. CAS Registration No. 1497669-55-2. Chemical Abstract Services. American Chemical Society. [Last Accessed Jul. 25, 2016].
SciFinder Database. CAS Registration No. 1501166-65-9. Chemical Abstract Services. American Chemical Society. [Last Accessed Jul. 25, 2016].
SciFinder Database. CAS Registration No. 1511831-42-7. Chemical Abstract Services. American Chemical Society. [Last Accessed Jul. 25, 2016].
SciFinder Database. CAS Registration No. 1516653-16-9. Chemical Abstract Services. American Chemical Society. [Last Accessed Jul. 25, 2016].
SciFinder Database. CAS Registration No. 1522224-86-7. Chemical Abstract Services. American Chemical Society. [Last Accessed Jul. 25, 2016].
SciFinder Database. CAS Registration No. 1567296-86-9. Chemical Abstract Services. American Chemical Society. [Last Accessed Jul. 25, 2016].
SciFinder Database. CAS Registration No. 1567311-64-1. Chemical Abstract Services. American Chemical Society. [Last Accessed Jul. 25, 2016].

(56) References Cited

OTHER PUBLICATIONS

SciFinder Database. CAS Registration No. 1567490-89-4. Chemical Abstract Services. American Chemical Society. [Last Accessed Jul. 25, 2016].
SciFinder Database. CAS Registration No. 1574576-07-0. Chemical Abstract Services. American Chemical Society. [Last Accessed Jul. 25, 2016].
SciFinder Database. CAS Registration No. 1574592-26-9. Chemical Abstract Services. American Chemical Society. [Last Accessed Jul. 25, 2016].
SciFinder Database. CAS Registration No. 1574626-86-0. Chemical Abstract Services. American Chemical Society. [Last Accessed Jul. 25, 2016].
SciFinder Database. CAS Registration No. 1574640-97-3. Chemical Abstract Services. American Chemical Society. [Last Accessed Jul. 25, 2016].
SciFinder Database. CAS Registration No. 1609742-77-9. Chemical Abstract Services. American Chemical Society. [Last Accessed Jul. 25, 2016].
International Search Report with Written Opinion corresponding to International Patent Application No. PCT/US2015/068059, dated Jun. 29, 2016.
International Search Report with Written Opinion corresponding to International Patent Application No. PCT/US2015/068091, dated Jun. 29, 2016.
International Search Report with Written Opinion corresponding to International Patent Application No. PCT/US2015/068099, dated Jun. 29, 2016.

DERIVATIVES AND METHODS OF TREATING HEPATITIS B INFECTIONS

RELATED APPLICATIONS

This application is a continuation of U.S. application Ser. No. 15/375,652, filed on Dec. 12, 2016 which is a continuation of U.S. application Ser. No. 14/984,654, filed Dec. 30, 2015, now U.S. Pat. No. 9,550,779, which claims priority to U.S. Provisional Application No. 62/097,835, filed Dec. 30, 2014, and U.S. Provisional Application No. 62/163,150, filed May 18, 2015. The contents of these applications are incorporated herein by reference in their entireties.

BACKGROUND

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon alpha and nucleoside analogues/inhibitors of the viral polymerase); drug resistance, low efficacy, and tolerability issues limit their impact. The low cure rates of HBV are attributed at least in part to the fact that complete suppression of virus production is difficult to achieve with a single antiviral agent. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma.

There is a need in the art for therapeutic agents that can increase the suppression of virus production and that can treat, ameliorate, and/or prevent HBV infection. Administration of such therapeutic agents to an HBV infected patient, either as monotherapy or in combination with other HBV treatments or ancillary treatments, will lead to significantly reduced virus burden, improved prognosis, diminished progression of the disease and enhanced seroconversion rates.

SUMMARY

Provided herein are compounds useful for the treatment of HBV infection in a subject in need thereof, having the structure:

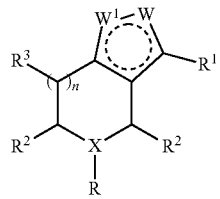

or a pharmaceutically acceptable salt thereof.

In one aspect, provided herein is a compound of Formula I:

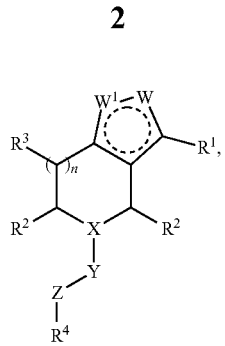

or a pharmaceutically acceptable salt thereof.

In an embodiment, the compound of Formula I is a compound of Formula II:

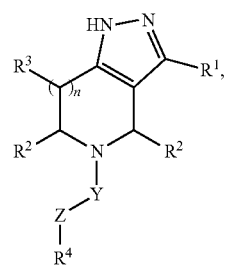

or a pharmaceutically acceptable salt thereof.

In another embodiment, the compound of Formula I is a compound of Formula III:

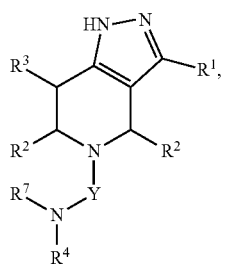

or a pharmaceutically acceptable salt thereof.

In another embodiment, the compound of Formula I is a compound of Formula IV:

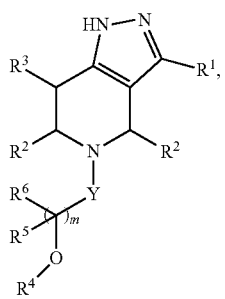

or a pharmaceutically acceptable salt thereof.

In another aspect, provided herein are pharmaceutical compositions comprising a compound of Formula I, II, III, or IV, or a pharmaceutically acceptable salt thereof, together with a pharmaceutically acceptable carrier.

In one aspect, provided herein is a method of treating an HBV infection in an individual in need thereof, comprising administering to the individual a therapeutically effective amount of a compound of Formula I, II, III, or IV, or a pharmaceutically acceptable salt thereof.

In another aspect, provided herein is a method of eradicating an HBV infection in an individual in need thereof, comprising administering to the individual a therapeutically effective amount of a compound of Formula I, II, III, or IV, or a pharmaceutically acceptable salt thereof.

In another aspect, provided herein is a method of reducing the viral load associated with an HBV infection in an individual in need thereof, comprising administering to the individual a therapeutically effective amount of a compound of Formula I, II, III, or IV, or a pharmaceutically acceptable salt thereof.

In another aspect, provided herein is a method of reducing reoccurrence of an HBV infection in an individual in need thereof, comprising administering to the individual a therapeutically effective amount of a compound of Formula I, II, III, or IV, or a pharmaceutically acceptable salt thereof.

In another aspect, provided herein is a method of inhibiting or reducing the formation or presence of HBV DNA-containing particles or HBV RNA-containing particles in an individual in need thereof, comprising administering to the individual a therapeutically effective amount of a compound of Formula I, II, III, or IV, or a pharmaceutically acceptable salt thereof.

In another aspect, provided herein is a method of reducing an adverse physiological impact of an HBV infection in an individual in need thereof, comprising administering to the individual a therapeutically effective amount of a compound of Formula I, II, III, or IV, or a pharmaceutically acceptable salt thereof.

In another aspect, provided herein is a method of inducing remission of hepatic injury from an HBV infection in an individual in need thereof, comprising administering to the individual a therapeutically effective amount of a compound of Formula I, II, III, or IV, or a pharmaceutically acceptable salt thereof.

In another aspect, provided herein is a method of reducing the physiological impact of long-term antiviral therapy for HBV infection in an individual in need thereof, comprising administering to the individual a therapeutically effective amount of a compound of Formula I, II, III, or IV, or a pharmaceutically acceptable salt thereof.

In another aspect, provided herein is a method of prophylactically treating an HBV infection in an individual in need thereof, wherein the individual is afflicted with a latent HBV infection, comprising administering to the individual a therapeutically effective amount of a compound of Formula I, II, III, or IV, or a pharmaceutically acceptable salt thereof.

In an embodiment, the methods provided herein can further comprise administering to the individual at least one additional therapeutic agent selected from the group consisting of an HBV polymerase inhibitor, immunomodulatory agents, pegylated interferon, viral entry inhibitor, viral maturation inhibitor, literature-described capsid assembly modulator, reverse transcriptase inhibitor, a cyclophilin/TNF inhibitor, a TLR-agonist, an HBV vaccine, and agents of distinct or unknown mechanism, and a combination thereof. In a further embodiment, the methods provided herein allow for administering of the at least one additional therapeutic agent at a lower dose or frequency as compared to the administering of the at least one additional therapeutic agent alone that is required to achieve similar results in prophylactically treating an HBV infection in an individual in need thereof.

In another embodiment, the methods provided herein reduce the viral load in the individual to a greater extent or at a faster rate compared to the administering of a compound selected from the group consisting of an HBV polymerase inhibitor, interferon, viral entry inhibitor, viral maturation inhibitor, distinct capsid assembly modulator, antiviral compounds of distinct or unknown mechanism, and any combination thereof.

In another embodiment, the methods provided herein cause a lower incidence of viral mutation and/or viral resistance than the administering of a compound selected from the group consisting of an HBV polymerase inhibitor, interferon, viral entry inhibitor, viral maturation inhibitor, distinct capsid assembly modulator, antiviral compounds of distinct or unknown mechanism, and combination thereof.

In another embodiment, the methods provided herein further comprise administering to the individual at least one HBV vaccine, a nucleoside HBV inhibitor, an interferon or any combination thereof.

In an aspect, provided herein is a method of treating an HBV infection in an individual in need thereof, comprising reducing the HBV viral load by administering to the individual a therapeutically effective amount of a compound of Formula I, II, III, or IV, or a pharmaceutically acceptable salt thereof, alone or in combination with a reverse transcriptase inhibitor; and further administering to the individual a therapeutically effective amount of HBV vaccine.

In an embodiment, the methods provided herein further comprise monitoring the HBV viral load of the subject, wherein the method is carried out for a period of time such that the HBV virus is undetectable.

DETAILED DESCRIPTION

Provided herein are compounds, e.g., the compounds of Formulas I, II, III, or IV, or pharmaceutically acceptable salts thereof, that are useful in the treatment and prevention of HBV infection in subject. In a non-limiting aspect, these compounds may modulate or disrupt HBV assembly and other HBV core protein functions necessary for HBV replication or the generation of infectious particles, may inhibit the production of infectious virus particles or infection or may interact with HBV capsid to afford defective viral particles with greatly reduced infectivity or replication capacity. In other words, the compounds provided herein may act as capsid assembly modulators. The compounds provided herein have potent antiviral activity, exhibit favorable metabolic properties, tissue distribution, safety and pharmaceutical profiles, and are suitable for use in humans.

The HBV capsid protein plays essential functions during the viral life cycle. HBV capsid/core proteins form metastable viral particles or protein shells that protect the viral genome during intercellular passage, and also play a central role in viral replication processes, including genome encapsidation, genome replication, and virion morphogenesis and egress. Capsid structures also respond to environmental cues to allow un-coating after viral entry. Consistently, the appropriate timing of capsid assembly and disassembly, the appropriate capsid stability and the function of core protein have been found to be critical for viral infectivity.

The crucial function of HBV capsid proteins imposes stringent evolutionary constraints on the viral capsid protein sequence, leading to the observed low sequence variability and high conservation. Consistently, mutations in HBV capsid that disrupt its assembly are lethal, and mutations that perturb capsid stability severely attenuate viral replication. The high functional constraints on the multi-functional HBV core/capsid protein is consistent with a high sequence conservation, as many mutations are deleterious to function. Indeed, the core/capsid protein sequences are >90% identical across HBV genotypes and show only a small number of polymorphic residues. Resistance selection to HBV core/capsid protein binding compounds may therefore be difficult to select without large impacts on virus replication fitness.

Reports describing compounds that bind viral capsids and inhibit replication of HIV, rhinovirus and HBV provide strong pharmacological proof of concept for viral capsid proteins as antiviral drug targets.

In one aspect, the compounds provided herein are useful in HBV treatment by disrupting, accelerating, reducing, delaying and/or inhibiting normal viral capsid assembly and/or disassembly of immature or mature particles, thereby inducing aberrant capsid morphology and leading to antiviral effects such as disruption of virion assembly and/or disassembly, virion maturation, virus egress and/or infection of target cells. In one embodiment, a disruptor of capsid assembly interacts with mature or immature viral capsid to perturb the stability of the capsid, thus affecting assembly and/or disassembly. In another embodiment, a disruptor of capsid assembly perturbs protein folding and/or salt bridges required for stability, function and/or normal morphology of the viral capsid, thereby disrupting and/or accelerating capsid assembly and/or disassembly. In yet another embodiment, the compounds of the invention bind capsid and alter metabolism of cellular polyproteins and precursors, leading to abnormal accumulation of protein monomers and/or oligomers and/or abnormal particles, which causes cellular toxicity and death of infected cells. In another embodiment, the compounds provided herein cause failure of the formation of capsids of optimal stability, affecting efficient uncoating and/or disassembly of viruses (e.g., during infectivity).

In one embodiment, the compounds provided herein disrupt and/or accelerate capsid assembly and/or disassembly when the capsid protein is immature. In another embodiment, the compounds provided herein disrupt and/or accelerate capsid assembly and/or disassembly when the capsid protein is mature. In yet another embodiment, the compounds provided herein disrupt and/or accelerate capsid assembly and/or disassembly during viral infectivity. In yet another embodiment, the disruption and/or acceleration of capsid assembly and/or disassembly attenuates HBV viral infectivity and/or reduces viral load. In yet another embodiment, disruption, acceleration, inhibition, delay and/or reduction of capsid assembly and/or disassembly eradicates the virus from the host organism. In yet another embodiment, eradication of the HBV from a host advantageously obviates the need for chronic long-term therapy and/or reduces the duration of long-term therapy.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds proided herein can be used in methods of modulating (e.g., inhibiting or disrupting) the activity, stability, function, and viral replication properties of HBV cccDNA. In yet another embodiment, the compounds of the invention can be used in methods of diminishing or preventing the formation of HBV cccDNA.

In another embodiment, the the compounds provided herein can be used in methods of modulating (e.g., inhibiting or disrupting) the activity of HBV cccDNA. In yet another embodiment, the compounds of the invention can be used in methods of diminishing the formation of HBV cccDNA.

In another embodiment, the the compounds provided herein can be used in methods of modulating, inhibiting, or disrupting the generation or release of HBV RNA particles from within the infected cell. In a further embodiment, the total burden (or concentration) of HBV RNA particles is modulated. In a preferred embodiment, the total burden of HBV RNA is diminished.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

As used herein, the term "capsid assembly modulator" refers to a compound that disrupts or accelerates or inhibits or hinders or delays or reduces or modifies normal capsid assembly (e.g., during maturation) or normal capsid disassembly (e.g., during infectivity) or perturbs capsid stability, thereby inducing aberrant capsid morphology and function. In one embodiment, a capsid assembly modulator accelerates capsid assembly or disassembly, thereby inducing aberrant capsid morphology. In another embodiment, a capsid assembly modulator interacts (e.g. binds at an active site, binds at an allosteric site, modifies and/or hinders folding and the like) with the major capsid assembly protein (CA), thereby disrupting capsid assembly or disassembly. In yet another embodiment, a capsid assembly modulator causes a perturbation in structure or function of CA (e.g., ability of CA to assemble, disassemble, bind to a substrate, fold into a suitable conformation, or the like), which attenuates viral infectivity and/or is lethal to the virus.

As used herein, the term "treatment" or "treating," is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has an HBV infection, a symptom of HBV infection or the potential to develop an HBV infection, with the purpose to cure, heal, alleviate, relieve, alter, remedy, ameliorate, improve or affect the HBV infection, the symptoms of HBV infection or the potential to develop an HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "alkyl," by itself or as part of another substituent means, unless otherwise stated, a straight or branched chain hydrocarbon having the number of carbon atoms designated (i.e., $C_1$-$C_6$-alkyl means one to six carbon atoms) and includes straight, branched chain Examples include methyl, ethyl, propyl, isopropyl, butyl, isobutyl, tert-butyl, pentyl, neopentyl, and hexyl. Other examples of $C_1$-$C_6$-alkyl include ethyl, methyl, isopropyl, isobutyl, n-pentyl, and n-hexyl.

As used herein, the term "alkenyl," denotes a monovalent group derived from a hydrocarbon moiety containing at least two carbon atoms and at least one carbon-carbon double bond. The double bond may or may not be the point of attachment to another group. Alkenyl groups (e.g., $C_2$-$C_8$-alkenyl) include, but are not limited to, for example, ethenyl, propenyl, prop-1-en-2-yl, butenyl, 1-methyl-2-buten-1-yl, heptenyl, octenyl and the like.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "haloalkyl" refers to alkl radicals wherein any one or more of the alkyl carbon atoms is substituted with halo as defined above. Haloalkyl embraces monohaloalkyl, dihaloalkyl, and polyhaloalkyl radicals. The term "haloalkyl" includes, but is not limited to, fluoromethyl, difluoromethyl, trifluoromethyl, chloromethyl, dichloromethyl, trichloromethyl, and pentafluoroethyl.

As used herein, the term "cycloalkyl" refers to a mono cyclic or polycyclic nonaromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having 3 to 10 ring atoms ($C_3$-$C_{10}$-cycloalkyl), groups having 3 to 8 ring atoms ($C_3$-$C_8$-cycloalkyl), groups having 3 to 7 ring atoms ($C_3$-$C_7$-cycloalkyl), and groups having 3 to 6 ring atoms ($C_3$-$C_6$-cycloalkyl). Illustrative examples of cycloalkyl groups include, but are not limited to, the following moieties:

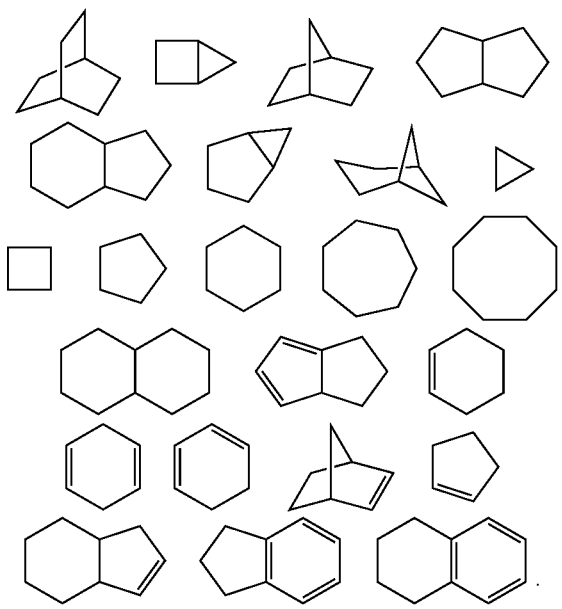

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocyclyl group has from 3 to 10 atoms in its ring system, with the proviso that the ring of said group does not contain two adjacent O or S atoms. Heterocyclyl substituents may be alternatively defined by the number of carbon atoms, e.g., $C_2$-$C_8$-heterocyclyl indicates the number of carbon atoms contained in the heterocyclic group without including the number of heteroatoms. For example, a $C_2$-$C_8$-heterocyclyl will include an additional one to four heteroatoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure.

An example of a 3-membered heterocyclyl group includes, and is not limited to, aziridine. Examples of 4-membered heterocyclyl groups include, and are not limited to, azetidine and a beta lactam. Examples of 5-membered heterocyclyl groups include, and are not limited to, pyrrolidine, oxazolidine and thiazolidinedione. Examples of 6-membered heterocycloalkyl groups include, and are not limited to, piperidine, morpholine and piperazine.

Other non-limiting examples of heterocyclyl groups are:

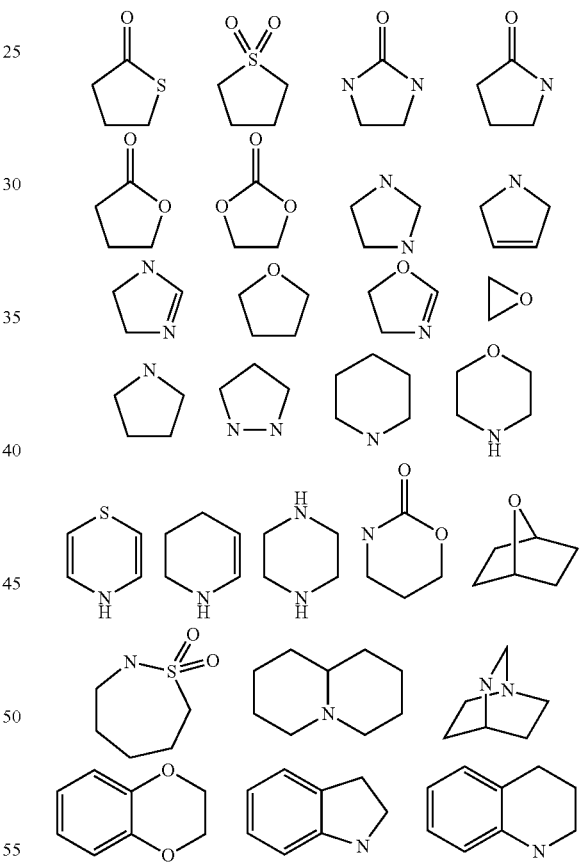

Examples of heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e., having (4n+2) delocalized 7E (pi) electrons, where n is an integer.

As used herein, the term "aryl," employed alone or in combination with other terms, means, unless otherwise stated, a carbocyclic aromatic system containing one or more rings (typically one, two, or three rings), wherein such rings may be attached together in a pendent manner, such as a biphenyl, or may be fused, such as naphthalene. Examples of aryl groups include phenyl, anthracyl, and naphthyl. Preferred examples are phenyl (e.g., $C_6$-aryl) and biphenyl (e.g., $C_{12}$-aryl). In some embodiments, aryl groups have from six to sixteen carbon atoms. In some embodiments, aryl groups have from six to twelve carbon atoms (e.g., $C_6$-$C_{12}$-aryl). In some embodiments, aryl groups have six carbon atoms (e.g., $C_6$-aryl).

As used herein, the term "heteroaryl" or "heteroaromatic" refers to a heterocycle having aromatic character. Heteroaryl substituents may be defined by the number of carbon atoms, e.g., $C_1$-$C_9$-heteroaryl indicates the number of carbon atoms contained in the heteroaryl group without including the number of heteroatoms. For example, a $C_1$-$C_9$-heteroaryl will include an additional one to four heteroatoms. A polycyclic heteroaryl may include one or more rings that are partially saturated. Non-limiting examples of heteroaryls include:

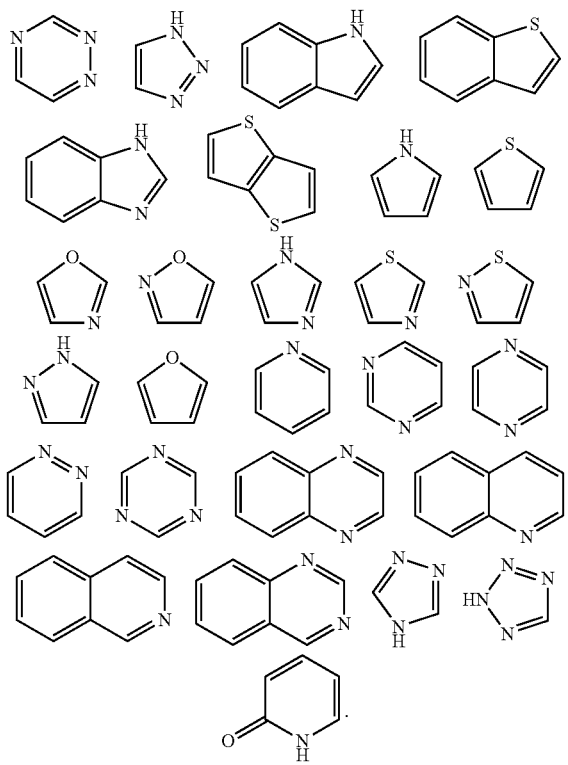

Additional non-limiting examples of heteroaryl groups include pyridyl, pyrazinyl, pyrimidinyl (including, e.g., 2- and 4-pyrimidinyl), pyridazinyl, thienyl, furyl, pyrrolyl (including, e.g., 2-pyrrolyl), imidazolyl, thiazolyl, oxazolyl, pyrazolyl (including, e.g., 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Non-limiting examples of polycyclic heterocycles and heteroaryls include indolyl (including, e.g., 3-, 4-, 5-, 6- and 7-indolyl), indolinyl, quinolyl, tetrahydroquinolyl, isoquinolyl (including, e.g., 1- and 5-isoquinolyl), 1,2,3,4-tetrahydroisoquinolyl, cinnolinyl, quinoxalinyl (including, e.g., 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (including, e.g., 3-, 4-, 5-, 6- and 7-benzofuryl), 2,3-dihydrobenzofuryl, 1,2-benzisoxazolyl, benzothienyl (including, e.g., 3-, 4-, 5-, 6-, and 7-benzothienyl), benzoxazolyl, benzothiazolyl (including, e.g., 2-benzothiazolyl and 5-benzothiazolyl), purinyl, benzimidazolyl (including, e.g., 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group.

Compounds of the Invention

Provided herein are compounds useful for the treatment of HBV infection in a subject in need thereof, having the structure:

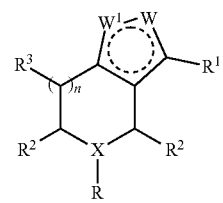

or pharmaceutically acceptable salts thereof.

In one aspect, provided herein is a compound of Formula Ia

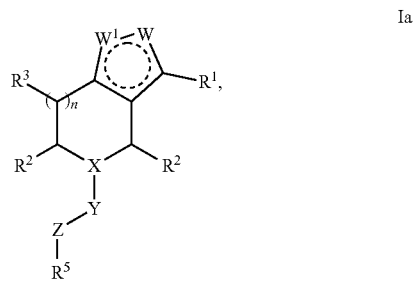

Ia or a pharmaceutically acceptable salt thereof,
wherein
$W^1$ and W are each independently selected from N, $NR^a$, and $CR^a$, wherein one of $W^1$ and W is $NR^a$;
X is N or $CR^b$;
Y is selected from a bond, —C(O)—, and —SO$_2$—;
Z is selected from —(CR$^5$R$^6$)$_m$, —(CR$^5$R$^6$)$_m$O—, —(CR$^5$R$^6$)$_m$CR$^5$=CR$^5$—, —(CR$^5$R$^6$)$_m$—C$_3$-C$_6$-cycloalkylene-, and —(CR$^5$R$^6$)$_m$—NR$^7$—;
$R^1$ is selected from $C_6$-$C_{12}$-aryl, $C_1$-$C_9$-heteroaryl, $C_3$-$C_8$-cycloalkyl, $C_2$-$C_8$-heterocyclyl, —OR$^c$, $C_1$-$C_6$-alkyl, C(O)OR$^c$, C(O)R$^c$, C(O)NR$^d$R$^e$, NR$^d$C(O)R$^c$, —OC(O)R$^c$, halo, and $C_2$-$C_8$-alkenyl, wherein alkyl, aryl, heteroaryl, cycloalkyl, heterocyclyl, and alkenyl are optionally substituted with 1, 2, 3, or 4 groups each independently selected from —OH, halo, $C_1$-$C_6$-alkyl, $C_1$-$C_6$-haloalkyl, —O—$C_1$-$C_6$-alkyl, and $C_1$-$C_6$-alkyl-OH;

$R^2$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^3$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^4$ is selected from $C_1$-$C_6$-alkyl, $(CR^8R^9)_p$—$C_3$-$C_8$-cycloalkyl, $(CR^8R^9)_p$—$C_2$-$C_8$-heterocyclyl, $(CR^8R^9)_p$—$C_6$-$C_{12}$-aryl, and $(CR^8R^9)_p$—$C_1$-$C_9$-heteroaryl, wherein alkyl, cycloalkyl, heterocyclyl, aryl, and heteroaryl are optionally substituted with 1, 2, 3, or 4 groups, each independently selected from —OH, halo, CN, $C_1$-$C_6$-alkyl, $C_1$-$C_6$-haloalkyl, —O—$C_1$-$C_6$-alkyl, $C(O)N(R^f)_2$, $C(O)OR^f$, —OCH$_2$C(O)OR$^f$, —SO$_2$R$^f$, $C_1$-$C_6$-alkyl-OH, and $C_3$-$C_8$-cycloalkyl;

$R^5$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

alternatively, $R^4$ and $R^5$ are optionally joined to form a ring;

$R^6$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^7$ is selected from H, $C_1$-$C_6$-alkyl, and $C_1$-$C_6$-alkyl-OH;

$R^8$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^9$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^a$ is selected from H, $C_1$-$C_6$-alkyl, and $C_1$-$C_6$-alkyl-OH;

$R^b$ is selected from H and $C_1$-$C_6$-alkyl;

$R^c$ is selected from H, $C_1$-$C_6$-alkyl, $C_1$-$C_6$-alkyl-OH, $C_3$-$C_5$-cycloalkyl, $C_2$-$C_5$-heterocyclyl, $C_6$-$C_{12}$-aryl, and $C_1$-$C_9$-heteroaryl;

$R^d$ is selected from H, $C_1$-$C_6$-alkyl, and $C_1$-$C_6$-alkyl-OH;

$R^e$ is selected from H, $C_1$-$C_6$-alkyl, $C_1$-$C_6$-alkyl-OH, $C_3$-$C_5$-cycloalkyl, $C_2$-$C_5$-heterocyclyl, $C_6$-$C_{12}$-aryl, $C_1$-$C_9$-heteroaryl, and —O—$C_1$-$C_6$-alkyl;

alternatively, $R^d$ and $R^e$ are optionally joined to form a heterocyclic ring;

$R^f$ is, at each occurrence, independently selected from H and $C_1$-$C_6$-alkyl;

m is 0, 1, 2, 3, or 4;

n is 0, 1, 2, or 3; and p is 0, 1, 2, 3, or 4.

In another aspect, provided herein is a compound of Formula I

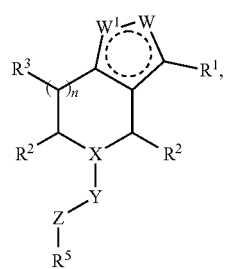

I or a pharmaceutically acceptable salt thereof, wherein $W^1$ and W are each independently selected from N, NR$^a$, and CR$^a$, wherein one of $W^1$ and W is NR$^a$.

X is N or CR$^b$;

Y is selected from a bond, —C(O)—, and —SO$_2$—;

Z is selected from —(CR$^5$R$^6$)$_m$—, —(CR$^5$R$^6$)$_m$O—, —(CR$^5$R$^6$)$_m$CR$^5$=CR$^5$—, —(CR$^5$R$^6$)$_m$—C$_3$-C$_6$-cycloalkylene-, and —(CR$^5$R$^6$)$_m$—NR$^7$—;

$R^1$ is selected from $C_6$-$C_{12}$-aryl and $C_1$-$C_9$-heteroaryl, wherein aryl and heteroaryl are optionally substituted with 1, 2, 3, or 4 groups each independently selected from —OH, halo, $C_1$-$C_6$-alkyl, $C_1$-$C_6$-haloalkyl, —O—$C_1$-$C_6$-alkyl, $C_1$-$C_6$-alkyl-OH, CN, and C(O)H;

$R^2$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^3$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^4$ is selected from $C_1$-$C_6$-alkyl, $(CR^8R^9)_p$—$C_3$-$C_8$-cycloalkyl, $(CR^8R^9)_p$—$C_2$-$C_8$-heterocyclyl, $(CR^8R^9)_p$—$C_6$-$C_{12}$-aryl, and $(CR^8R^9)_p$—$C_1$-$C_9$-heteroaryl, wherein alkyl, cycloalkyl, heterocyclyl, aryl, and heteroaryl are optionally substituted with 1, 2, 3, or 4 groups, each independently selected from —OH, halo, CN, $C_1$-$C_6$-alkyl, $C_1$-$C_6$-haloalkyl, —O—$C_1$-$C_6$-alkyl, $C(O)N(R^f)_2$, $C(O)OR^f$, —OCH$_2$C(O)OR$^f$, —SO$_2$R$^f$, $C_1$-$C_6$-alkyl-OH, $C_3$-$C_8$-cycloalkyl, and $C_6$-aryl;

$R^5$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

alternatively, $R^4$ and $R^5$ are optionally joined to form a heterocyclic ring;

$R^6$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^7$ is selected from H, $C_1$-$C_6$-alkyl, and $C_1$-$C_6$-alkyl-OH;

$R^8$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^9$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

$R^a$ is selected from H, $C_1$-$C_6$-alkyl, and $C_1$-$C_6$-alkyl-OH;

$R^b$ is selected from H and $C_1$-$C_6$-alkyl;

$R^f$ is, at each occurrence, independently selected from H and $C_1$-$C_6$-alkyl;

m is 0, 1, 2, 3, or 4;

n is 0, 1, 2, or 3; and p is 0, 1, 2, 3, or 4.

In an embodiment of the compound of Formula I

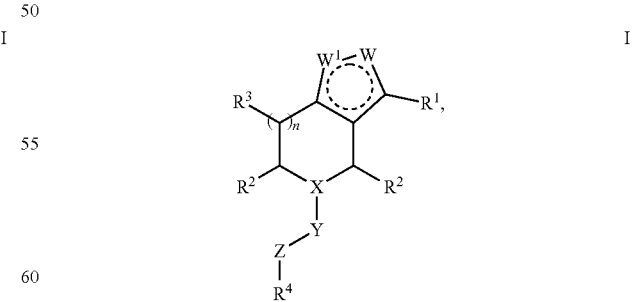

I or a pharmaceutically acceptable salt thereof, $W^1$ and W are each independently selected from N, NR$^a$, and CR$^a$, wherein one of $W^1$ and W is NR$^a$;

X is N or CR$^b$;

Y is selected from a bond, —C(O)—, and —SO$_2$—;

Z is selected from $-(CR^5R^6)_m-$, $-(CR^5R^6)_mO-$, $-(CR^5R^6)_mCR^5=CR^5-$, $-(CR^5R^6)_m-C_3-C_6$-cycloalkylene-, and $-(CR^5R^6)_m-NR^7-$;

$R^1$ is selected from $C_6-C_{12}$-aryl and $C_1-C_9$-heteroaryl, wherein aryl and heteroaryl are optionally substituted with 1 or 2 groups each independently selected from —OH, halo, $C_1-C_6$-alkyl, $C_1-C_6$-haloalkyl, —O—$C_1-C_6$-alkyl, $C_1-C_6$-alkyl-OH, CN, and C(O)HH;

$R^2$ is, at each occurrence, independently selected from H, —OH, halo, $C_1-C_6$-alkyl, $C_1-C_6$-haloalkyl, —O—$C_1-C_6$-alkyl, and $C_1-C_6$-alkyl-OH;

$R^3$ is, at each occurrence, independently selected from H, —OH, halo, $C_1-C_6$-alkyl, $C_1-C_6$-haloalkyl, —O—$C_1-C_6$-alkyl, and $C_1-C_6$-alkyl-OH;

$R^4$ is selected from $C_1-C_6$-alkyl, $(CR^8R^9)_p-C_3-C_8$-cycloalkyl, $(CR^8R^9)_p-C_2-C_8$-heterocyclyl, $(CR^8R^9)_p-C_6-C_{12}$-aryl, and $(CR^8R^9)_p-C_1-C_9$-heteroaryl, wherein alkyl, cycloalkyl, heterocyclyl, aryl, and heteroaryl are optionally substituted with 1, 2, 3, or 4 groups, each independently selected from —OH, halo, CN, $C_1-C_6$-alkyl, $C_1-C_6$-haloalkyl, —O—$C_1-C_6$-alkyl, C(O)N($R^f$)$_2$, C(O)O$R^f$, —OCH$_2$C(O)O$R^f$, —SO$_2R^f$, and $C_1-C_6$-alkyl-OH;

$R^5$ is, at each occurrence, independently selected from H, —OH, halo, $C_1-C_6$-alkyl, $C_1-C_6$-haloalkyl, —O—$C_1-C_6$-alkyl, and $C_1-C_6$-alkyl-OH;

alternatively, $R^4$ and $R^5$ are optionally joined to form a ring;

$R^6$ is, at each occurrence, independently selected from H, —OH, halo, $C_1-C_6$-alkyl, $C_1-C_6$-haloalkyl, —O—$C_1-C_6$-alkyl, and $C_1-C_6$-alkyl-OH;

$R^7$ is selected from H, $C_1-C_6$-alkyl, and $C_1-C_6$-alkyl-OH;

$R^8$ is, at each occurrence, independently selected from H, —OH, halo, $C_1-C_6$-alkyl, $C_1-C_6$-haloalkyl, —O—$C_1-C_6$-alkyl, and $C_1-C_6$-alkyl-OH;

$R^9$ is, at each occurrence, independently selected from H, —OH, halo, $C_1-C_6$-alkyl, $C_1-C_6$-haloalkyl, —O—$C_1-C_6$-alkyl, and $C_1-C_6$-alkyl-OH;

$R^a$ is selected from H, $C_1-C_6$-alkyl, and $C_1-C_6$-alkyl-OH;

$R^b$ is selected from H and $C_1-C_6$-alkyl;

$R^f$ is, at each occurrence, independently selected from H and $C_1-C_6$-alkyl;

m is 0, 1, 2, 3, or 4;
n is 0, 1, 2, or 3; and
p is 0, 1, 2, 3, or 4.

In another embodiment of the compound of Formula I, $W^1$ is N$R^a$ and W is N or C$R^a$. In a further embodiment, $W^1$ is NH.

In another embodiment of the compound of Formula I, $W^1$ is N or C$R^a$ and W is N$R^a$.

In another embodiment of the compound of Formula I, X is N.

In an embodiment of the compound of Formula I, Y is —C(O)— or —SO$_2$—.

In a further embodiment of the compound of Formula I, Z is $-(CR^5R^6)_m-$, $-(CR^5R^6)_mO-$, or $-(CR^5R^6)_m-NR^7-$.

In an embodiment of the compound of Formula I,
m is 0 or 1;
$R^5$ is H, —OH, or $C_1-C_6$-alkyl;
$R^6$ is H or $C_1-C_6$-alkyl; and
$R^7$ is H or $C_1-C_6$-alkyl.

In an embodiment of the compound of Formula I, $R^1$ is $C_6$-aryl or $C_1-C_9$-heteroaryl wherein aryl and heteroaryl are optionally substituted with 1 or 2 groups independently selected from —OH, halo, $C_1-C_6$-alkyl, $C_1-C_6$-haloalkyl, —O—$C_1-C_6$-alkyl, $C_1-C_6$-alkyl-OH, CN, and C(O)H.

In another embodiment of the compound of Formula I, $R^1$ is $C_6$-aryl, pyrimidinyl, pyridinyl, pyrazolyl, thiophenyl, thiazolyl, isothiazolyl, oxazolyl, pyridazinyl, pyrazinyl, or pyrrolyl, any of which are optionally substituted by 1 or 2 groups independently selected from —OH, halo, $C_1-C_6$-alkyl, $C_1-C_6$-haloalkyl, —O—$C_1-C_6$-alkyl, $C_1-C_6$-alkyl-OH, CN, and C(O)H.

In an embodiment of the compound of Formula I, each $R^2$ is independently selected from H, $C_1-C_6$-alkyl, or $C_1-C_6$-alkyl-OH. In a further embodiment of the compound of Formula I, each $R^2$ is independently selected from $C_1-C_6$-alkyl or H. In yet a further embodiment of the compound of Formula I, $R^2$ is H.

In an embodiment of the compound of Formula I, $R^3$ is H or $C_1-C_6$-alkyl.

In an embodiment of the compound of Formula I, $R^4$ is $(CR^8R^9)_p-C_3-C_8$-cycloalkyl, $(CR^8R^9)_p-C_2-C_8$-heterocyclyl, $(CR^8R^9)_p-C_6-C_{12}$-aryl, or $(CR^8R^9)_p-C_1-C_9$-heteroaryl, wherein cycloalkyl, heterocyclyl, aryl, and heteroaryl are optionally substituted with 1, 2, 3, or 4 groups each independently selected from —OH, halo, CN, $C_1-C_6$-alkyl, $C_1-C_6$-haloalkyl, —O—$C_1-C_6$-alkyl, C(O)N($R^f$)$_2$, C(O)O$R^f$, —OCH$_2$C(O)O$R^f$, —SO$_2R^f$, and $C_1-C_6$-alkyl-OH.

In another embodiment of the compound of Formula I, $R^4$ is $(CR^8R^9)_p-C_6-C_{12}$-aryl, or $(CR^8R^9)_p-C_1-C_9$-heteroaryl, wherein aryl, and heteroaryl are optionally substituted with 1, 2, 3, or 4 groups, each independently selected from —OH, halo, CN, $C_1-C_6$-alkyl, $C_1-C_6$-haloalkyl, —O—$C_1-C_6$-alkyl, C(O)N($R^f$)$_2$, C(O)O$R^f$, —OCH$_2$C(O)O$R^f$, —SO$_2R^f$, and $C_1-C_6$-alkyl-OH.

In another embodiment of the compound of Formula I,
p is 0 or 1;
$R^8$ is H, —OH, or $C_1-C_6$-alkyl; and
$R^9$ is H or $C_1-C_6$-alkyl.

In an embodiment of the compound of Formula I, n is 1.

In another embodiment of the compound of Formula I,
X is N;
Y is —C(O)—;
Z is N$R^7$; and
$R^7$ is H or $C_{1-4}$-alkyl.

In a further embodiment of the compound of Formula I,
X is N;
Y is —C(O)—;
Z is N$R^7$;
$R^7$ is H or $C_{1-4}$-alkyl; and
n is 1.

Also provided herein is a compound of Formula I, having the structure of Formula II (also referred to as "a compound of Formula II"):

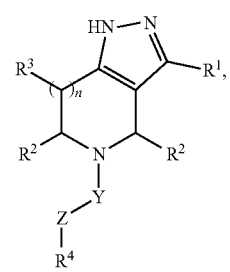

or a pharmaceutically acceptable salt thereof.

In an embodiment of the compound of Formula II, Y is —C(O)— or —SO$_2$—.

In an embodiment of the compound of Formula II, Z is —$(CR^5R^6)_m$—, —$(CR^5R^6)_mO$— or —$(CR^5R^6)_m$—$NR^7$—.

In an embodiment of the compound of Formula II,
m is 0 or 1;
$R^5$ is H, —OH, or $C_1$-$C_6$-alkyl;
$R^6$ is H or $C_1$-$C_6$-alkyl; and
$R^7$ is H or $C_1$-$C_6$-alkyl.

In an embodiment of the compound of Formula II, $R^1$ is $C_6$-$C_{12}$-aryl or $C_1$-$C_9$-heteroaryl, wherein aryl and heteroaryl are optionally substituted with 1 or 2 groups each independently selected from —OH, halo, $C_1$-$C_6$-alkyl, $C_1$-$C_6$-haloalkyl, —O—$C_1$-$C_6$-alkyl, $C_1$-$C_6$-alkyl-OH, CN, and C(O)H.

In another embodiment of the compound of Formula II, $R^1$ is $C_6$-aryl, pyrimidinyl, pyridinyl, pyrazolyl, thiophenyl, thiazolyl, isothiazolyl, oxazolyl, pyridazinyl, pyrazinyl, or pyrrolyl, any of which are optionally substituted by 1 or 2 groups independently selected from —OH, halo, $C_1$-$C_6$-alkyl, $C_1$-$C_6$-haloalkyl, —O—$C_1$-$C_6$-alkyl, $C_1$-$C_6$-alkyl-OH, CN, and C(O)H.

In an embodiment of the compound of Formula II, each $R^2$ is independently selected from H, $C_1$-$C_6$-alkyl, or $C_1$-$C_6$-alkyl-OH. In a further embodiment of the compound of Formula II, each $R^2$ is independently selected from $C_1$-$C_6$-alkyl or H. In yet a further embodiment of the compound of Formula II, $R^2$ is H.

In an embodiment of the compound of Formula II, $R^3$ is H or $C_1$-$C_6$-alkyl. In a further embodiment, $R^3$ is H.

In an embodiment of the compound of Formula II, n is 1.

In an embodiment of the compound of Formula II, $R^4$ is $(CR^8R^9)_p$—$C_3$-$C_8$-cycloalkyl, $(CR^8R^9)_p$—$C_2$-$C$ s-heterocyclyl, $(CR^8R^9)_p$—$C_6$-$C_{12}$-aryl, or $(CR^8R^9)_p$—$C_1$-$C_9$-heteroaryl, wherein cycloalkyl, heterocyclyl, aryl, and heteroaryl are optionally substituted with 1, 2, 3, or 4 groups, each independently selected from —OH, halo, CN, $C_1$-$C_6$-alkyl, $C_1$-$C_6$-haloalkyl, —O—$C_1$-$C_6$-alkyl, $C(O)N(R^f)_2$, $C(O)OR^f$, —$OCH_2C(O)OR^f$, —$SO_2R^f$, and $C_1$-$C_6$-alkyl-OH.

In an embodiment of the compound of Formula II, $R^4$ is $(CR^8R^9)_p$—$C_6$-$C_{12}$-aryl, or $(CR^8R^9)_p$—$C_1$-$C_9$-heteroaryl, and wherein aryl and heteroaryl are optionally substituted with 1, 2, 3, or 4 groups, each independently selected from —OH, halo, CN, $C_1$-$C_6$-alkyl, $C_1$-$C_6$-haloalkyl, —O—$C_1$-$C_6$-alkyl, $C(O)N(R^f)_2$, $C(O)OR^f$, —$OCH_2C(O)OR^f$, —$SO_2R^f$, and $C_1$-$C_6$-alkyl-OH.

In an embodiment of the compound of Formula II,
Y is —C(O)—;
Z is —$(CR^5R^6)_m$—, —$(CR^5R^6)_mO$— or —$(CRR^6)_m$—$NR^7$—;
$R^1$ is $C_6$-aryl, pyrimidinyl, pyridinyl, pyrazolyl, thiophenyl, thiazolyl, isothiazolyl, oxazolyl, pyridazinyl, pyrazinyl, or pyrrolyl, any of which are optionally substituted by 1 or 2 groups independently selected from —OH, halo, $C_1$-$C_6$-alkyl, $C_1$-$C_6$-haloalkyl, —O—$C_1$-$C_6$-alkyl, $C_1$-$C_6$-alkyl-OH, CN, and C(O)Heach $R^2$ is independently selected from H, $C_1$-$C_6$-alkyl, or $C_1$-$C_6$-alkyl-OH and $R^3$ is H;
$R^4$ is $(CR^8R^9)_p$—$C_6$-$C_{12}$-aryl, or $(CR^8R^9)_p$—$C_1$-$C_9$-heteroaryl, and wherein aryl and heteroaryl are optionally substituted with 1, 2, 3, or 4 groups, each independently selected from —OH, halo, CN, $C_1$-$C_6$-alkyl, $C_1$-$C_6$-haloalkyl, —O—$C_1$-$C_6$-alkyl, $C(O)N(R^f)_2$, $C(O)OR^f$, —$OCH_2C(O)OR^f$, —$SO_2R^f$, and $C_1$-$C_6$-alkyl-OH;
$R^5$ is H, —OH, or $C_1$-$C_6$-alkyl;
$R^6$ is H or $C_1$-$C_6$-alkyl;
$R^7$ is H or $C_1$-$C_6$-alkyl;
$R^8$ is, at each occurrence, independently selected from H, —OH, halo, and $C_1$-$C_6$-alkyl;
$R^9$ is, at each occurrence, independently selected from H, —OH, halo, and $C_1$-$C_6$-alkyl;
$R^f$ is, at each occurrence, independently selected from H and $C_1$-$C_6$-alkyl;
m is 1 or 2;
n is 1; and
p is 0, 1, or 2.

In an embodiment of this embodiment, $R^1$ is $C_6$-aryl, optionally substituted by —OH or halo.

In an embodiment of this embodiment, $R^1$ is $C_6$-aryl, optionally substituted with halo.

In an embodiment of this embodiment, $R^4$ is $(CR^8R^9)_p$—$C_6$-$C_{12}$-aryl, or $(CR^8R^9)_p$—$C_1$-$C_9$-heteroaryl, and wherein aryl and heteroaryl are optionally substituted with 1, 2, or 3 groups, each independently selected from —OH, halo, CN, $C_1$-$C_6$-alkyl, $C_1$-$C_6$-haloalkyl, —O—$C_1$-$C_6$-alkyl, and $C_1$-$C_6$-alkyl-OH.

In an embodiment of the compound of Formula II,
p is 0 or 1;
$R^8$ is independently selected from H, —OH, and $C_1$-$C_6$-alkyl; and
$R^9$ is independently selected from H and $C_1$-$C_6$-alkyl.

In an embodiment of the compound of Formula II, n is 1.

In an embodiment of the compound of Formula II,
Y is —C(O)—;
Z is $NR^7$; and
$R^7$ is H or $C_{1-4}$-alkyl.

In an embodiment of the compound of Formula II,
Y is —C(O)—;
Z is $NR^7$;
$R^7$ is H or $C_{1-4}$-alkyl; and
n is 1.

Also provided herein is a compound of Formula I, having the structure of Formula III (also referred to as "a compound of Formula III"):

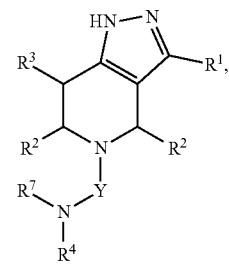

III or a pharmaceutically acceptable salt thereof, wherein
Y is —C(O)— or —$SO_2$—;
$R^1$ is $C_6$-$C_{12}$-aryl or $C_1$-$C_9$-heteroaryl, wherein aryl and heteroaryl are optionally substituted with 1 or 2 groups each independently selected from —OH, halo, $C_1$-$C_6$-alkyl, $C_1$-$C_6$-haloalkyl, —O—$C_1$-$C_6$-alkyl, $C_1$-$C_6$-alkyl-OH, CN, and C(O)H;
$R^2$ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;
$R^3$ is selected from H, —OH, halo, $C_1$-$C_6$-alkyl, $C_1$-$C_6$-haloalkyl, —O—$C_1$-$C_6$-alkyl, and $C_1$-$C_6$-alkyl-OH;
$R^4$ is selected from $(CR^8R^9)_p$—$C_1$-$C_9$-heteroaryl, $(CR^8R^9)_p$—$C_6$-$C_{12}$-aryl, and $C_3$-$C_5$-cycloalkyl wherein heteroaryl, aryl, and cycloalkyl are optionally substituted with 1, 2, or 3 groups, each independently selected from —OH, halo, CN, $C_1$-$C_6$-alkyl, $C_1$-$C_6$-haloalkyl, —O—$C_1$-$C_6$-alkyl, $C_1$-$C_6$-alkyl-OH, and $C_3$-$C_5$-cycloalkyl.

R⁷ is selected from H, $C_1$-$C_6$-alkyl, and $C_1$-$C_6$-alkyl-OH;

R⁸ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

R⁹ is, at each occurrence, independently selected from H and $C_1$-$C_6$-alkyl; and p is 0, 1, 2, 3, or 4.

In an embodiment of the Compound of Formula III

Y is —C(O)— or —SO$_2$—;

R¹ is $C_6$-aryl, pyrimidinyl, pyridinyl, pyrazolyl, thiophenyl, thiazolyl, isothiazolyl, oxazolyl, pyridazinyl, pyrazinyl, or pyrrolyl, any of which are optionally substituted by 1 or 2 groups independently selected from —OH, halo, $C_1$-$C_6$-alkyl, $C_1$-$C_6$-haloalkyl, —O—$C_1$-$C_6$-alkyl, $C_1$-$C_6$-alkyl-OH, CN, and C(O)H;

R² is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

R³ is selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

R⁴ is selected from $(CR^8R^9)_p$—$C_1$-$C_9$-heteroaryl and $(CR^8R^9)_p$—$C_6$-$C_{12}$-aryl, wherein heteroaryl and aryl are optionally substituted with 1, 2, or 3 groups, each independently selected from —OH, halo, CN, $C_1$-$C_6$-alkyl, $C_1$-$C_6$-haloalkyl, —O—$C_1$-$C_6$-alkyl, and $C_1$-$C_6$-alkyl-OH.

R⁷ is selected from H, $C_1$-$C_6$-alkyl, and $C_1$-$C_6$-alkyl-OH;

R⁸ is, at each occurrence, independently selected from H, —OH, halo, $C_1$-$C_6$-alkyl, $C_1$-$C_6$-haloalkyl, —O—$C_1$-$C_6$-alkyl, and $C_1$-$C_6$-alkyl-OH;

R⁹ is, at each occurrence, independently selected from H and $C_1$-$C_6$-alkyl; and p is 0, 1, 2, 3, or 4.

In an embodiment of the compound of Formula III, Y is —C(O)—.

In an embodiment of the compound of Formula III, R¹ is $C_6$-aryl, or $C_1$-$C_9$-heteroaryl, wherein aryl or heteroaryl are optionally substituted by —OH, halo, $C_1$-$C_6$-alkyl, or —O—$C_1$-$C_6$-alkyl.

In an embodiment of the compound of Formula III, R¹ is $C_6$-aryl, $C_6$-aryl, pyrimidinyl, pyridinyl, pyrazolyl, thiophenyl, thiazolyl, isothiazolyl, oxazolyl, or pyridazinyl, any of which are optionally substituted by 1 or 2 groups independently selected from —OH, halo, $C_1$-$C_6$-alkyl, $C_1$-$C_6$-haloalkyl, —O—$C_1$-$C_6$-alkyl, $C_1$-$C_6$-alkyl-OH, CN, and C(O)H.

In another embodiment of the compound of Formula III, R¹ is $C_6$-aryl.

In another embodiment of the compound of Formula III, each R² is independently selected from H, $C_1$-$C_6$-alkyl, or $C_1$-$C_6$-alkyl-OH. In a further embodiment of the compound of Formula III, each R² is idependantly selected from $C_1$-$C_6$-alkyl or H. In yet a further embodiment of the compound of Formula III, R² is H.

In an embodiment of the compound of Formula III, R³ is H or $C_1$-$C_6$-alkyl. In a further embodiment of the compound of Formula III, R³ is H.

In an embodiment of the compound of Formula III, R⁷ is H or $C_1$-$C_4$-alkyl. In a further embodiment, R⁷ is H or —CH$_3$. In yet another embodiment, R⁷ is H.

In an embodiment of the compound of Formula III, R⁴ is $(CR^8R^9)_p$—$C_1$-$C_5$-heteroaryl or $(CR^8R^9)_p$—$C_6$-aryl, or $C_3$-$C_5$-cycloalkyl, wherein heteroaryl, aryl and cycloalkyl are optionally substituted with 1, 2, or 3 groups, each independently selected from —OH, halo, CN, and $C_1$-$C_6$-alkyl;

R⁸ is H or $C_1$-$C_6$-alkyl;

R⁹ is H or $C_1$-$C_6$-alkyl; and p is 0 or 1.

In an embodiment of the compound of Formula III, R⁴ is $(CR^8R^9)_p$—$C_1$-$C_5$-heteroaryl or $(CR^8R^9)_p$—$C_6$-aryl, wherein heteroaryl and aryl are optionally substituted with 1, 2, or 3 groups, each independently selected from —OH, halo, CN, and $C_1$-$C_6$-alkyl;

R⁸ is H or $C_1$-$C_6$-alkyl;

R⁹ is H or $C_1$-$C_6$-alkyl; and p is 0 or 1.

In a particular embodiment of the compound of Formula III, R⁴ is

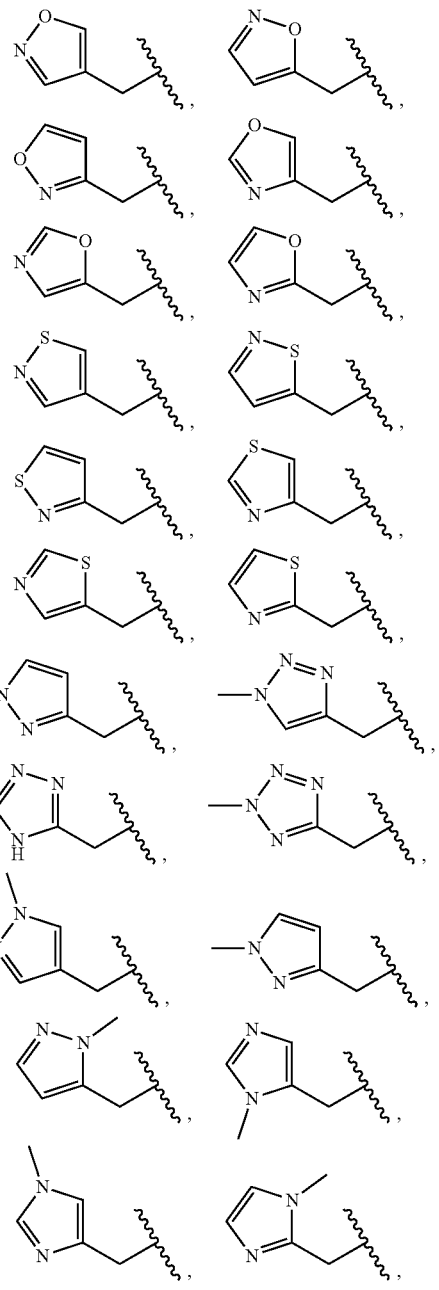

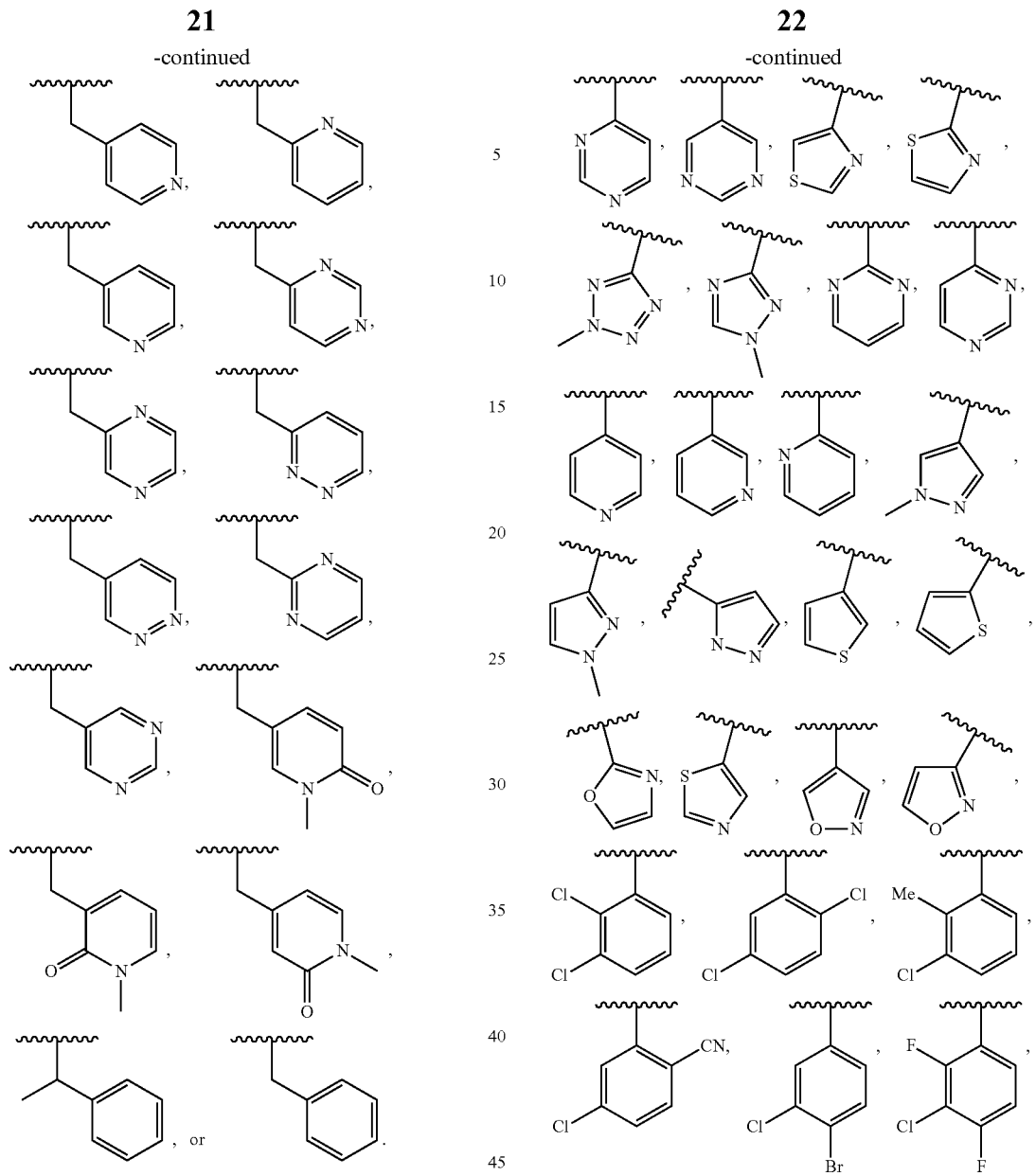
In another particular embodiment of the compound of Formula III, $R^4$ is
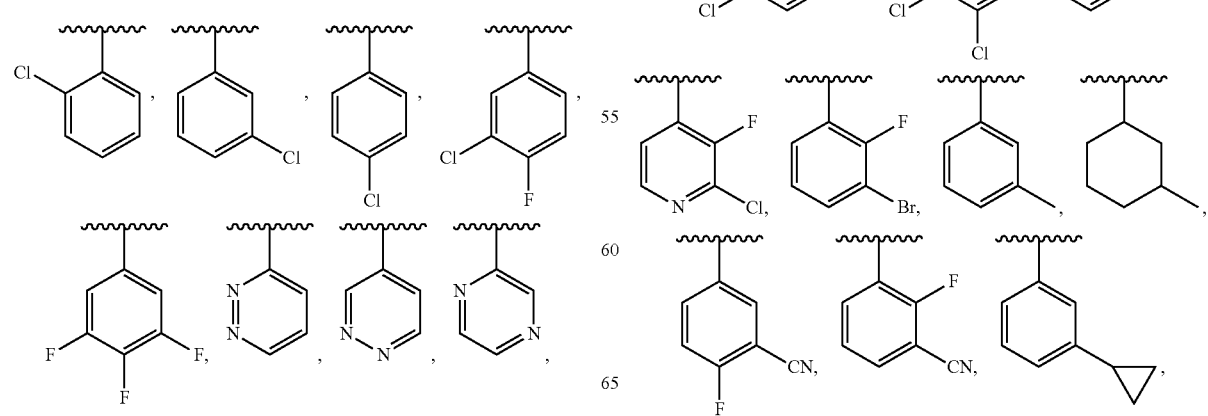

-continued

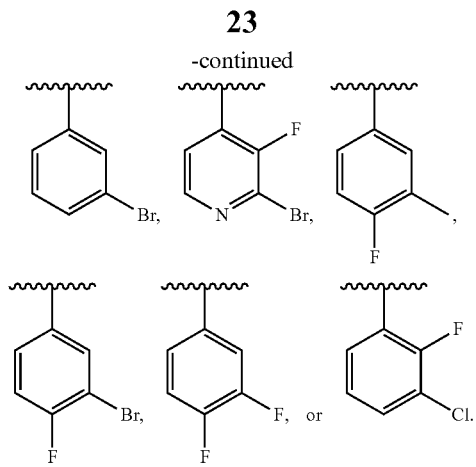

In another particular embodiment of the compound of Formula III, R⁴ is

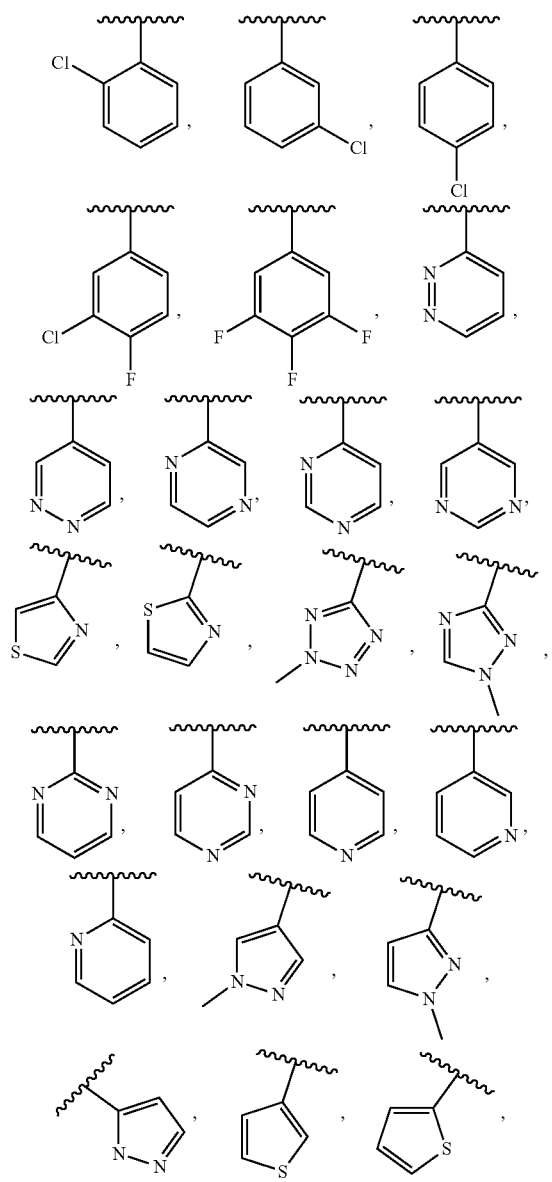

-continued

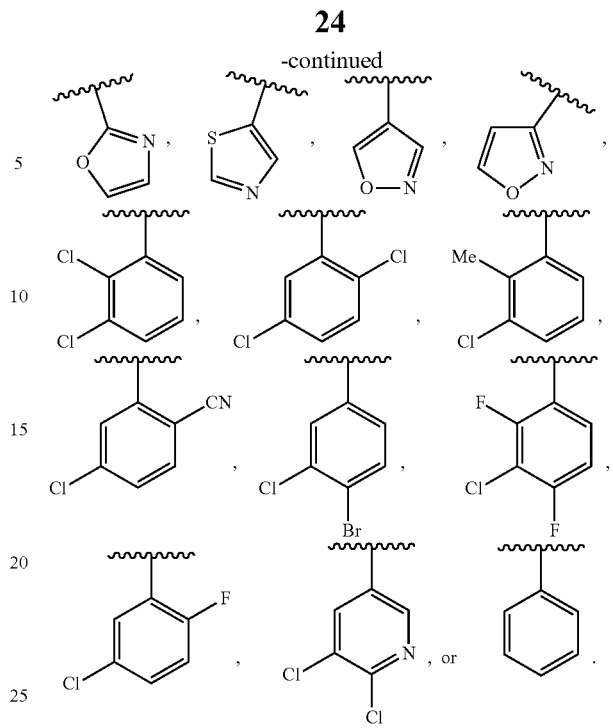

Also provided herein is a compound of Formula I, having the structure of Formula IV (also referred to as "a compound of Formula IV"):

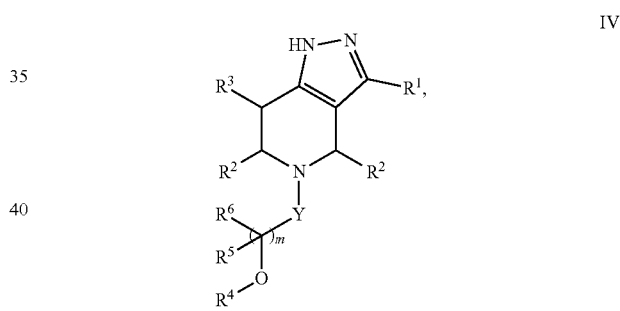

IV or a pharmaceutically acceptable salt thereof wherein,
Y is —C(O)— or —SO₂—; and
m is 0, 1, or 2.

In an embodiment of the compound of Formula IV, Y is —C(O)—.

In an embodiment of the compound of Formula IV, $R^1$ is $C_6$-$C_{12}$-aryl or $C_1$-$C_9$-heteroaryl, wherein aryl and heteroaryl are optionally substituted with 1 or 2 groups each independently selected from —OH, halo, $C_1$-$C_6$-alkyl, $C_1$-$C_6$-haloalkyl, —O—$C_1$-$C_6$-alkyl, $C_1$-$C_6$-alkyl-OH, and CN. In an embodiment of the compound of Formula IV, $R^1$ is $C_6$-aryl optionally substituted by —OH or halo.

In an embodiment of the compound of Formula IV, $R^2$ is H.

In an embodiment of the compound of Formula IV, $R^3$ is H.

In another embodiment of the compound of Formula IV, m is 1, $R^5$ is H or $C_1$-$C_6$-alkyl, $R^6$ is H or $C_1$-$C_6$-alkyl, and wherein $R^5$ and $R^4$ are optionally joined to form a ring. In another embodiment of the compound of Formula IV, m is 1; $R^5$ is $C_1$-$C_6$-alkyl; $R^6$ is H or $C_1$-$C_6$-alkyl; and $R^5$ and $R^4$ are optionally joined to form a ring. For example, in an embodiment,

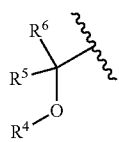

is

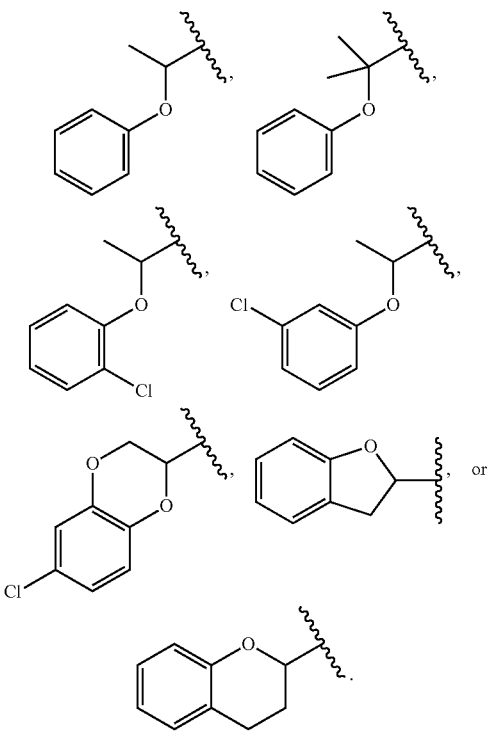

In another embodiment of the compound of Formula IV, $R^4$ is $C_1$-$C_6$-alkyl or $(CR^8R^9)_p C_6$-$C_{12}$-aryl, wherein alkyl and aryl are optionally substituted with 1, 2, or 3, groups, each independently selected from —OH, halo, CN, $C_1$-$C_6$-alkyl, $C_1$-$C_6$-haloalkyl, —O—$C_1$-$C_6$-alkyl, C(O)N($R^f$)$_2$, C(O)O$R^f$, —OCH$_2$C(O)O$R^f$, —SO$_2R^f$, and $C_1$-$C_6$-alkyl-OH.

In further embodiments of the compound of Formula IV, $R^4$ is

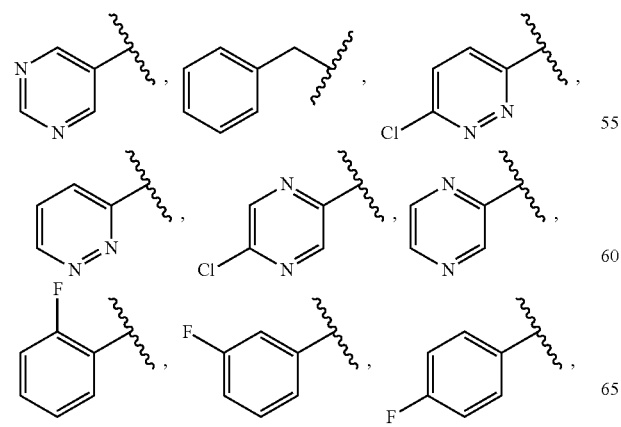

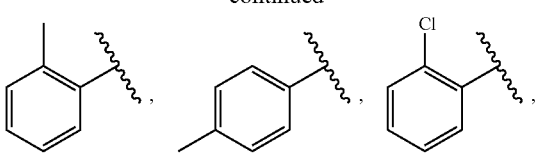

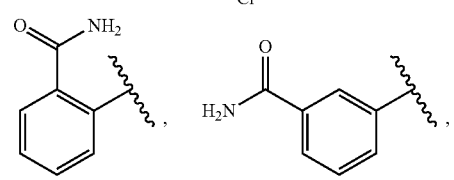

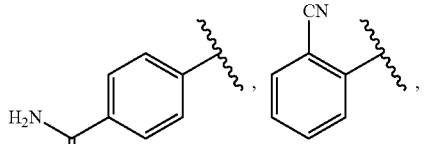

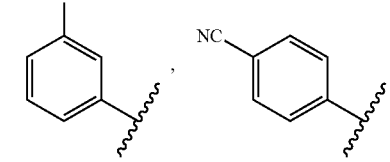

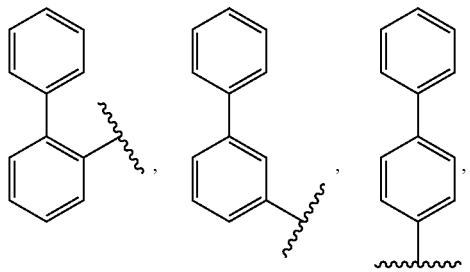

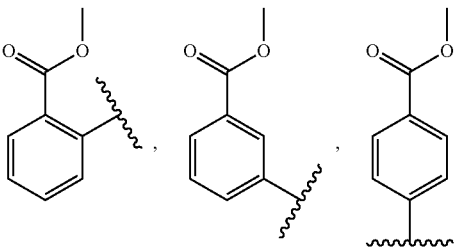

-continued

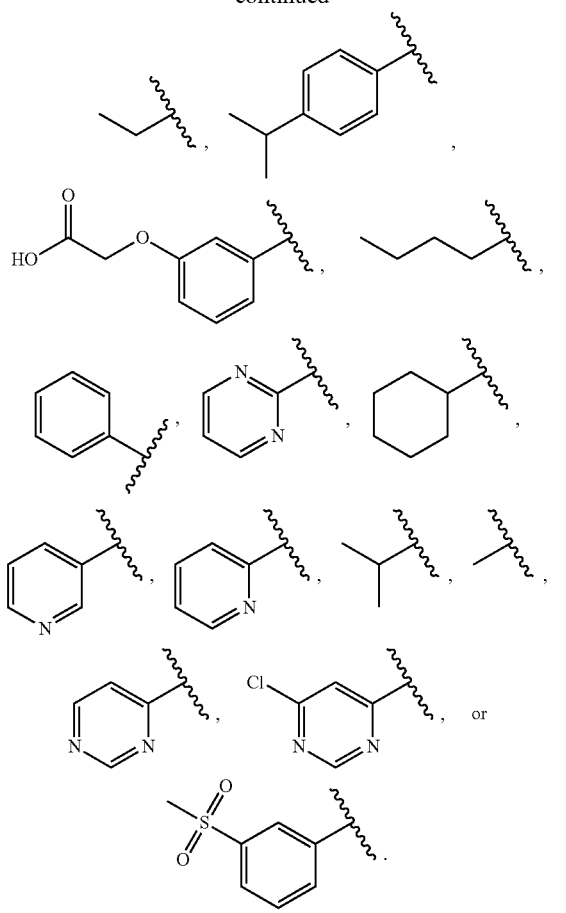

Certain embodiments of Formulas I-IV, including pharmaceutically acceptable salts thereof, are shown below in Table 1. All compounds of Formula I, II, III, and IV as well as pharmaceutically acceptable salts thereof, and the compounds of Table 1, as well as pharmaceutically acceptable salts thereof, are considered to be "compounds of the invention."

TABLE 1

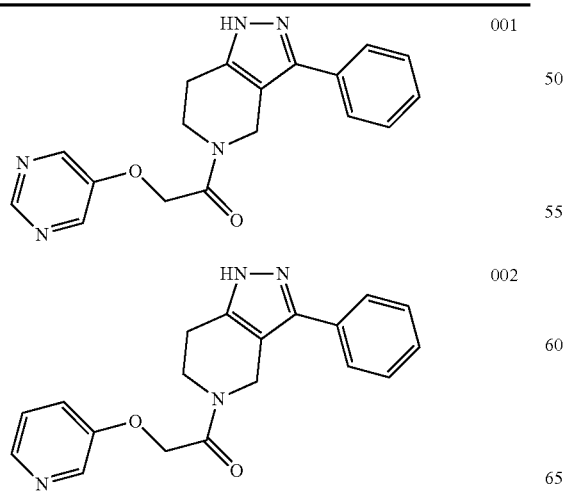

TABLE 1-continued

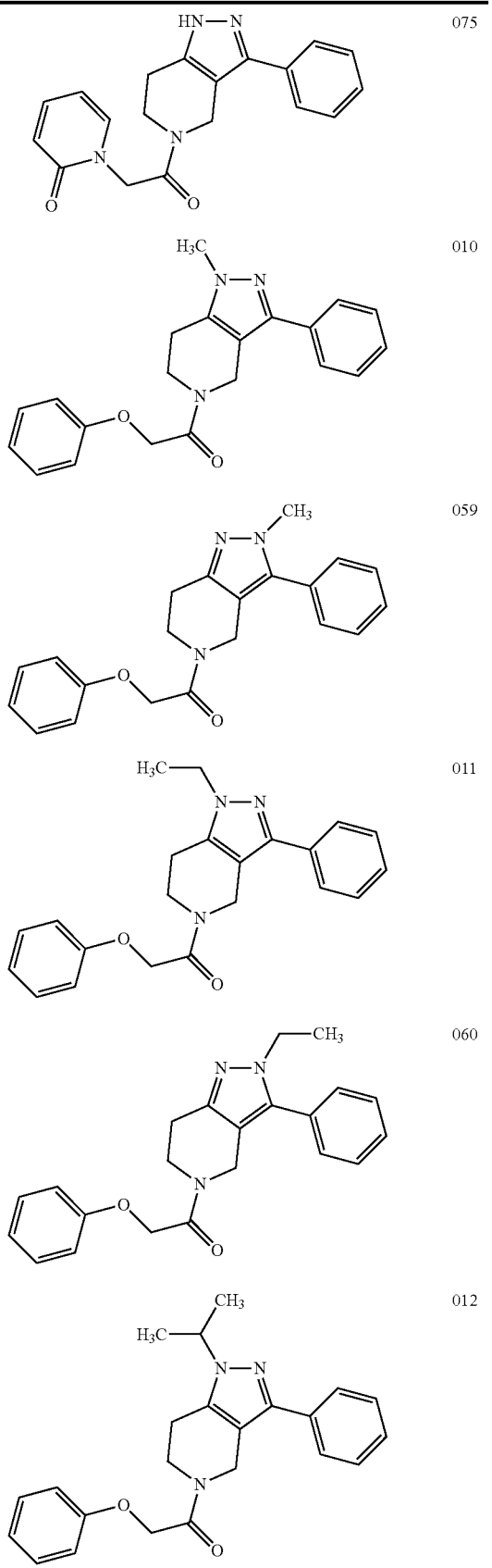

TABLE 1-continued
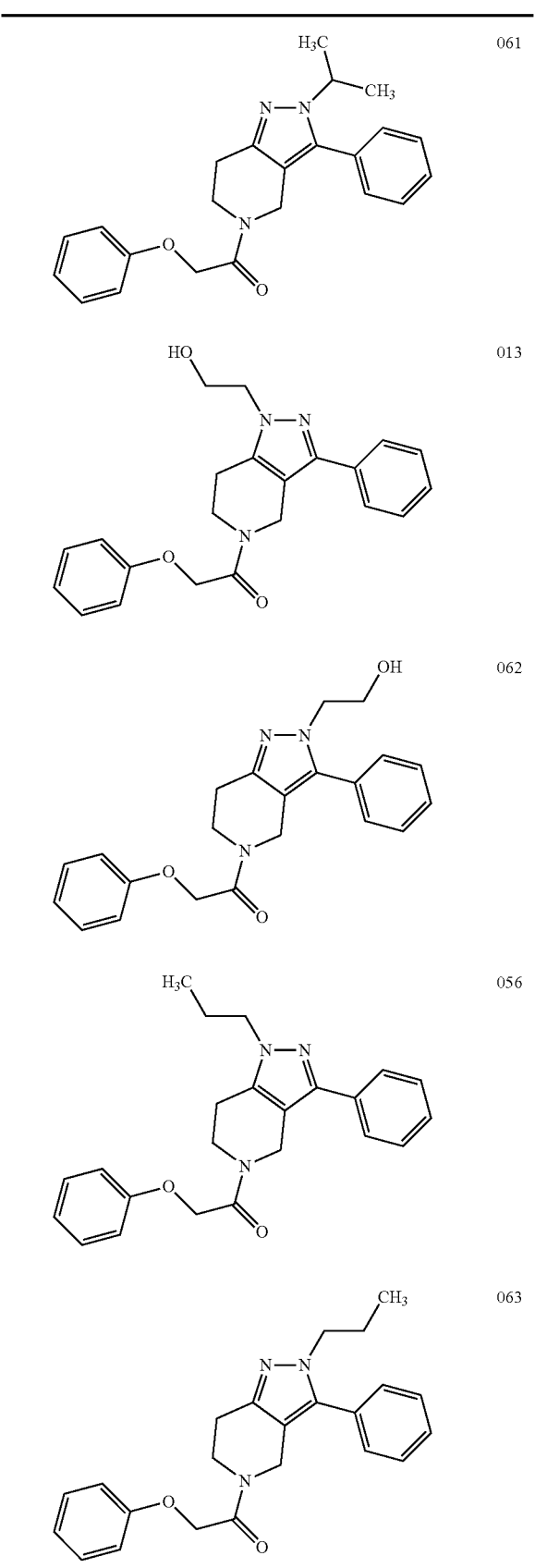
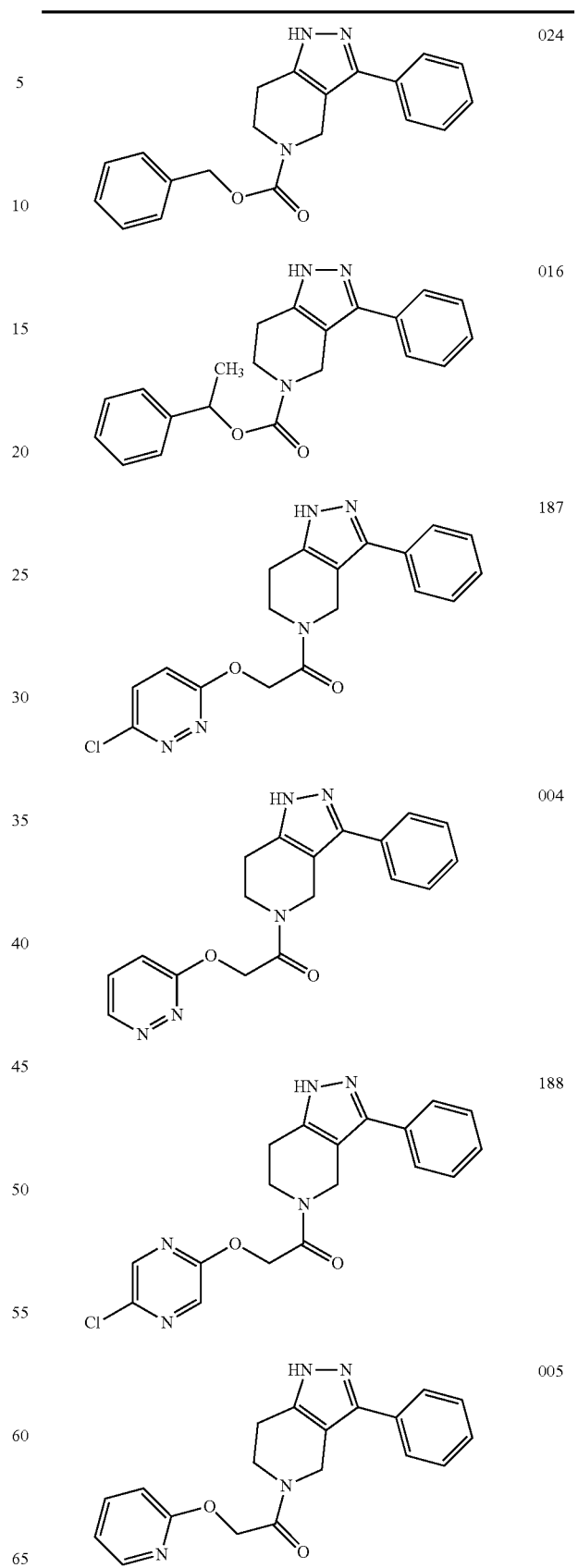

TABLE 1-continued
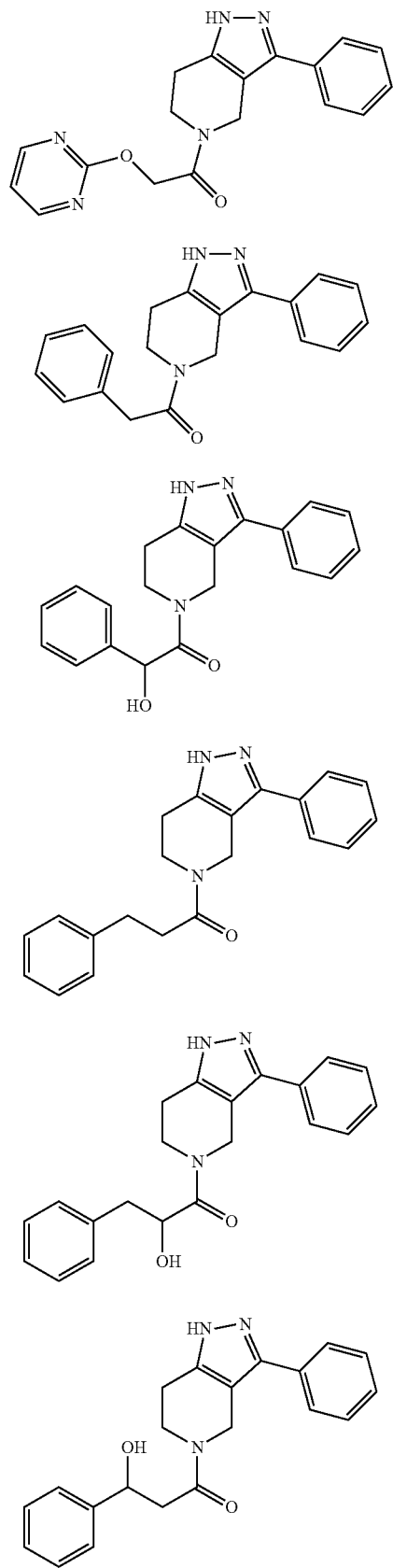
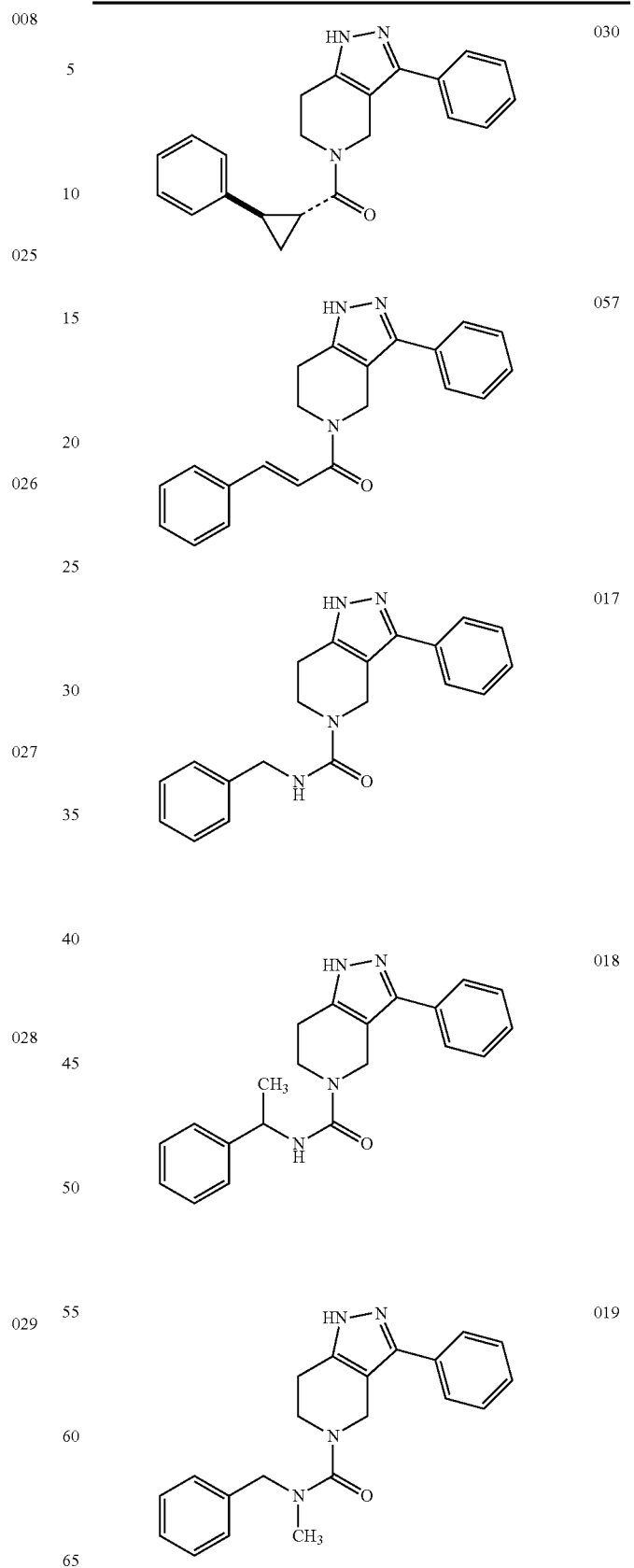

TABLE 1-continued
020 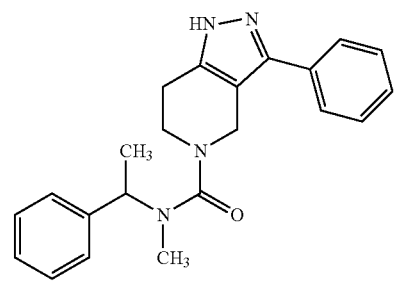 [SMILES: CC(c1ccccc1)N(C)C(=O)N1CCc2[nH]nc(-c3ccccc3)c2C1]
021 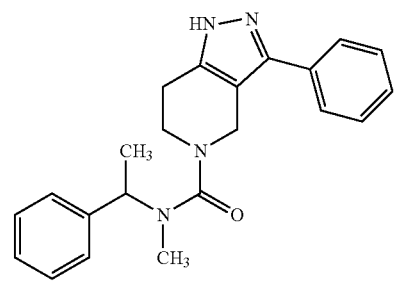 [SMILES: CC(c1ccccc1)N(C)C(=O)N1CCc2[nH]nc(-c3ccccc3)c2C1]
022 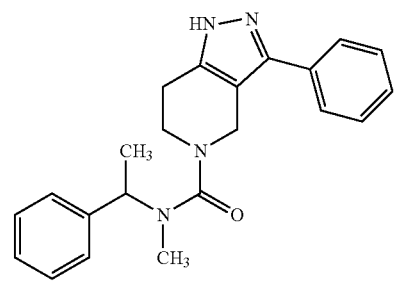 [SMILES: CC(c1ccccc1)N(C)C(=O)N1CCc2[nH]nc(-c3ccccc3)c2C1]
023 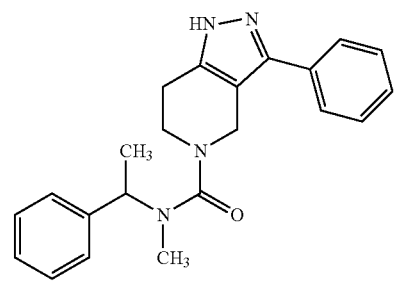 [SMILES: CC(c1ccccc1)N(C)C(=O)N1CCc2[nH]nc(-c3ccccc3)c2C1]
014 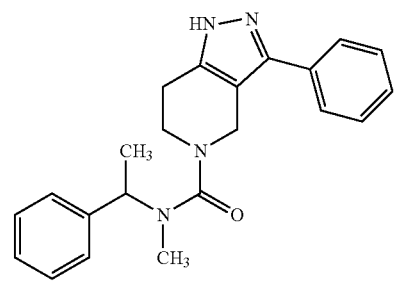 [SMILES: CC(c1ccccc1)N(C)C(=O)N1CCc2[nH]nc(-c3ccccc3)c2C1]
015 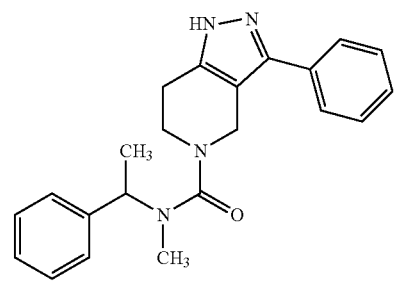 [SMILES: CC(c1ccccc1)N(C)C(=O)N1CCc2[nH]nc(-c3ccccc3)c2C1]
TABLE 1-continued
064 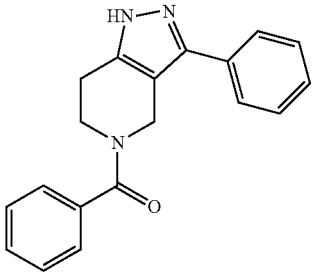 [SMILES: O=C(c1ccccc1)N1CCc2[nH]nc(-c3ccccc3)c2C1]
065 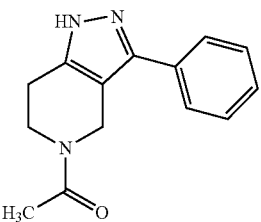 [SMILES: CC(=O)N1CCc2[nH]nc(-c3ccccc3)c2C1]
066 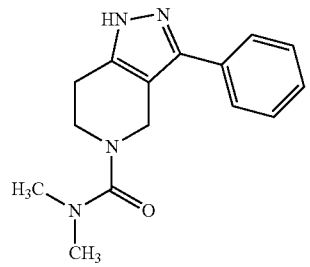 [SMILES: CN(C)C(=O)N1CCc2[nH]nc(-c3ccccc3)c2C1]
067 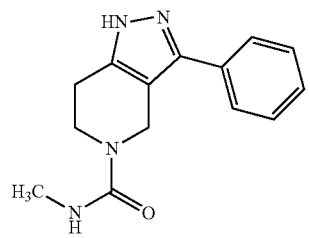 [SMILES: CNC(=O)N1CCc2[nH]nc(-c3ccccc3)c2C1]
068 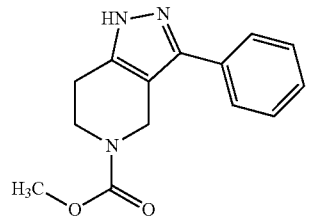 [SMILES: COC(=O)N1CCc2[nH]nc(-c3ccccc3)c2C1]
069 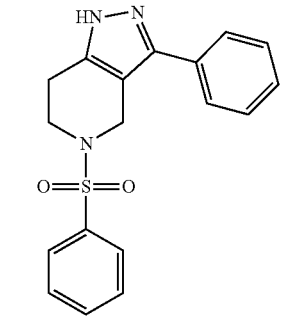 [SMILES: O=S(=O)(c1ccccc1)N1CCc2[nH]nc(-c3ccccc3)c2C1]

TABLE 1-continued
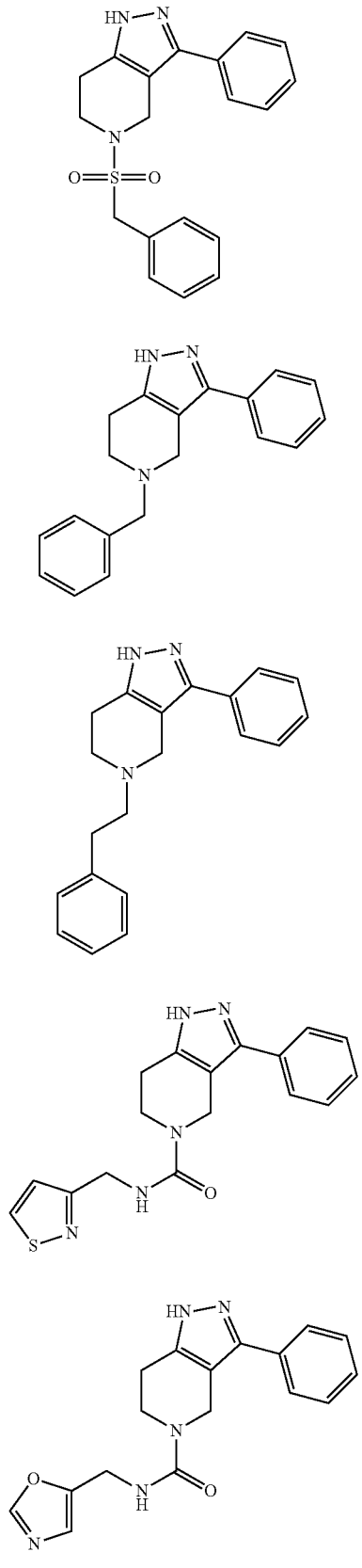
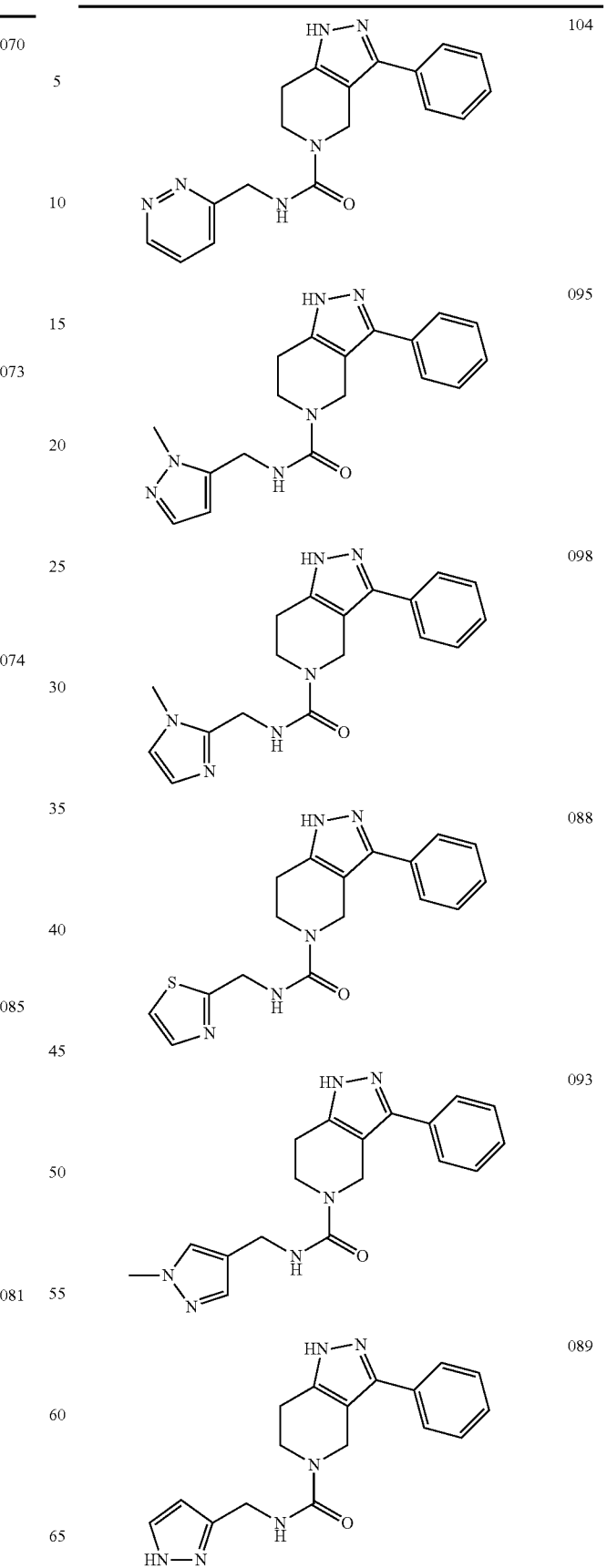

TABLE 1-continued
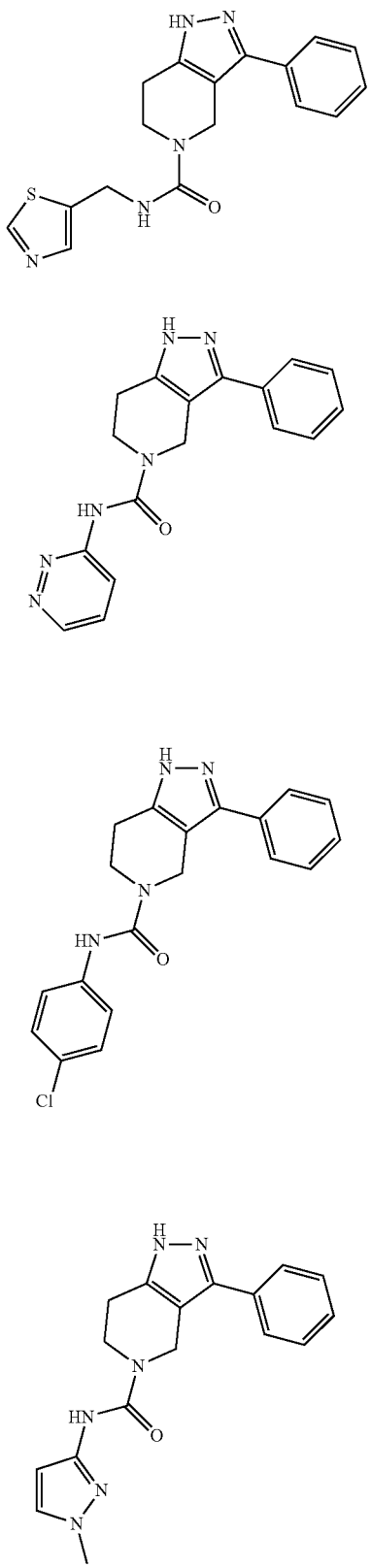
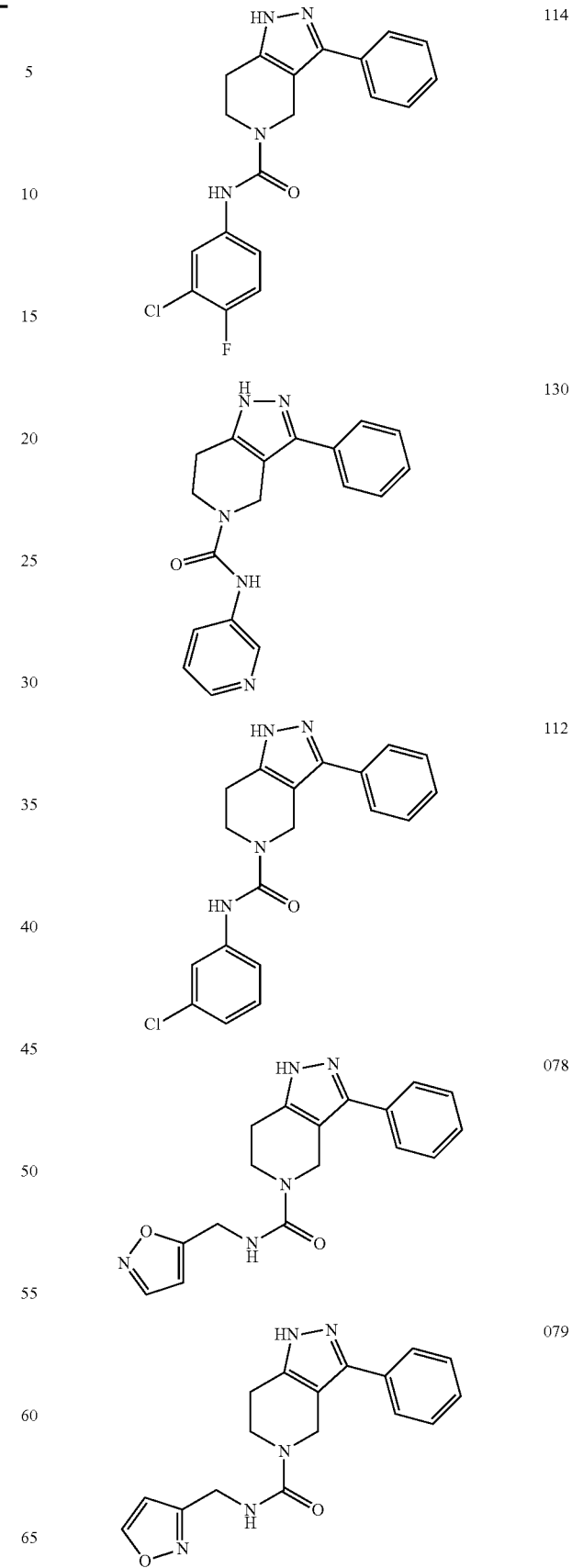

TABLE 1-continued
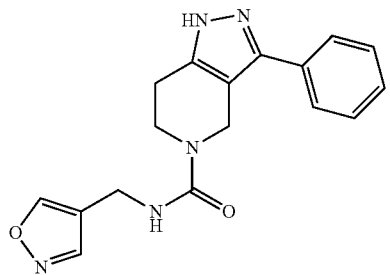 [SMILES: O=C(NCc1cnoc1)N1CCc2[nH]nc(-c3ccccc3)c2C1] 077
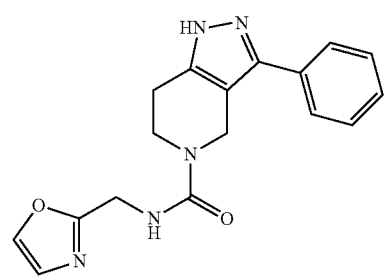 [SMILES: O=C(NCc1ncco1)N1CCc2[nH]nc(-c3ccccc3)c2C1] 082
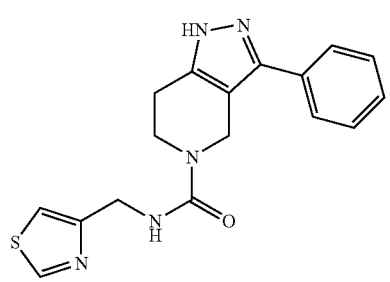 [SMILES: O=C(NCc1cscn1)N1CCc2[nH]nc(-c3ccccc3)c2C1] 086
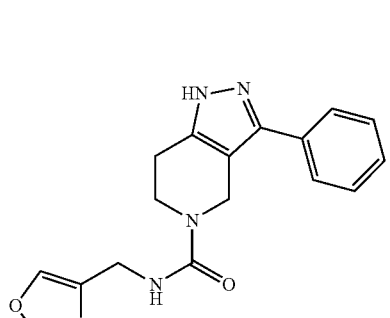 080
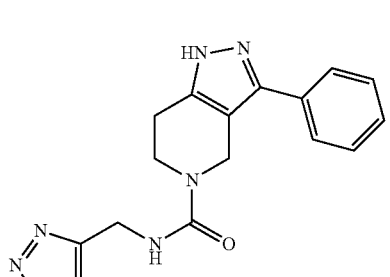 092
TABLE 1-continued
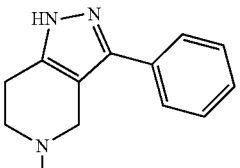 094
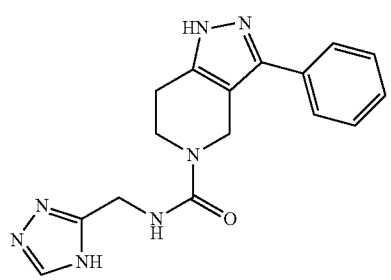 [SMILES: O=C(NCc1nnc[nH]1)N1CCc2[nH]nc(-c3ccccc3)c2C1] 091
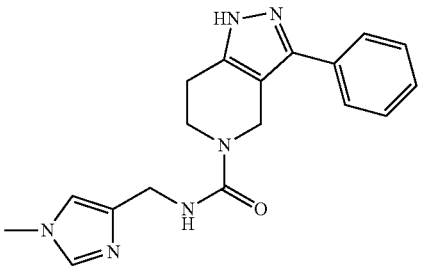 [SMILES: Cn1cnc(CNC(=O)N2CCc3[nH]nc(-c4ccccc4)c3C2)c1] 097
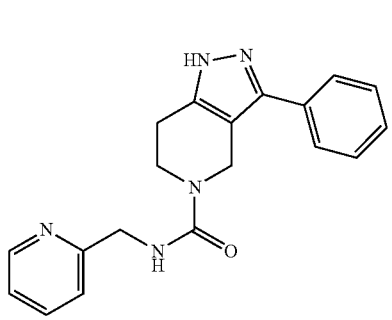 100
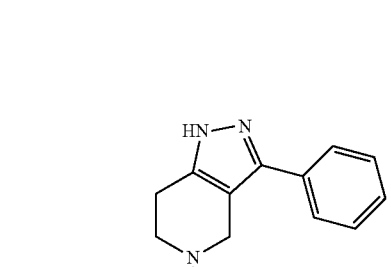 096

TABLE 1-continued
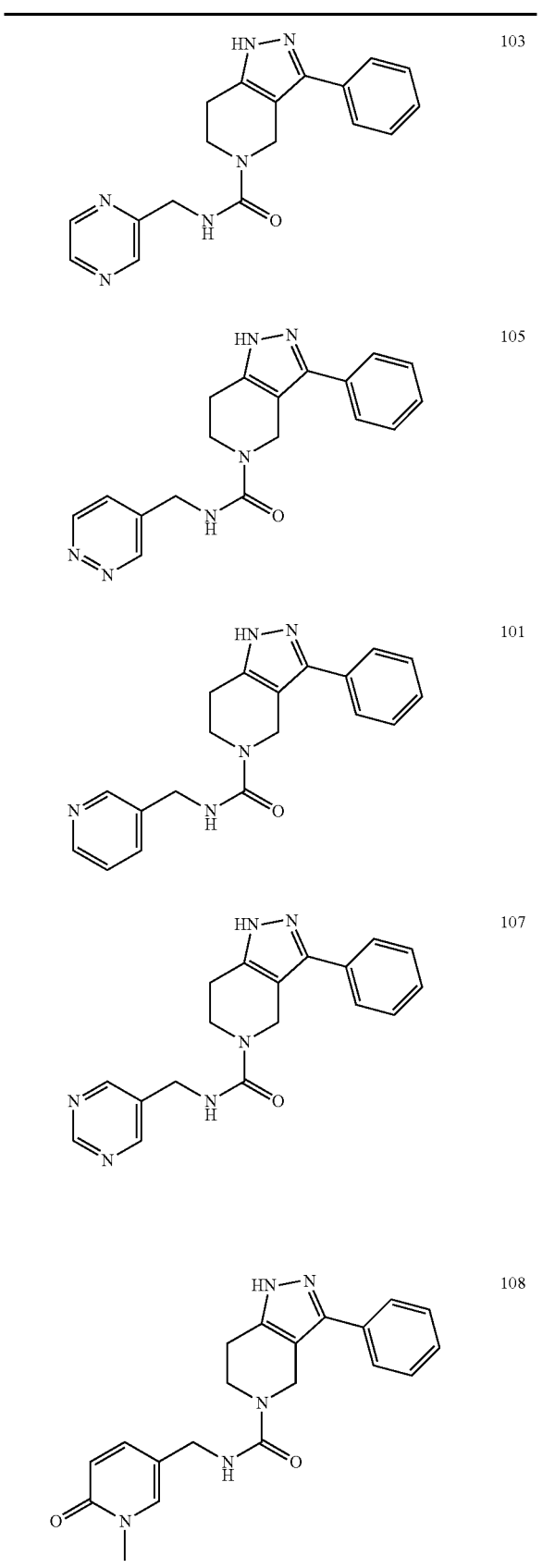
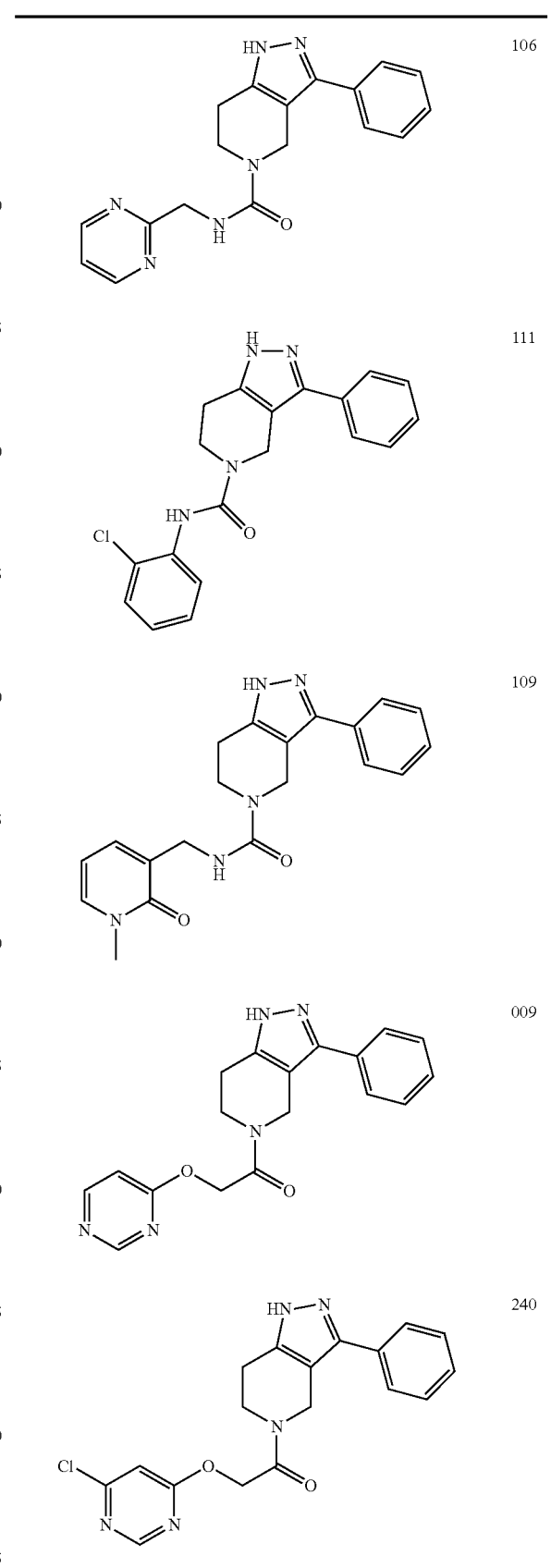

TABLE 1-continued
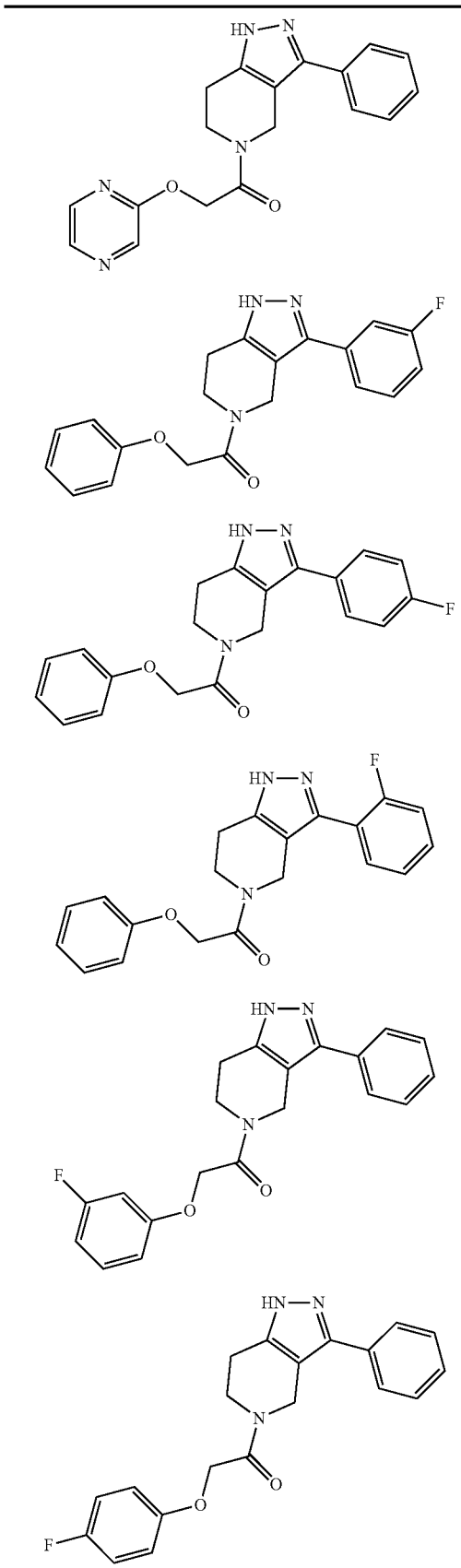
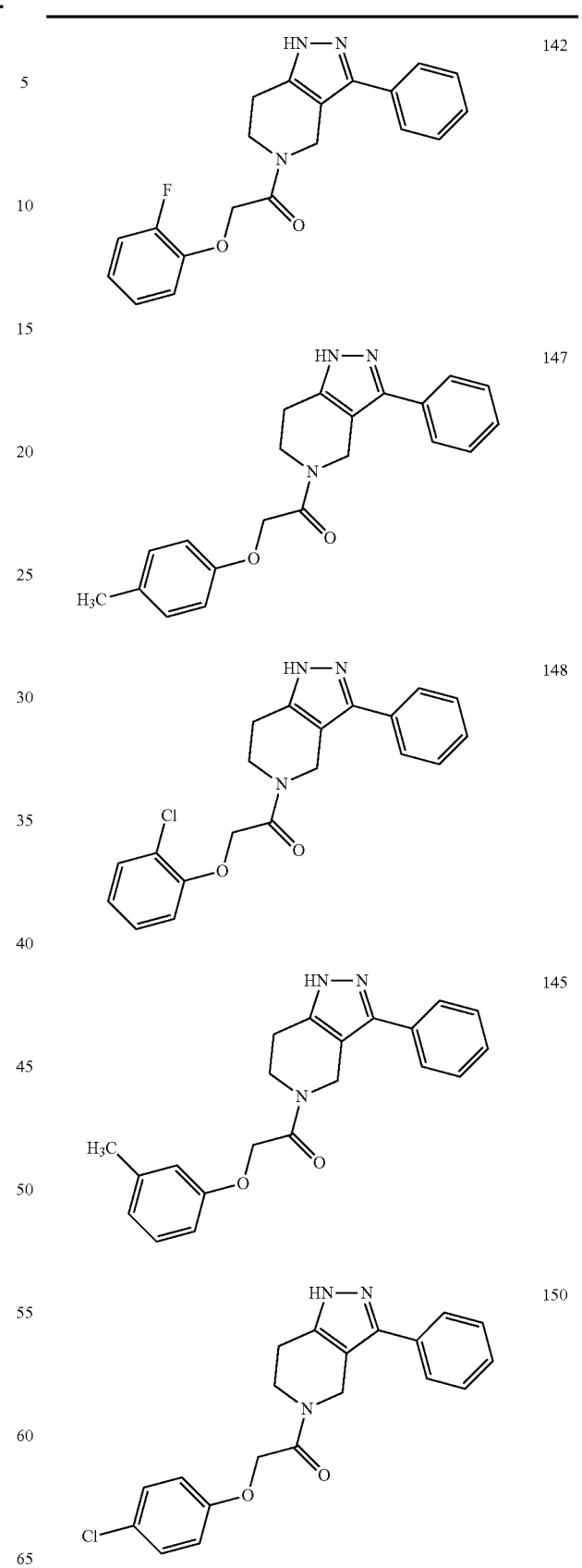

TABLE 1-continued
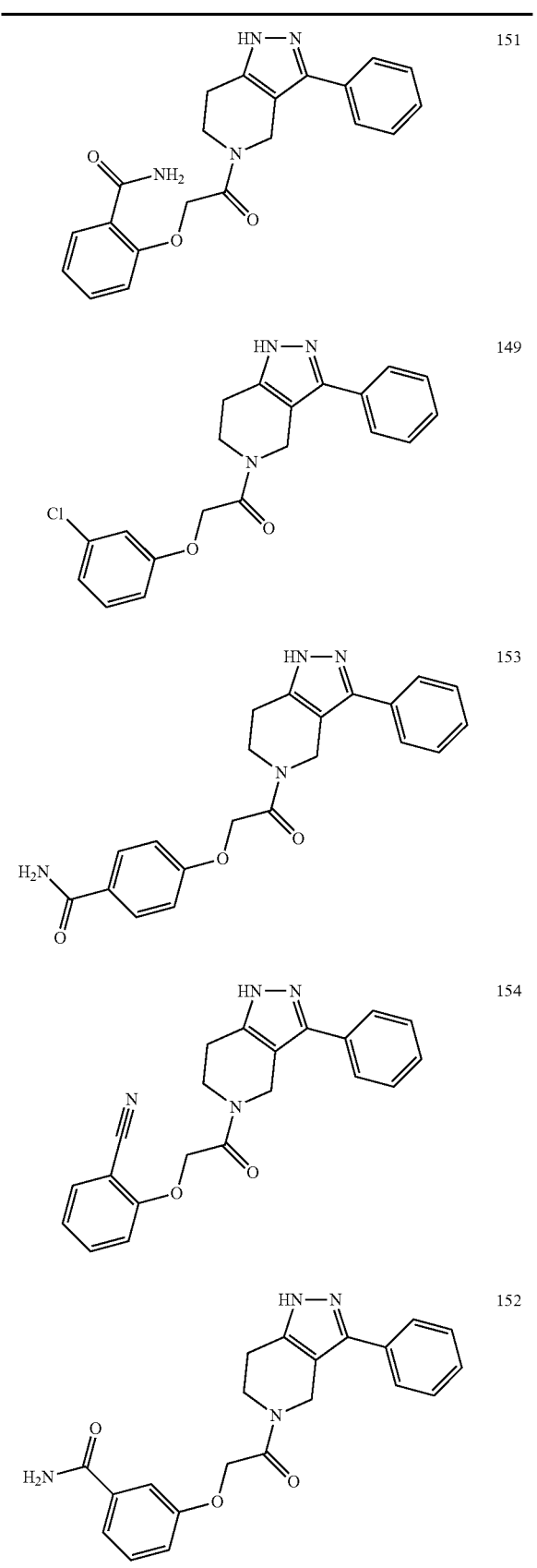
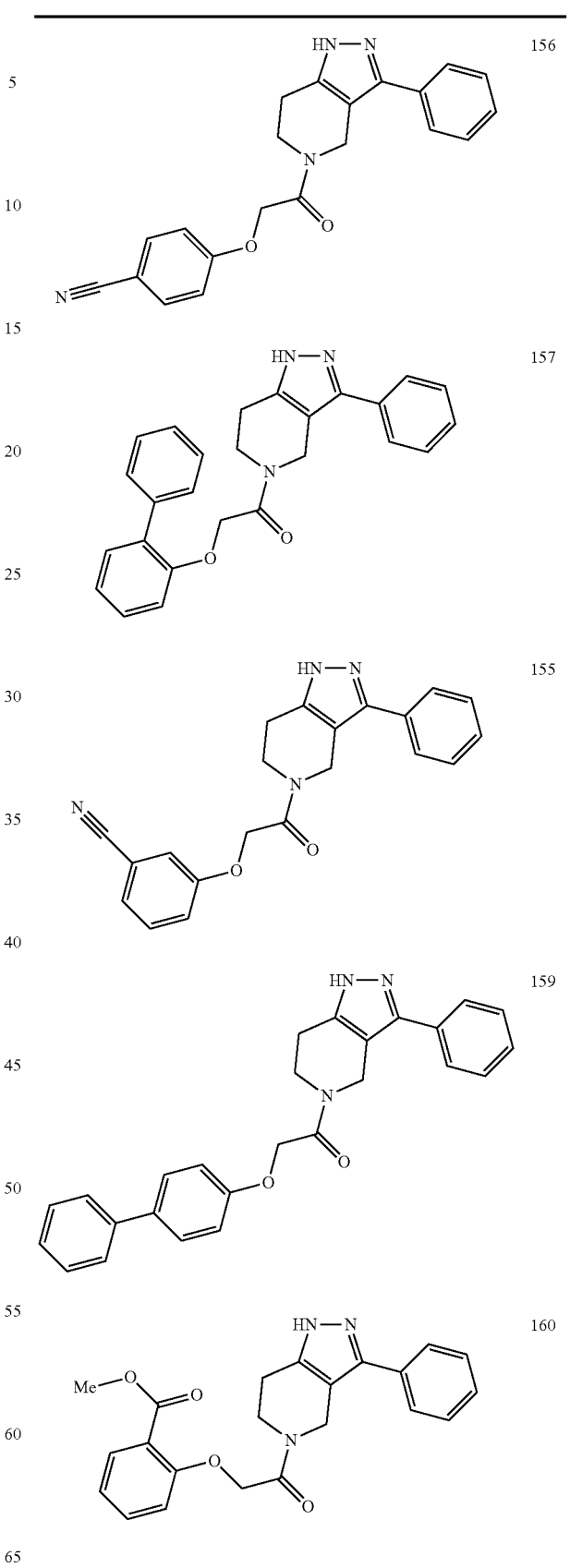

TABLE 1-continued
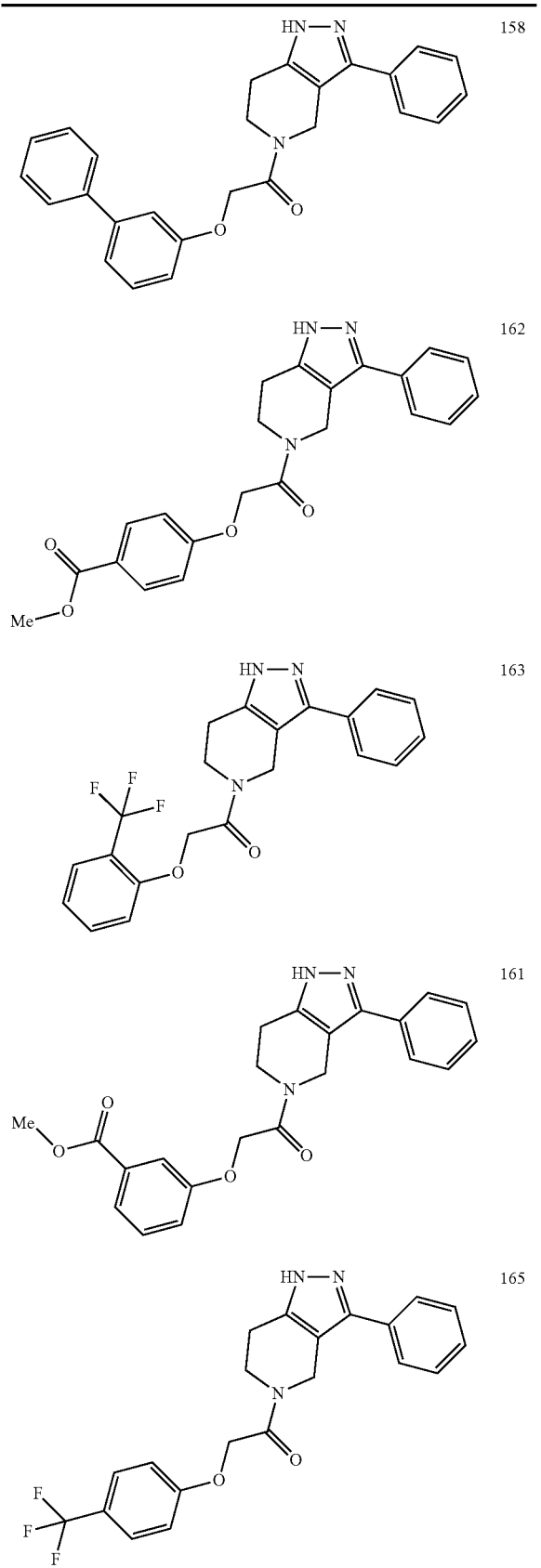
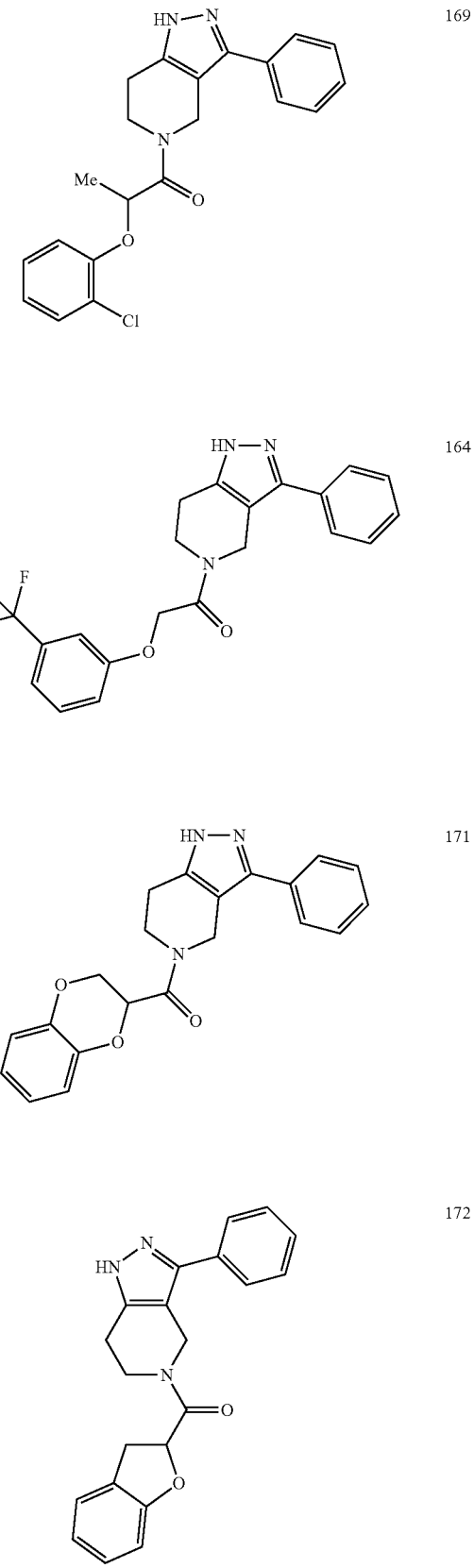

TABLE 1-continued
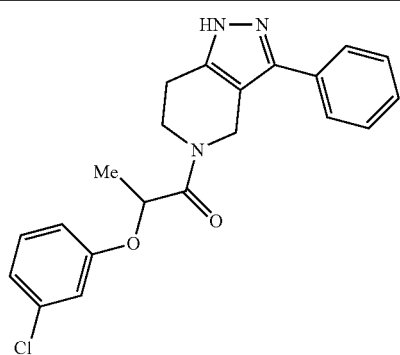
170
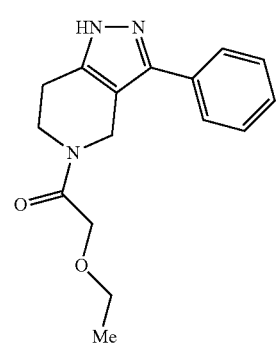 [SMILES: CCOCC(=O)N1CCc2[nH]nc(-c3ccccc3)c2C1]
174
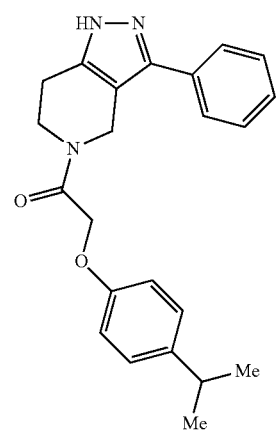 [SMILES: CC(C)c1ccc(OCC(=O)N2CCc3[nH]nc(-c4ccccc4)c3C2)cc1]
175
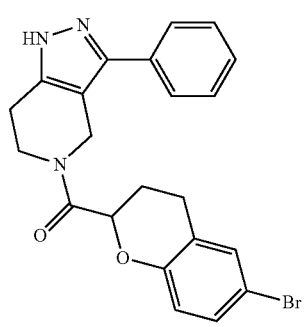 [SMILES: O=C(C1CCc2cc(Br)ccc2O1)N1CCc2[nH]nc(-c3ccccc3)c2C1]
173
TABLE 1-continued
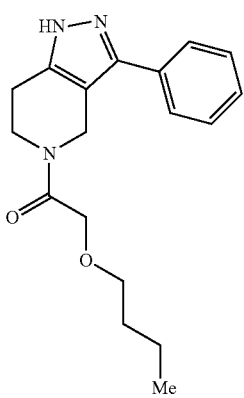 [SMILES: CCCCOCC(=O)N1CCc2[nH]nc(-c3ccccc3)c2C1]
177
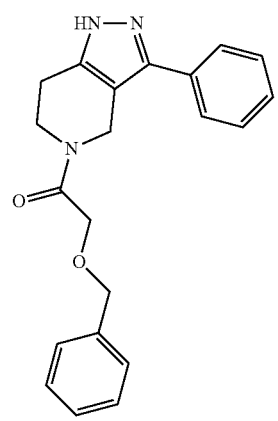 [SMILES: O=C(COCc1ccccc1)N1CCc2[nH]nc(-c3ccccc3)c2C1]
178
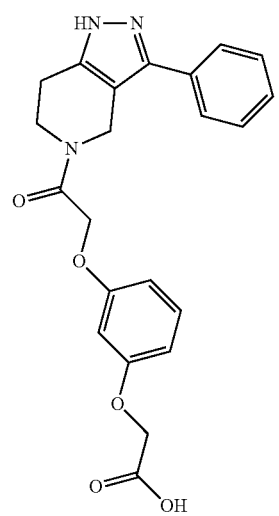 [SMILES: O=C(O)COc1cccc(OCC(=O)N2CCc3[nH]nc(-c4ccccc4)c3C2)c1]
176

TABLE 1-continued
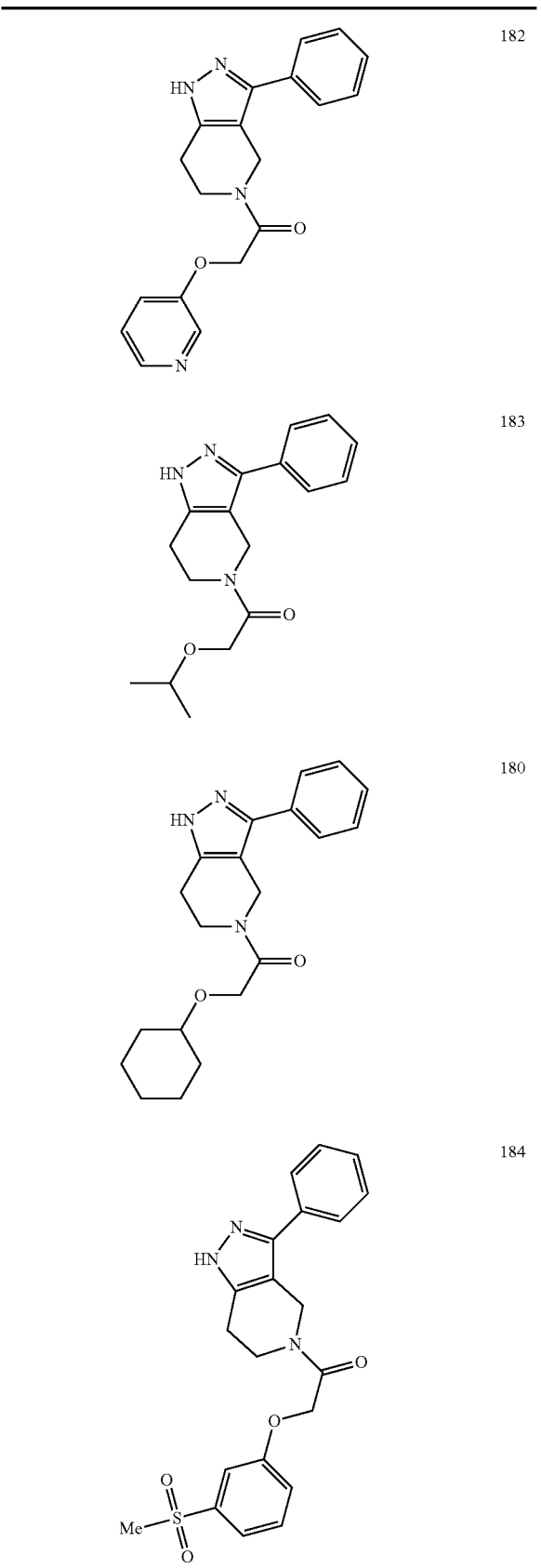
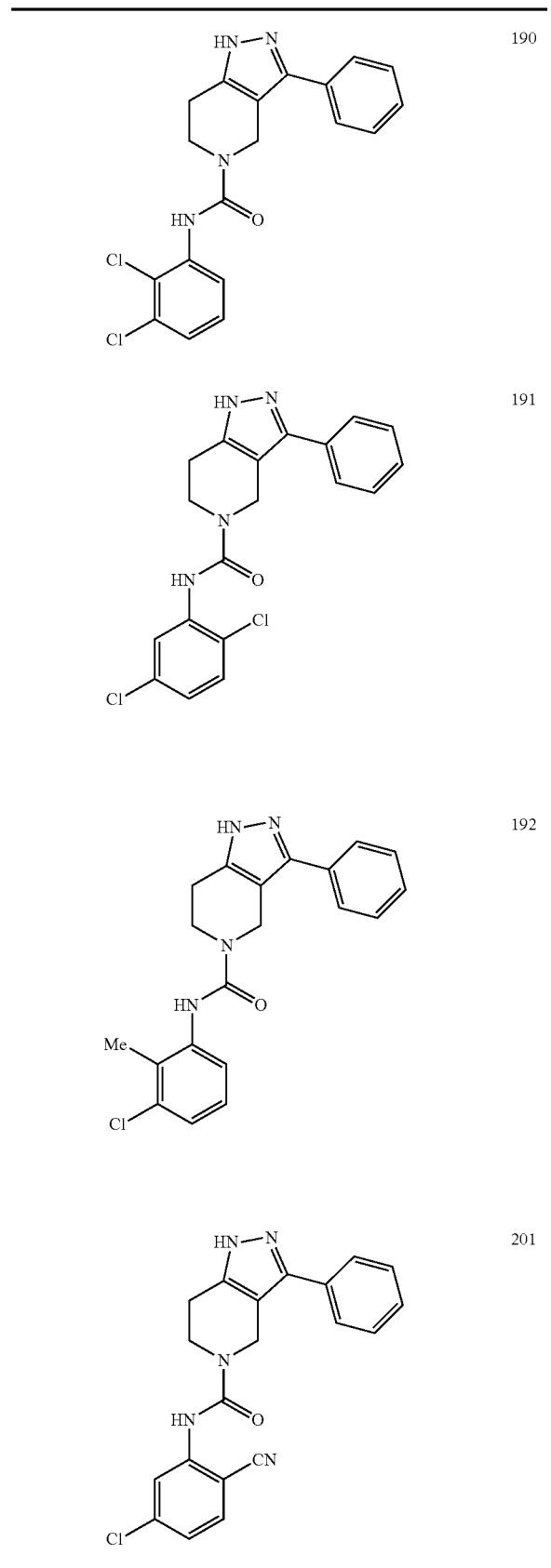

TABLE 1-continued
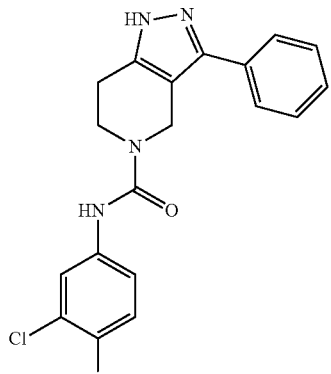 204
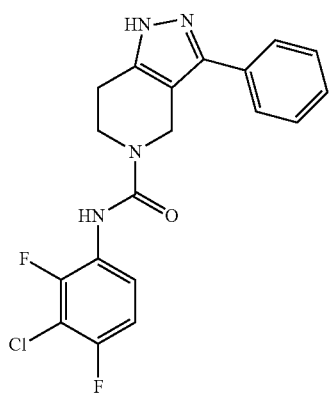 [SMILES: O=C(Nc1ccc(F)c(Cl)c1F)N1CCc2[nH]nc(-c3ccccc3)c2C1] 205
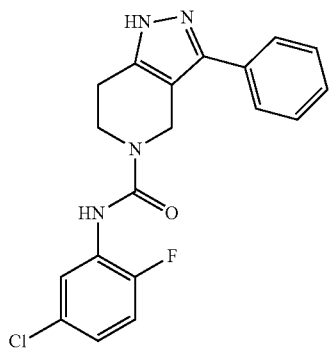 [SMILES: O=C(Nc1cc(Cl)ccc1F)N1CCc2[nH]nc(-c3ccccc3)c2C1] 214
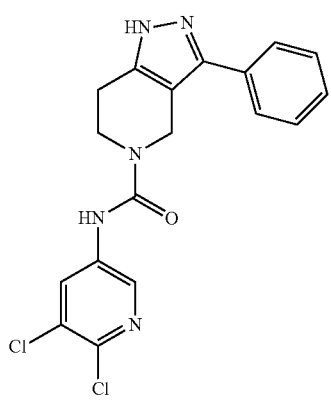 [SMILES: O=C(Nc1cnc(Cl)c(Cl)c1)N1CCc2[nH]nc(-c3ccccc3)c2C1] 226
TABLE 1-continued
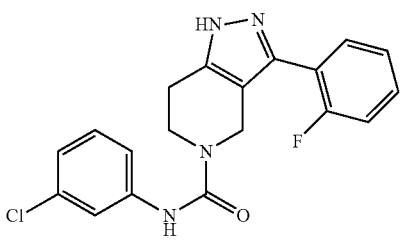 [SMILES: O=C(Nc1cccc(Cl)c1)N1CCc2[nH]nc(-c3ccccc3F)c2C1] 276
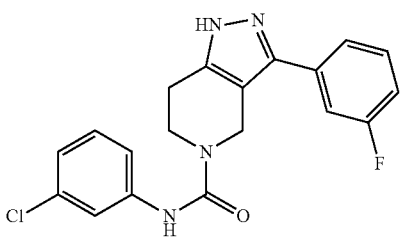 [SMILES: O=C(Nc1cccc(Cl)c1)N1CCc2[nH]nc(-c3cccc(F)c3)c2C1] 277
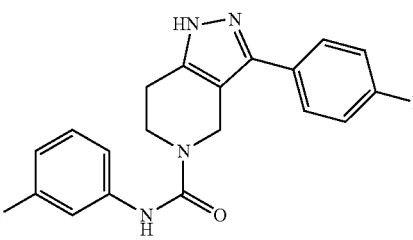 278
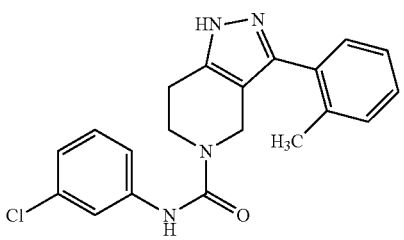 279
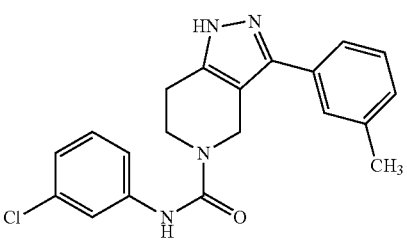 [SMILES: Cc1cccc(-c2n[nH]c3c2CN(C(=O)Nc2cccc(Cl)c2)CC3)c1] 280
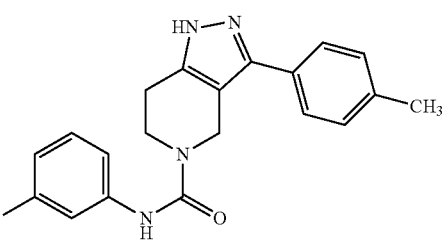 281

TABLE 1-continued
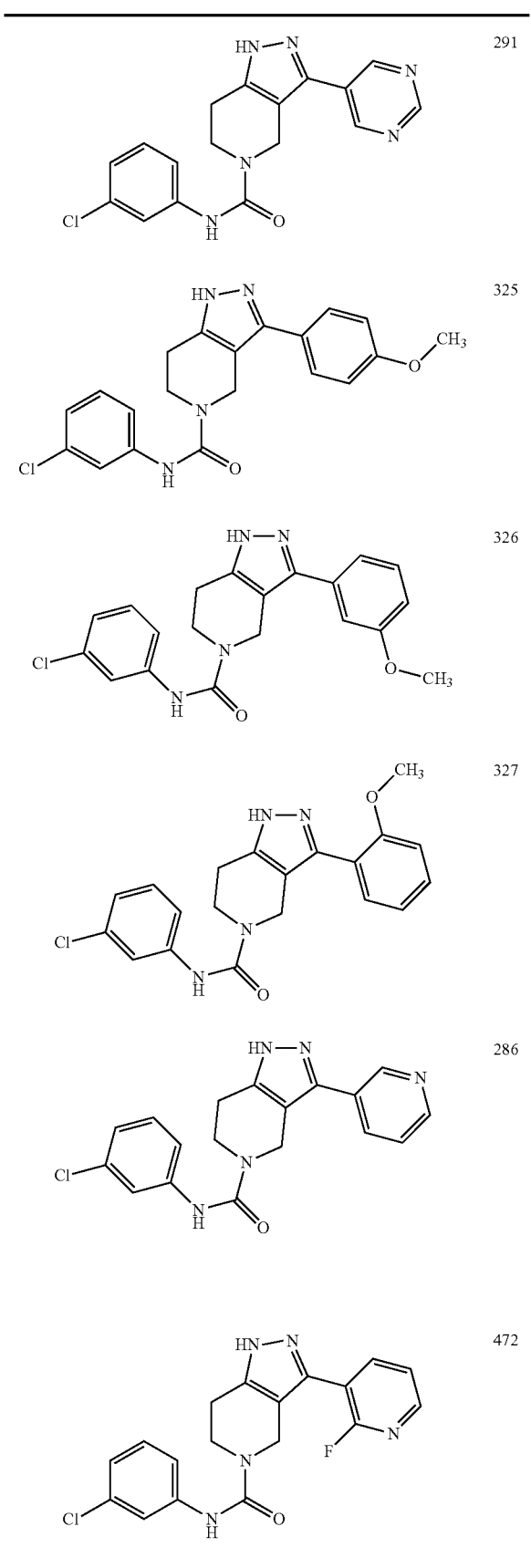
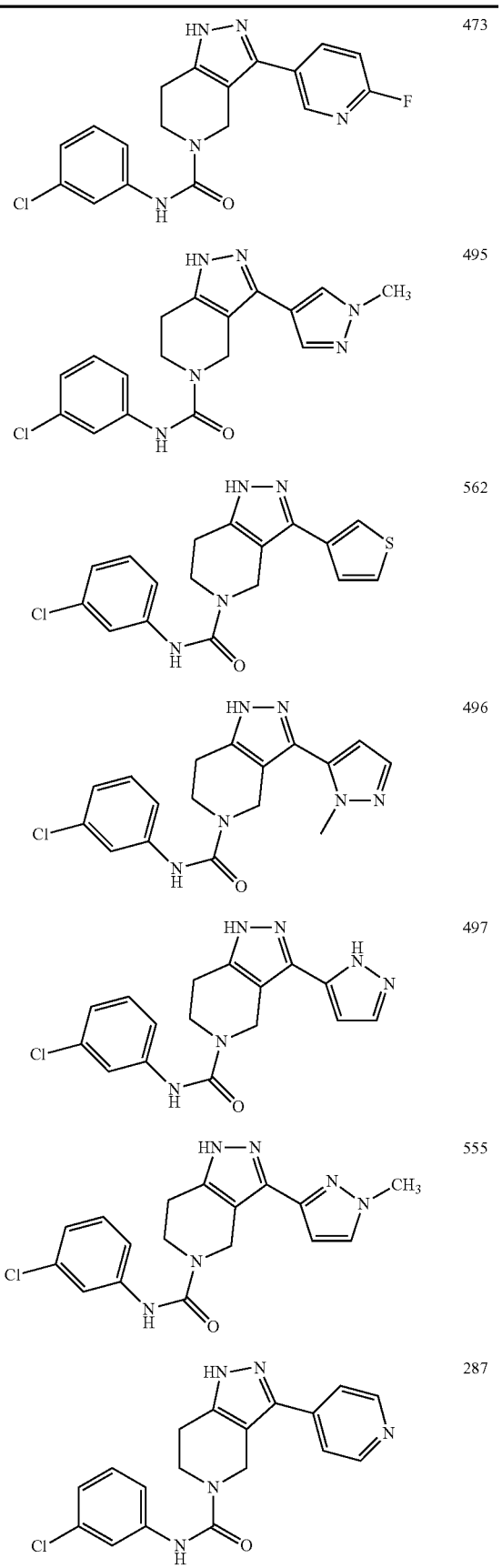

TABLE 1-continued
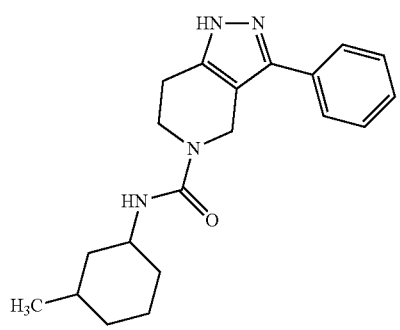 [SMILES: CC1CCCC(NC(=O)N2CCc3[nH]nc(-c4ccccc4)c3C2)C1] 436
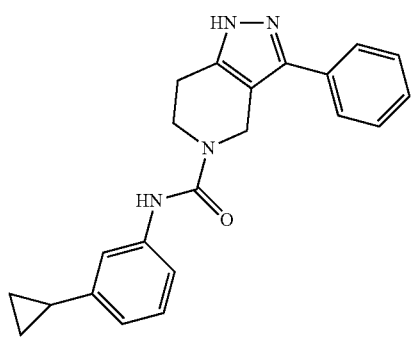 [SMILES: O=C(Nc1cccc(C2CC2)c1)N1CCc2[nH]nc(-c3ccccc3)c2C1] 556
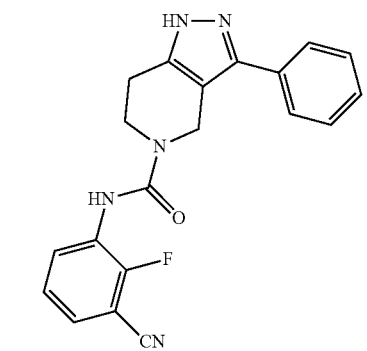 [SMILES: N#Cc1cccc(NC(=O)N2CCc3[nH]nc(-c4ccccc4)c3C2)c1F] 559
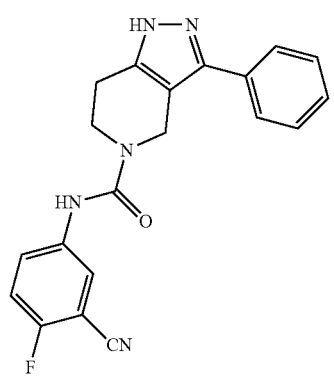 [SMILES: N#Cc1cc(NC(=O)N2CCc3[nH]nc(-c4ccccc4)c3C2)ccc1F] 560
TABLE 1-continued
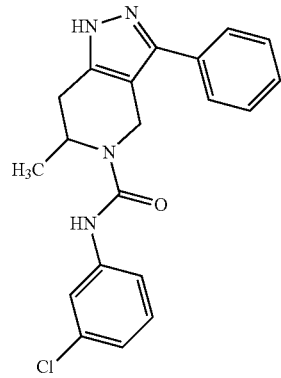 [SMILES: CC1Cc2[nH]nc(-c3ccccc3)c2CN1C(=O)Nc1cccc(Cl)c1] 317
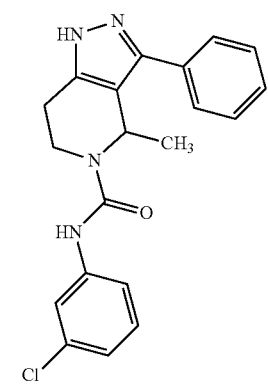 [SMILES: CC1c2c(-c3ccccc3)n[nH]c2CCN1C(=O)Nc1cccc(Cl)c1] 318
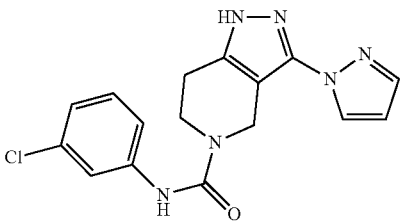 [SMILES: O=C(Nc1cccc(Cl)c1)N1CCc2[nH]nc(-n3cccn3)c2C1] 576
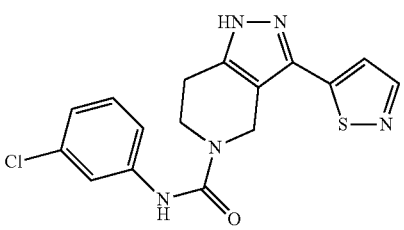 [SMILES: O=C(Nc1cccc(Cl)c1)N1CCc2[nH]nc(-c3ccns3)c2C1] 751
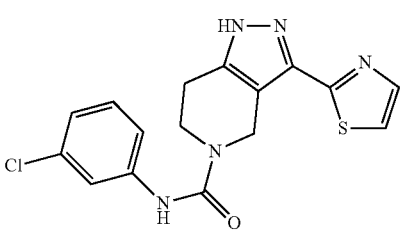 [SMILES: O=C(Nc1cccc(Cl)c1)N1CCc2[nH]nc(-c3nccs3)c2C1] 569

TABLE 1-continued
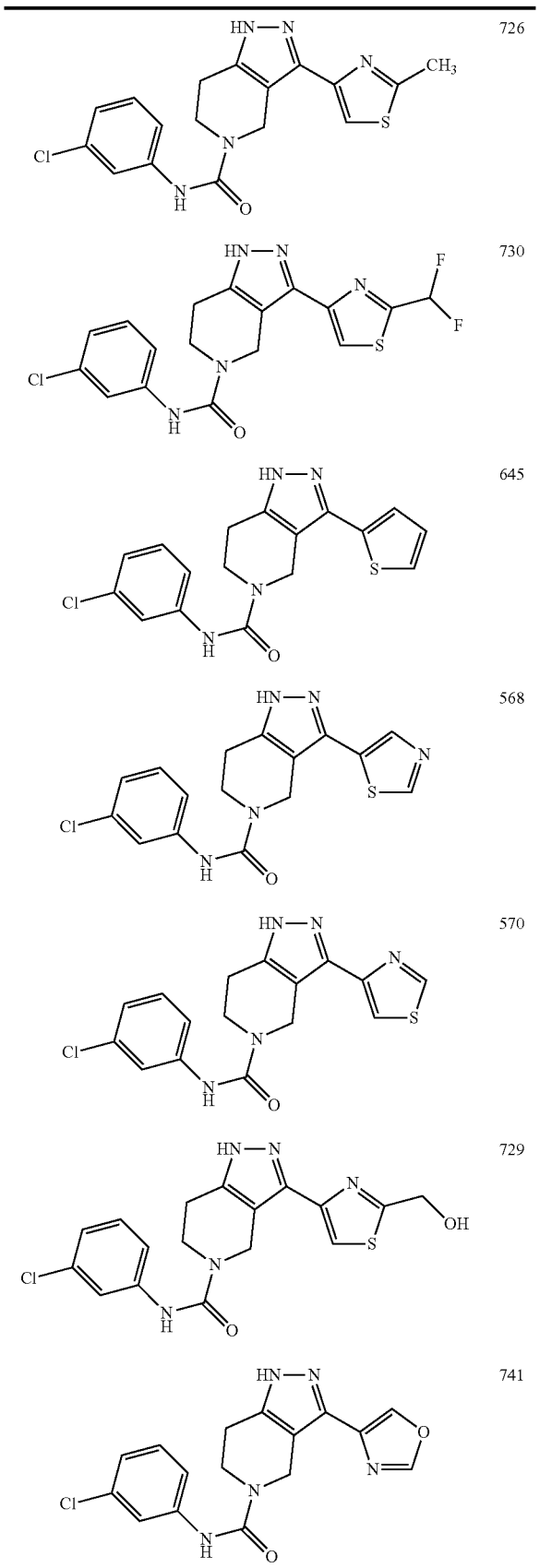
TABLE 1-continued
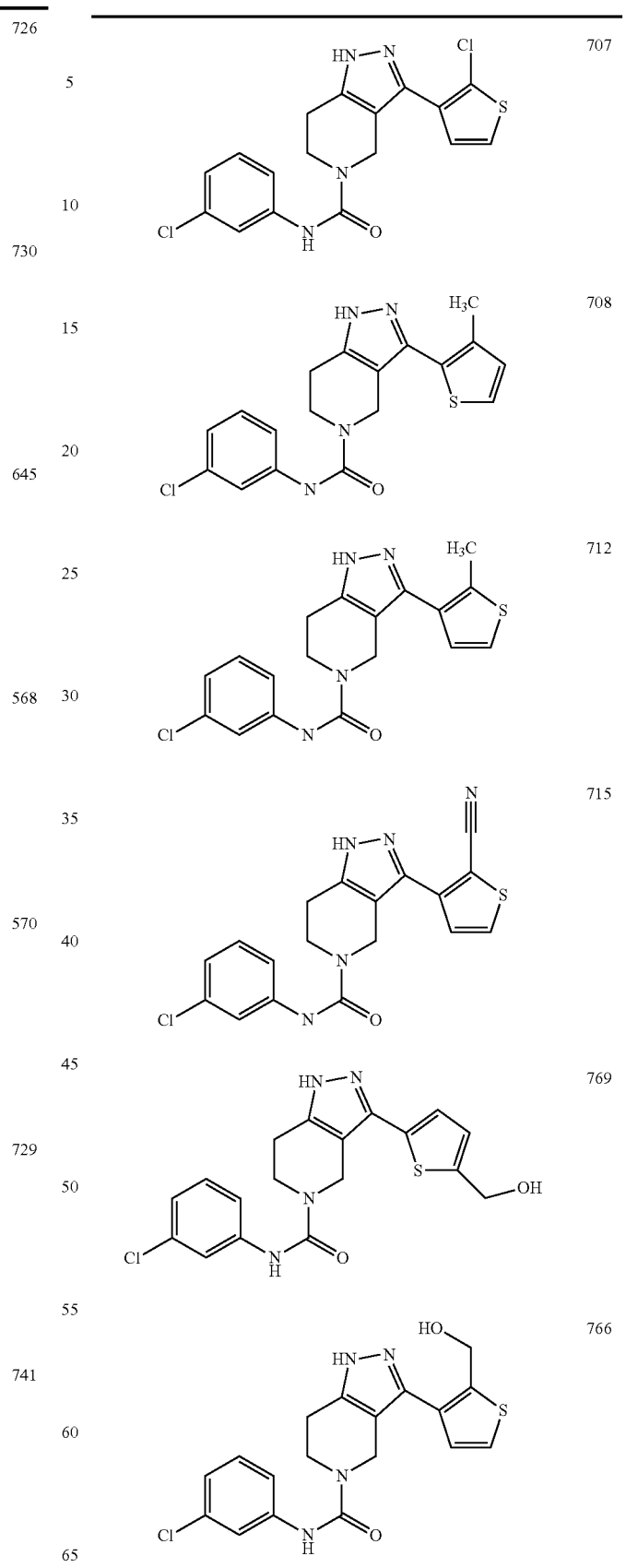

TABLE 1-continued
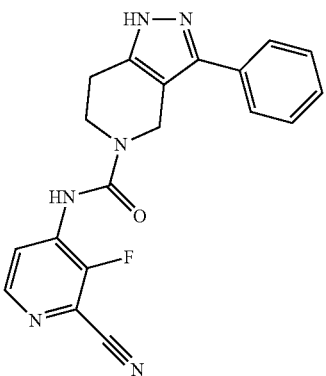 [SMILES: N#Cc1nccc(NC(=O)N2CCc3[nH]nc(-c4ccccc4)c3C2)c1F] 747
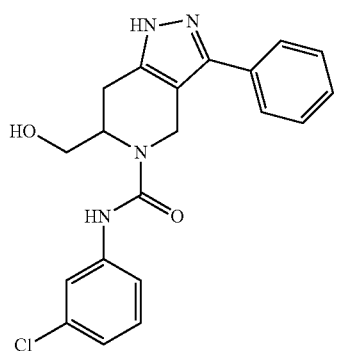 [SMILES: O=C(Nc1cccc(Cl)c1)N1Cc2c(-c3ccccc3)n[nH]c2CC1CO] 756
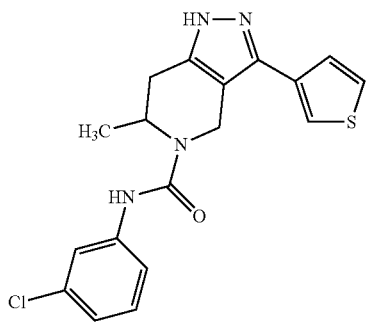 [SMILES: CC1Cc2[nH]nc(-c3ccsc3)c2CN1C(=O)Nc1cccc(Cl)c1] 754
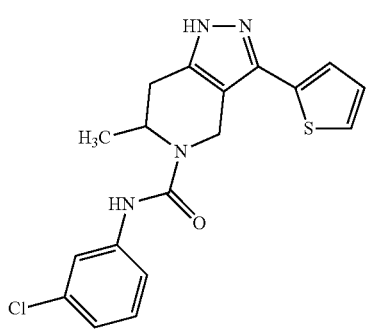 753
TABLE 1-continued
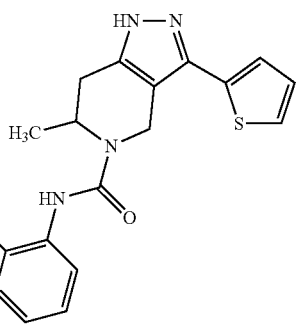 819
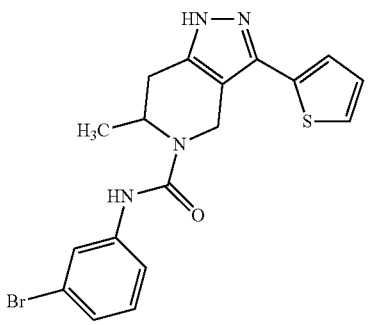 [SMILES: CC1Cc2[nH]nc(-c3cccs3)c2CN1C(=O)Nc1cccc(Cl)c1] 820 (851)
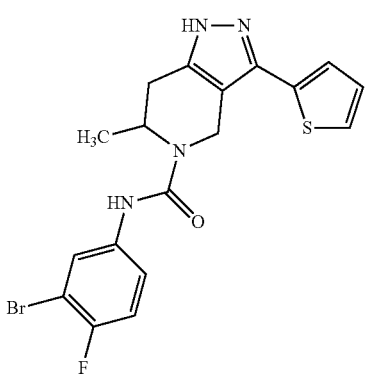 821 (852)
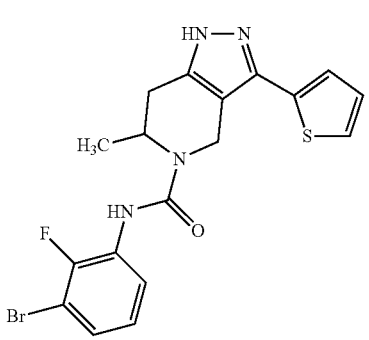 [SMILES: CC1Cc2[nH]nc(-c3cccs3)c2CN1C(=O)Nc1cccc(Cl)c1F] 822

TABLE 1-continued
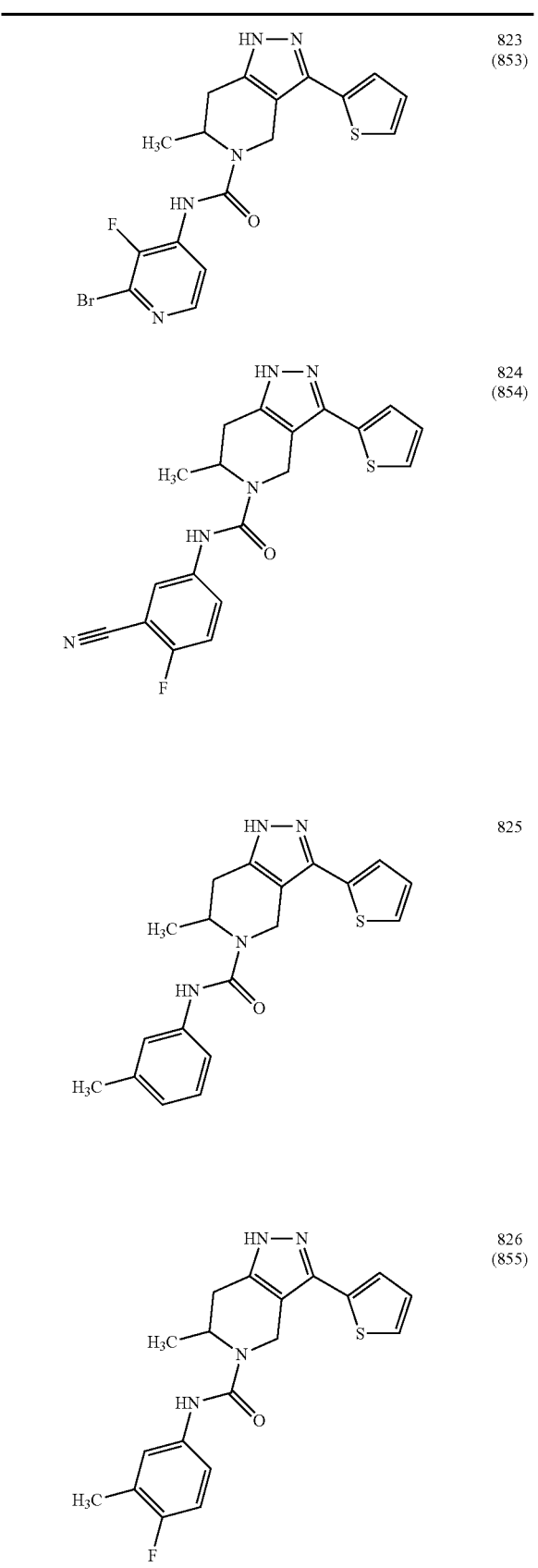
823 (853)
824 (854)
825
826 (855)
TABLE 1-continued
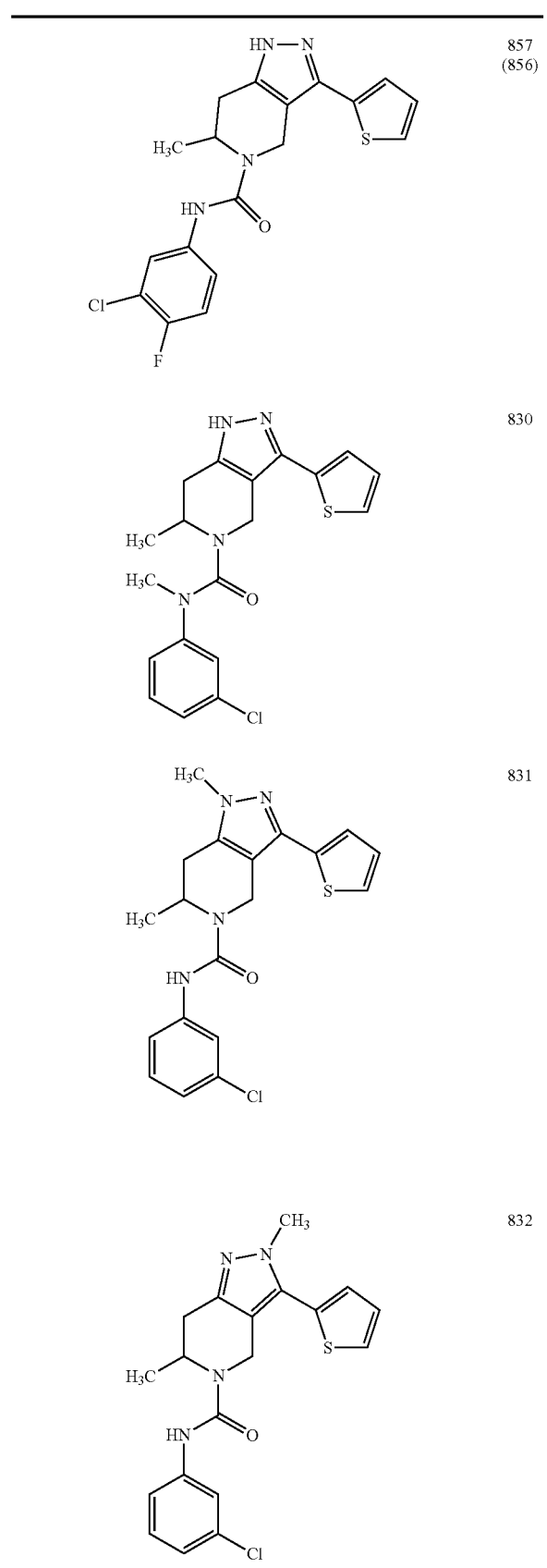
857 (856)
830
831
832

TABLE 1-continued
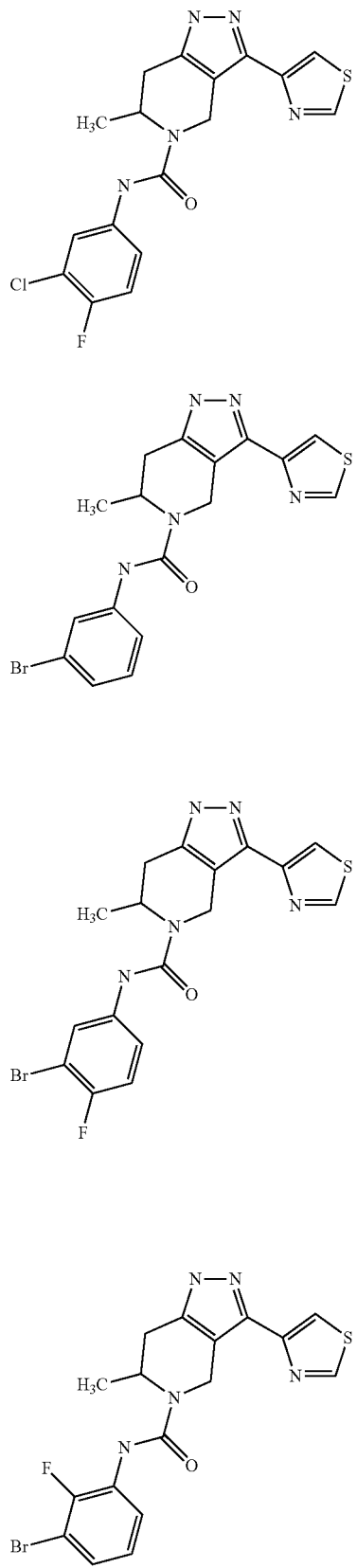
917
918
919
920
TABLE 1-continued
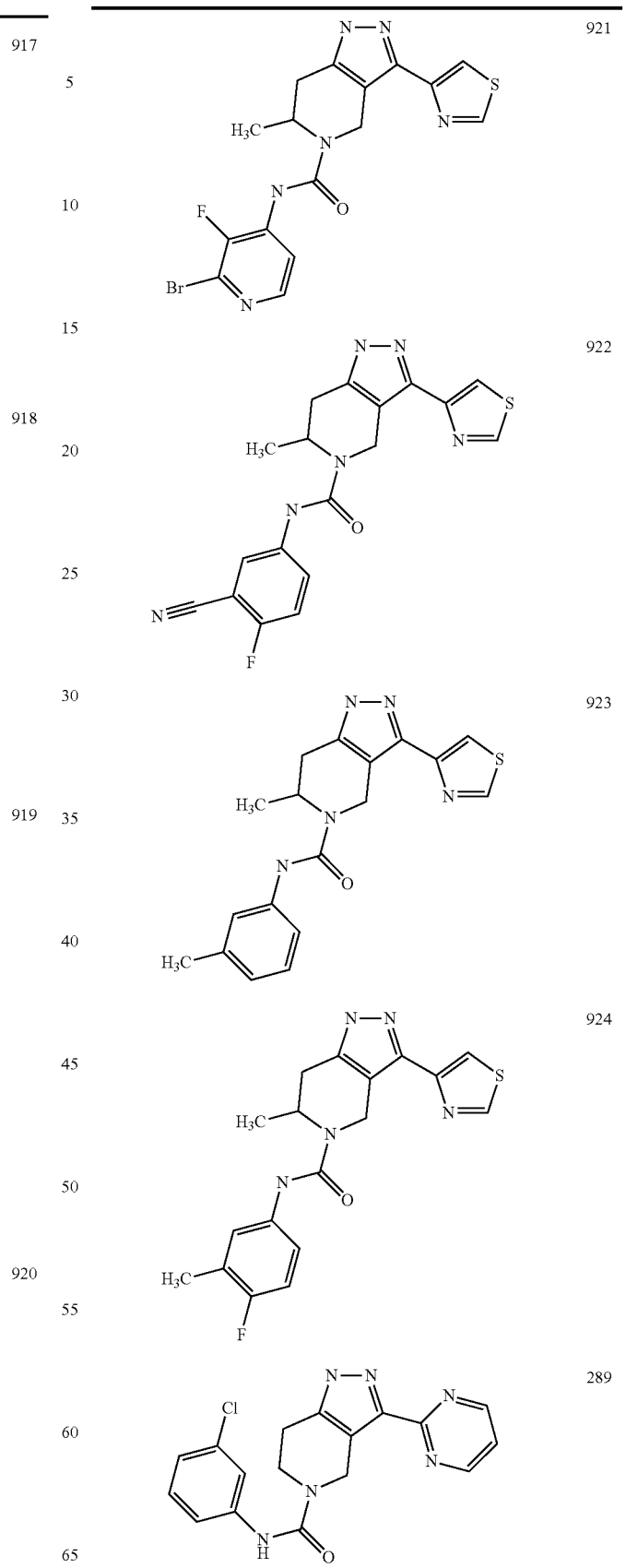
921
922
923
924
289

TABLE 1-continued
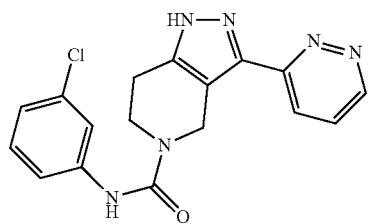 [SMILES: O=C(Nc1cccc(Cl)c1)N1CCc2[nH]nc(-c3cccnn3)c2C1]
290
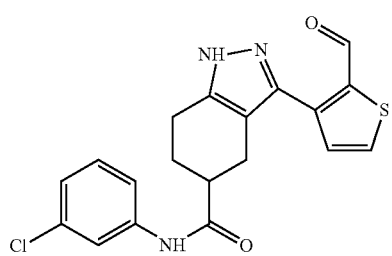 [SMILES: O=Cc1sccc1-c1n[nH]c2c1CC(C(=O)Nc1cccc(Cl)c1)CC2]
716
In yet another embodiment of Formula I provided herein, the compound of Formula III, or a pharmaceutically acceptable salt thereof, is selected from compounds shown in Table 2 and pharmaceutically acceptable salts thereof.
TABLE 2
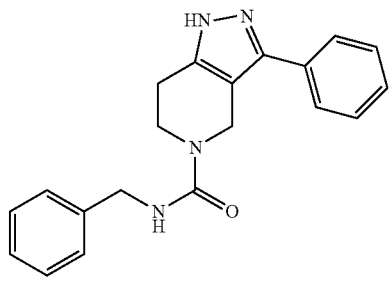
017
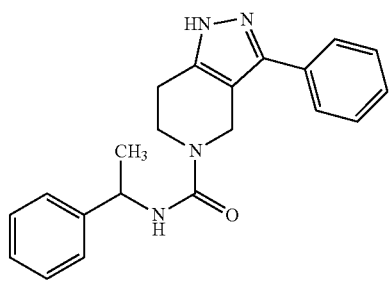 [SMILES: CC(NC(=O)N1CCc2[nH]nc(-c3ccccc3)c2C1)c1ccccc1]
018
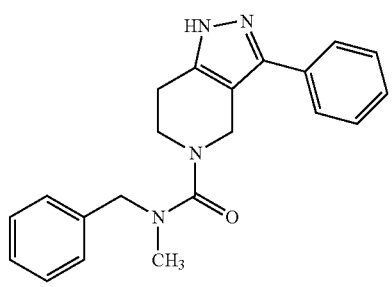
019
TABLE 2-continued
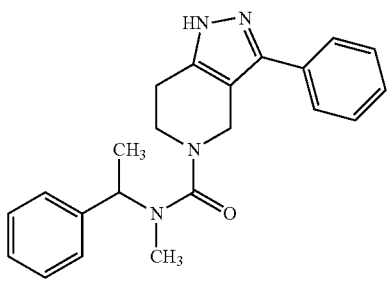 [SMILES: CC(c1ccccc1)N(C)C(=O)N1CCc2[nH]nc(-c3ccccc3)c2C1]
020
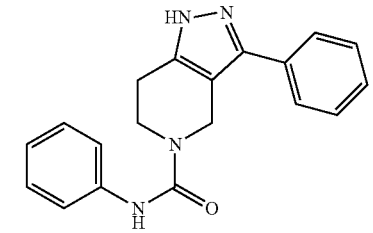 [SMILES: O=C(Nc1ccccc1)N1CCc2[nH]nc(-c3ccccc3)c2C1]
022
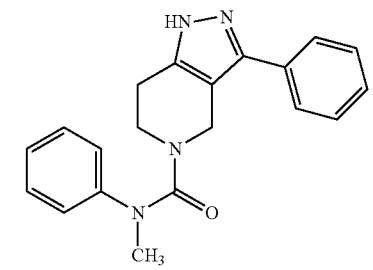 [SMILES: CN(C(=O)N1CCc2[nH]nc(-c3ccccc3)c2C1)c1ccccc1]
023
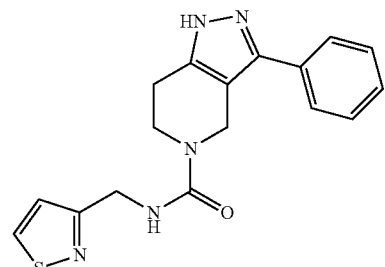
085
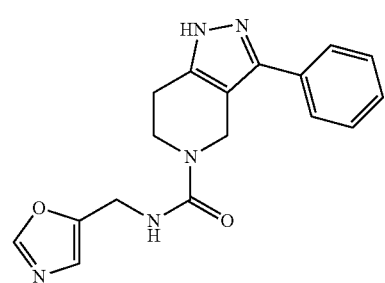
081
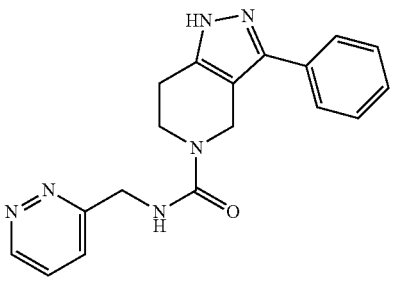 [SMILES: O=C(NCc1cccnn1)N1CCc2[nH]nc(-c3ccccc3)c2C1]
104

TABLE 2-continued
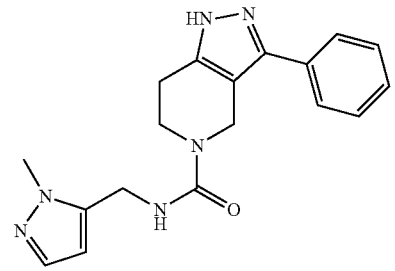 [SMILES: Cn1nccc1CNC(=O)N1CCc2[nH]nc(-c3ccccc3)c2C1] 095
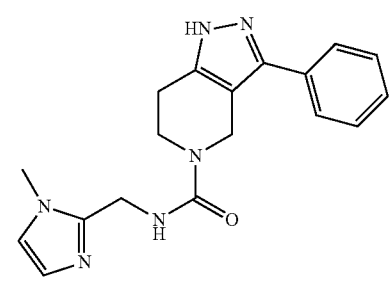 [SMILES: Cn1ccnc1CNC(=O)N1CCc2[nH]nc(-c3ccccc3)c2C1] 098
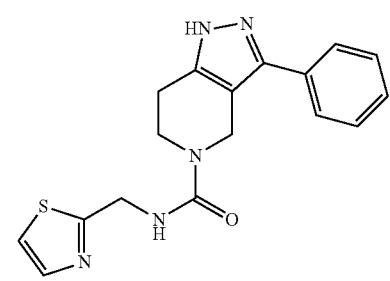 [SMILES: O=C(NCc1nccs1)N1CCc2[nH]nc(-c3ccccc3)c2C1] 088
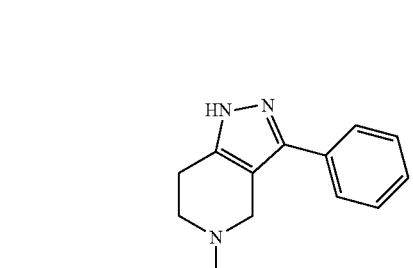 093
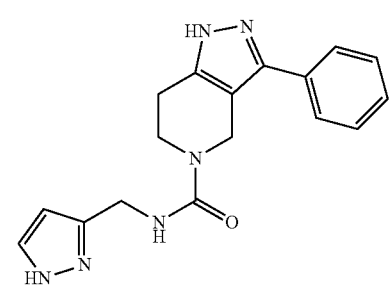 [SMILES: O=C(NCc1cc[nH]n1)N1CCc2[nH]nc(-c3ccccc3)c2C1] 089
TABLE 2-continued
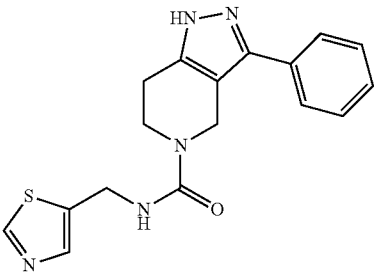 [SMILES: O=C(NCc1cncs1)N1CCc2[nH]nc(-c3ccccc3)c2C1] 087
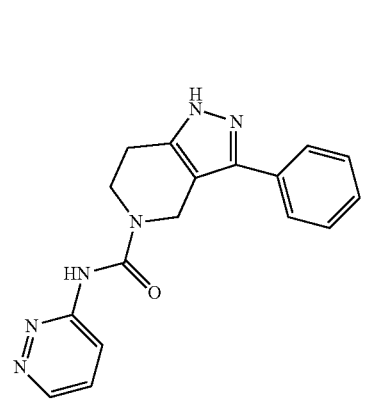 [SMILES: O=C(Nc1cccnn1)N1CCc2[nH]nc(-c3ccccc3)c2C1] 119
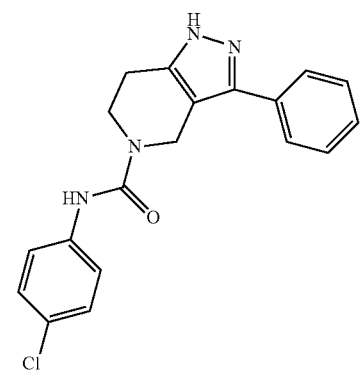 [SMILES: O=C(Nc1ccc(Cl)cc1)N1CCc2[nH]nc(-c3ccccc3)c2C1] 113
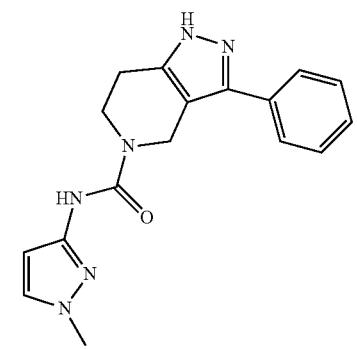 [SMILES: Cn1ccc(NC(=O)N2CCc3[nH]nc(-c4ccccc4)c3C2)n1] 117

TABLE 2-continued
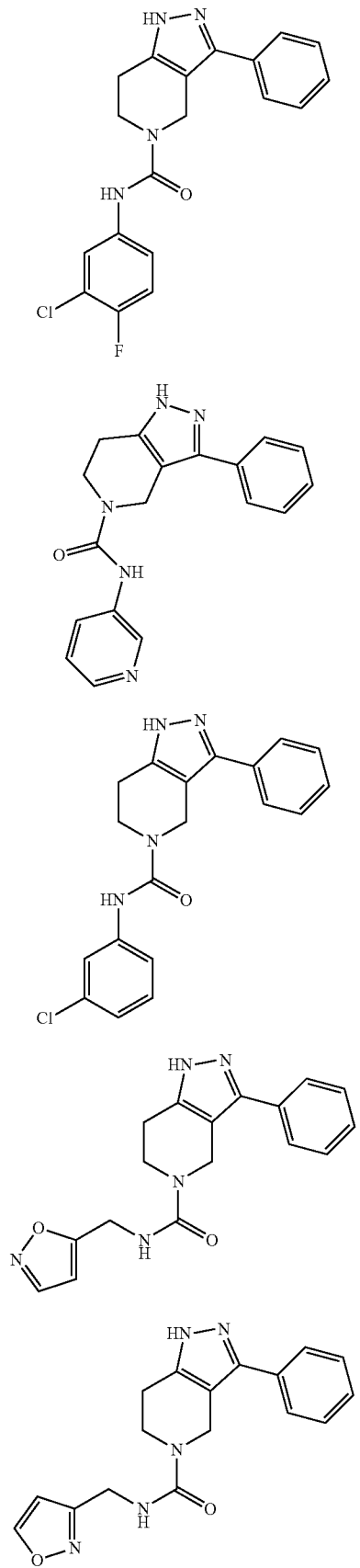
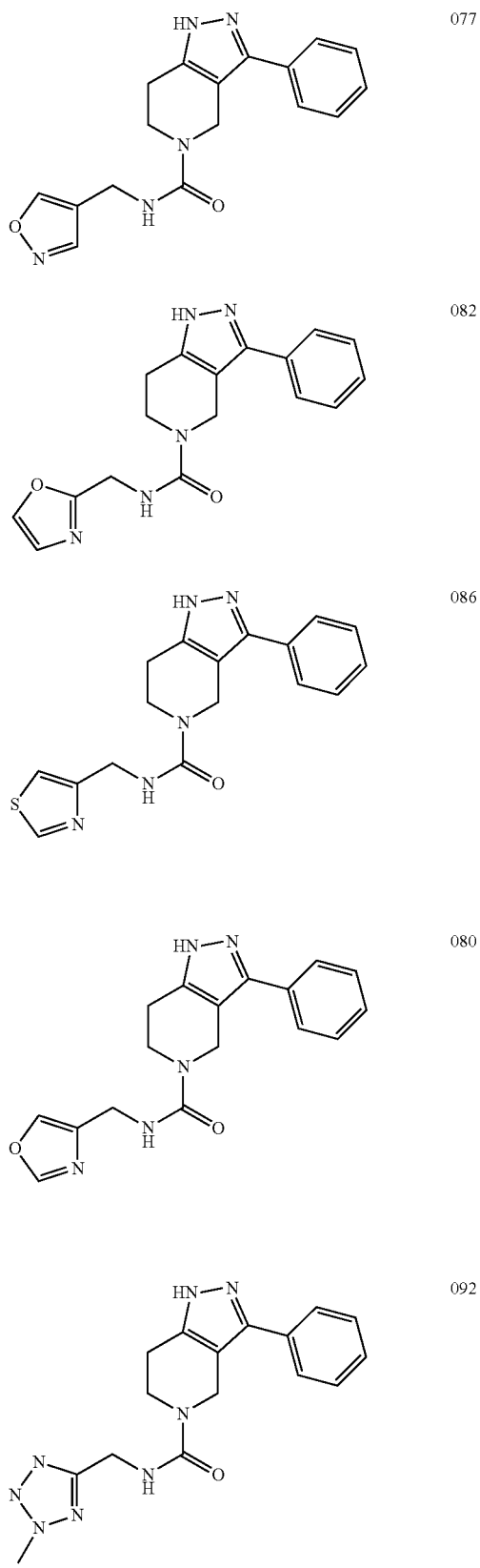

TABLE 2-continued
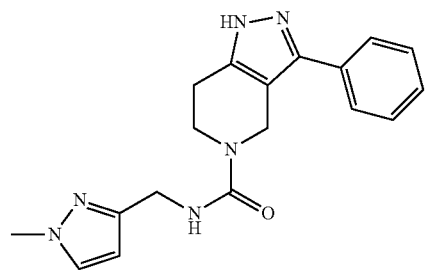 [SMILES: Cn1ccc(CNC(=O)N2CCc3[nH]nc(-c4ccccc4)c3C2)n1] 094
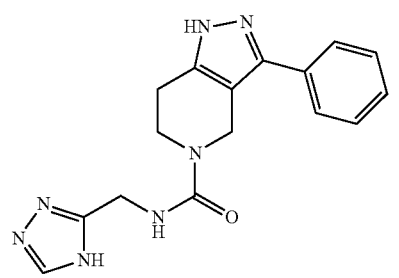 [SMILES: O=C(NCc1nnc[nH]1)N1CCc2[nH]nc(-c3ccccc3)c2C1] 091
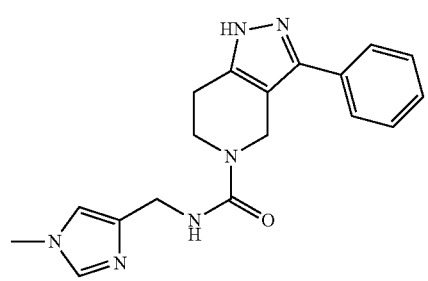 [SMILES: Cn1cnc(CNC(=O)N2CCc3[nH]nc(-c4ccccc4)c3C2)c1] 097
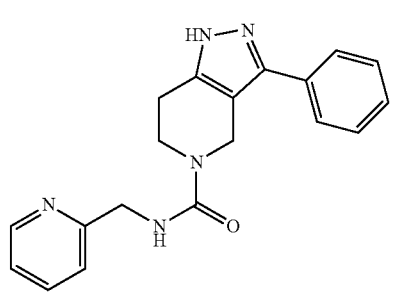 [SMILES: O=C(NCc1ccccn1)N1CCc2[nH]nc(-c3ccccc3)c2C1] 100
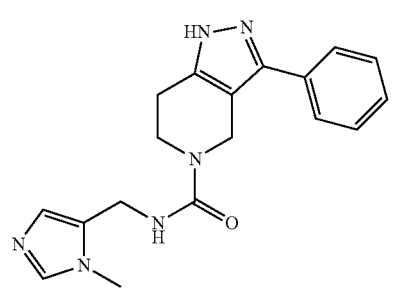 [SMILES: Cn1cncc1CNC(=O)N1CCc2[nH]nc(-c3ccccc3)c2C1] 096
TABLE 2-continued
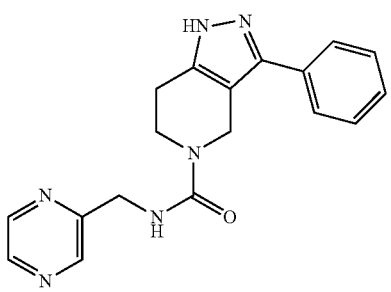 [SMILES: O=C(NCc1cnccn1)N1CCc2[nH]nc(-c3ccccc3)c2C1] 103
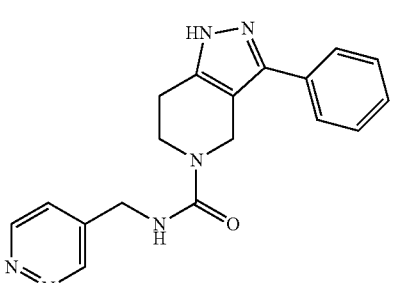 105
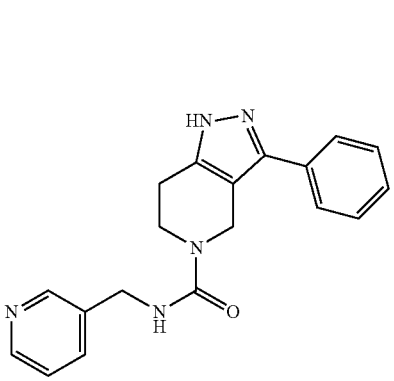 [SMILES: O=C(NCc1cccnc1)N1CCc2[nH]nc(-c3ccccc3)c2C1] 101
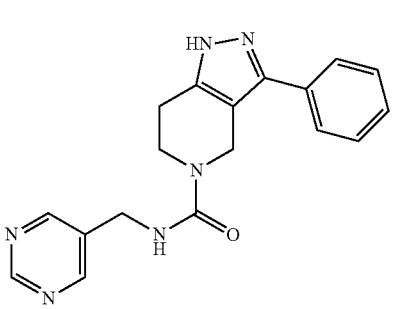 [SMILES: O=C(NCc1cncnc1)N1CCc2[nH]nc(-c3ccccc3)c2C1] 107
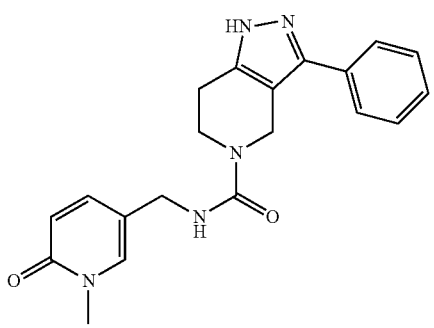 [SMILES: Cn1cc(CNC(=O)N2CCc3[nH]nc(-c4ccccc4)c3C2)ccc1=O] 108

TABLE 2-continued
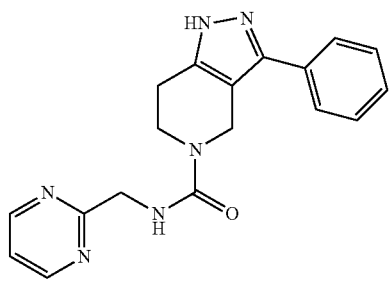 [SMILES: O=C(NCc1ncccn1)N1CCc2[nH]nc(-c3ccccc3)c2C1] 106
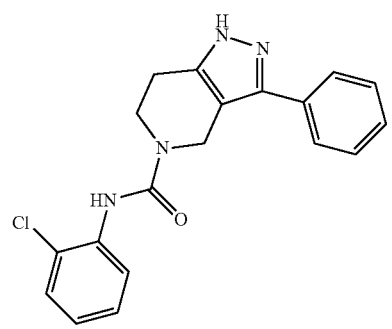 [SMILES: O=C(Nc1ccccc1Cl)N1CCc2[nH]nc(-c3ccccc3)c2C1] 111
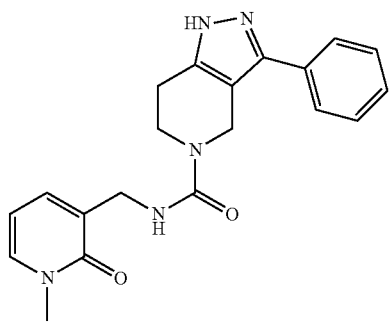 [SMILES: Cn1cccc(CNC(=O)N2CCc3[nH]nc(-c4ccccc4)c3C2)c1=O] 109
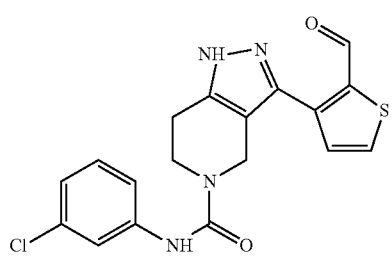 [SMILES: O=Cc1sccc1-c1n[nH]c2c1CN(C(=O)Nc1cccc(Cl)c1)CC2] 716
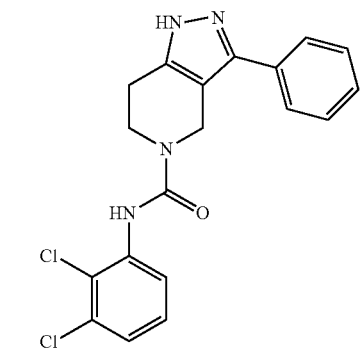 [SMILES: O=C(Nc1cccc(Cl)c1Cl)N1CCc2[nH]nc(-c3ccccc3)c2C1] 190
TABLE 2-continued
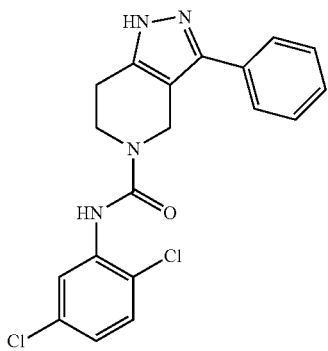 191
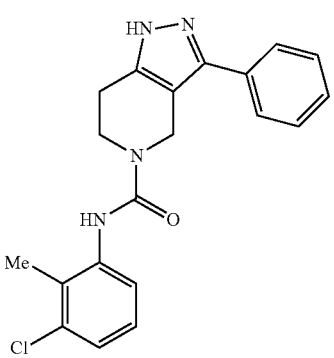 [SMILES: Cc1c(Cl)cccc1NC(=O)N1CCc2[nH]nc(-c3ccccc3)c2C1] 192
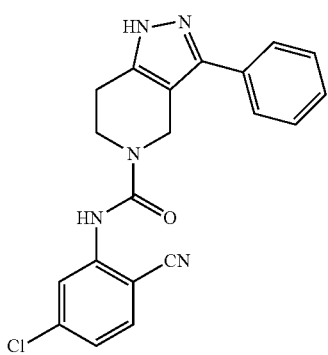 201
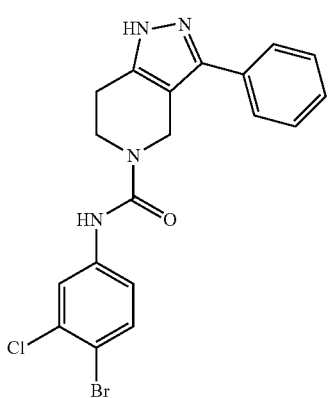 [SMILES: O=C(Nc1ccc(Br)c(Cl)c1)N1CCc2[nH]nc(-c3ccccc3)c2C1] 204

TABLE 2-continued
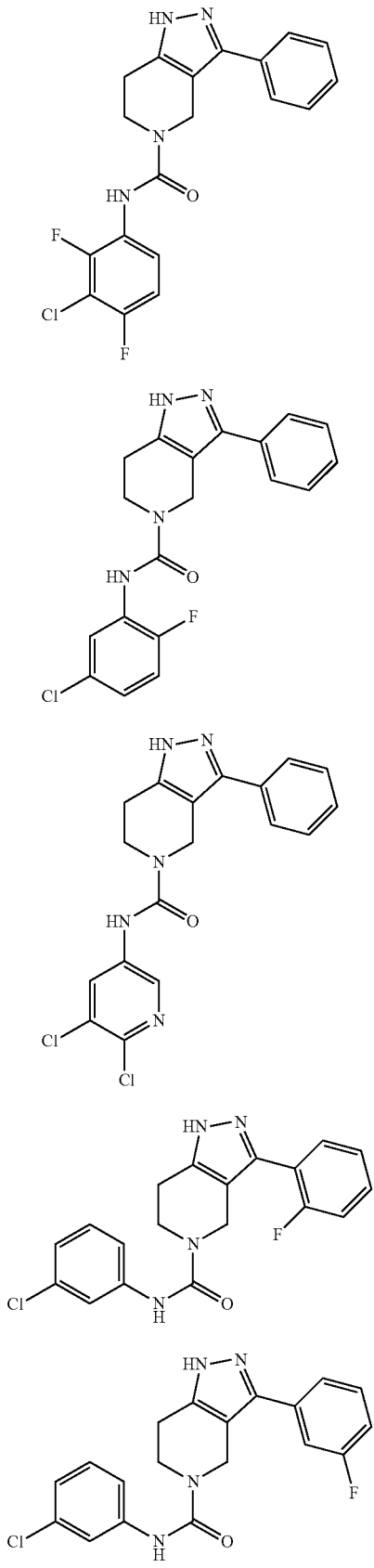
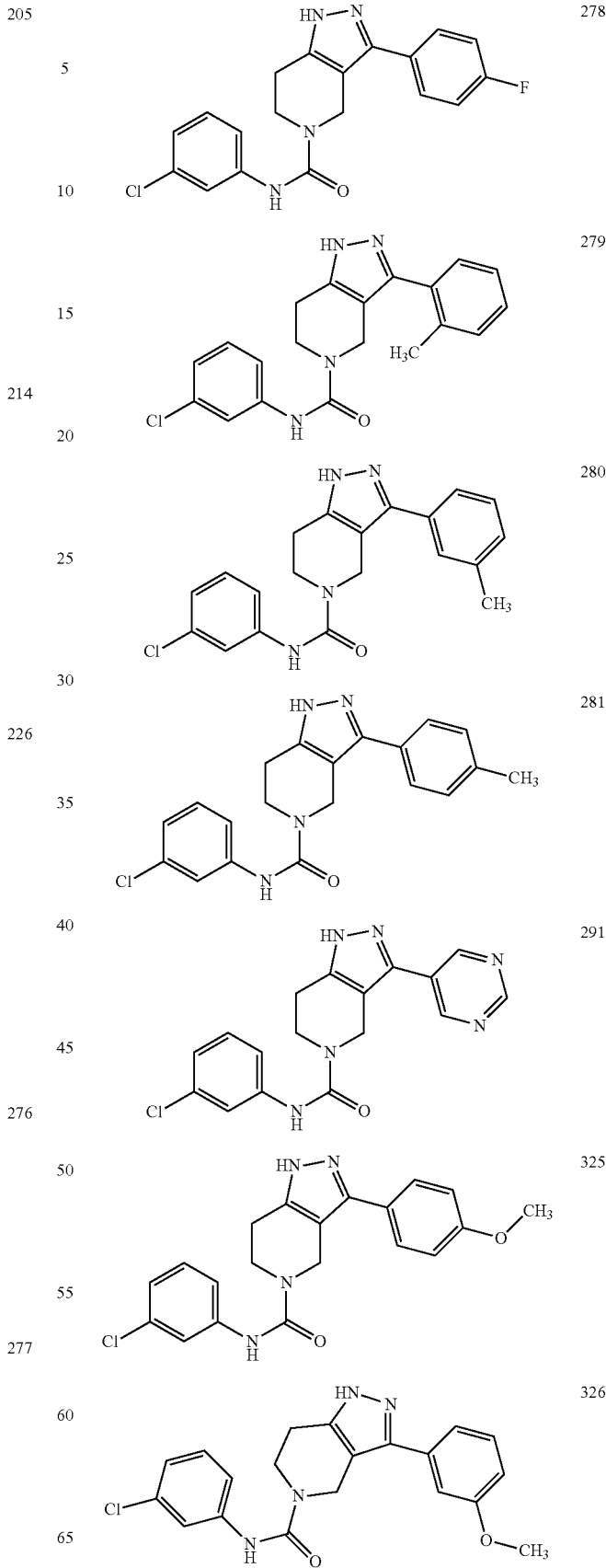

TABLE 2-continued
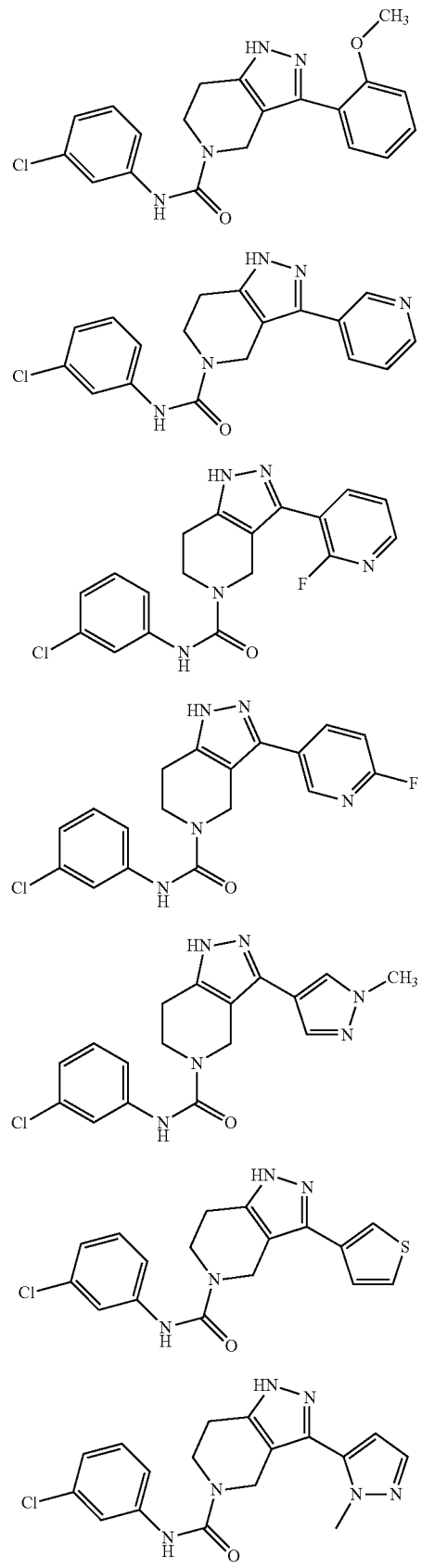
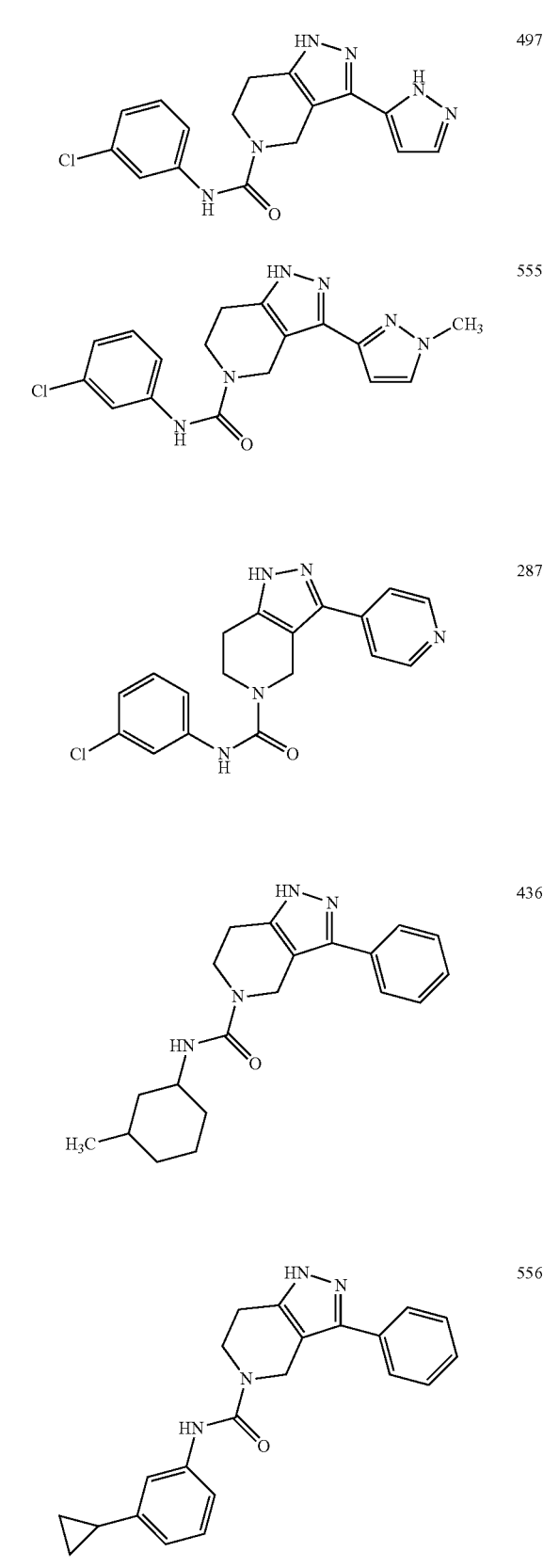

TABLE 2-continued
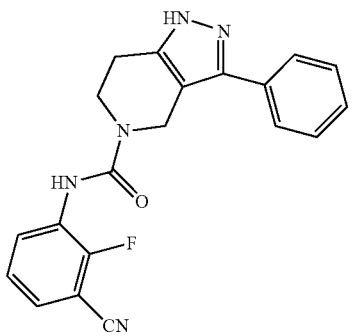 [SMILES: N#Cc1cccc(NC(=O)N2CCc3[nH]nc(-c4ccccc4)c3C2)c1F] 559
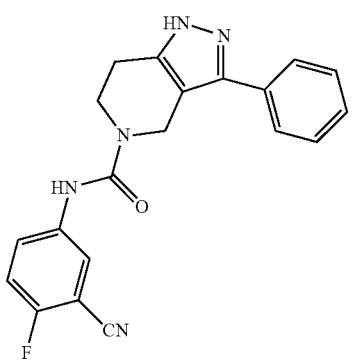 [SMILES: N#Cc1cc(NC(=O)N2CCc3[nH]nc(-c4ccccc4)c3C2)ccc1F] 560
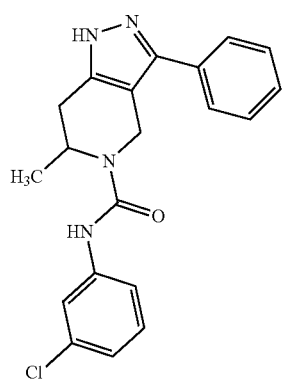 [SMILES: CC1Cc2[nH]nc(-c3ccccc3)c2CN1C(=O)Nc1cccc(Cl)c1] 317
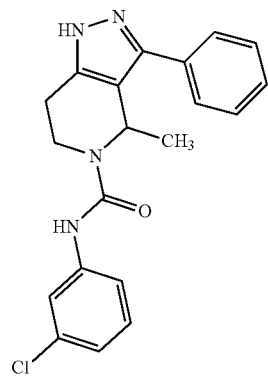 [SMILES: CC1c2c(-c3ccccc3)n[nH]c2CCN1C(=O)Nc1cccc(Cl)c1] 318
TABLE 2-continued
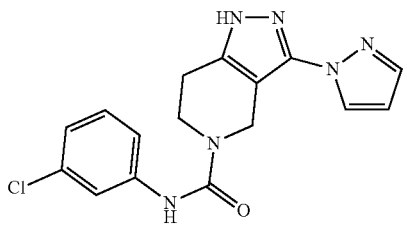 [SMILES: O=C(Nc1cccc(Cl)c1)N1CCc2[nH]nc(-n3cccn3)c2C1] 576
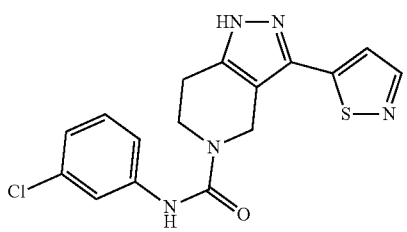 [SMILES: O=C(Nc1cccc(Cl)c1)N1CCc2[nH]nc(-c3ccns3)c2C1] 751
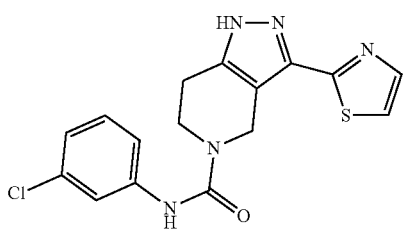 [SMILES: O=C(Nc1cccc(Cl)c1)N1CCc2[nH]nc(-c3nccs3)c2C1] 569
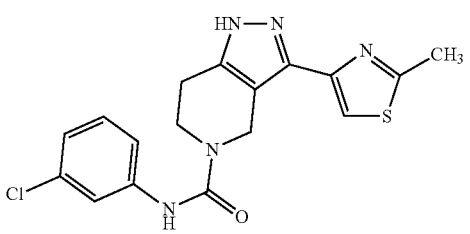 [SMILES: Cc1nc(-c2n[nH]c3c2CN(C(=O)Nc2cccc(Cl)c2)CC3)cs1] 726
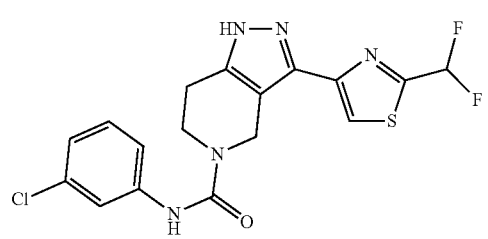 [SMILES: O=C(Nc1cccc(Cl)c1)N1CCc2[nH]nc(-c3csc(C(F)F)n3)c2C1] 730
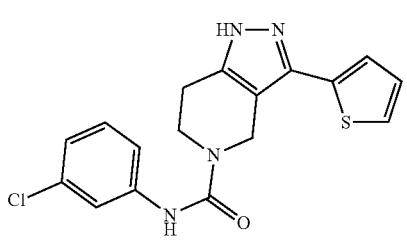 [SMILES: O=C(Nc1cccc(Cl)c1)N1CCc2[nH]nc(-c3cccs3)c2C1] 645
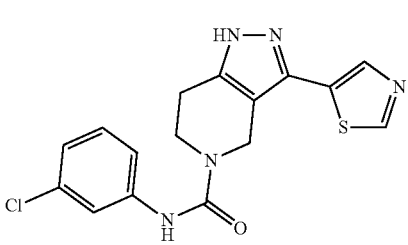 [SMILES: O=C(Nc1cccc(Cl)c1)N1CCc2[nH]nc(-c3cncs3)c2C1] 568

TABLE 2-continued
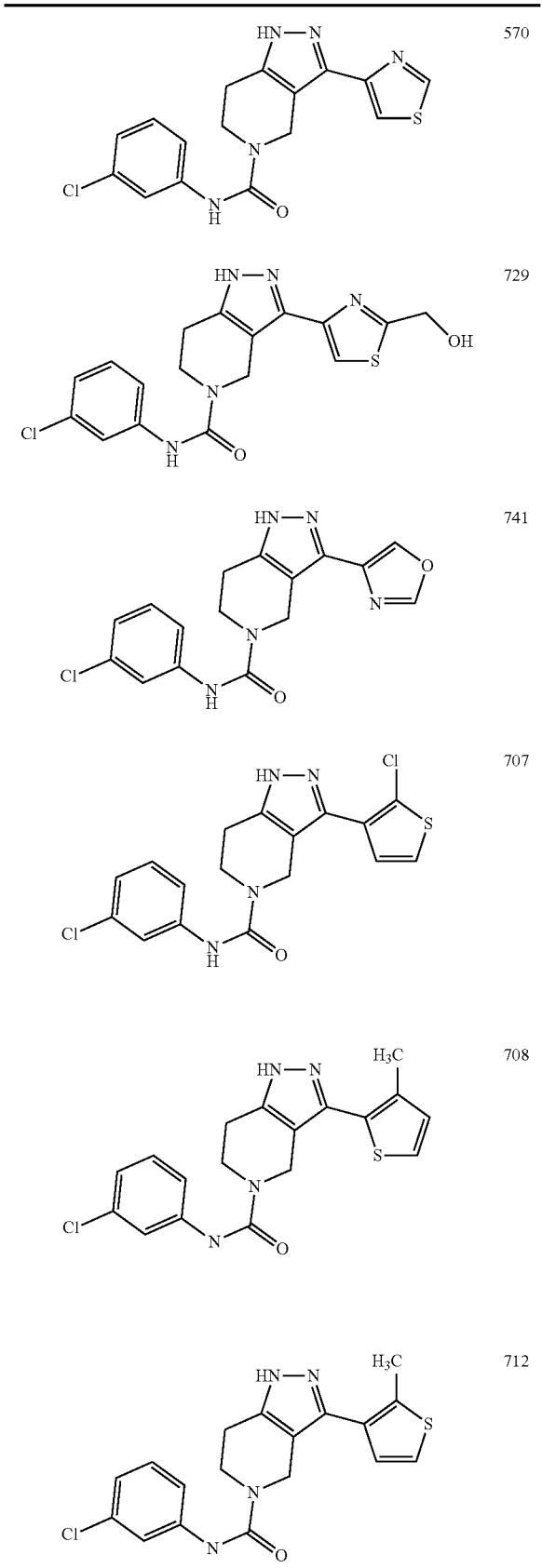
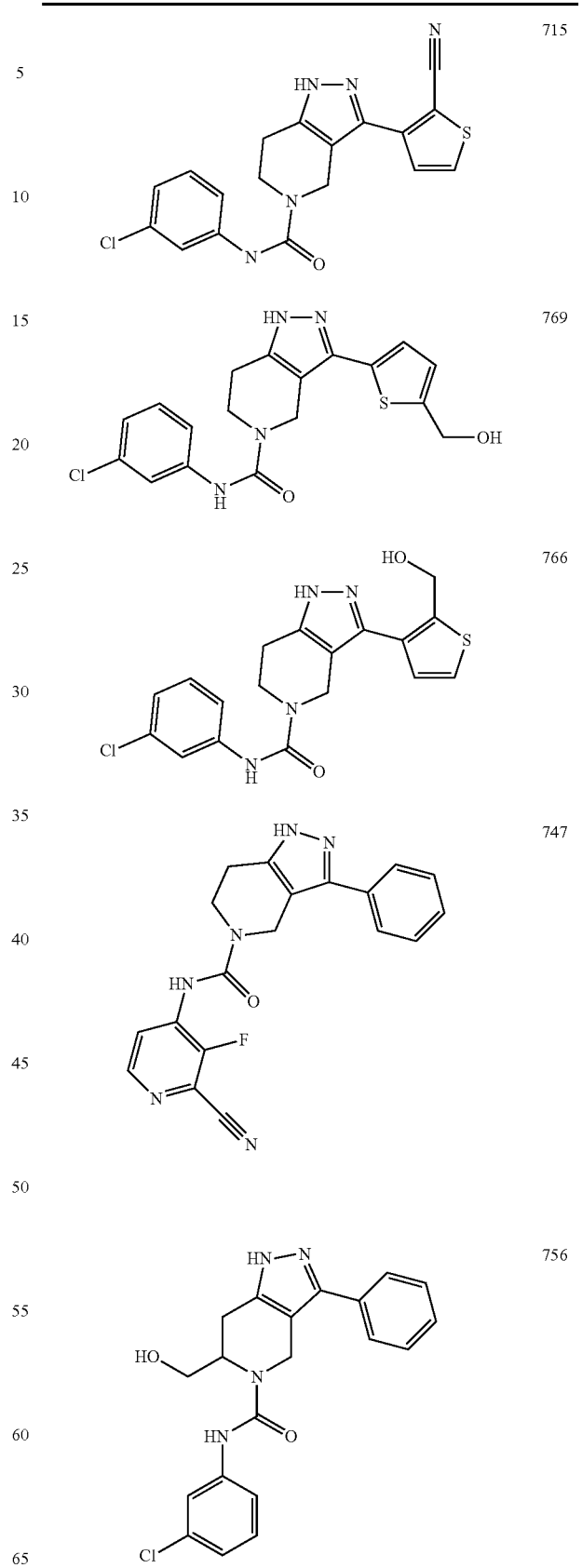

TABLE 2-continued
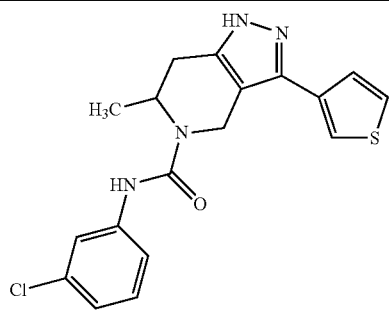 754
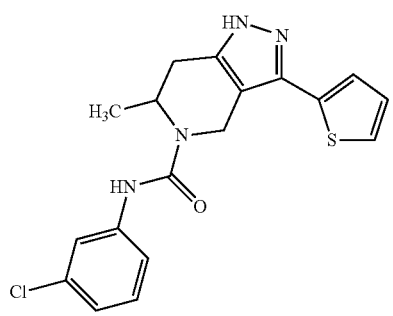 [SMILES: CC1Cc2[nH]nc(-c3cccs3)c2CN1C(=O)Nc1cccc(Cl)c1] 753
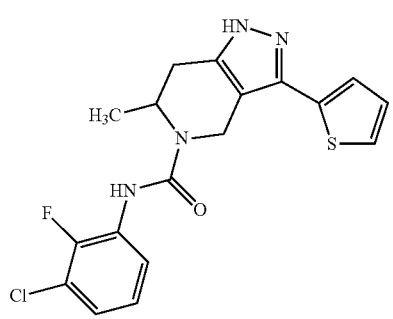 [SMILES: CC1Cc2[nH]nc(-c3cccs3)c2CN1C(=O)Nc1cccc(Cl)c1F] 819
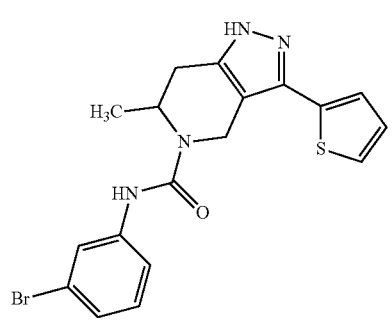 [SMILES: CC1Cc2[nH]nc(-c3cccs3)c2CN1C(=O)Nc1cccc(Br)c1] 820 (851)
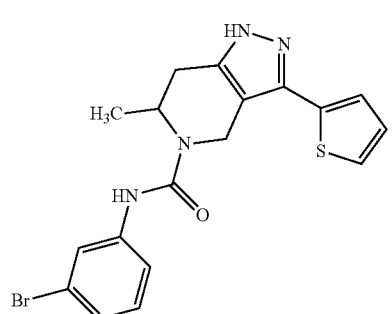 821 (852)
TABLE 2-continued
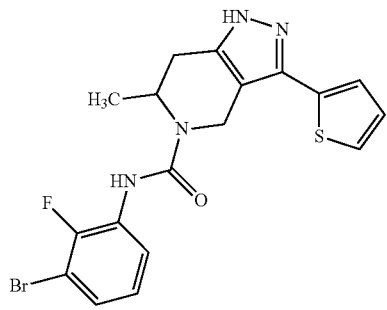 [SMILES: CC1Cc2[nH]nc(-c3cccs3)c2CN1C(=O)Nc1cccc(Br)c1F] 822
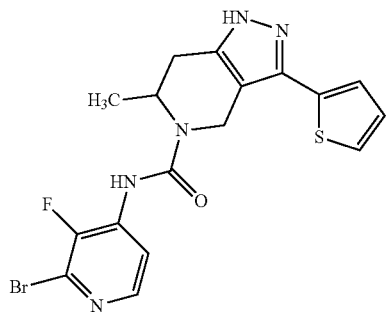 [SMILES: CC1Cc2[nH]nc(-c3cccs3)c2CN1C(=O)Nc1ccnc(Br)c1F] 823 (853)
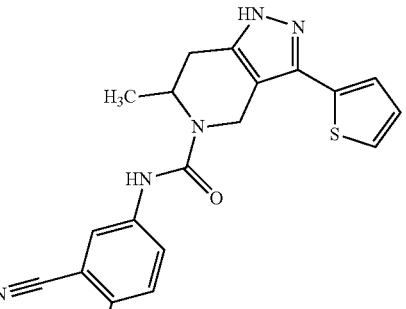 824 (854)
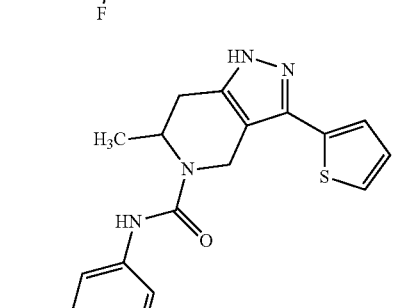 825
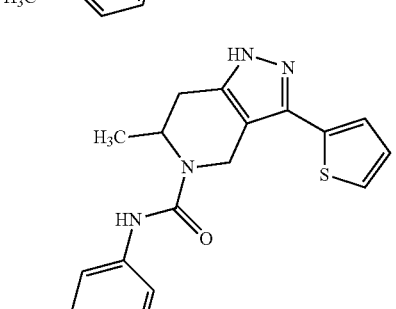 826 (855)

TABLE 2-continued
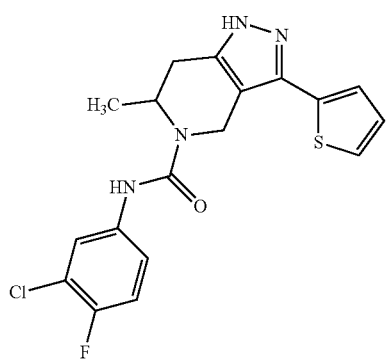 [SMILES: CC1Cc2[nH]nc(-c3cccs3)c2CN1C(=O)Nc1ccc(F)c(Cl)c1]
857
(856)
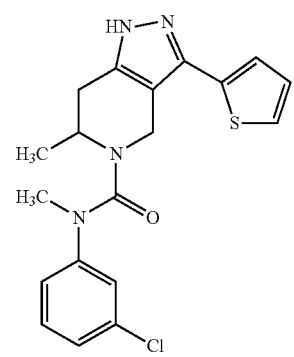 [SMILES: CC1Cc2[nH]nc(-c3cccs3)c2CN1C(=O)N(C)c1cccc(Cl)c1]
830
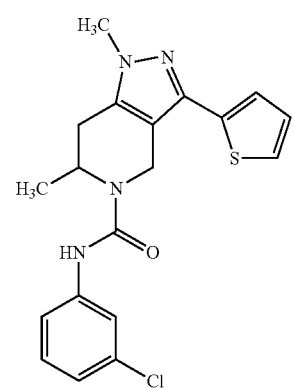 [SMILES: CC1Cc2c(c(-c3cccs3)nn2C)CN1C(=O)Nc1cccc(Cl)c1]
831
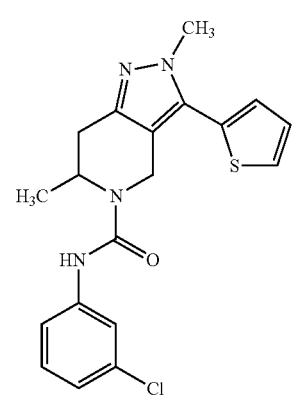 [SMILES: CC1Cc2nn(C)c(-c3cccs3)c2CN1C(=O)Nc1cccc(Cl)c1]
832
TABLE 2-continued
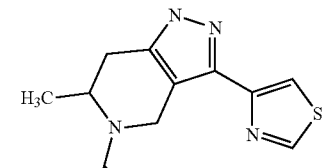
917
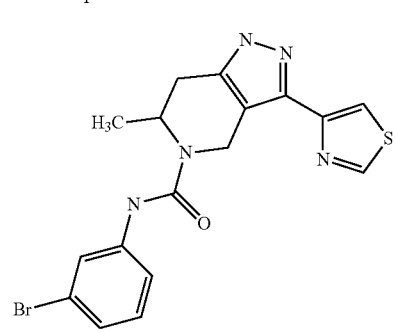
918
919
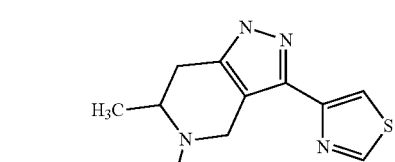
920
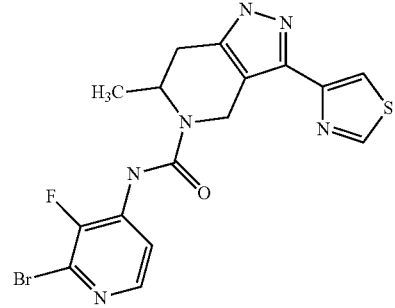 [SMILES: CC1Cc2[nH]nc(-c3cscn3)c2CN1C(=O)Nc1ccnc(Br)c1F]
921

TABLE 2-continued

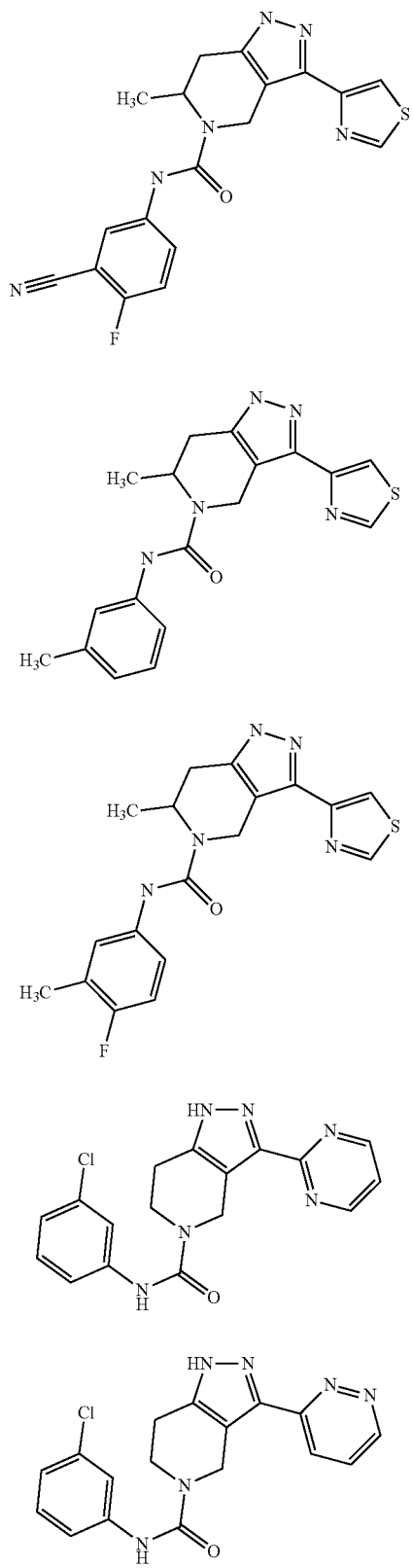

and pharmaceutically acceptable salts thereof.

Also provided herein are the following compounds:

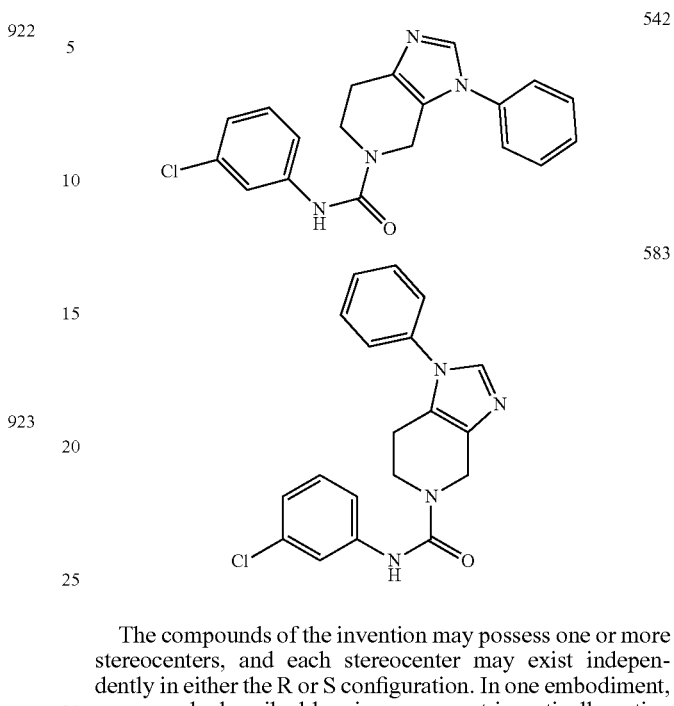

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

In one embodiment, the compounds of the invention may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

Methods of the Invention

The invention provides a method of treating an HBV infection in an individual in need thereof, comprising administering to the individual a therapeutically effective amount of a compound of the invention.

The invention also provides a method of eradicating an HBV infection in an individual in need thereof, comprising administering to the individual a therapeutically effective amount of a compound of the invention.

The invention also provides a method of reducing viral load associated with an HBV infection in an individual in need thereof, comprising administering to the individual a therapeutically effective amount of a compound of the invention.

The invention further provides a method of reducing reoccurrence of an HBV infection in an individual in need thereof, comprising administering to the individual a therapeutically effective amount of a compound of the invention.

The invention further provides a method of inhibiting or reducing the formation or presence of HBV DNA-containing particles or HBV RNA-containing particles in an individual in need thereof, comprising administering to the individual a therapeutically effective amount of a compound of the invention.

The invention also provides a method of reducing an adverse physiological impact of an HBV infection in an individual in need thereof, comprising administering to the individual a therapeutically effective amount of a compound of the invention.

The invention further provides a method of reducing, slowing, or inhibiting an HBV infection in an individual in need thereof, comprising administering to the individual a therapeutically effective amount of a compound of the invention.

The invention also provides a method of inducing remission of hepatic injury from an HBV infection in an individual in need thereof, comprising administering to the individual a therapeutically effective amount of a compound of the invention.

The invention further provides a method of reducing the physiological impact of long-term antiviral therapy for HBV infection in an individual in need thereof, comprising administering to the individual a therapeutically effective amount of a compound of the invention.

The invention further provides a method of prophylactically treating an HBV infection in an individual in need thereof, wherein the individual is afflicted with a latent HBV infection, comprising administering to the individual a therapeutically effective amount of a compound of the invention.

In one embodiment, the methods described herein further comprise administering at least one additional therapeutic agent selected from the group consisting of nucleotide/nucleoside analogs, entry inhibitors, fusion inhibitors, and any combination of these or other antiviral mechanisms. In another embodiment, the compound of the invention and the at least one additional therapeutic agent are co-formulated. In yet another embodiment, the compound of the invention and the at least one additional therapeutic agent are co-administered.

In one embodiment, the individual is refractory to other therapeutic classes of HBV drugs (e.g, HBV polymerase inhibitors, interferons, viral entry inhibitors, viral maturation inhibitors, literature-described capsid assembly modulators, antiviral compounds of distinct or unknown mechanism, and the like, or combinations thereof). In another embodiment, the method of the invention reduces viral load in an individual suffering from an HBV infection to a greater extent or at a faster rate compared to the extent that other therapeutic classes of HBV drugs reduce viral load in the individual.

In one embodiment, the administering of a compound of the invention, or a pharmaceutically acceptable salt thereof, allows for administering of the at least one additional therapeutic agent at a lower dose or frequency as compared to the administering of the at least one additional therapeutic agent alone that is required to achieve similar results in prophylactically treating an HBV infection in an individual in need thereof.

In one embodiment, the administering of a compound of the invention, or a pharmaceutically acceptable salt thereof, reduces the viral load in the individual to a greater extent or at a faster rate compared to the administering of a compound selected from the group consisting of an HBV polymerase inhibitor, interferon, viral entry inhibitor, viral maturation inhibitor, distinct capsid assembly modulator, antiviral compounds of distinct or unknown mechanism, and any combination thereof.

In one embodiment, the method of the invention reduces viral load in an individual suffering from an HBV infection, thus allowing lower doses or varying regimens of combination therapies to be used.

In one embodiment, the method of the invention causes a lower incidence of viral mutation and/or viral resistance compared to other classes of HBV drugs, thereby allowing for long term therapy and minimizing the need for changes in treatment regimens.

In one embodiment, the administering of a compound the invention, or a pharmaceutically acceptable salt thereof, causes a lower incidence of viral mutation and/or viral resistance than the administering of a compound selected from the group consisting of an HBV polymerase inhibitor, interferon, viral entry inhibitor, viral maturation inhibitor, distinct capsid assembly modulator, antiviral compounds of distinct or unknown mechanism, and combination thereof.

In one embodiment, the method of the invention increases the seroconversion rate beyond that of current treatment regimens.

In one embodiment, the method of the invention increases and/or normalizes and/or restores normal health, elicits full recovery of normal health, restores life expectancy, and/or resolves the viral infection in the individual in need thereof.

In one embodiment, the method of the invention eliminates or decreases the number of HBV RNA particles that are released from HBV infected cells thus enhancing, prolonging, or increasing the therapeutic benefit of the compounds of the invention.

In one embodiment, the method of the invention eradicates HBV from an individual infected with HBV, thereby obviating the need for long term and/or life-long treatment, or shortening the duration of treatment, and/or allowing for reduction in dosing of other antiviral agents.

In another embodiment, the method of the invention further comprises monitoring the HBV viral load of the subject, and wherein the method is carried out for a period of time such that the HBV virus is undetectable.

Accordingly, in one embodiment, provided herein is a method of treating an HBV infection in an individual in need thereof, comprising administering to the individual a therapeutically effective amount of a compound of Formula I, or a pharmaceutically acceptable salt thereof.

In another embodiment, provided herein is a method of treating an HBV infection in an individual in need thereof, comprising administering to the individual a therapeutically effective amount of a compound of Formula II, or a pharmaceutically acceptable salt thereof.

In another embodiment, provided herein is a method of treating an HBV infection in an individual in need thereof, comprising administering to the individual a therapeutically effective amount of a compound of Formula III, or a pharmaceutically acceptable salt thereof.

In another embodiment, provided herein is a method of treating an HBV infection in an individual in need thereof, comprising administering to the individual a therapeutically effective amount of a compound of Formula IV, or a pharmaceutically acceptable salt thereof.

In another embodiment, provided herein is a method of treating an HBV infection in an individual in need thereof, comprising administering to the individual a therapeutically effective amount of a compound of Table 1, or a pharmaceutically acceptable salt thereof.

In another embodiment, provided herein is a method of treating an HBV infection in an individual in need thereof, comprising administering to the individual a therapeutically effective amount of a compound of Table 2, or a pharmaceutically acceptable salt thereof.

In an embodiment of any of the methods provided herein, the method can further comprise monitoring the HBV viral load of the subject, wherein the method is carried out for a period of time such that the HBV virus is undetectable.

Combination Therapies

The compounds of the present invention are intended to be useful in combination with one or more additional compounds useful for treating HBV infection. These additional compounds may comprise compounds of the present invention or compounds known to treat, prevent, or reduce the symptoms or effects of HBV infection. Such compounds include but are not limited to HBV polymerase inhibitors, interferons, viral entry inhibitors, viral maturation inhibitors, literature-described capsid assembly modulators, reverse transcriptase inhibitor, immunomodulatory agents, a TLR-agonist, and other agents with distinct or unknown mechanisms that affect the HBV life cycle and/or affect the consequences of HBV infection.

In non-limiting examples, the compounds of the invention may be used in combination with one or more drugs (or a salt thereof) selected from the group consisting of HBV reverse transcriptase inhibitors, and DNA and RNA polymerase inhibitors, including but not limited to: lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

interferons, including but not limited to interferon alpha (IFN-α), interferon beta (IFN-β), interferon lambda (IFN-λ), and interferon gamma (IFN-γ);

viral entry inhibitors;

viral maturation inhibitors;

literature-described capsid assembly modulators, such as, but not limited to BAY 41-4109;

reverse transcriptase inhibitor;

an immunomodulatory agent such as a TLR-agonist; and agents of distinct or unknown mechanism, such as but not limited to AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl)prop-1-en-2-yl)-4-nitrobenzamide), and similar analogs.

In one embodiment, the additional therapeutic agent is an interferon. The term "interferon" or "IFN" refers to any member the family of highly homologous species-specific proteins that inhibit viral replication and cellular proliferation, and modulate immune response. Human interferons are grouped into three classes; Type I, which include interferon-alpha (IFN-α), interferon-beta (IFN-β), and interferon-omega (IFN-ω), Type II, which includes interferon-gamma (IFN-γ), and Type III, which includes interferon-lambda (IFN-λ). Recombinant forms of interferons that have been developed and are commercially available are encompassed by the term "interferon" as used herein. Subtypes of interferons, such as chemically modified or mutated interferons, are also encompassed by the term "interferon" as used herein. Chemically modified interferons include pegylated interferons and glycosylated interferons. Examples of interferons also include, but are not limited to, interferon-alpha-2a, interferon-alpha-2b, interferon-alpha-n1, interferon-beta-1a, interferon-beta-1b, interferon-lamda-1, interferon-lamda-2, and interferon-lamda-3. Examples of pegylated interferons include pegylated interferon-alpha-2a and pegylated interferson alpha-2b.

Accordingly, in one embodiment, the compounds of Formula I, II, III, or IV, can be administered in combination with an interferon selected from the group consisting of interferon alpha (IFN-α), interferon beta (IFN-β), interferon lambda (IFN-λ), and interferon gamma (IFN-γ). In one specific embodiment, the interferon is interferon-alpha-2a, interferon-alpha-2b, or interferon-alpha-n1. In another specific embodiment, the interferon-alpha-2a or interferon-alpha-2b is pegylated. In a preferred embodiment, the interferon-alpha-2a is pegylated interferon-alpha-2a (PEGASYS).

In another embodiment, the additional therapeutic agent is selected from immune modulator or immune stimulator therapies, which includes biological agents belonging to the interferon class.

Further, the additional therapeutic agent may be an agent of distinct or unknown mechanism including agents that disrupt the function of other essential viral protein(s) or host proteins required for HBV replication or persistence.

In another embodiment, the additional therapeutic agent is an antiviral agent that blocks viral entry or maturation or targets the HBV polymerase such as nucleoside or nucleotide or non-nucleos(t)ide polymerase inhibitors. In a further embodiment of the combination therapy, the reverse transcriptase inhibitor and/or DNA and/or RNA polymerase inhibitor is Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In an embodiment, the additional therapeutic agent is an immunomodulatory agent that induces a natural, limited immune response leading to induction of immune responses against unrelated viruses. In other words, the immunomodulatory agent can effect maturation of antigen presenting cells, proliferation of T-cells and cytokine release (e.g., IL-12, IL-18, IFN-alpha, -beta, and -gamma and TNF-alpha among others).

In a further embodiment, the additional therapeutic agent is a TLR modulator or a TLR agonist, such as a TLR-7 agonist or TLR-9 agonist. In further embodiment of the combination therapy, the TLR-7 agonist is selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl)propyl]amino}methyl)phenyl] acetate).

In any of the methods provided herein, the method may further comprise administering to the individual at least one HBV vaccine, a nucleoside HBV inhibitor, an interferon or any combination thereof. In an embodiment, the HBV vaccine is at least one of RECOMBIVAX HB, ENGERIX-B, ELOVAC B, GENEVAC-B, or SHANVAC B.

In another aspect, provided herein is method of treating an HBV infection in an individual in need thereof, comprising reducing the HBV viral load by administering to the individual a therapeutically effective amount of a compound of the invention alone or in combination with a reverse transcriptase inhibitor; and further administering to the individual a therapeutically effective amount of HBV vaccine. The reverse transcriptase inhibitor may be one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

For any combination therapy described herein, synergistic effect may be calculated, for example, using suitable methods such as the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

In an embodiment of any of the methods of administering combination therapies provided herein, the method can further comprise monitoring the HBV viral load of the subject, wherein the method is carried out for a period of time such that the HBV virus is undetectable.

Administration/Dosage/Formulations

In another aspect, provided herein is pharmaceutical composition comprising a compound of the invention, or a pharmaceutically acceptable salt thereof, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of HBV infection in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., another drug for HBV treatment) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of HBV infection in a patient.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Preparation of Compounds 010 and 059

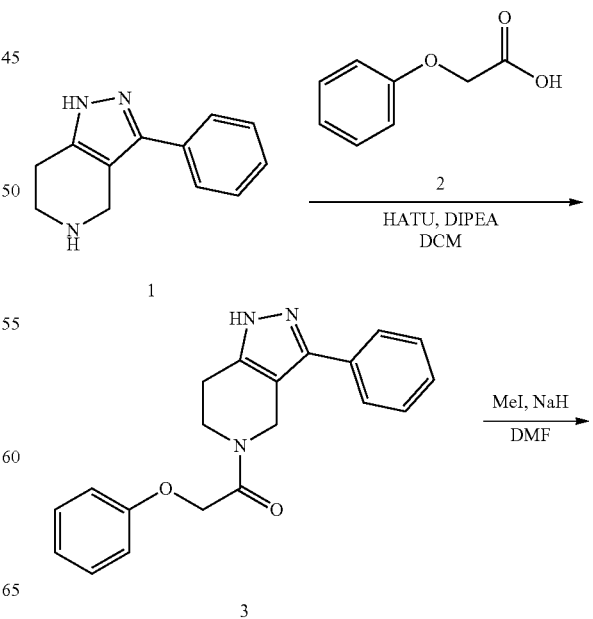

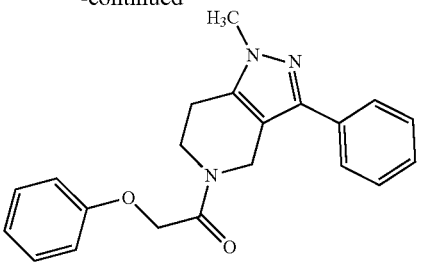

3.82 (m, 3H), 2.73-2.95 (m, 2H). LCMS: 348 [M+1]. Characterization of Compound 059: $^1$H NMR (400 MHz, Methanol-d$_4$) δ 7.39-7.67 (m, 5H), 7.19-7.33 (m, 2H), 6.83-7.02 (m, 3H), 4.88-4.90 (m, 2H), 4.54-4.61 (m, 2H), 3.84-4.00 (m, 2H), 3.77 (s, 3H), 2.71-2.92 (m, 2H). LCMS: 348 [M+1].

Example 2: Preparation of Compounds 011 and 060

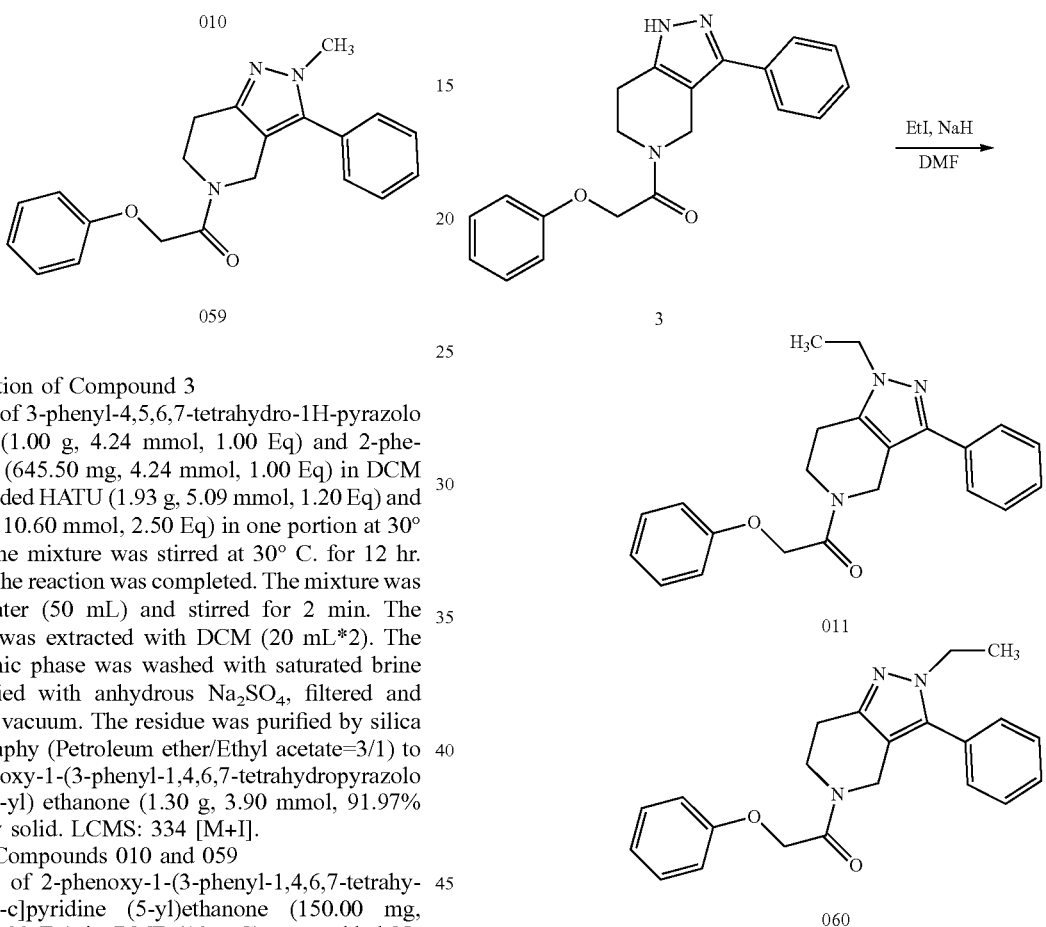

Step 1: Preparation of Compound 3

To a mixture of 3-phenyl-4,5,6,7-tetrahydro-1H-pyrazolo[4,3-c]pyridine (1.00 g, 4.24 mmol, 1.00 Eq) and 2-phenoxyacetic acid (645.50 mg, 4.24 mmol, 1.00 Eq) in DCM (40 mL), was added HATU (1.93 g, 5.09 mmol, 1.20 Eq) and DIPEA (1.37 g, 10.60 mmol, 2.50 Eq) in one portion at 30° C. under N$_2$. The mixture was stirred at 30° C. for 12 hr. LCMS showed the reaction was completed. The mixture was poured into water (50 mL) and stirred for 2 min. The aqueous phase was extracted with DCM (20 mL*2). The combined organic phase was washed with saturated brine (20 mL*2), dried with anhydrous Na$_2$SO$_4$, filtered and concentrated in vacuum. The residue was purified by silica gel chromatography (Petroleum ether/Ethyl acetate=3/1) to afford 2-phenoxy-1-(3-phenyl-1,4,6,7-tetrahydropyrazolo[4,3-c]pyridin-5-yl) ethanone (1.30 g, 3.90 mmol, 91.97% yield) as yellow solid. LCMS: 334 [M+I].

Preparation of Compounds 010 and 059

To a mixture of 2-phenoxy-1-(3-phenyl-1,4,6,7-tetrahydropyrazolo[4,3-c]pyridine (5-yl)ethanone (150.00 mg, 449.94 umol, 1.00 Eq) in DMF (10 mC), was added Na (36.00 mg, 899.88 umol, 2.00 Eq) in one portion at 0° C. under N. The mixture was stirred at 0° C. for 0.5 hr, then MeI (191.59 mg, 1.35 mmol, 3.00 Eq) was added to the mixture at 0° C. The mixture was heated to 30° C. and stirred for 12 hours. LCMS showed the reaction was completed. The mixture was quenched with water. The aqueous phase was extracted with ethyl acetate (10 mL*2). The combined organic phase was washed with saturated brine (10 mL*2), dried with anhydrous Na$_2$SO$_4$, filtered and concentrated in vacuum. The residue was purified by pre-HPLC(FA) to afford a region-isomeric mixture (85.34 mg, 245.65 umol, 54.60% yield) as yellow solid. The yellow solid was separated by SFC to afford 1-(1-methyl-3-phenyl-6,7-dihydro-4H-pyrazolo[4,3-c]pyridin-5-yl)-2-phenoxy-ethanone (21.34 mg, 61.43 umol) and 1-(2-methyl-3-phenyl-6,7-dihydro-4H-pyrazolo[4,3-c]pyridin-5-yl)-2-phenoxy-ethanone (32.11 mg, 92.43 umol). Characterization of Compound 010: $^1$H NMR (400 MHz, Methanol-d$_4$) δ 7.56-7.66 (m, 2H), 7.43 (s, 5H), 6.84-7.04 (m, 3H), 4.89-4.92 (m, 1H), 4.85 (s, 1H), 4.76-4.80 (m, 2H), 3.87-4.00 (m, 2H), 3.74-

To a mixture of 2-phenoxy-1-(3-phenyl-1,4,6,7-tetrahydropyrazolo[4,3-c]pyridin-5-yl) ethanone (150.00 mg, 449.94 umol, 1.00 Eq) in DMF (10 mL), was added NaH (36.00 mg, 899.88 umol, 2.00 Eq) in one portion at 0° C. under N$_2$. The mixture was stirred at 0° C. for 0.5 hr, then iodoethane (210.53 mg, 1.35 mmol, 3.00 Eq) was added to the mixture at 0° C. The mixture was heated to 30° C. and stirred for 12 hours. LCMS showed the reaction was completed. The mixture was quenched with water (5 mL) and stirred for 5 min. The aqueous phase was extracted with ethyl acetate (15 mL*2). The combined organic phase was washed with saturated brine (15 mL*2), dried with anhydrous Na$_2$SO$_4$, filtered and concentrated in vacuum. The residue was purified by pre-HPLC (FA) to afford 1-(1-ethyl-3-phenyl-6,7-dihydro-4H-pyrazolo[4,3-c]pyridin-5-yl)-2-phenoxy-ethanone (71.20 mg, 196.99 umol, 43.78% yield) and 1-(2-ethyl-3-phenyl-6,7-dihydro-4H-pyrazolo[4,3-c]pyridin-5-yl)-2-phenoxy-ethanone (21.49 mg, 59.46 umol, 13.21% yield) as white solid.

Charactertization of Compound 011: ¹H NMR (400 MHz, Methanol-d₄) δ 7.57-7.66 (m, 2H), 7.38-7.50 (m, 2H), 7.15-7.38 (m, 3H), 6.83-7.05 (m, 3H), 4.91 (s, 1H), 4.83-4.86 (m, 1H), 4.75-4.81 (m, 2H), 4.05-4.18 (m, 2H), 3.85-4.03 (m, 2H), 2.87-2.96 (m, 1H), 2.75-2.83 (m, 1H), 1.40 (s, 3H). LCMS: 362 [M+1].

Characterization of Compound 060: ¹H NMR (400 MHz, Methanol-d₄) δ 7.44-7.59 (m, 3H), 7.37-7.44 (m, 2H), 7.19-7.33 (m, 2H), 6.84-7.02 (m, 3H), 4.89 (br. s., 2H), 4.51-4.62 (m, 2H), 4.08 (d, J=7.28 Hz, 2H), 3.89 (s, 2H), 2.85-2.91 (m, 1H), 2.74-2.81 (m, 1H), 1.31 (t, J=7.22 Hz, 3H). LCMS: 362 [M+1].

Example 3: Preparation of Compounds 012 and 061

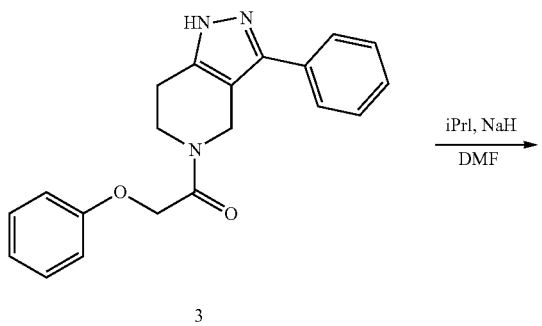

3

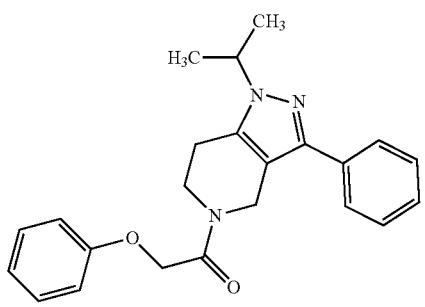

012

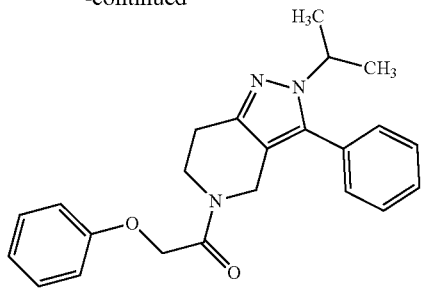

061

To a mixture of 2-phenoxy-1-(3-phenyl-1,4,6,7-tetrahydropyrazolo[4,3-c]pyridine-5-yl)ethanone (150.00 mg, 449.94 umol, 1.00 Eq) in DMF (10 mL), was added NaH (36.00 mg, 899.88 umol, 2.00 Eq) in one portion at 0° C. under N₂. The mixture was stirred at 0° C. for 0.5 hr, then 2-iodopropane (229.46 mg, 1.35 mmol, 3.00 Eq) was added to the mixture, the mixture was heated to 30° C. and stirred for 12 hours. LCMS showed the reaction was completed. The mixture was poured into water (10 mL) and stirred for 5 min. The aqueous phase was extracted with ethyl acetate (20 mL*2). The combined organic phase was washed with saturated brine (10 mL*2), dried with anhydrous Na₂SO₄, filtered and concentrated in vacuum. The residue was purified by pre-HPLC(FA) to afford 1-(1-isopropyl-3-phenyl-6,7-dihydro-4H-pyrazolo [4,3-c] pyridin-5-yl)-2-phenoxy-ethanone (22.18 mg, 59.07 umol, 13.13% yield) and 1-(2-isopropyl-3-phenyl-6,7-dihydro-4H-pyrazolo[4,3-c]pyridin-5-yl)-2-phenoxy-ethanone (54.13 mg, 144.17 umol, 32.04% yield) as yellow solid. Characterization of Compound 012: ¹H NMR (400 MHz, Methanol-d₄) δ 7.57-7.69 (m, 2H), 7.39-7.49 (m, 2H), 7.17-7.38 (m, 3H), 6.84-7.06 (m, 3H), 4.91 (s, 2H), 4.75-4.81 (m, 2H), 4.40-4.58 (m, 1H), 3.84-4.04 (m, 2H), 2.75-3.00 (m, 2H), 1.49 (d, J=6.53 Hz, 6H). LCMS: 376 [M+1]. Characterization of Compound 061: ¹H NMR (400 MHz, Methanol-d₄) δ 7.43-7.60 (m, 3H), 7.34-7.41 (m, 2H), 7.18-7.33 (m, 2H), 6.82-7.02 (m, 3H), 4.89 (br. s., 2H), 4.43-4.63 (m, 3H), 3.81-4.01 (m, 2H), 2.74-2.94 (m, 2H), 1.41 (d, J=6.65 Hz, 6H). LCMS: 376 [M+1].

Example 4: Preparation of Compounds 013, 056, 062, and 063

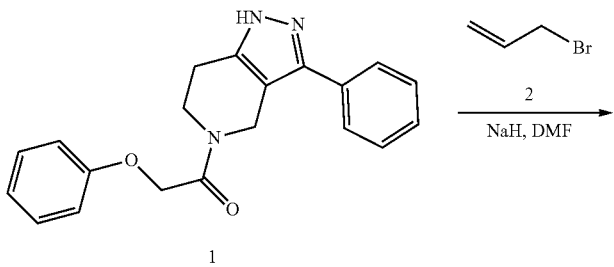

1

-continued
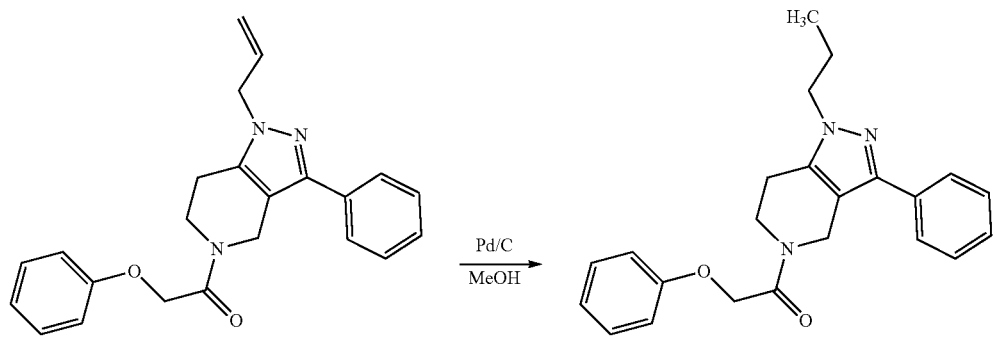
3
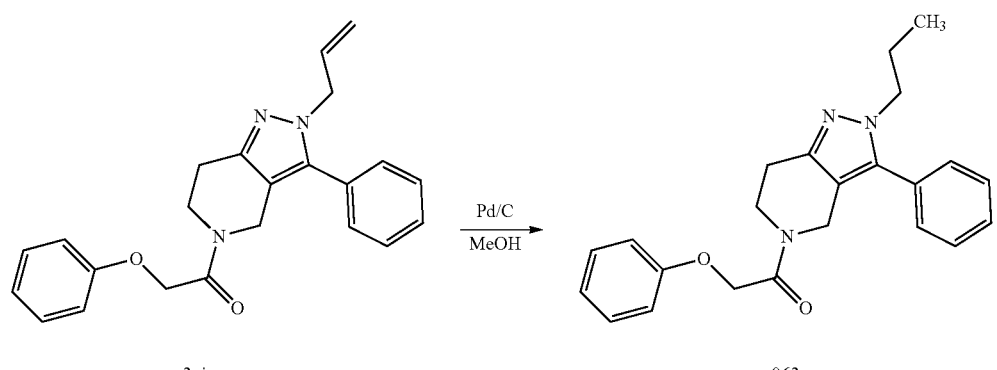
3_isomer
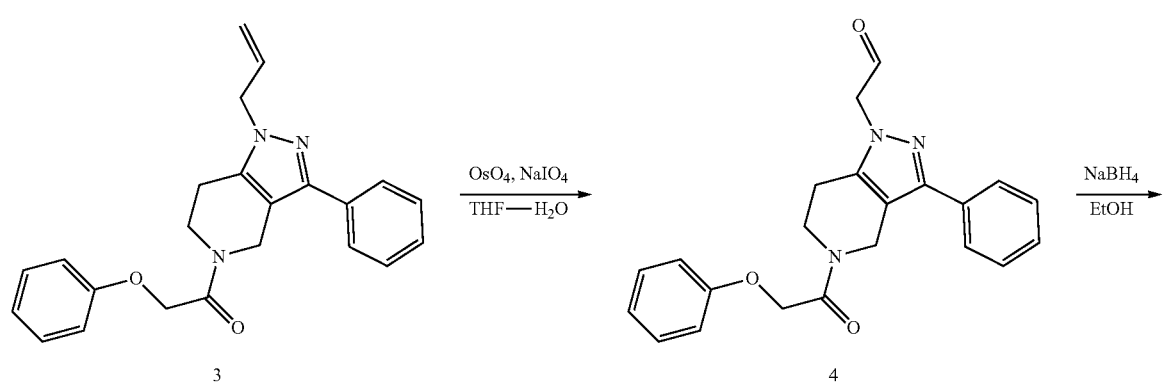
3
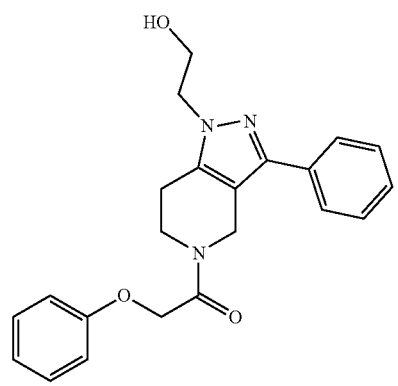
013

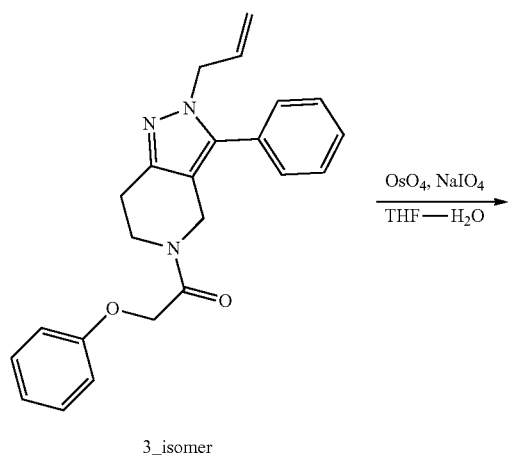

3_isomer

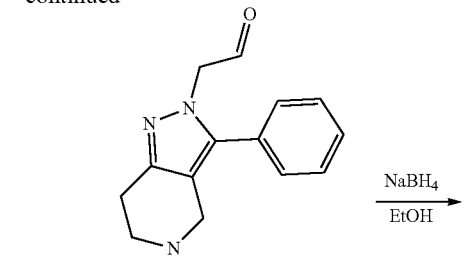

4_isomer

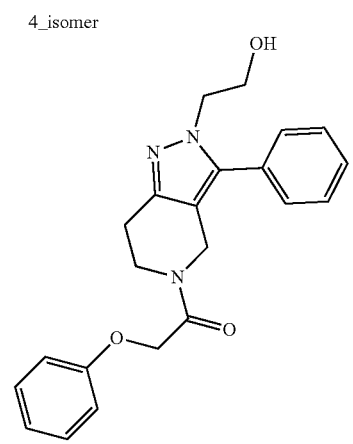

062

Step 1: Preparation of Compound 3 and Compound 3-isomer

To a mixture of 2-phenoxy-1-(3-phenyl-1,4,6,7-tetrahydropyrazolo[4,3-c]pyridin-5-yl)ethanone (400.00 mg, 1.20 mmol, 1.00 Eq) in DMF (10 mL), was added NaH (95.99 mg, 2.40 mmol, 2.00 Eq) in one portion at 0° C. under $N_2$. The mixture was stirred at 0° C. for 1 hr, 10 then 3-bromoprop-1-ene (362.94 mg, 3.00 mmol, 2.50 Eq) was added to the mixture, the mixture was heated to 30 HC and stirred for 12 hours. LCMS showed the reaction was completed. The mixture was poured into ice-water (w/w=1/1) (20 mL) and stirred for 5 min. The aqueous phase was extracted with ethyl acetate (40 mL*2). The combined organic phase was washed with saturated brine (30 L*2, dried with anhydrous $Na_2SO_4$, filtered and concentrated in vacuum. The residue was purified by silica gel chromatography (Petroleum ether/Ethyl acetate=3/1) to afford 1-(1-allyl-3-phenyl-6,7-dihydro-4H-pyrazolo[4,3-c]pyridin-5-yl)-2-phenoxy-ethanone (330.00 mg, 883.65 umol, 73.64% yield) and 1-(2-allyl-3-phenyl-6,7-dihydro-4H-pyrazolo[4,3-c]pyridin-5-yl)-2-phenoxy-ethanone (120.00 mg, 267.77 umol, 22.31% yield) as yellow solid. LCMS: 374 [M+1].

Preparation of Compound 056

To a solution of 1-(1-allyl-3-phenyl-6,7-dihydro-4H-pyrazolo[4,3-c]pyridin-5-yl)-2-phenoxy-ethanone (100.00 mg, 267.77 umol, 1.00 Eq) in MeOH (10 mL) was added Pd—C (10%, 20.00 mg) under $N_2$. The suspension was degassed under vacuum and purged with $H_2$ several times. The mixture was stirred under $H_2$ (15 psi) at 30° C. for 12 hours. LCMS showed the starting material was consumed completely. The reaction mixture was filtered and the filter was concentrated. The crude product was purified by pre-HPLC(FA) to give 2-phenoxy-1-(3-phenyl-1-propyl-6,7-dihydro-4H-pyrazolo[4,3-c]pyridin-5-yl)ethanone (45.32 mg, 120.71 umol, 45.08% yield) as white solid. $^1$H NMR (400 MHz, DMSO-$d_6$) δ 7.56-7.70 (m, 2H), 7.35-7.48 (m, 2H), 7.20-7.34 (m, 3H), 6.85-7.00 (m, 3H), 4.87-5.01 (m, 2H), 4.60-4.77 (m, 2H), 3.89-4.07 (m, 2H), 3.67-3.85 (m, 2H), 2.80-2.95 (m, 1H), 2.65-2.76 (m, 1H), 1.69-1.84 (m, 2H), 0.86 (t, J=7.34 Hz, 3H). LCMS: 376 [M+1].

Preparation of Compound 063

To a solution of 1-(2-allyl-3-phenyl-6,7-dihydro-4H-pyrazolo [4,3-c]pyridin-5-yl)-2-phenoxy-ethanone (50.00 mg, 133.89 umol, 1.00 Eq) in MeOH (10 mL) was added Pd—C (10%, 5 mg) under $N_2$. The suspension was degassed under vacuum and purged with $H_2$ several times. The mixture was stirred under $H_2$ (15 psi) at 30° C. for 10 hours. LCMS showed the starting material was consumed completely. The reaction mixture was filtered and the filter was concentrated. The crude product was purified by pre-HPLC (FA) to give 2-phenoxy-1-(3-phenyl-2-propyl-6,7-dihydro-4H-pyrazolo[4,3-c]pyridin-5-yl)ethanone (25.34 mg, 67.49 umol, 50.41% yield) as white solid. LCMS: 376 [M+1].

Preparation of Compound 013

To a mixture of 1-(1-allyl-3-phenyl-6,7-dihydro-4H-pyrazolo[4,3-c]pyridin-5-yl)-2-phenoxy-ethanone (150.00 mg, 401.66 umol, 1.00 Eq) in THF (10 mL) and H2O (2 mL), was added NaIO4 (189.00 mg, 883.65 umol, 2.20 Eq) and OsO4 (10.21 mg, 40.17 umol, 0.10 Eq) in one portion under $N_2$. The mixture was stirred at 30° C. for 5 hr. The mixture was washed with saturated $Na_2SO_3$ (20 mL*2), The aqueous phase was extracted with ethyl acetate (10 mL*2). The combined organic phase was dried with anhydrous $Na_2SO_4$, filtered and concentrated in vacuum. The residue was diluted in EtOH (10 mL), NaBH4 (15.20 mg, 401.66 umol, 1.00 Eq) was added to the mixture. The mixture was stirred at 30° C. for 5 hr. LCMS showed the reaction was completed. The mixture was poured into water (20 mL) and stirred for 5 min. The aqueous phase was extracted with ethyl acetate (15 mL*2). The combined organic phase was washed with saturated brine (15 mL*2), dried with anhydrous $Na_2SO_4$, filtered and concentrated in vacuum. The residue was purified by pre-HPLC(FA) to afford 1-[1-(2-hydroxyethyl)-3-phenyl-6,7-dihydro-4H-pyrazolo[4,3-c]pyridin-5-yl]-2-phenoxy-ethanone (45.32 mg, 120.07 umol, 29.89% yield) as white solid. LCMS: 378 [M+1].

Preparation of Compound 062

To a mixture of 1-(2-allyl-3-phenyl-6,7-dihydro-4H-pyrazolo[4,3-c]pyridin-5-yl)-2-phenoxy-ethanone (70.00 mg, 187.44 umol, 1.00 Eq) in THF (10 mL) and H2O (2 mL), was added NaIO4 (88.20 mg, 412.37 umol, 2.20 Eq) and OsO4 (4.77 mg, 18.74 umol, 0.10 Eq) in one portion under $N_2$. The mixture was stirred at 30° C. for 5 hr. The mixture was washed with saturated $Na_2SO_3$ (20 mL*2), The aqueous phase was extracted with ethyl acetate (10 mL*2). The combined organic phase was dried with anhydrous $Na_2SO_4$, filtered and concentrated in vacuum. The residue was diluted in EtOH (10 mL), NaBH4 (8.51 mg, 224.93 umol, 1.20 Eq) was added to the mixture. The mixture was stirred at 30° C. for 5 hr. LCMS showed the reaction was completed. The mixture was poured into water (20 mL) and stirred for 5 min. The aqueous phase was extracted with ethyl acetate (15 mL*2). The combined organic phase was washed with saturated brine (15 mL*2), dried with anhydrous $Na_2SO_4$, filtered and concentrated in vacuum. The residue was purified by pre-HPLC(FA) to afford 1-[2-(2-hydroxyethyl)-3-phenyl-6,7-dihydro-4H-pyrazolo[4,3-c]pyridin-5-yl]-2-phenoxy-ethanone (18.24 mg, 48.33 umol, 25.78% yield) as white solid. LCMS: 378 [M+1].

Example 5: Preparation of Compound 024

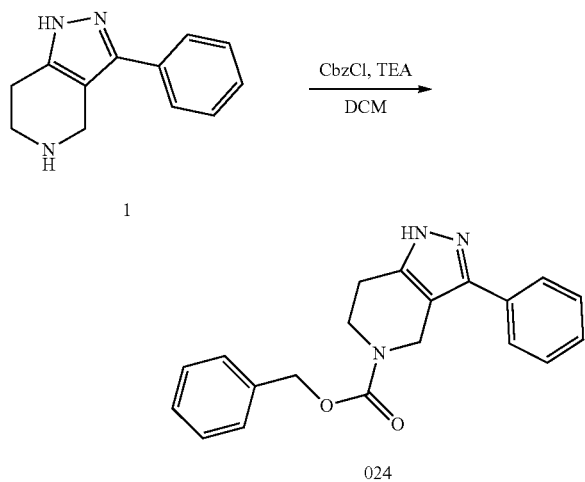

To a mixture of 3-phenyl-4,5,6,7-tetrahydro-1H-pyrazolo[4,3-c]pyridine (150.00 mg, 636.38 umol, 1.00 Eq) in DCM (5 mL), was added CbzCl (130.27 mg, 763.66 umol, 1.20 Eq) and TEA (193.19 mg, 1.91 mmol, 3.00 Eq) in one portion under $N_2$. The mixture was stirred at 30° C. for 12 hr. LCMS showed the reaction was completed. The mixture was washed with saturated brine (10 mL*2), dried with anhydrous $Na_2SO_4$, filtered and concentrated in vacuum. The residue was purified by pre-HPLC (FA) to afford benzyl 3-phenyl-1,4,6,7-tetrahydropyrazolo[4,3-c]pyridine-5-carboxylate (48.97 mg, 146.89 umol, 23.08% yield) as white solid. $^1$H NMR (400 MHz, Methanol-$d_4$) 7.50-7.64 (m, 2H), 7.41-7.50 (m, 2H), 7.24-7.41 (m, 6H), 5.12-5.22 (m, 2H), 4.69-4.77 (m, 2H), 3.78-3.89 (m, 2H), 2.74-2.85 (m, 2H). LCMS: 334 [M+1].

Example 6: Preparation of Compound 016

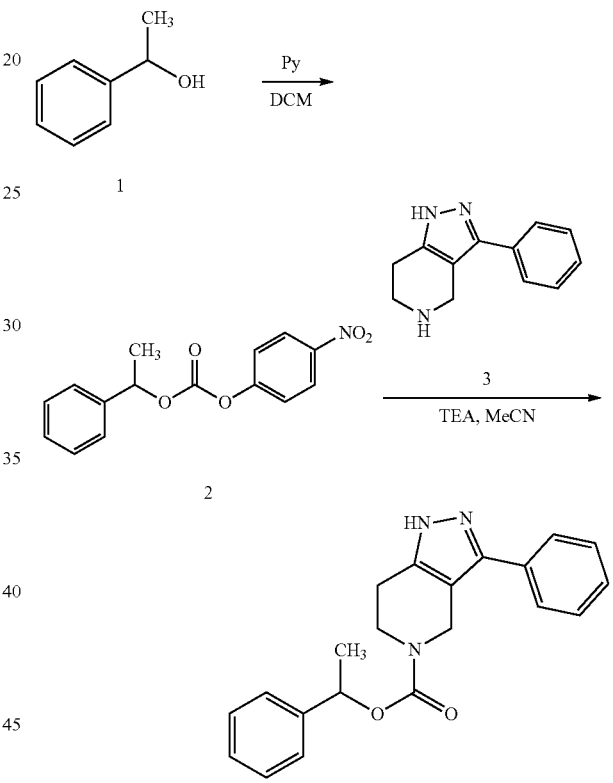

Step 1: Preparation of Compound 2

To a mixture of 1-phenylethanol (2.00 g, 16.37 mmol, 1.00 eq) and Py (3.24 g, 40.93 mmol, 2.50 eq) in DCM (75.00 mL), was added (4-nitrophenyl) carbonochloridate (3.30 g, 16.37 mmol, 1.00 eq) in DCM (75.00 mL) dropwise at 0° C. under $N_2$. The mixture was stirred at 0° C. for 1 hr, then heated to 30° C. and stirred for 12 hours. TLC showed the reaction was completed. The mixture was poured into water (30 mL) and stirred for 5 min. The aqueous phase was extracted with ethyl acetate (20 mL*2). The combined organic phase was washed with saturated brine (20 mL*2), dried with anhydrous $Na_2SO_4$, filtered and concentrated in vacuum. The residue was purified by silica gel chromatography (Petroleum ether/Ethyl acetate=10/1) to afford (4-nitrophenyl) 1-phenylethyl carbonate (2.90 g, 10.10 mmol, 61.67% yield) as yellow solid. LCMS: 288 [M+1].

Preparation of Compound 016

To a mixture of (4-nitrophenyl) 1-phenylethyl carbonate (150.00 mg, 522.16 umol, 1.00 eq) and 3-phenyl-4,5,6,7-tetrahydro-1H-pyrazolo [4,3-c]pyridine (123.08 mg, 522.16 umol, 1.00 eq) in MeCN (10.00 mL), was added TEA (158.51 mg, 1.57 mmol, 3.00 eq) in one portion at 30° C. under N$_2$. The mixture was stirred at 30° C. for 5 hours. LCMS showed the reaction was completed. The mixture was poured into water (10 mL) and stirred for 5 min. The aqueous phase was extracted with ethyl acetate (10 mL*2). The combined organic phase was washed with saturated brine (10 mL*2), dried with anhydrous Na$_2$SO$_4$, filtered and concentrated in vacuum. The residue was purified by pre-HPLC(FA) to afford 1-phenylethyl 3-phenyl-1,4,6,7-tetrahydropyrazolo[4,3-c]pyridine-5-carboxylate (54.40 mg, 156.59 umol, 29.99% yield) as white solid. LCMS: 348 [M+1].

Example 7: Preparation of Compounds 025-030 and 057

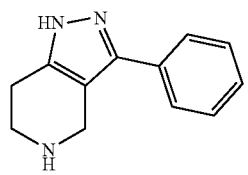

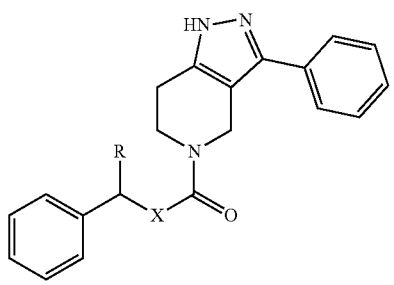

025-030 and 057

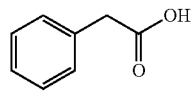

2

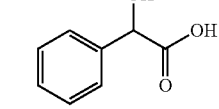

3

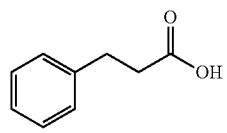

4

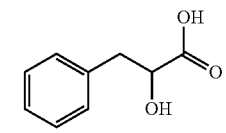

5

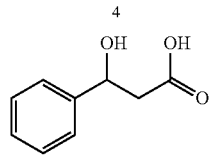

6

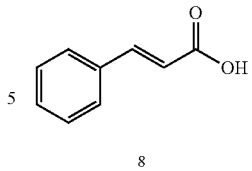

8

Preparation of Compound 025

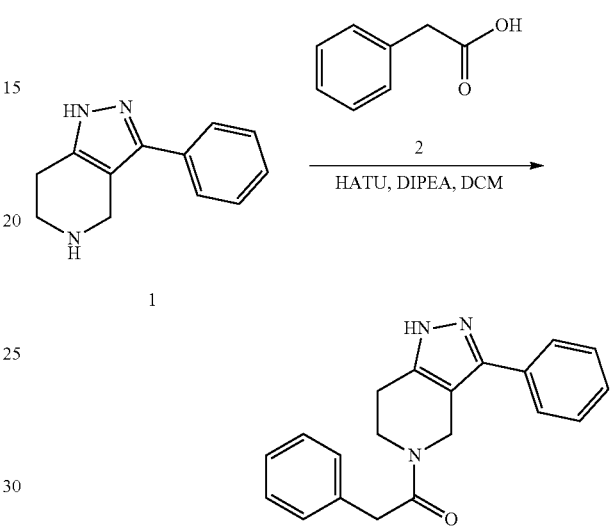

025

To a mixture of 3-phenyl-4,5,6,7-tetrahydro-1H-pyrazolo [4,3-c]pyridine (100.00 mg, 424.25 umol, 1.00 Eq) and 2-phenylacetic acid (57.76 mg, 424.25 umol, 1.00 Eq) in DCM (10 mL), was added HATU (241.97 mg, 636.38 umol, 1.50 Eq) and DIPEA (137.08 mg, 1.06 mmol, 2.50 Eq) in one portion at 30° C. under N$_2$. The mixture was stirred at 30° C. for 8 hr. LCMS showed the reaction was completed. The mixture was poured into water (20 mL) and stirred for 5 min. The aqueous phase was extracted with DCM (20 mL*2). The combined organic phase was washed with saturated brine (20 mL*2), dried with anhydrous Na$_2$SO$_4$, filtered and concentrated in vacuum. The residue was purified by pre-HPLC (FA) to afford 2-phenyl-1-(3-phen yl-1, 4,6,7-tetrahydropyrazolo[4,3-c]pyridin-5-yl)ethanone (32.58 mg, 102.65 umol, 24.20% yield) as white solid. LCMS: 318 [M+1].

Preparation of Compound 026

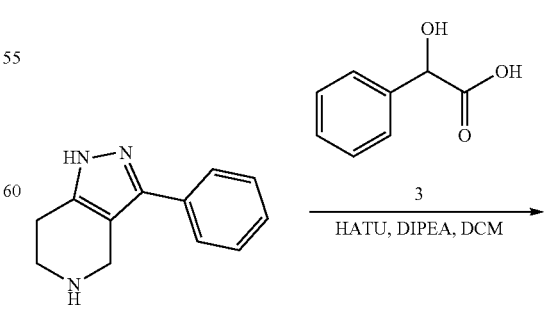

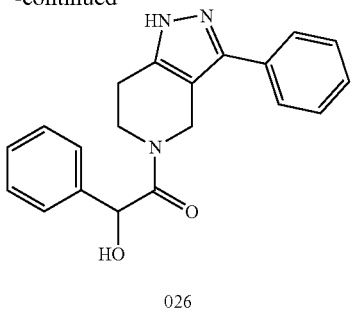

026

To a mixture of 3-phenyl-4,5,6,7-tetrahydro-1H-pyrazolo[4,3-c]pyridine (100.00 mg, 424.25 umol, 1.00 Eq) and 2-hydroxy-2-phenyl-acetic acid (64.55 mg, 424.25 umol, 1.00 Eq) in DCM (10 mL), was added HATU (241.97 mg, 636.38 umol, 1.50 Eq) and DIPEA (137.08 mg, 1.06 mmol, 2.50 Eq) in one portion at 30° C. under N₂. The mixture was stirred at 30° C. for 8 hr. LCMS showed the reaction was completed. The mixture was poured into water (20 mL) and stirred for 5 min. The aqueous phase was extracted with DCM (20 mL*2). The combined organic phase was washed with saturated brine (20 mL*2), dried with anhydrous Na₂SO₄, filtered and concentrated in vacuum. The residue was purified by pre-HPLC (FA) to afford 2-hydroxy-2-phenyl-1-(3-phenyl-1,4,6,7-tetrahydropyrazolo[4,3-c]pyridin-5-yl)ethanone (46.19 mg, 138.55 umol, 32.66% yield) as white solid. ¹H NMR (400 MHz, DMSO-d₆) 7.13-7.69 (m, 10H), 5.75 (d, J=6.53 Hz, 1H), 5.51 (br. s., 1H), 4.62-4.83 (m, 2H), 3.74 (br. s., 3H), 2.67 (br. s., 1H), 2.15 (d, J=15.18 Hz, 1H). LCMS: 334 [M+1].

Preparation of Compound 027

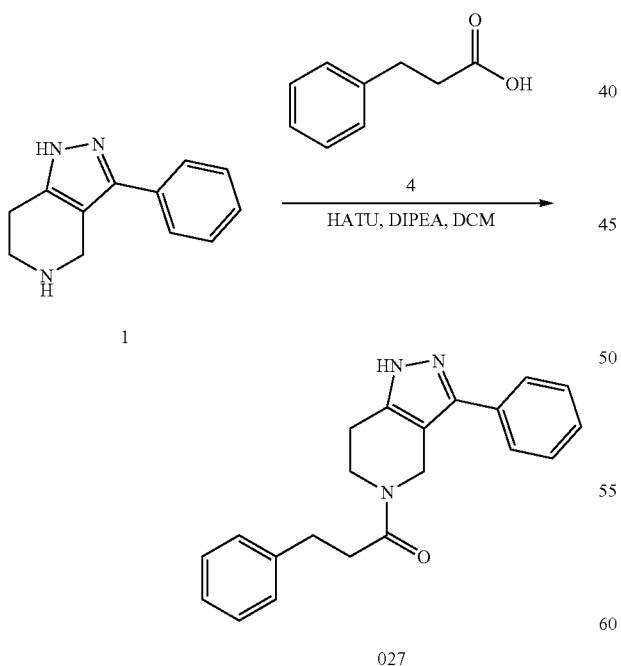

027

To a mixture of 3-phenyl-4,5,6,7-tetrahydro-1H-pyrazolo[4,3-c]pyridine (100.00 mg 424.25 umol, 1.00 Eq) and 3-phenylpropanoic acid (63.71 mg, 424.25 umol, 1.00 Eq) in DCM (10 mL), was added HATU (241.97 mg, 636.38 umol, 1.50 Eq) and DIPEA (137.08 mg, 1.06 mmol, 2.50 Eq) at 30° C. The mixture was stirred at 30° C. for 14 hr. LCMS showed the reaction was completed. The mixture was poured into water (20 mL) and stirred for 5 min. The aqueous phase was extracted with DCM (20 mL*2). The combined organic phase was washed with saturated brine (20 mL*2), dried with anhydrous Na₂SO₄, filtered and concentrated in vacuum. The residue was purified by pre-HPLC(FA) to afford 3-phenyl-1-(3-phenyl-1,4,6,7-tetrahydropyrazolo[4,3-c]pyridin-5-yl)propan-1-one (24.76 mg, 74.71 umol, 17.61% yield) as white solid. LCMS: 332 [M+1].

Preparation of Compound 028

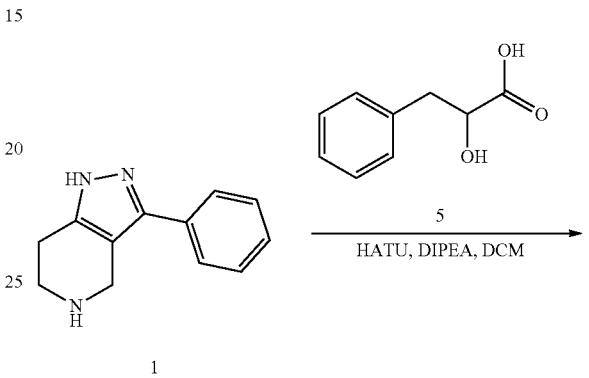

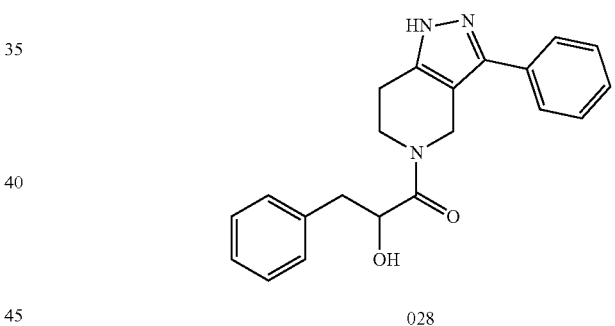

028

To a mixture of 3-phenyl-4,5,6,7-tetrahydro-1H-pyrazolo[4,3-c]pyridine (100.00 mg, 424.25 umol, 1.00 Eq) and 2-hydroxy-3-phenyl-propanoic acid (70.50 mg, 424.25 umol, 1.00 Eq), was added HATU (241.97 mg, 636.38 umol, 1.50 Eq) and DIPEA (137.08 mg, 1.06 mmol, 2.50 Eq) at 30° C. The mixture was stirred at 30° C. for 15 hr. LCMS showed the reaction was completed. The mixture was poured into water (20 mL) and stirred for 5 min. The aqueous phase was extracted with DCM (20 mL*2). The combined organic phase was washed with saturated brine (20 mL*2), dried with anhydrous Na₂SO₄, filtered and concentrated in vacuum. The residue was purified by pre-HPLC (FA) to afford 2-hydroxy-3-phenyl-1-(3-phenyl-1,4,6,7-tetrahydropyrazolo[4,3-c]pyridine-5-yl)propan-1-one (58.00 mg, 166.95 umol, 39.35% yield) as white solid. LCMS: 348 [M+1].

Preparation of Compound 029

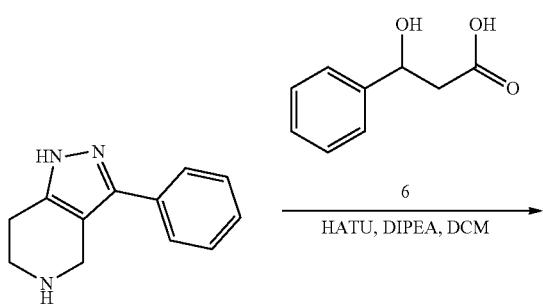

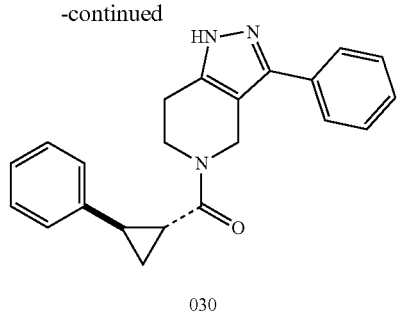

To a mixture of 3-phenyl-4,5,6,7-tetrahydro-1H-pyrazolo[4,3-c]pyridine (100.00 mg, 424.25 umol, 1.00 Eq) and 3-hydroxy-3-phenyl-propanoic acid (70.50 mg, 424.25 umol, 1.00 Eq) in DCM (10 mL) was added HATU (241.97 mg, 636.38 umol, 1.50 Eq) and DIPEA (137.08 mg, 1.06 mmol, 2.50 Eq) at 30° C. The mixture was stirred at 30° C. for 15 hr. LCMS showed the reaction was completed. The mixture was poured into water (20 mL) and stirred for 5 min. The aqueous phase was extracted with DCM (20 mL*2). The combined organic phase was washed with saturated brine (20 mL*2), dried with anhydrous $Na_2SO_4$, filtered and concentrated in vacuum. The residue was purified by pre-HPLC (FA) to afford 3-hydroxy-3-phenyl-1-(3-phenyl-1,4,6,7-tetrahydropyrazolo[4,3-c]pyridin-5-yl)propan-1-one (95.00 mg, 273.45 umol, 64.46% yield) as white solid. LCMS: 348 [M+1].

Preparation of Compound 030

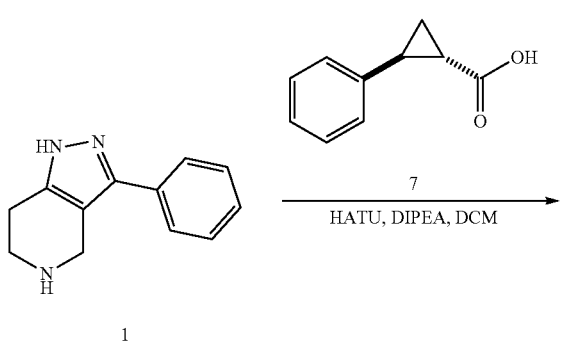

To a mixture of 3-phenyl-4,5,6,7-tetrahydro-1H-pyrazolo[4,3-c]pyridine (100.00 mg, 424.25 umol, 1.00 Eq) and 2-phenylcyclopropanecarboxylic acid (68.80 mg, 424.25 umol, 1.00 Eq) in DCM (10 mL), was added DIPEA (137.08 mg, 1.06 mmol, 2.50 Eq) and HATU (241.97 mg, 636.38 umol, 1.50 Eq) in one portion at 30° C. under $N_2$. The mixture was stirred at 30° C. for 4 hr. LCMS showed the reaction was completed. The mixture was poured into water (20 mL) and stirred for 5 min. The aqueous phase was extracted with DCM (10 mL*2). The combined organic phase was washed with saturated brine (10 mL*2), dried with anhydrous $Na_2SO_4$, filtered and concentrated in vacuum. The residue was purified by pre-HPLC (FA) to afford (2-phenylcyclopropyl)-(3-phenyl-2,4,6,7-tetrahydropyrazolo[4,3-c]pyridin-5-yl)methanone (27.92 mg, 81.30 umol, 19.16% yield) as white solid. $^1$H NMR (400 MHz, DMSO-$d_6$) 7.11-7.63 (m, 10H), 4.88 (d, J=14.56 Hz, 1H), 4.72 (s, 1H), 3.67-3.99 (m, 2H), 2.63-2.86 (m, 2H), 2.27-2.47 (m, 2H), 1.43 (td, J=8.97, 4.52 Hz, 1H), 1.18-1.28 (m, 1H). LCMS: 344 [M+1].

Preparation of Compound 057

To a mixture of 3-phenyl-4,5,6,7-tetrahydro-1H-pyrazolo[4,3-c]pyridine (100.00 mg, 424.25 umol, 1.00 Eq) and (E)-3-phenylprop-2-enoic acid (62.86 mg, 424.25 umol, 1.00 Eq) in DCM (10 mL), was added HATU (241.97 mg, 636.38 umol, 1.50 Eq) and DIPEA (137.08 mg, 1.06 mmol, 2.50 Eq) at 30° C. The mixture was stirred at 30° C. for 5 hr. LCMS showed the reaction was completed. The mixture was poured into water (20 mL) and stirred for 5 min. The aqueous phase was extracted with DCM (20 mL*2). The combined organic phase was washed with saturated brine (20 mL*2), dried with anhydrous $Na_2SO_4$, filtered and concentrated in vacuum. The residue was purified by pre-HPLC (FA) to afford (E)-3-phenyl-1-(3-phenyl-1,4,6,7-tetrahydropyrazolo[4,3-c]pyridin-5-yl)prop-2-en-1-one (61.85 mg, 187.77 umol, 44.26% yield) as white solid. $^1$H NMR (400 MHz, DMSO-$d_6$) 12.63-13.14 (m, 1H), 7.32-7.80 (m, 12H), 4.75-5.00 (m, 2H), 3.86-4.06 (m, 2H), 2.67-2.90 (m, 2H). LCMS: 330 [M+1].

Example 8: Preparation of Compounds 017 Through 023

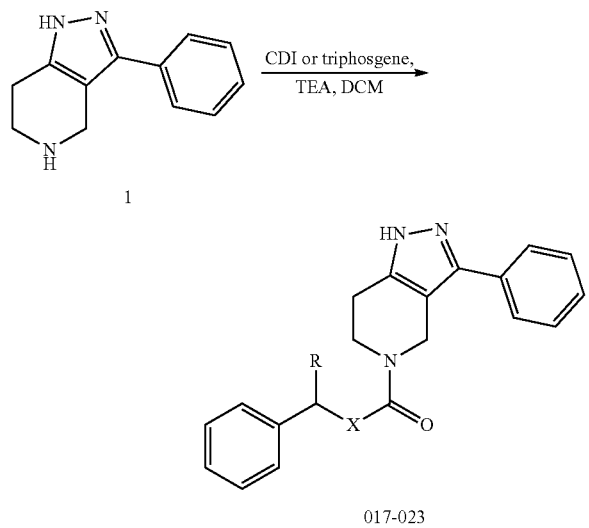

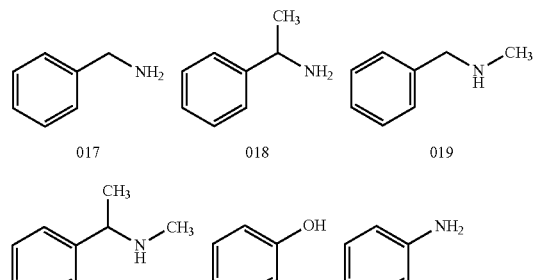

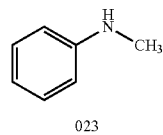

Preparation of Compound 017

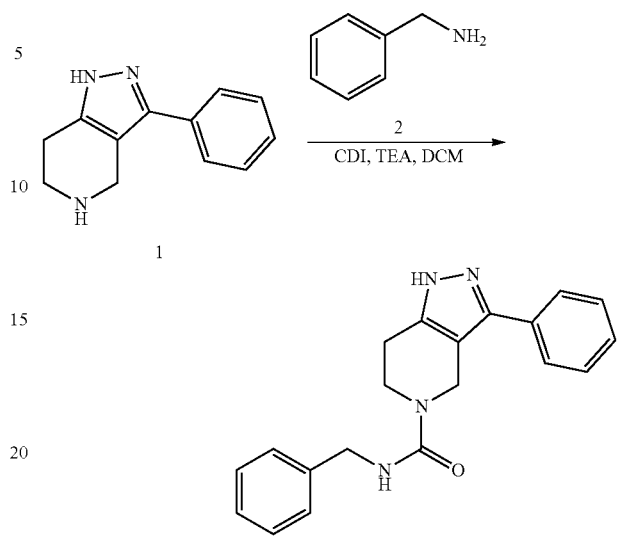

To a mixture of 3-phenyl-4,5,6,7-tetrahydro-1H-pyrazolo[4,3-c]pyridine (100.00 mg, 424.25 umol, 1.00 Eq) and phenylmethanamine (45.46 mg, 424.25 umol, 1.00 Eq) in DCM (10 mL), was added TEA (51.52 mg, 509.10 umol, 1.20 Eq) and CDI (68.79 mg, 424.25 umol, 1.00 Eq) at 30° C. The mixture was stirred at 30° C. for 5 hr. LCMS showed the reaction was completed. The mixture was poured into water (20 mL) and stirred for 5 min. The aqueous phase was extracted with DCM (20 mL*2). The combined organic phase was washed with saturated brine (20 mL*2), dried with anhydrous $Na_2SO_4$, filtered and concentrated in vacuum. The residue was purified by pre-HPLC (FA) to afford N-benzyl-3-phenyl-1,4,6,7-tetrahydropyrazolo[4,3-c]pyridine-5-carboxamide (29.09 mg, 87.52 umol, 20.63% yield) as white solid. LCMS: 333 [M+1].

Preparation of Compound 018

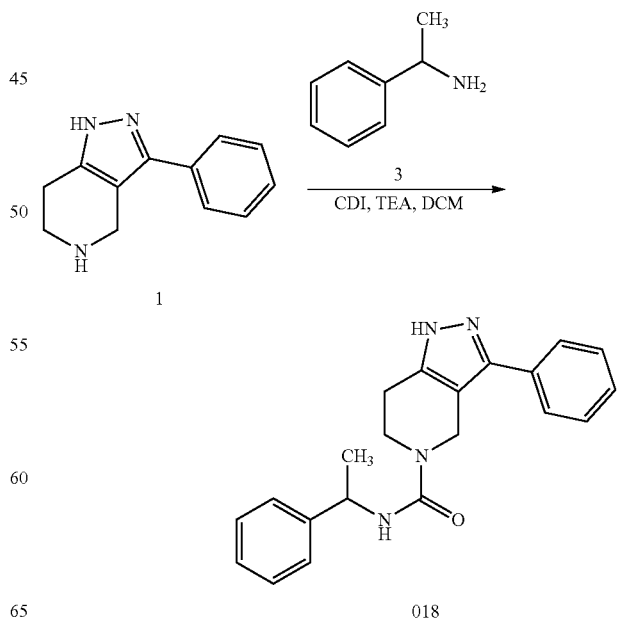

To a mixture of 3-phenyl-4,5,6,7-tetrahydro-1H-pyrazolo[4,3-c]pyridine (100.00 mg, 424.25 umol, 1.00 Eq) and 1-phenylethanamine (51.41 mg, 424.25 umol, 1.00 Eq) in DCM (10 mL), was added TEA (51.52 mg, 509.10 umol, 1.20 Eq) and CDI (68.79 mg, 424.25 umol, 1.00 Eq) at 30° C. The mixture was stirred at 30° C. for 14 hr. LCMS showed the reaction was completed. The mixture was poured into water (20 mL) and stirred for 5 min. The aqueous phase was extracted with DCM (20 mL*2). The combined organic phase was washed with saturated brine (20 mL*2), dried with anhydrous Na₂SO₄, filtered and concentrated in vacuum. The residue was purified by pre-HPLC (FA) to afford 3-phenyl-N-(1-phenylethyl)-1,4,6,7-tetrahydropyrazolo [4,3-c]pyridine-5-carboxamide (39.91 mg, 115.21 umol, 27.16% yield) as white solid. LCMS: 347 [M+1].

Preparation of Compound 019

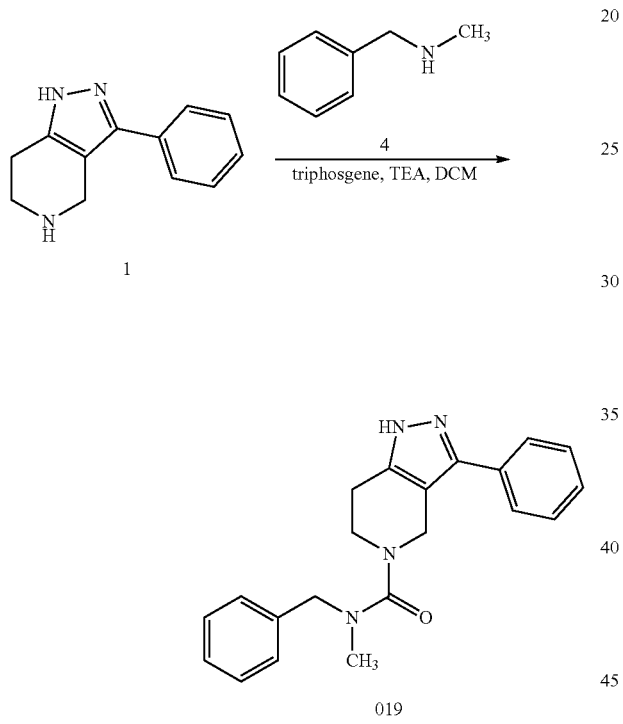

To a mixture of N-methyl-1-phenyl-methanamine (51.41 mg, 424.25 umol, 1.00 Eq) and TEA (214.65 mg, 2.12 mmol, 5.00 Eq) in DCM (15 mL), was added TRIPHOSGENE (50.36 mg, 169.70 umol, 0.40 Eq) at 0° C. under N₂. The mixture was stirred at 0° C. for 5 min, then added 3-phenyl-4,5,6,7-tetrahydro-1H-pyrazolo[4,3-c]pyridine (100.00 mg, 424.25 umol, 1.00 Eq) and stirred at 0° C. for 2 hours. LCMS showed the reaction was completed. The mixture was poured into water (20 mL) and stirred for 5 min. The aqueous phase was extracted with DCM (20 mL*2). The combined organic phase was washed with saturated brine (20 mL*2), dried with anhydrous Na₂SO₄, filtered and concentrated in vacuum. The residue was purified by pre-HPLC (FA) to afford N-benzyl-N-methyl-3-phenyl-1,4,6,7-tetrahydropyrazolo [4,3-c]pyridine-5-carboxamide (23.51 mg, 67.87 umol, 16.00% yield) as white solid. LCMS: 347 [M+1].

Preparation of Compound 020

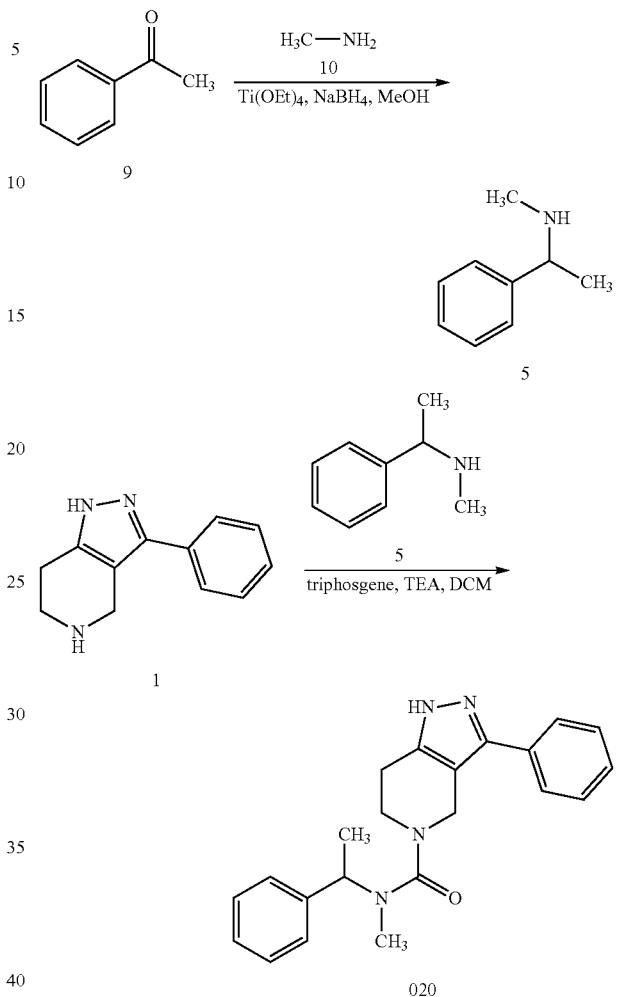

Step 1: Preparation of Compound 5:

To a mixture of 1-phenylethanone (1.00 g, 8.32 mmol, 1.00 eq) and Titanium ethoxide (3.80 g, 16.64 mmol, 2.00 eq) in MeOH (15 mL), was added methanamine (2.58 g, 83.20 mmol, 10.00 eq) at 30° C. under N₂. The mixture was stirred at 30° C. for 5 hr, then added NaBH₄ (472.12 mg, 12.48 mmol, 1.50 eq) at 0° C. under N₂ and stirred for 10 min. The mixture was heated to 30° C. and stirred for 19 hours. LCMS showed the reaction was completed. The mixture was added water (20 mL) in one portion and stirred for 10 min. The aqueous phase was extracted with EA (20 mL*2). The combined organic phase was washed with saturated brine (20 mL*2), dried with anhydrous Na₂SO₄, filtered and concentrated in vacuum to afford N-methyl-1-phenyl-ethanamine (700.00 mg, crude) as yellow oil. The crude product was used for next step directly without purification. LCMS: 136 [M+1].

Step 2: Preparation of Compound 020:

To a mixture of 3-phenyl-4,5,6,7-tetrahydro-1H-pyrazolo[4,3-c]pyridine (100.00 mg, 424.25 umol, 1.00 Eq) and phenol (39.93 mg, 424.25 umol, 1.00 Eq) in DCM (10 mL), was added TEA (51.52 mg, 509.10 umol, 1.20 Eq) and CDI (68.79 mg, 424.25 umol, 1.00 Eq) at 30° C. The mixture was stirred at 30° C. for 8 hr. LCMS showed the reaction was completed. The mixture was poured into water (20 mL) and stirred for 5 min. The aqueous phase was extracted with DCM (20 mL*2). The combined organic phase was washed with saturated brine (20 mL*2), dried with anhydrous Na₂SO₄, filtered and concentrated in vacuum. The residue was purified by pre-HPLC (FA) to afford phenyl3-phenyl-1,4,6,7-tetrahydropyrazolo[4,3-c]pyridine-5-carboxylate (42.83 mg, 134.11 umol, 31.61% yield) as white solid. ¹H NMR (400 MHz, METHANOL-d₄) ppm 7.11-7.66 (m, 10H), 5.20 (d, J=7.15 Hz, 1H), 4.42-4.58 (m, 2H), 3.61 (q, J=5.98 Hz, 2H), 2.89 (t, J=5.58 Hz, 2H), 2.65 (s, 3H), 1.57 (d, J=7.03 Hz, 3H). LCMS: 361 [M+1].

Preparation of Compound 021

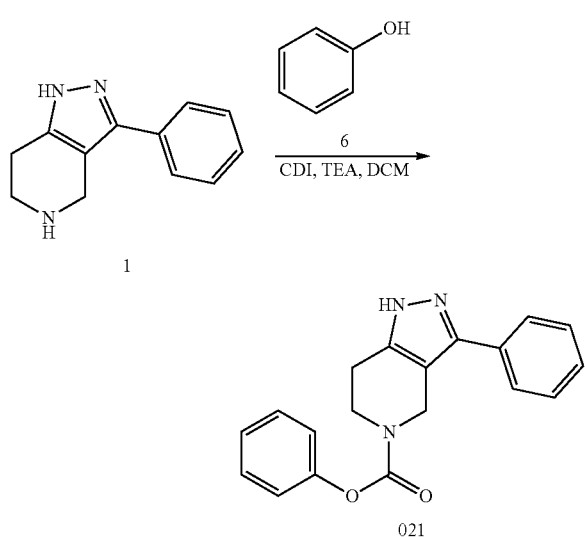

To a mixture of 3-phenyl-4,5,6,7-tetrahydro-1H-pyrazolo[4,3-c]pyridine (100.00 mg, 424.25 umol, 1.00 Eq) and phenol (39.93 mg, 424.25 umol, 1.00 Eq) in DCM (10 mL), was added TEA (51.52 mg, 509.10 umol, 1.20 Eq) and CDI (68.79 mg, 424.25 umol, 1.00 Eq) at 30° C. The mixture was stirred at 30° C. for 8 hr. LCMS showed the reaction was completed. The mixture was poured into water (20 mL) and stirred for 5 min. The aqueous phase was extracted with DCM (20 mL*2). The combined organic phase was washed with saturated brine (20 mL*2), dried with anhydrous Na₂SO₄, filtered and concentrated in vacuum. The residue was purified by pre-HPLC (FA) to afford phenyl3-phenyl-1,4,6,7-tetrahydropyrazolo[4,3-c]pyridine-5-carboxylate (42.83 mg, 134.11 umol, 31.61% yield) as white solid. LCMS: 320 [M+1].

Preparation of Compound 022

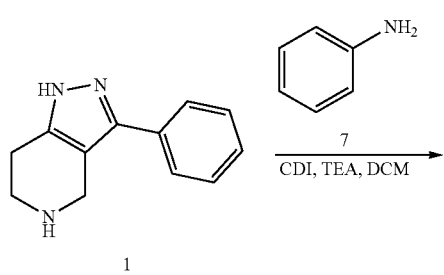

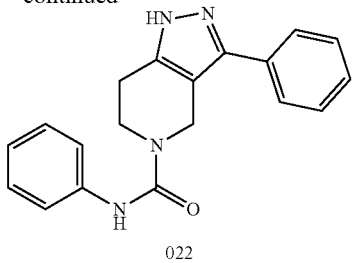

To a mixture of 3-phenyl-4,5,6,7-tetrahydro-1H-pyrazolo[4,3-c]pyridine (100.00 mg, 424.25 umol, 1.00 Eq) and aniline (39.51 mg, 424.25 umol, 1.00 Eq) in DCM (10 mL), was added TEA (51.52 mg, 509.10 umol, 1.20 Eq) and CDI (68.79 mg, 424.25 umol, 1.00 Eq) at 30° C. The mixture was stirred at 30° C. for 8 hr. LCMS showed the reaction was completed. The mixture was poured into water (20 mL) and stirred for 5 min. The aqueous phase was extracted with DCM (20 mL*2). The combined organic phase was washed with saturated brine (20 mL*2), dried with anhydrous Na₂SO₄, filtered and concentrated in vacuum. The residue was purified by pre-HPLC (FA) to afford N,3-diphenyl-1,4,6,7-tetrahydropyrazolo[4,3-c]pyridine-5-carboxamide (20.23 mg, 63.54 umol, 14.98% yield) as white solid. ¹H NMR (400 MHz, DMSO-d₆) ppm 12.58-13.11 (m, 1H), 8.68 (s, 1H), 7.65 (br. s., 2H), 7.44 (d, J=7.53 Hz, 5H), 7.23 (t, J=7.97 Hz, 2H), 6.90-6.97 (m, 1H), 4.72 (s, 2H), 3.78 (t, J=5.33 Hz, 2H), 2.76 (br. s., 2H). LCMS: 319 [M+1].

Preparation of Compound 023

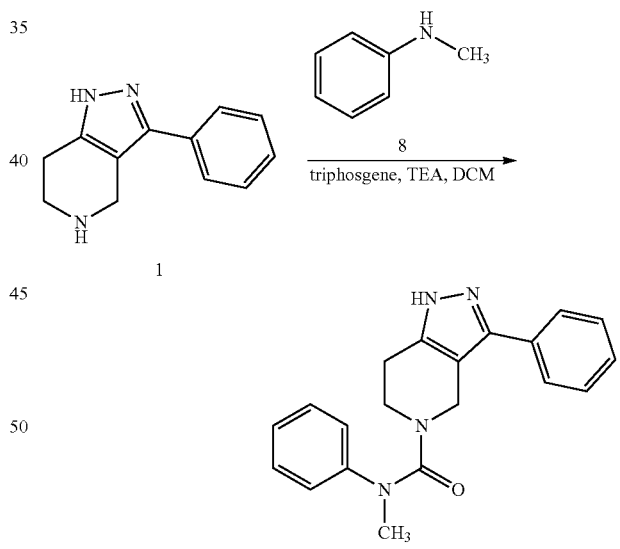

To a mixture of N-methylaniline (45.46 mg, 424.25 umol, 1.00 Eq) and TEA (214.65 mg, 2.12 mmol, 5.00 Eq) in DCM (15 mL), was added triphosgene (50.36 mg, 169.70 umol, 0.40 Eq) at 0° C. under N₂. The mixture was stirred at 0° C. for 5 min, then added 3-phenyl-4,5,6,7-tetrahydro-1H-pyrazolo[4,3-c]pyridine (100.00 mg, 424.25 umol, 1.00 Eq) and stirred at 0° C. for 2 hours. LCMS showed the reaction was completed. The mixture was poured into water (20 mL) and stirred for 5 min. The aqueous phase was extracted with DCM (20 mL*2). The combined organic phase was washed with saturated brine (20 mL*2), dried with anhydrous Na$_2$SO$_4$, filtered and concentrated in vacuum. The residue was purified by pre-HPLC (FA) to afford N-methyl-N,3-diphenyl-1,4,6,7-tetrahydropyrazolo[4,3-c]pyridine-5-carboxamide (32.10 mg, 96.57 umol, 22.76% yield) as white solid. $^1$H NMR (400 MHz, DMSO-d$_6$) ppm 12.47-13.04 (m, 1H), 7.38 (dd, J=16.00, 8.09 Hz, 7H), 7.10-7.22 (m, 3H), 4.28 (s, 2H), 3.45 (d, J=5.52 Hz, 2H), 3.11 (s, 3H), 2.38 (br. s., 2H). LCMS: 333 [M+1].

Example 9: Preparation of Compound 014

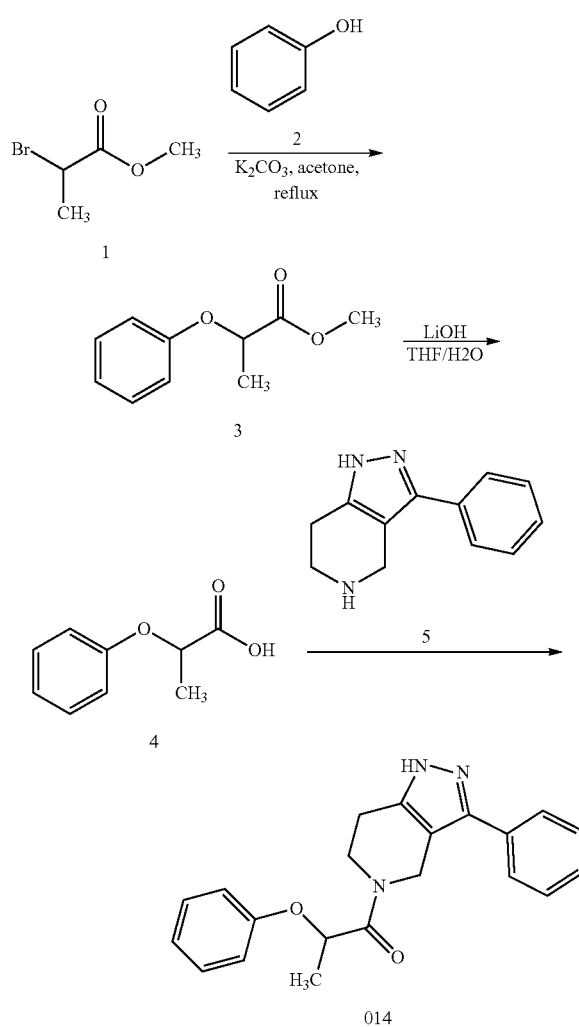

Step 1: Preparation of Compound 3

To a mixture of methyl 2-bromopropanoate (2.00 g, 11.98 mmol, 1.00 Eq) and phenol (1.13 g, 11.98 mmol, 1.00 Eq) in ACETONE (30 mL), was added K$_2$CO$_3$ (2.48 g, 17.97 mmol, 1.50 Eq) at 30° C. The mixture was stirred at 30° C. for 5 hr. LCMS showed the reaction was completed. The mixture was concentrated in reduced pressure at 45° C. The residue was poured into water (50 mL) and stirred for 5 min. The aqueous phase was extracted with ethyl acetate (50 mL*2). The combined organic phase was washed with saturated brine (50 mL*2), dried with anhydrous Na$_2$SO$_4$, filtered and concentrated in vacuum to afford methyl 2-phenoxypropanoate (3.30 g, crude). The crude product was used for next step directly without purification. LCMS: 181 [M+1].

Step 2: Preparation of Compound 4

To a mixture of methyl 2-phenoxypropanoate (3.30 g, 18.31 mmol, 1.00 Eq) and LiOH (877.05 mg, 36.62 mmol, 2.00 Eq) in THF (50 mL). The mixture was stirred at 30° C. for 15 hr. TLC showed the reaction was completed. The mixture was poured into water (100 mL) and stirred for 10 min, and acidified with diluted hydrochloride acid, then the aqueous phase was extracted with ethyl acetate (50 mL*3). The combined organic phase was washed with saturated brine (50 mL*3), dried with anhydrous Na$_2$SO$_4$, filtered and concentrated in vacuum to afford 2-phenoxypropanoic acid (1.03 g, 6.20 mmol, 33.85% yield).

Preparation of Compound 014

To a mixture of 3-phenyl-4,5,6,7-tetrahydro-1H-pyrazolo[4,3-c]pyridine (100.00 mg, 424.25 umol, 1.00 Eq) and 2-phenoxypropanoic acid (70.50 mg, 424.25 umol, 1.00 Eq) in DCM (10 mL) was added HATU (241.97 mg, 636.38 umol, 1.50 Eq) and DIPEA (137.08 mg, 1.06 mmol, 2.50 Eq) at 30° C. The mixture was stirred at 30° C. for 15 hr. LCMS showed the reaction was completed. The mixture was poured into water (20 mL) and stirred for 5 min. The aqueous phase was extracted with DCM (20 mL*2). The combined organic phase was washed with saturated brine (20 mL*2), dried with anhydrous Na$_2$SO$_4$, filtered and concentrated in vacuum. The residue was purified by pre-HPLC (FA) to afford 2-phenoxy-1-(3-phenyl-1,4,6,7-tetrahydropyrazolo[4,3-c]pyridin-5-yl)propan-1-one (96.00 mg, 276.33 umol, 65.13% yield) as white solid. LCMS: 348 [M+1].

Example 10: Preparation of Compound 015

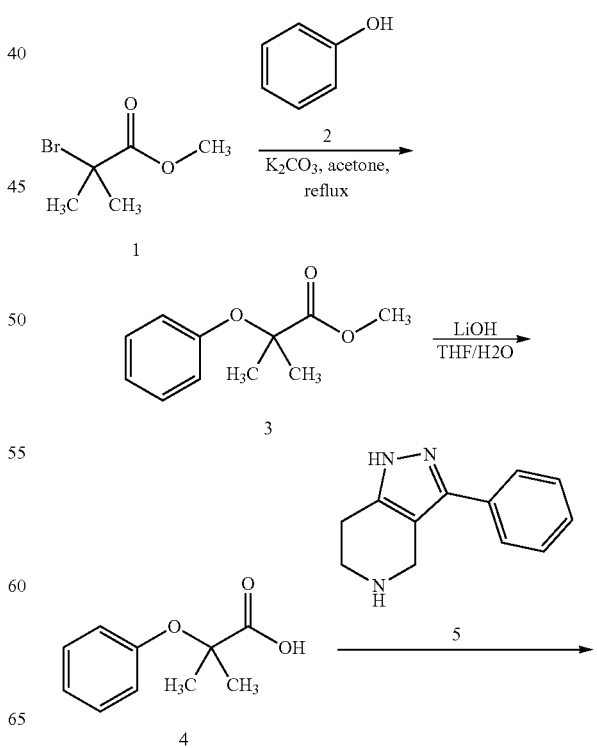

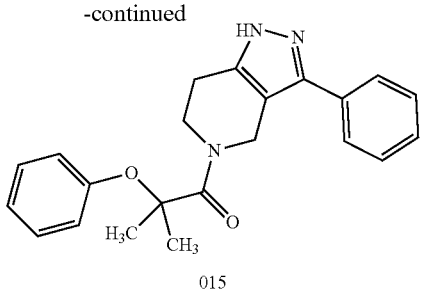

015

Step 1: Preparation of Compound 3

To a mixture of methyl 2-bromo-2-methyl-propanoate (2.00 g, 11.05 mmol, 1.00 Eq) and phenol (1.04 g, 11.05 mmol, 1.00 Eq) in ACETONE (30 mL), was added K2CO3 (2.29 g, 16.58 mmol, 1.50 Eq) at 30° C. Then heated to 60° C. and stirred for 5 hours. LCMS showed the reaction was completed. The mixture was cooled to 30° C. and concentrated in reduced pressure at 45° C. The residue was poured into water (50 mL) and stirred for 5 min. The aqueous phase was extracted with ethyl acetate (50 mL*2). The combined organic phase was washed with saturated brine (50 mL*2), dried with anhydrous Na$_2$SO$_4$, filtered and concentrated in vacuum to afford methyl 2-methyl-2-phenoxy-propanoate (1.50 g, crude) as yellow oil. The crude product was used for next step directly without purification. LCMS: 195 [M+1].

Step 2: Preparation of Compound 4

To a mixture of methyl 2-methyl-2-phenoxy-propanoate (1.50 g, 7.72 mmol, 1.00 Eq) and LiOH (369.79 mg, 15.44 mmol, 2.00 Eq) in THF (50 mL) and H2O (10 mL). The mixture was stirred at 30° C. for 15 hr. TLC showed the reaction was completed. The mixture was poured into water (100 mL) and stirred for 10 min. Acidify the aqueous phase with diluted hydrochloride acid, then the aqueous phase was extracted with ethyl acetate (50 mL*3). The combined organic phase was washed with saturated brine (50 mL*3), dried with anhydrous Na$_2$SO$_4$, filtered and concentrated in vacuum to afford 2-methyl-2-phenoxy-propanoic acid (850.00 mg, 4.72 mmol, 61.10% yield).

Preparation of Compound 015

To a mixture of 3-phenyl-4,5,6,7-tetrahydro-1H-pyrazolo[4,3-c]pyridine (100.00 mg, 424.25 umol, 1.00 eq) and 2-methyl-2-phenoxy-propanoic acid (76.45 mg, 424.25 umol, 1.00 eq) in DCM (10 mL), was added HATU (241.97 mg, 636.38 umol, 1.50 eq) and DIPEA (137.08 mg, 1.06 mmol, 2.50 eq) at 30° C. The mixture was stirred at 30° C. for 18 hr. LCMS showed the reaction was completed. The mixture was poured into water (20 mL) and stirred for 5 min. The aqueous phase was extracted with DCM (20 mL*2). The combined organic phase was washed with saturated brine (20 mL*2), dried with anhydrous Na$_2$SO$_4$, filtered and concentrated in vacuum. The residue was purified by pre-HPLC (FA) to afford 2-methyl-2-phenoxy-1-(3-phenyl-1,4,6,7-tetrahydropyrazolo[4,3-c]pyridin-5-yl)propan-1-one (21.30 mg, 58.93 umol, 13.89% yield) as white solid. $^1$H NMR (400 MHz, DMSO-d$_6$) ppm 7.59 (d, J=7.40 Hz, 1H), 7.43-7.52 (m, 3H), 7.34 (t, J=7.03 Hz, 1H), 7.25 (t, J=7.53 Hz, 1H), 7.11-7.18 (m, 1H), 6.77-6.99 (m, 2H), 6.68 (d, J=7.65 Hz, 1H), 5.02 (br. s., 1H), 4.74 (br. s., 1H), 4.08 (br. s., 2H), 3.81 (br. s., 2H), 1.42-1.64 (m, 6H). LCMS: 362 [M+1].

Example 11: Preparation of Compound 067

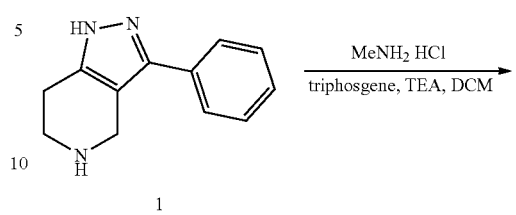

1

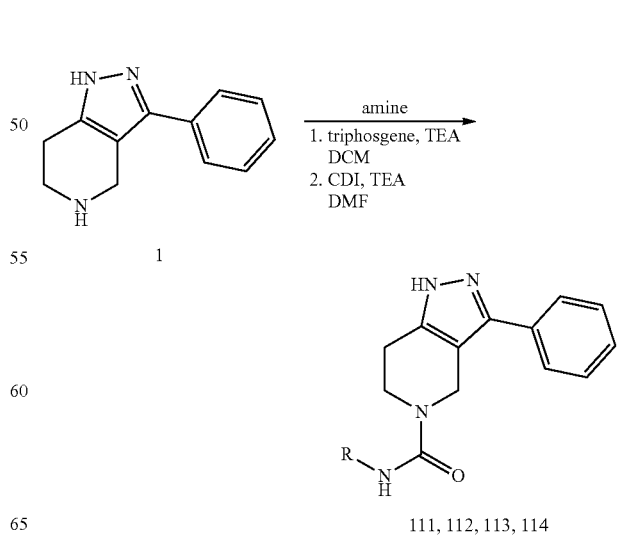

067

To a mixture of 3-phenyl-4,5,6,7-tetrahydro-1H-pyrazolo[4,3-c]pyridine (100.00 mg, 424.25 umol, 1.00 eq) and methanamine hydrochloride (28.64 mg, 424.25 umol, 1.00 eq) in DCM (15.00 mL), was added TEA (429.30 mg, 4.24 mmol, 10.00 eq) at 0° C. under N$_2$. The mixture was stirred at 0° C. for 5 min, then added TRIPHOSGENE (50.36 mg, 169.70 umol, 0.40 eq) and heated to 30° C. for 15 hours. LCMS showed the reaction was completed. The mixture was poured into water (20 mL) and stirred for 5 min. The aqueous phase was extracted with DCM (20 mL*2). The combined organic phase was washed with saturated brine (20 mL*2), dried with anhydrous Na$_2$SO$_4$, filtered and concentrated in vacuum. The residue was purified by pre-HPLC (FA) to afford N-methyl-3-phenyl-1,4,6,7-tetrahydropyrazolo[4,3-c] pyridine-5-carboxamide (11.68 mg, 45.57 umol, 10.74% yield) as white solid. LCMS: 257 [M+1].

Example 12: Preparation of Compounds 111, 112, 113, and 114

1

111, 112, 113, 114

Condition 1:

To a mixture of triphosgene (0.6 eq) and amine (1.05 eq) in DCM (5 mL) was added Et₃N (1.0 eq) in one portion at 0° C. The mixture was stirred at 0-10° C. for 20 min, and then added intermediate 1 (1.0 eq) and Et₃N (2.2 eq) at 0° C. The mixture was stirred at 0-10° C. for 5 min. The desired product was detected by LCMS. The reaction mixture was concentrated under reduced pressure. The residue was purified by pre-HPLC to give the desired products.

Condition 2:

To a mixture of amine (1.05 eq) in DMF (5.00 mL) was added CDI (1.05 eq) in one portion at 25° C. The mixture was stirred for 20 min, and then added intermediate 1 (1.0 eq) and Et₃N (2.2 eq). The mixture was stirred for 16-48 hours (25° C.-40° C.). The desired product was detected by LCMS. The reaction mixture was concentrated under reduced pressure. The residue was purified by pre-HPLC to give the desired products.

| Compound ID/ Conditions | Analytical Data |
|---|---|
| 113/Condition 2 | LCMS: 353[M + 1] |
| 112/Condition 2 | LCMS: 353[M + 1] |
| 114/Condition 2 | LCMS: 371[M + 1] |
| 111/Condition 2 | LCMS: 353[M + 1]<br>¹H NMR(CDCl₃, 400 MHz): δ 8.17 (d, 1H, J = 9.6 Hz), 7.56 (d, 2H, J = 7.2 Hz), 7.48 (t, 2H, J = 8.0 Hz) 7.42-7.34 (m, 2H), 7.12 (s, 1H), 6.98 (t, 1H, J = 8.0 Hz), 4.82 (s, 2H), 3.90 (t, 2H, J = 5.6 Hz), 2.98 (t, 2H, J = 5.6 Hz). |

Example 13: Preparation of Compounds 242-244

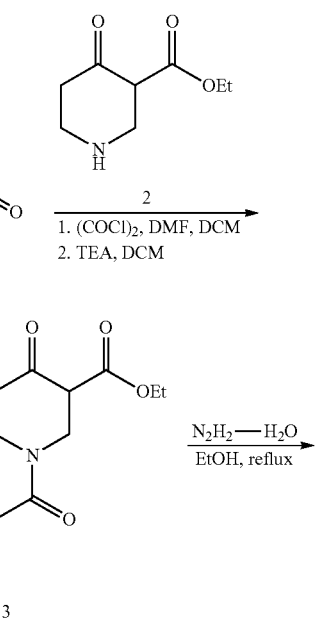

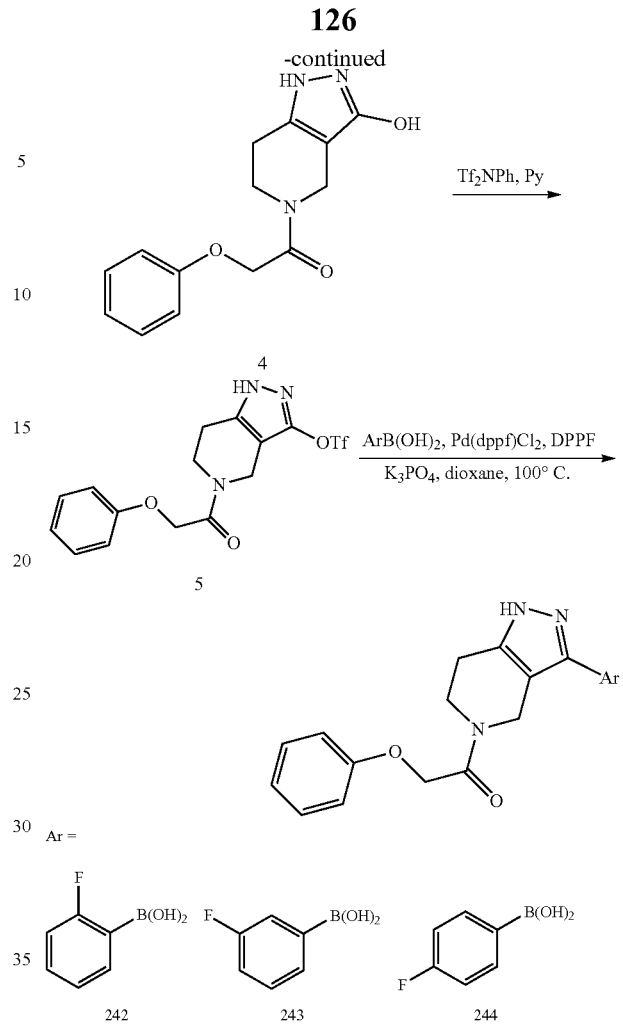

Step 1: Preparation of Compound 3

To a mixture of 2-phenoxyacetic acid (7.33 g, 48.16 mmol, 1.00 eq) in DCM (100.00 mL) was added oxalyl chloride (9.17 g, 72.24 mmol, 1.50 eq) dropwise at 0° C. under N₂, followed by catalytic amount DMF. The mixture was stirred at 0° C. for 2 hours. TLC showed the reaction was completed. The mixture was concentrated in vacuum. The residue was diluted in DCM (50.00 mL), added to ethyl 4-oxopiperidine-3-carboxylate (10.00 g, 48.16 mmol, 1.00 eq) and TEA (14.62 g, 144.48 mmol, 3.00 eq) in DCM (80.00 mL) at 0° C. under N₂. The mixture was stirred at 20° C. for 10 hours. TLC showed the reaction was completed. The mixture was poured into water (100 mL) and stirred for 5 min. The aqueous phase was extracted with DCM (50 mL*2). The combined organic phase was washed with saturated brine (50 mL*2), dried over anhydrous Na₂SO₄, filtered and concentrated in vacuum. The residue was purified by silica gel chromatography (Petroleum ether/Ethyl acetate=5/1) to afford ethyl 4-oxo-1-(2-phenoxyacetyl)piperidine-3-carboxylate (14.20 g, 46.51 mmol, 96.57% yield) as yellow solid. LCMS: 306 [M+1].

Step 2: Preparation of Compound 4

To a mixture of ethyl 4-oxo-1-(2-phenoxyacetyl)piperidine-3-carboxylate (12.00 g, 39.30 mmol, 1.00 eq) in EtOH (200.00 mL) was added N2H4-H2O (2.36 g, 47.16 mmol, 1.20 eq) in one portion under N₂. The mixture was stirred at 80° C. for 3 hours. TLC showed the reaction was completed. The mixture was cooled and concentrated in vacuum to afford 1-(3-hydroxy-1,4,6,7-tetrahydropyrazolo[4,3-c]pyridin-5-yl)-2-phenoxy-ethanone (10.00 g, 36.59 mmol, 93.11% yield) as white solid. LCMS: 274 [M+I].

Step 3: Preparation of Compound 5

To a mixture of 1-(3-hydroxy-1,4,6,7-tetrahydropyrazolo[4,3-c]pyridin-5-yl)-2-phenoxy-ethanone (3.00 g, 10.98 mmol, 1.00 eq) in Py (30.00 mL) was added 1,1,1-trifluoro-N-phenyl-N-(trifluoromethylsulfonyl)methanesulfonamide (5.10 g, 14.27 mmol, 1.30 eq) in one portion at 20° C. under N₂. The mixture was stirred at 20° C. for 16 hours. TLC showed the reaction was completed. The mixture was concentrated in vacuum. The residue was poured into water (15 mL) and stirred for 2 min. The aqueous phase was extracted with ethyl acetate (15 mL*2). The combined organic phase was washed with saturated brine (10 mL*2), dried over anhydrous Na₂SO₄, filtered and concentrated in vacuum. The residue was purified by silica gel chromatography (Petroleum ether/Ethyl acetate=1/1) to afford [5-(2-phenoxyacetyl)-1,4,6,7-tetrahydropyrazolo [4,3-c]pyridin-3-yl]trifluoromethanesulfonate (4.10 g, 10.11 mmol, 92.12% yield) as yellow solid. LCMS: 406 [M+1].

Preparation of Compound 242

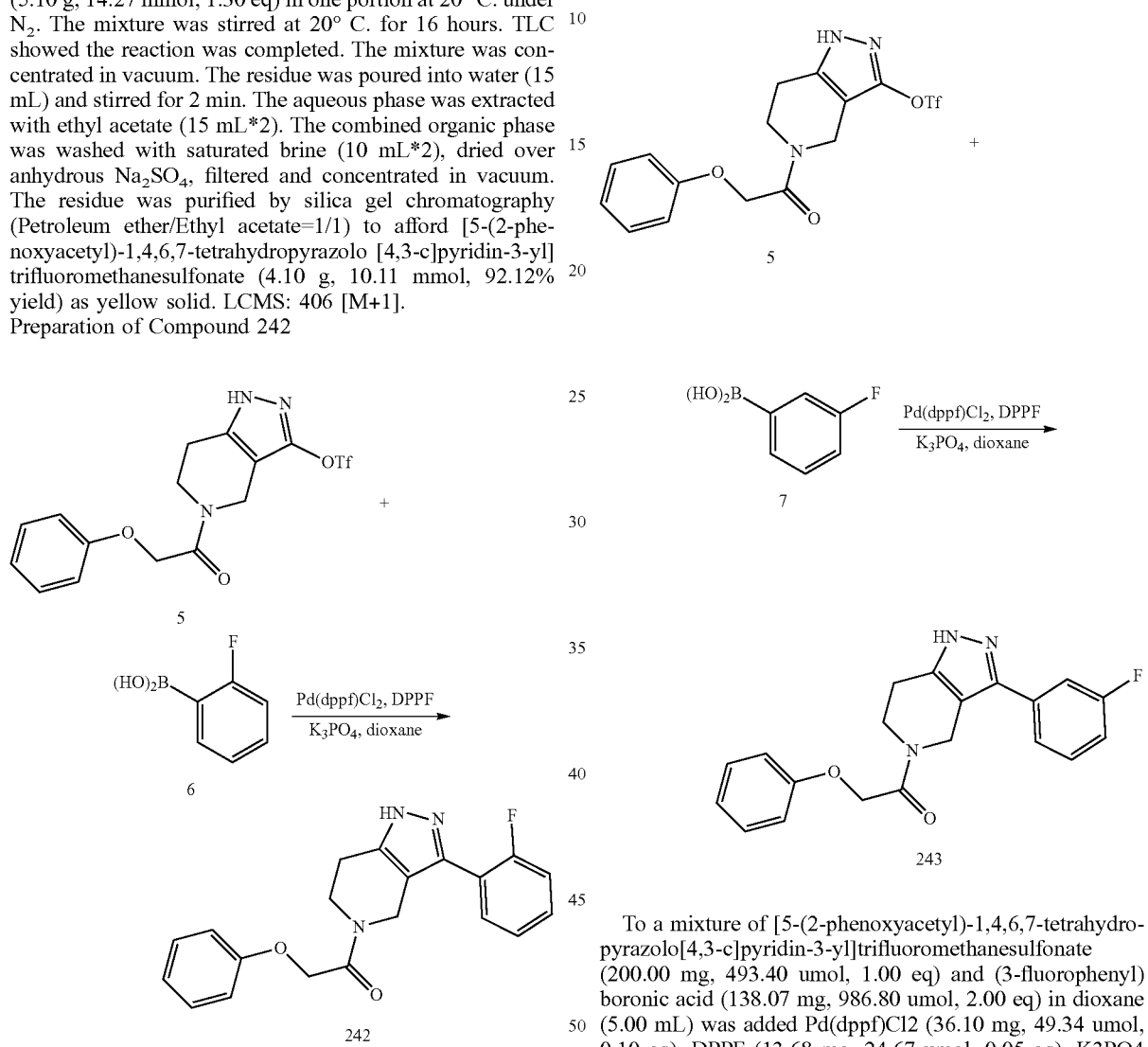

To a mixture of [5-(2-phenoxyacetyl)-1,4,6,7-tetrahydropyrazolo[4,3-c]pyridin-3-yl]trifluoromethanesulfonate (200.00 mg, 493.40 umol, 1.00 eq) and (2-fluorophenyl) boronic acid (138.07 mg, 986.80 umol, 2.00 eq) in dioxane (5.00 mL) was added Pd(dppf)Cl2 (36.10 mg, 49.34 umol, 0.10 eq), DPPF (13.68 mg, 24.67 umol, 0.05 eq), K3PO4 (314.20 mg, 1.48 mmol, 3.00 eq) in one portion under N₂. The mixture was stirred at 110° C. for 10 hours. LCMS showed the reaction was completed. The mixture was poured into water (10 mL) and stirred for 2 min. The aqueous phase was extracted with ethyl acetate (10 mL*2). The combined organic phase was washed with saturated brine (10 mL*2), dried over anhydrous Na₂SO₄, filtered and concentrated in vacuum. The residue was purified by pre-HPLC(FA) to afford 1-[3-(2-fluorophenyl)-1,4,6,7-tetrahydropyrazolo[4,3-c]pyridin-5-yl]-2-phenoxy-ethanone (35.46 mg, 100.11 umol, 20.29% yield, 99.2% purity) as white solid. ¹H NMR (400 MHz, METHANOL-d₄) δ 7.51-7.61 (m, 1H), 7.39-7.49 (m, 1H), 7.18-7.33 (m, 4H), 6.83-7.02 (m, 3H), 4.90 (s, 1H), 4.80-4.82 (m, 1H), 4.64-4.70 (m, 2H), 3.87-4.00 (m, 2H), 2.78-2.97 (m, 2H). LCMS: 352 [M+1].

Preparation of Compound 243

To a mixture of [5-(2-phenoxyacetyl)-1,4,6,7-tetrahydropyrazolo[4,3-c]pyridin-3-yl]trifluoromethanesulfonate (200.00 mg, 493.40 umol, 1.00 eq) and (3-fluorophenyl) boronic acid (138.07 mg, 986.80 umol, 2.00 eq) in dioxane (5.00 mL) was added Pd(dppf)Cl2 (36.10 mg, 49.34 umol, 0.10 eq), DPPF (13.68 mg, 24.67 umol, 0.05 eq), K3PO4 (314.20 mg, 1.48 mmol, 3.00 eq) in one portion under N₂. The mixture was stirred at 110° C. for 10 hours. LCMS showed the reaction was completed. The mixture was poured into water (10 mL) and stirred for 2 min. The aqueous phase was extracted with ethyl acetate (10 mL*2). The combined organic phase was washed with saturated brine (10 mL*2), dried over anhydrous Na₂SO₄, filtered and concentrated in vacuum. The residue was purified by pre-HPLC(FA) to afford 1-[3-(3-fluorophenyl)-1,4,6,7-tetrahydropyrazolo[4,3-c]pyridin-5-yl]-2-phenoxy-ethanone (45.32 mg, 126.61 umol, 25.66% yield, 98.16% purity) as white solid. ¹H NMR (400 MHz, METHANOL-d₄) δ 7.33-7.53 (m, 3H), 7.19-7.32 (m, 2H), 7.05-7.15 (m, 1H), 6.99 (d, J=7.91 Hz, 3H), 4.92 (br. s., 2H), 4.80-4.85 (m, 2H), 3.86-3.99 (m, 2H), 2.88-2.96 (m, 1H), 2.77-2.84 (m, 1H). LCMS: 352 [M+1].

Preparation of Compound 244

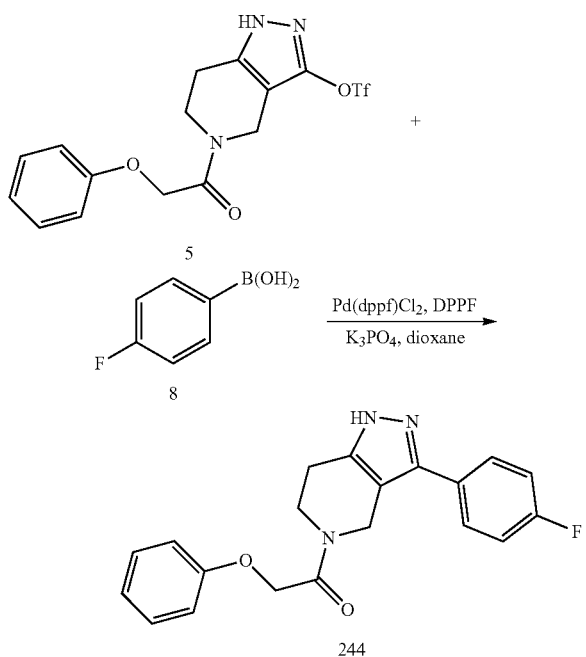

To a mixture of [5-(2-phenoxyacetyl)-1,4,6,7-tetrahydropyrazolo[4,3-c]pyridin-3-yl]trifluoromethanesulfonate (100.00 mg, 246.70 umol, 1.00 eq) and (4-fluorophenyl)boronic acid (69.04 mg, 493.40 umol, 2.00 eq) in dioxane (5.00 mL) was added Pd(dppf)Cl2 (18.05 mg, 24.67 umol, 0.10 eq), DPPF (13.68 mg, 24.67 umol, 0.10 eq) and K3PO4 (157.10 mg, 740.10 umol, 3.00 eq) in one portion under $N_2$. The mixture was stirred at 110° C. for 12 hours. LCMS showed the reaction was completed. The mixture was poured into water (10 mL) and stirred for 1 min. The aqueous phase was extracted with ethyl acetate (10 mL*2). The combined organic phase was washed with saturated brine (10 mL*2), dried over anhydrous $Na_2SO_4$, filtered and concentrated in vacuum. The residue was purified by pre-HPLC(FA) to afford 1-[3-(4-fluorophenyl)-1,4,6,7-tetrahydropyrazolo[4,3-c]pyridin-5-yl]-2-phenoxy-ethanone (8.00 mg, 20.80 umol, 8.43% yield, 91.35% purity) as yellow solid. $^1$H NMR (400 MHz, METHANOL-$d_4$) δ 7.62 (br. s., 2H), 7.14-7.34 (m, 4H), 6.87-7.03 (m, 3H), 5.00-5.12 (m, 2H), 4.80 (br. s., 2H), 3.90 (br. s., 2H), 2.75-2.95 (m, 2H). LCMS: 352 [M+1].

Example 14: Preparation of Compounds 142, 143, 144, 145, 147, 148, 150, 163, 164, and 165

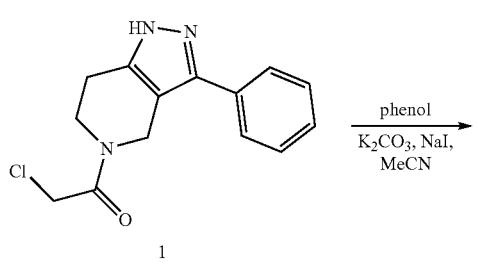

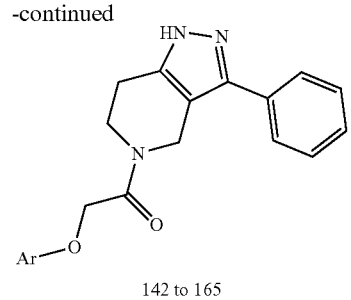

General Procedure

To a mixture of phenol (0.35 mmol, 1.2 eq) in MeCN (5 mL) was added $K_2CO_3$ (60 mg, 0.435 mmol, 1.5 eq) and NaI (2.17 mg, 14.51 umol, 0.05 eq) at 25° C., followed by compound 1 (80 mg, 0.29 mmol, 1 eq). The mixture was heated to 80° C. and stirred for 18 hours. TLC showed the reaction was completed. The mixture was cooled to 25° C. The mixture added into 10 mL water. The aqueous phase was extracted with DCM (10 mL*2). The combined organic phase was dried over anhydrous $Na_2SO_4$, filtered and concentrated in vacuum. The residue was purified by pre-TLC to give the desired product.

| Comp. ID | Analytical Data |
|---|---|
| 142 | LCMS(M + 1): 352 |
| 143 | LCMS(M + 1): 352 |
| 144 | LCMS(M + 1): 352 |
| 145 | LCMS(M + 1): 348 |
| 147 | LCMS(M + 1): 348 |
| 148 | LCMS(M + 1): 368 |
| 150 | LCMS(M + 1): 368 |
|  | 1H NMR (400 MHz, DMSO-d6) d 12.66-13.16 (m, 1H), 7.21-7.76 (m, 7H), 6.87-7.09 (m, 2H), 4.94-5.05 (m, 2H), 4.71 (br. s., 2H), 3.77 (d, J = 15.18 Hz, 2H), 2.85 (br. s., 1H), 2.68 (d, J = 1.63 Hz, 1H) |
| 163 | LCMS(M + 1): 402 |
| 164 | LCMS(M + 1): 402 |
| 165 | LCMS(M + 1): 402 |

Example 15: Preparation of Compound 169

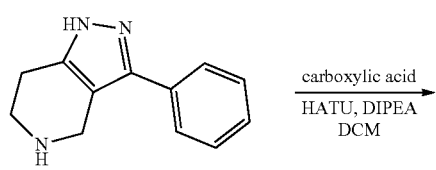

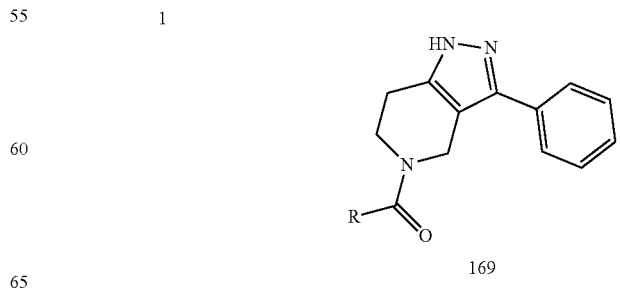

General Procedure

To a mixture of Compound 1 (80 mg, 0.40 mml, 1 eq) and carboxylic acid (0.48 mmol, 1.2 eq) in DCM (5.00 mL) was added DIPEA (62.27 mg, 0.48 mmol, 1.2 eq) and HATU (305.3 mg, 0.80 mmol, 2 eq) at 25° C. The mixture was stirred at 25° C. for 5 h. TLC showed the reaction was completed. The mixture was added into 10 mL water. The aqueous phase was extracted with DCM (10 mL*2). The combined organic phase was dried with anhydrous $Na_2SO_4$, filtered and concentrated in vacuum. The residue was purified by pre-TLC to give the desired product.

| Compound ID | Analytical Data |
|---|---|
| 169 | LCMS (M + 1): 382 |

Example 16: Preparation of Compound 276

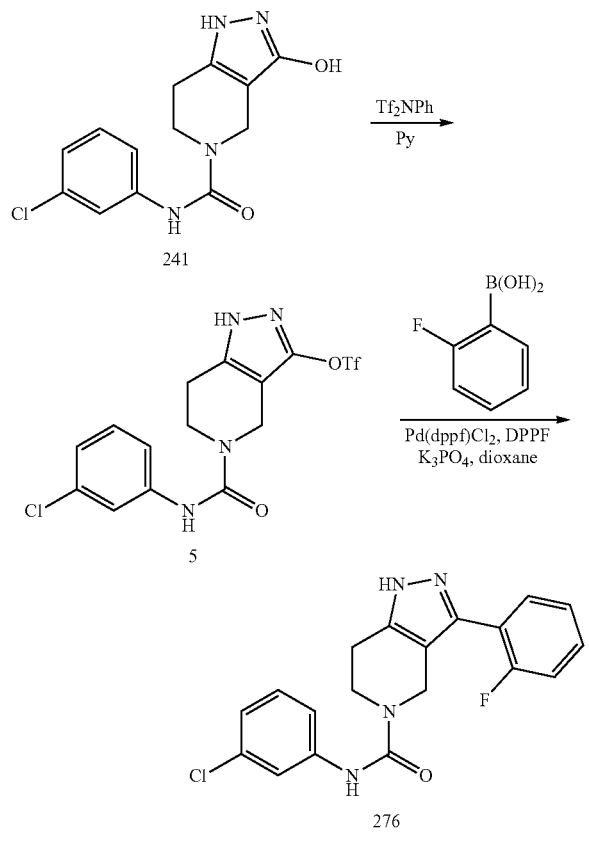

Step 1: Preparation of Compound 5

To a mixture of N-(3-chlorophenyl)-3-hydroxy-1,4,6,7-tetrahydropyrazolo[4,3-c]pyridine-5-carboxamide (3.60 g, 12.30 mmol, 1.00 eq) in Py (30.00 mL) was added 1,1,1-trifluoro-N-phenyl-N-(trifluoromethylsulfonyl)methanesulfonamide (6.15 g, 17.22 mmol, 1.40 eq) in one portion under $N_2$. The mixture was stirred at 10° C. for 16 hours. TLC showed the reaction was completed. The mixture was concentrated in vacuum. The residue was diluted with ethyl acetate (50 mL) and poured into 1N HCl (50 mL) and stirred for 3 min. The aqueous phase was extracted with ethyl acetate (50 mL*2). The combined organic phase was washed with saturated brine (30 mL*2), dried with anhydrous $Na_2SO_4$, filtered and concentrated in vacuum. The residue was purified by silica gel chromatography (Petroleum ether/Ethyl acetate=4/1, 1/1) to afford [5-[(3-chlorophenyl)carbamoyl]-1,4,6,7-tetrahydropyrazolo[4,3-c]pyridin-3-yl] trifluoromethanesulfonate (3.20 g, 7.19 mmol, 58.49% yield, 95.5% purity) as white solid. LCMS: 425 [M+1].

Step 2: Preparation of Compound 276

To a mixture of [5-[(3-chlorophenyl)carbamoyl]-1,4,6,7-tetrahydropyrazolo[4,3-c]pyridin-3-yl] trifluoromethanesulfonate (100.00 mg, 235.42 umol, 1.00 eq) and (2-fluorophenyl)boronic acid (65.88 mg, 470.84 umol, 2.00 eq) in dioxane (5.00 mL) was added Pd(dppf)Cl$_2$ (17.23 mg, 23.54 umol, 0.10 eq), DPPF (13.05 mg, 23.54 umol, 0.10 eq) and $K_3PO_4$ (149.92 mg, 706.26 umol, 3.00 eq) in one portion under $N_2$. The reaction vessel was sealed and heated in microwave at 120° C. for 2 hr. LCMS showed the reaction was completed. The mixture was poured into water (10 mL) and stirred for 3 min. The aqueous phase was extracted with ethyl acetate (10 mL*2). The combined organic phase was washed with saturated brine (10 mL*2), dried with anhydrous $Na_2SO_4$, filtered and concentrated in vacuum. The residue was purified by prep-HPLC(FA) to afford N-(3-chlorophenyl)-3-(2-fluorophenyl)-1,4,6,7-tetrahydropyrazolo[4,3-c]pyridine-5-carboxamide (13.56 mg, 35.69 umol, 15.16% yield, 97.59% purity) as white solid. $^1$H NMR (400 MHz, METHANOL-d$_4$) δ 7.54-7.62 (m, 1H), 7.50 (s, 1H), 7.40-7.48 (m, 1H), 7.18-7.34 (m, 4H), 6.96-7.03 (m, 1H), 4.58-4.66 (m, 2H), 3.83-3.92 (m, 2H), 2.86-2.95 (m, 2H). LCMS: 371 [M+1].

Example 17: Preparation of Compound 277

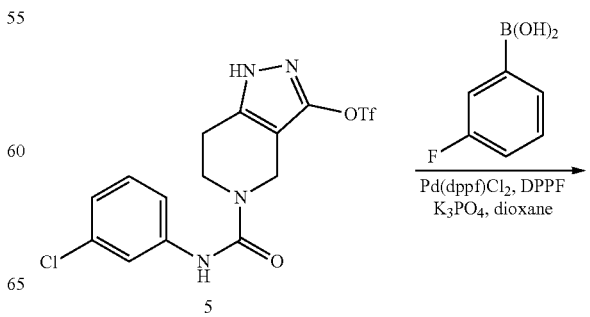

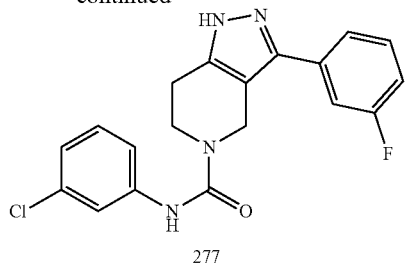

277

To a mixture of [5-[(3-chlorophenyl)carbamoyl]-1,4,6,7-tetrahydropyrazolo[4,3-c]pyridin-3-yl] trifluoromethanesulfonate (100.00 mg, 235.42 umol, 1.00 eq) and (3-fluorophenyl)boronic acid (65.88 mg, 470.84 umol, 2.00 eq) in dioxane (5.00 mL) was added Pd(dppf)Cl$_2$ (17.23 mg, 23.54 umol, 0.10 eq), DPPF (13.05 mg, 23.54 umol, 0.10 eq) and K$_3$PO$_4$ (149.92 mg, 706.26 umol, 3.00 eq) in one portion under N$_2$. The mixture was stirred at 110° C. for 12 hours. LCMS showed the reaction was completed. The mixture was poured into water (10 mL) and stirred for 2 min. The aqueous phase was extracted with ethyl acetate (10 mL*2). The combined organic phase was washed with saturated brine (10 mL*2), dried with anhydrous Na$_2$SO$_4$, filtered and concentrated in vacuum. The residue was purified by prep-HPLC(FA) to afford N-(3-chlorophenyl)-3-(3-fluorophenyl)-1,4,6,7-tetrahydropyrazolo[4,3-c]pyridine-5-carboxamide (15.36 mg, 40.97 umol, 17.40% yield, 98.9% purity) as white solid. $^1$H NMR (400 MHz, METHANOL-d$_4$) δ 7.38-7.56 (m, 1H), 7.26-7.33 (m, 1H), 7.19-7.26 (m, 1H), 7.06-7.15 (m, 1H), 6.97-7.03 (m, 1H), 4.76-4.81 (m, 2H), 3.84-3.92 (m, 2H), 2.84-2.92 (m, 2H). LCMS: 371 [M+1].

Example 18: Preparation of Compound 278

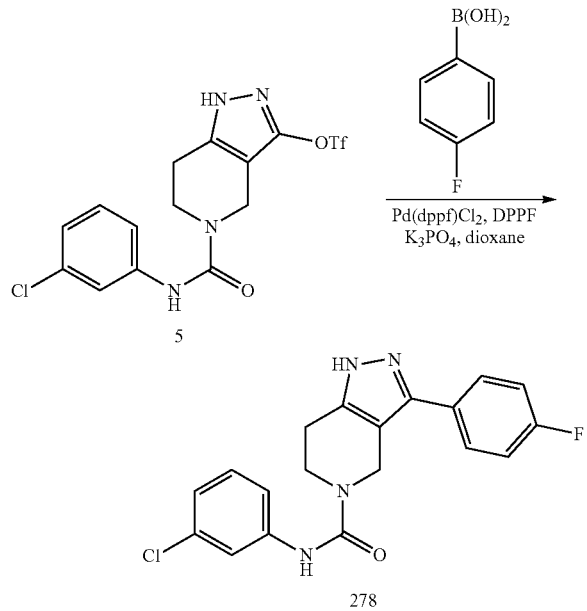

278

To a mixture of [5-[(3-chlorophenyl)carbamoyl]-1,4,6,7-tetrahydropyrazolo[4,3-c]pyridin-3-yl] trifluoromethanesulfonate (100.00 mg, 235.42 umol, 1.00 eq) and (4-fluorophenyl)boronic acid (65.88 mg, 470.84 umol, 2.00 eq) in dioxane (5.00 mL) was added Pd(dppf)Cl$_2$ (17.23 mg, 23.54 umol, 0.10 eq), DPPF (13.05 mg, 23.54 umol, 0.10 eq) and K$_3$PO$_4$ (149.92 mg, 706.26 umol, 3.00 eq) in one portion under N$_2$. The mixture was stirred at 110° C. for 12 hours. LCMS showed the reaction was completed. The mixture was poured into water (10 mL) and stirred for 2 min. The aqueous phase was extracted with ethyl acetate (10 mL*2). The combined organic phase was washed with saturated brine (10 mL*2), dried with anhydrous Na$_2$SO$_4$, filtered and concentrated in vacuum. The residue was purified by prep-HPLC(FA) to afford N-(3-chlorophenyl)-3-(4-fluorophenyl)-1,4,6,7-tetrahydropyrazolo[4,3-c]pyridine-5-carboxamide (35.42 mg, 92.53 umol, 39.30% yield, 96.87% purity) as white solid. $^1$H NMR (400 MHz, METHANOL-d$_4$) D 7.62-7.73 (m, 1H), 7.50-7.56 (m, 1H), 7.26-7.32 (m, 1H), 7.16-7.26 (m, 3H), 6.97-7.03 (m, 1H), 4.73-4.78 (m, 2H), 3.83-3.91 (m, 2H), 2.83-2.91 (m, 2H). LCMS: 371 [M+1].

Example 19: Preparation of Compound 279

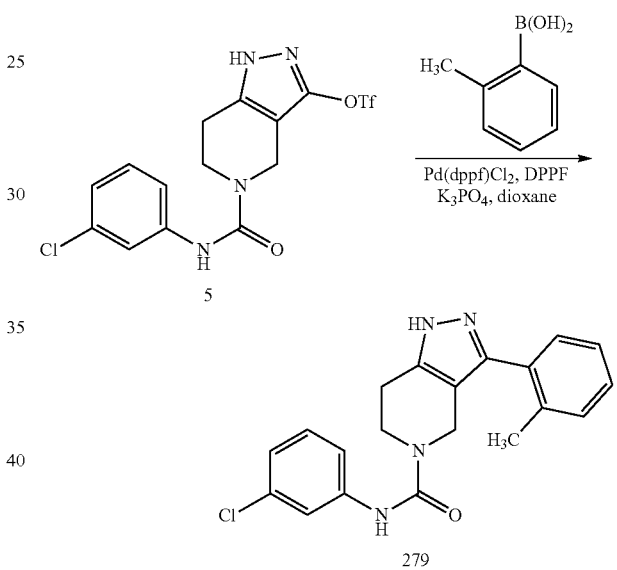

279

To a mixture of [5-[(3-chlorophenyl)carbamoyl]-1,4,6,7-tetrahydropyrazolo[4,3-c]pyridin-3-yl] trifluoromethanesulfonate (120.00 mg, 282.50 umol, 1.00 eq) and o-tolylboronic acid (76.82 mg, 565.00 umol, 2.00 eq) in dioxane (5.00 mL) was added Pd(dppf)Cl$_2$ (20.67 mg, 28.25 umol, 0.10 eq), DPPF (15.66 mg, 28.25 umol, 0.10 eq) and K$_3$PO$_4$ (179.90 mg, 847.50 umol, 3.00 eq) in one portion under N$_2$. The mixture was sealed and heated in microwave at 130° C. for 2 hr. LCMS showed the reaction was completed. The mixture was poured into water (10 mL) and stirred for 3 min. The aqueous phase was extracted with ethyl acetate (10 mL*2). The combined organic phase was washed with saturated brine (10 mL*2), dried with anhydrous Na$_2$SO$_4$, filtered and concentrated in vacuum. The residue was purified by prep-HPLC(FA) to afford N-(3-chlorophenyl)-3-(o-tolyl)-1,4,6,7-tetrahydropyrazolo[4,3-c]pyridine-5-carboxamide (25.25 mg, 68.18 umol, 24.14% yield, 99.06% purity) as white solid. $^1$H NMR (400 MHz, METHANOL-d$_4$) δ 7.47-7.52 (m, 1H), 7.16-7.36 (m, 6H), 6.94-7.03 (m, 1H), 4.46 (s, 2H), 3.82-3.94 (m, 2H), 2.84-2.95 (m, 2H), 2.29 (s, 3H). LCMS: 367 [M+1].

Example 20: Preparation of Compound 280

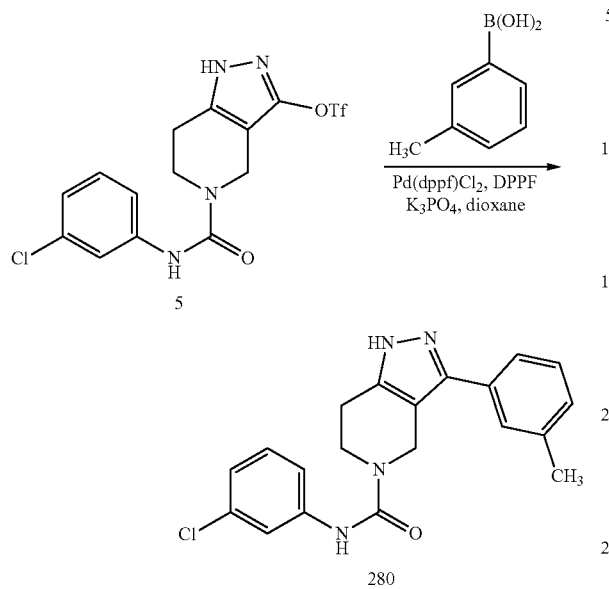

To a mixture of [5-[(3-chlorophenyl)carbamoyl]-1,4,6,7-tetrahydropyrazolo[4,3-c]pyridin-3-yl] trifluoromethanesulfonate (120.00 mg, 282.50 umol, 1.00 eq) and m-tolylboronic acid (76.82 mg, 565.00 umol, 2.00 eq) in dioxane (5.00 mL) was added Pd(dppf)Cl$_2$ (20.67 mg, 28.25 umol, 0.10 eq), DPPF (15.66 mg, 28.25 umol, 0.10 eq) and K$_3$PO$_4$ (179.90 mg, 847.50 umol, 3.00 eq) in one portion under N$_2$. The reaction vessel was sealed and heated in microwave at 130° C. for 2 hr. LCMS showed the reaction was completed. The mixture was poured into water (10 mL) and stirred for 1 min. The aqueous phase was extracted with ethyl acetate (10 mL*2). The combined organic phase was washed with brine (10 mL*2), dried with anhydrous Na$_2$SO$_4$, filtered and concentrated in vacuum. The residue was purified by pre-HPLC(FA) to afford N-(3-chlorophenyl)-3-(m-tolyl)-1,4,6,7-tetrahydropyrazolo[4,3-c]pyridine-5-carboxamide (15.32 mg, 41.05 umol, 14.53% yield, 98.3% purity) as white solid. LCMS: 367 [M+1].

Example 21: Preparation of Compound 281

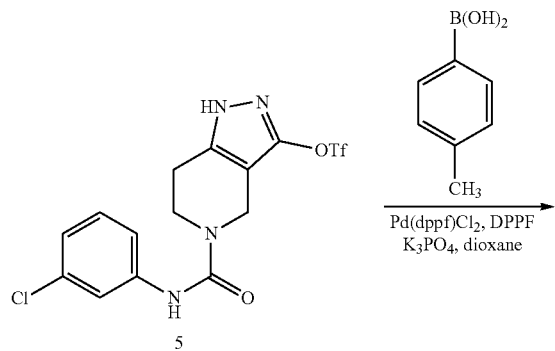

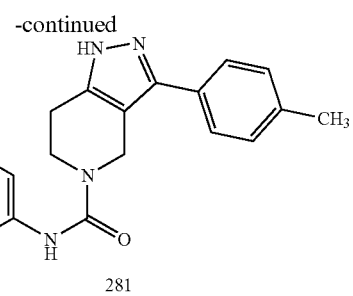

To a mixture of [5-[(3-chlorophenyl)carbamoyl]-1,4,6,7-tetrahydropyrazolo[4,3-c]pyridin-3-yl] trifluoromethanesulfonate (120.00 mg, 282.50 umol, 1.00 eq) and p-tolylboronic acid (76.82 mg, 565.00 umol, 2.00 eq) in dioxane (5.00 mL) was added Pd(dppf)Cl$_2$ (20.67 mg, 28.25 umol, 0.10 eq), DPPF (15.66 mg, 28.25 umol, 0.10 eq) and K$_3$PO$_4$ (179.90 mg, 847.50 umol, 3.00 eq) in one portion under N$_2$. The reaction vessel was sealed and heated in microwave at 130° C. for 2 hr. LCMS showed the reaction was completed. The mixture was poured into water (10 mL) and stirred for 1 min. The aqueous phase was extracted with ethyl acetate (10 mL*2). The combined organic phase was washed with brine (10 mL*2), dried with anhydrous Na$_2$SO$_4$, filtered and concentrated in vacuum. The residue was purified by prep-HPLC(FA) to afford N-(3-chlorophenyl)-3-(p-tolyl)-1,4,6,7-tetrahydropyrazolo[4,3-c]pyridine-5-carboxamide (20.35 mg, 54.25 umol, 19.20% yield, 97.8% purity) as white solid. LCMS: 367 [M+1].

Example 22: Preparation of Compound 291

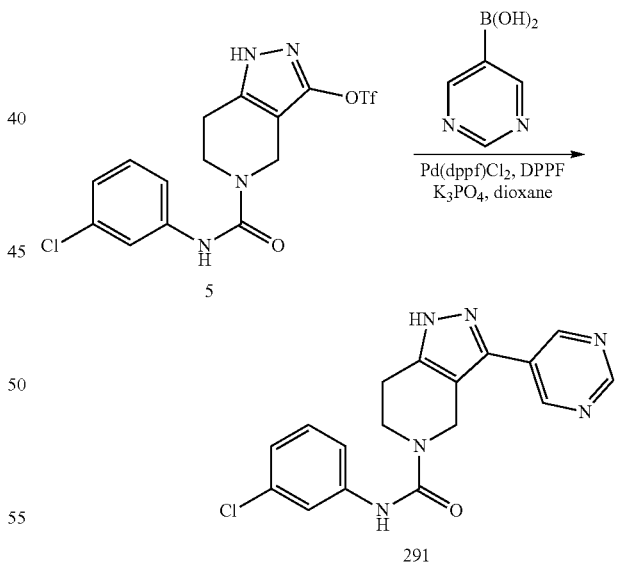

To a mixture of [5-[(3-chlorophenyl)carbamoyl]-1,4,6,7-tetrahydropyrazolo[4,3-c]pyridin-3-yl] trifluoromethanesulfonate (100.00 mg, 235.42 umol, 1.00 eq) and pyrimidin-5-ylboronic acid (58.34 mg, 470.84 umol, 2.00 eq) in dioxane (5.00 mL) was added Pd(dppf)Cl$_2$ (17.23 mg, 23.54 umol, 0.10 eq), DPPF (13.05 mg, 23.54 umol, 0.10 eq) and K$_3$PO$_4$ (149.92 mg, 706.26 umol, 3.00 eq) in one portion under N$_2$. The reaction vessel was sealed and heated in microwave at 145° C. for 2 hr. LCMS showed showed the reaction was completed. The mixture was poured into water (10 mL) and stirred for 2 min. The aqueous phase was extracted with ethyl acetate (10 mL*2). The combined organic phase was washed with saturated brine (10 mL*2), dried with anhydrous Na$_2$SO$_4$, filtered and concentrated in vacuum. The residue was purified by prep-HPLC(FA) to afford N-(3-chlorophenyl)-3-pyrimidin-5-yl-1,4,6,7-tetrahydropyrazolo[4,3-c]pyridine-5-carboxamide (25.63 mg, 69.47 umol, 29.51% yield, 96.16% purity) as white solid. $^1$H NMR (400 MHz, METHANOL-d$_4$) D 9.12 (d, J=5.02 Hz, 1H), 7.48-7.58 (m, 1H), 7.29 (s, 1H), 7.19-7.26 (m, 1H), 6.98-7.05 (m, 1H), 4.83 (s, 2H), 3.85-3.93 (m, 2H), 2.86-2.95 (m, 2H). LCMS: 355 [M+1].

Example 23: Preparation of Compound 325

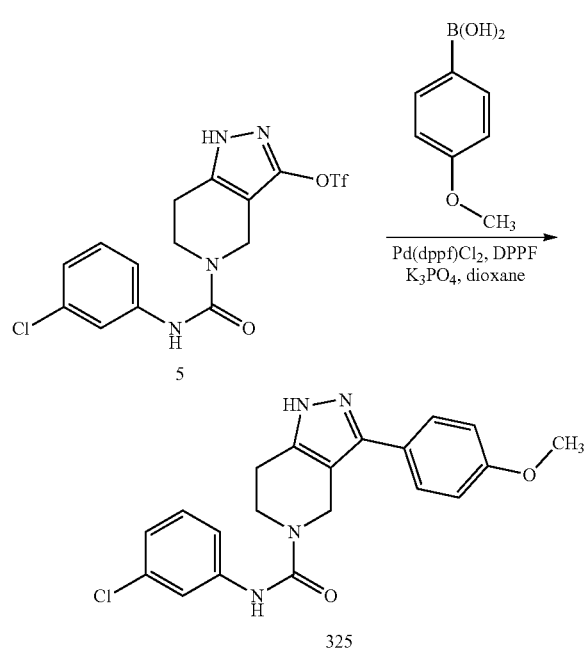

To a mixture of [5-[(3-chlorophenyl)carbamoyl]-1,4,6,7-tetrahydropyrazolo[4,3-c]pyridin-3-yl] trifluoromethanesulfonate (120.00 mg, 282.50 umol, 1.00 eq) and (4-methoxyphenyl)boronic acid (64.39 mg, 423.75 umol, 1.50 eq) in dioxane (5.00 mL) was added Pd(dppf)Cl$_2$ (20.67 mg, 28.25 umol, 0.10 eq), DPPF (15.66 mg, 28.25 umol, 0.10 eq) and K$_3$PO$_4$ (179.90 mg, 847.50 umol, 3.00 eq) in one portion under N$_2$. The reaction vessel was sealed and heated in microwave at 145° C. for 3 hr. LCMS showed the reaction was completed. The mixture was poured into water (10 mL) and stirred for 2 min. The aqueous phase was extracted with ethyl acetate (10 mL*2). The combined organic phase was washed with brine (10 mL*2), dried with anhydrous Na$_2$SO$_4$, filtered and concentrated in vacuum. The residue was purified by prep-HPLC(FA) to afford N-(3-chlorophenyl)-3-(4-methoxyphenyl)-1,4,6,7-tetrahydropyrazolo[4,3-c]pyridine-5-carboxamide (34.26 mg, 83.85 umol, 31.68% yield, 93.7% purity) as white solid. $^1$H NMR (400 MHz, METHANOL-d$_4$) D 7.55 (s, 3H), 7.19-7.32 (m, 2H), 7.03 (d, J=8.78 Hz, 3H), 4.73-4.77 (m, 2H), 3.85-3.89 (m, 2H), 3.84 (s, 3H), 2.83-2.89 (m, 2H). LCMS: 383 [M+1].

Example 24: Preparation of Compound 326

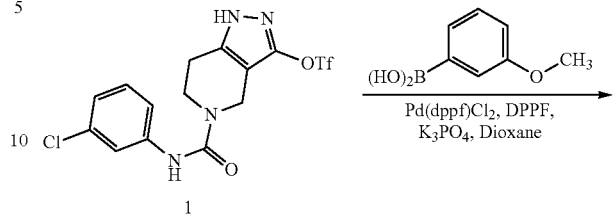

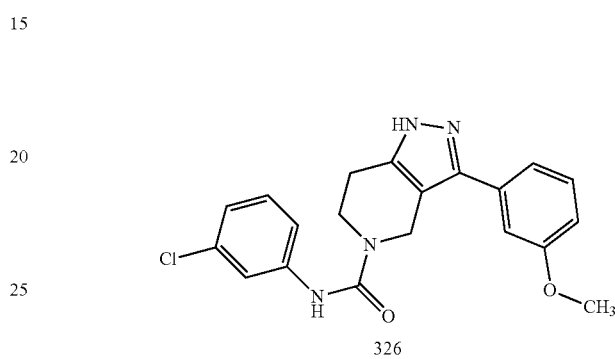

A mixture of [5-[(3-chlorophenyl)carbamoyl]-1,4,6,7-tetrahydropyrazolo[4,3-c]pyridine-3-yl]trifluoromethanesulfonate (120.00 mg, 282.50 umol, 1.00 eq), (3-methoxyphenyl)boronic acid (85.86 mg, 565.00 umol, 2.00 eq), Pd(dppf)Cl$_2$ (20.67 mg, 28.25 umol, 0.10 eq), DPPF (15.66 mg, 28.25 umol, 0.10 eq) and K$_3$PO$_4$ (179.90 mg, 847.50 umol, 3.00 eq) were taken up into a microwave tube in dioxane (5.00 mL). The sealed tube was heated at 145° C. for 3 hr under microwave. LCMS showed the reaction was completed. The mixture was filtered and concentrated under reduced pressure to give a residue. The residue was purified by prep-HPLC (FA) to give N-(3-chlorophenyl)-3-(3-methoxyphenyl)-1,4,6,7-tetrahydropyrazolo[4,3-c] pyridine-5-carboxamide (20.62 mg, 53.75 umol, 19.03% yield, 99.8% purity) as light yellow solid. $^1$H NMR (400 MHz, METHANOL-d$_4$) ppm 7.52 (s, 1H), 7.39 (t, J=7.84 Hz, 1H), 7.28 (s, 1H), 7.17-7.26 (m, 3H), 7.00 (d, J=7.91 Hz, 1H), 6.92-6.97 (m, 1H), 4.77 (s, 2H), 3.83-3.92 (m, 5H), 2.88 (t, J=5.65 Hz, 2H). LCMS: 383 [M+1].

Example 25: Preparation of Compound 327

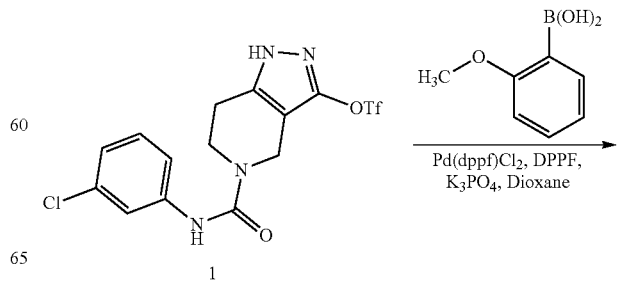

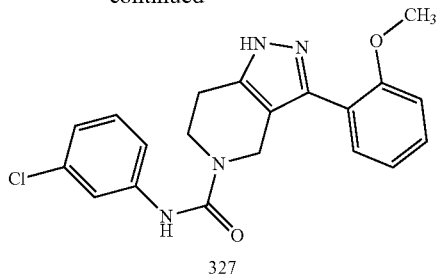

327

A mixture of [5-[(3-chlorophenyl)carbamoyl]-1,4,6,7-tetrahydropyrazolo[4,3-c]pyridine-3-yl]trifluoromethanesulfonate (120.00 mg, 282.50 umol, 1.00 eq), (2-methoxyphenyl)boronic acid (85.86 mg, 565.00 umol, 2.00 eq), Pd(dppf)Cl$_2$ (20.67 mg, 28.25 umol, 0.10 eq), DPPF (15.66 mg, 28.25 umol, 0.10 eq) and K$_3$PO$_4$ (179.90 mg, 847.51 umol, 3.00 eq) were taken up into a microwave tube in dioxane (5.00 mL). The sealed tube was heated at 145° C. for 3 hr under microwave. LCMS showed the starting material was consumed, the desired product was appeared. The mixture was filtered and concentrated under reduced pressure to give a residue. The residue was purified by prep-HPLC (FA) to give N-(3-chlorophenyl)-3-(2-methoxyphenyl)-1,4,6,7-tetrahydropyrazolo[4,3-c]pyridine-5-carboxamide (4.62 mg, 11.98 umol, 4.24% yield, 99.3% purity) as a light yellow solid. $^1$H NMR (400 MHz, METHANOL-d$_4$) ppm 7.50 (s, 1H), 7.37-7.44 (m, 2H), 7.25-7.30 (m, 1H), 7.18-7.24 (m, 1H), 7.12 (d, J=8.03 Hz, 1H), 7.05 (t, J=7.59 Hz, 1H), 6.99 (d, J=7.40 Hz, 1H), 4.60 (s, 2H), 3.82-3.96 (m, 5H), 2.88 (t, J=5.58 Hz, 2H). LCMS: 383 [M+1].

Example 26: Preparation of Compound 286

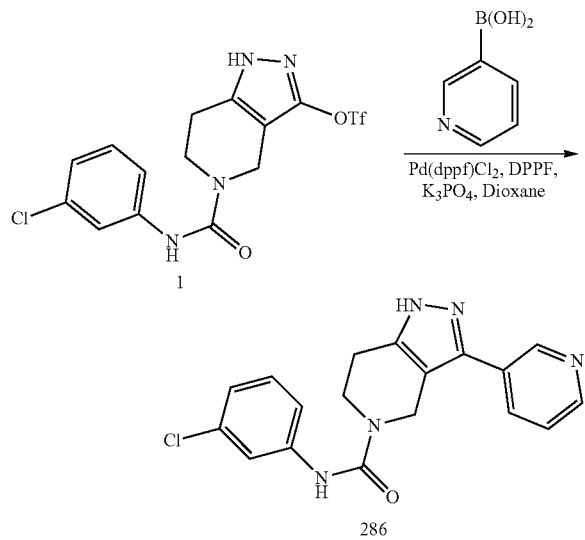

286

A mixture of [5-[(3-chlorophenyl)carbamoyl]-1,4,6,7-tetrahydropyrazolo[4,3-c]pyridine-3-yl]trifluoromethanesulfonate (120.00 mg, 282.50 umol, 1.00 eq), 3-pyridylboronic acid (69.45 mg, 565.00 umol, 2.00 eq), Pd(dppf)Cl$_2$ (20.67 mg, 28.25 umol, 0.10 eq), DPPF (15.66 mg, 28.25 umol, 0.10 eq) and K$_3$PO$_4$ (179.90 mg, 847.50 umol, 3.00 eq) were taken up into a microwave tube in dioxane (5.00 mL). The sealed tube was heated at 145° C. for 3 hr under microwave. LCMS showed the starting material/desired product=1/1. The mixture was filtered and concentrated under reduced pressure to give a residue. The residue was purified by pre-HPLC (FA) to give N-(3-chlorophenyl)-3-(3-pyridyl)-1,4,6,7-tetrahydropyrazolo [4,3-c]pyridine-5-carboxamide (13.00 mg, 34.02 umol, 12.04% yield, 92.6% purity) as a white solid.

$^1$H NMR (400 MHz, METHANOL-d$_4$) ppm 8.87 (d, J=1.51 Hz, 1H), 8.50-8.55 (m, 1H), 8.12 (td, J=1.77, 8.00 Hz, 1H), 7.51-7.57 (m, 2H), 7.27-7.32 (m, 1H), 7.20-7.26 (m, 1H), 6.98-7.03 (m, 1H), 4.81 (s, 2H), 3.89 (t, J=5.77 Hz, 2H), 2.90 (t, J=5.71 Hz, 2H). LCMS: 354 [M+1].

Example 27: Preparation of Compound 472

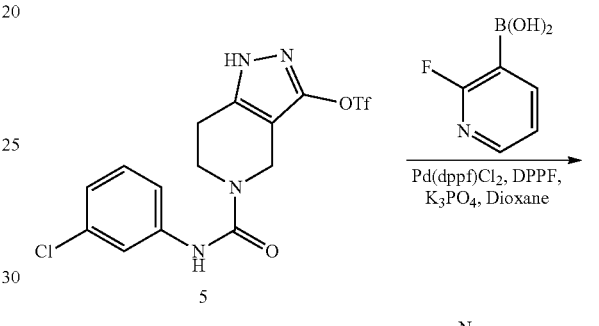

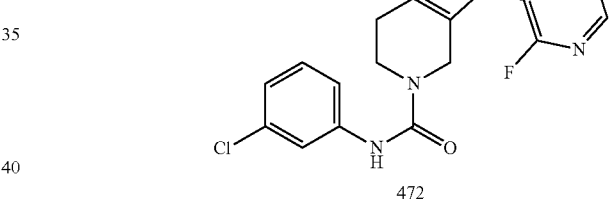

472

To a mixture of [5-[(3-chlorophenyl)carbamoyl]-1,4,6,7-tetrahydropyrazolo[4,3-c]pyridin-3-yl] trifluoromethanesulfonate (100.00 mg, 235.42 umol, 1.00 eq) and (2-fluoro-3-pyridyl)boronic acid (66.35 mg, 470.84 umol, 2.00 eq) in dioxane (5.00 mL) was added Pd(dppf)Cl$_2$ (17.23 mg, 23.54 umol, 0.10 eq), DPPF (13.05 mg, 23.54 umol, 0.10 eq), KBr (2.80 mg, 23.54 umol, 0.10 eq) and K$_3$PO$_4$ (149.92 mg, 706.26 umol, 3.00 eq) in one portion under N$_2$. The reaction vessel was sealed and heated in microwave at 145° C. for 2 hour. LCMS showed the desired compound was detected. The mixture was poured into water (10 mL) and stirred for 2 min. The aqueous phase was extracted with ethyl acetate (10 mL*2). The combined organic phase was washed with saturated brine (10 mL*2), dried with anhydrous Na$_2$SO$_4$, filtered and concentrated in vacuum. The residue was purified by prep-HPLC(FA) to afford N-(3-chlorophenyl)-3-(2-fluoro-3-pyridyl)-1,4,6,7-tetrahydropyrazolo[4,3-c]pyridine-5-carboxamide (17.56 mg, 46.71 umol, 19.84% yield, 98.9% purity) as white solid. $^1$H NMR (400 MHz, METHANOL-d$_4$) δ 8.22-8.28 (m, 1H), 8.10-8.19 (m, 1H), 7.48-7.52 (m, 1H), 7.40-7.46 (m, 1H), 7.18-7.30 (m, 2H), 6.96-7.02 (m, 1H), 4.62-4.69 (m, 2H), 3.85-3.93 (m, 2H), 2.86-2.94 (m, 2H). LCMS: 372 [M+1].

Example 28: Preparation of Compound 473

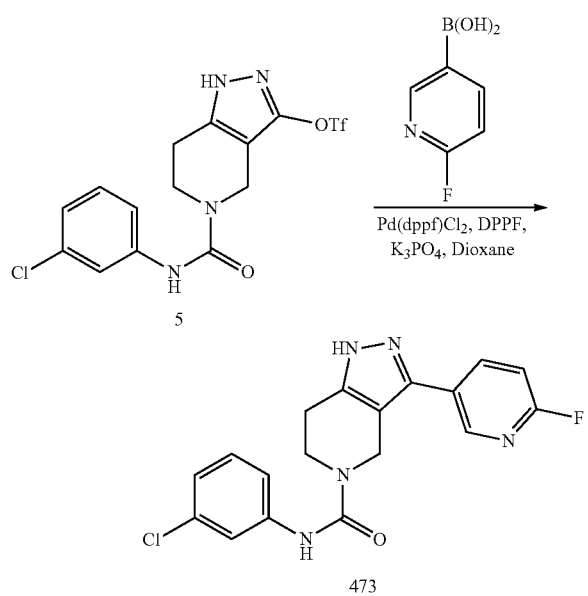

To a mixture of [5-[(3-chlorophenyl)carbamoyl]-1,4,6,7-tetrahydropyrazolo[4,3-c]pyridin-3-yl] trifluoromethanesulfonate (100.00 mg, 235.42 umol, 1.00 eq) and (6-fluoro-3-pyridyl)boronic acid (66.35 mg, 470.84 umol, 2.00 eq) in dioxane (5.00 mL) was added $Pd(dppf)Cl_2$ (17.23 mg, 23.54 umol, 0.10 eq), DPPF (13.05 mg, 23.54 umol, 0.10 eq) and $K_3PO_4$ (149.92 mg, 706.26 umol, 3.00 eq) in one portion under $N_2$. The reaction vessel was sealed and heated in microwave at 145° C. for 2 hr. LCMS showed showed the reaction was completed. The mixture was poured into water (10 mL) and stirred for 2 min. The aqueous phase was extracted with ethyl acetate (10 mL*2). The combined organic phase was washed with saturated brine (10 mL*2), dried with anhydrous $Na_2SO_4$, filtered and concentrated in vacuum. The residue was purified by prep-HPLC(FA) to afford N-(3-chlorophenyl)-3-(6-fluoro-3-pyridyl)-1,4,6,7-tetrahydropyrazolo[4,3-c]pyridine-5-carboxamide (21.36 mg, 57.05 umol, 24.23% yield, 99.3% purity) as white solid. $^1$H NMR (400 MHz, METHANOL-$d_4$) 8.46-8.54 (m, 1H), 8.18-8.28 (m, 1H), 7.49-7.57 (m, 1H), 7.16-7.32 (m, 3H), 6.98-7.04 (m, 1H), 4.78 (s, 2H), 3.88 (s, 2H), 2.84-2.95 (m, 2H). LCMS: 372 [M+1].

Example 29: Preparation of Compound 495

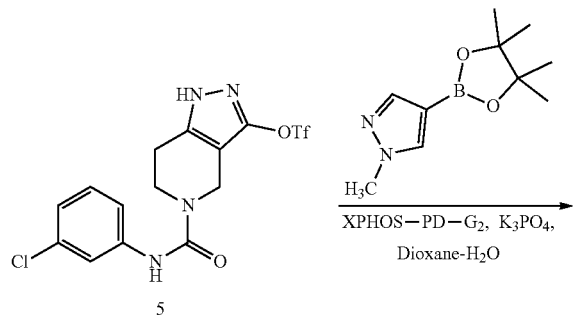

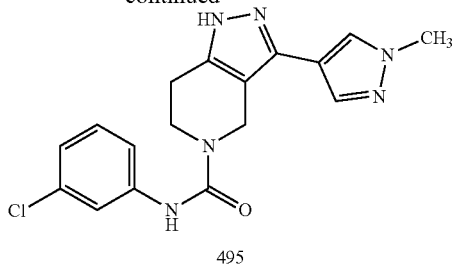

495

To a mixture of [5-[(3-chlorophenyl)carbamoyl]-1,4,6,7-tetrahydropyrazolo[4,3-c]pyridin-3-yl] trifluoromethanesulfonate (30.00 mg, 70.62 umol, 1.00 eq) and 1-methyl-4-(4,4,5,5-tetramethyl-1,3,2-dioxaborolan-2-yl)pyrazole (22.04 mg, 105.93 umol, 1.50 eq) in dioxane (2.00 mL) and $H_2O$ (200.00 uL) was added $K_3PO_4$ (29.98 mg, 141.24 umol, 2.00 eq), XPHOS-PD-$G_2$ (5.56 mg, 7.06 umol, 0.10 eq) in one portion under $N_2$. The mixture was stirred at 110° C. for 10 hour. LCMS showed the desired product was detected. The mixture was poured into water (10 mL) and stirred for 2 min. The aqueous phase was extracted with ethyl acetate (10 mL*2). The combined organic phase was washed with saturated brine (10 mL*2), dried with anhydrous $Na_2SO_4$, filtered and concentrated in vacuum. The residue was purified by prep-HPLC(FA) to afford N-(3-chlorophenyl)-3-(1-methylpyrazol-4-yl)-1,4,6,7-tetrahydropyrazolo[4,3-c]pyridine-5-carboxamide (5.20 mg, 14.25 umol, 20.18% yield, 97.8% purity) as white solid. $^1$H NMR (400 MHz, METHANOL-$d_4$) 7.90-7.95 (m, 1H), 7.79-7.83 (m, 1H), 7.52-7.56 (m, 1H), 7.29-7.34 (m, 1H), 7.20-7.28 (m, 1H), 6.99-7.05 (m, 1H), 4.63-4.69 (m, 2H), 3.93-4.00 (m, 3H), 3.81-3.89 (m, 2H), 2.79-2.89 (m, 2H). LCMS: 357 [M+1].

Example 30: Preparation of Compound 562

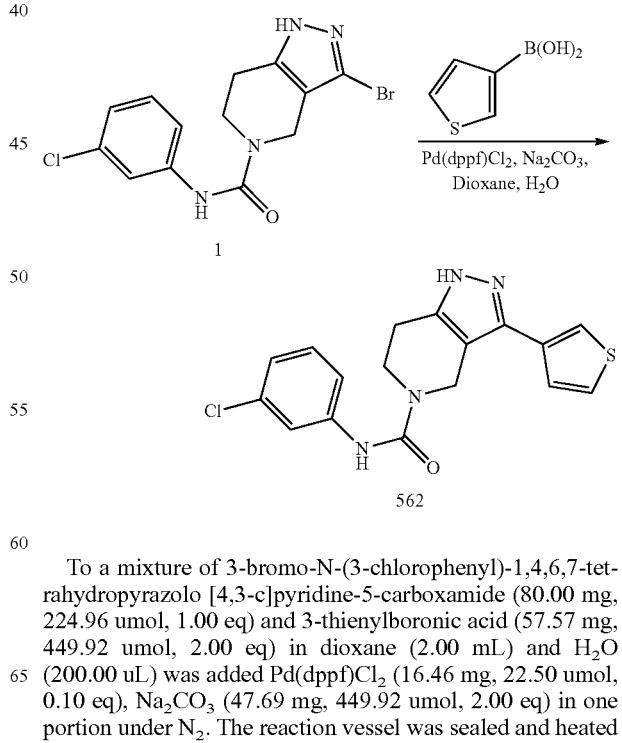

To a mixture of 3-bromo-N-(3-chlorophenyl)-1,4,6,7-tetrahydropyrazolo [4,3-c]pyridine-5-carboxamide (80.00 mg, 224.96 umol, 1.00 eq) and 3-thienylboronic acid (57.57 mg, 449.92 umol, 2.00 eq) in dioxane (2.00 mL) and $H_2O$ (200.00 uL) was added $Pd(dppf)Cl_2$ (16.46 mg, 22.50 umol, 0.10 eq), $Na_2CO_3$ (47.69 mg, 449.92 umol, 2.00 eq) in one portion under $N_2$. The reaction vessel was sealed and heated in microwave at 110° C. for 2 hour. LCMS showed the starting material was consumed completely. The mixture was poured into water (10 mL) and stirred for 2 min. The aqueous phase was extracted with ethyl acetate (10 mL*2). The combined organic phase was washed with brine (10 mL*2), dried with anhydrous $Na_2SO_4$, filtered and concentrated in vacuum. The residue was purified by prep-HPLC (FA) to afford N-(3-chlorophenyl)-3-(3-thienyl)-1,4,6,7-tetrahydropyrazolo[4,3-c]pyridine-5-carboxamide (16.00 mg, 44.05 umol, 19.58% yield, 98.8% purity) as white solid. $^1$H NMR (400 MHz, METHANOL-$d_4$) δ 7.61-7.66 (m, 1H), 7.51-7.57 (m, 2H), 7.46-7.51 (m, 1H), 7.28-7.35 (m, 1H), 7.20-7.27 (m, 1H), 6.97-7.05 (m, 1H), 4.72-4.78 (m, 2H), 3.83-3.92 (m, 2H), 2.82-2.90 (m, 2H). LCMS: 359 [M+1].

Example 31: Preparation of Compounds 496, and 497

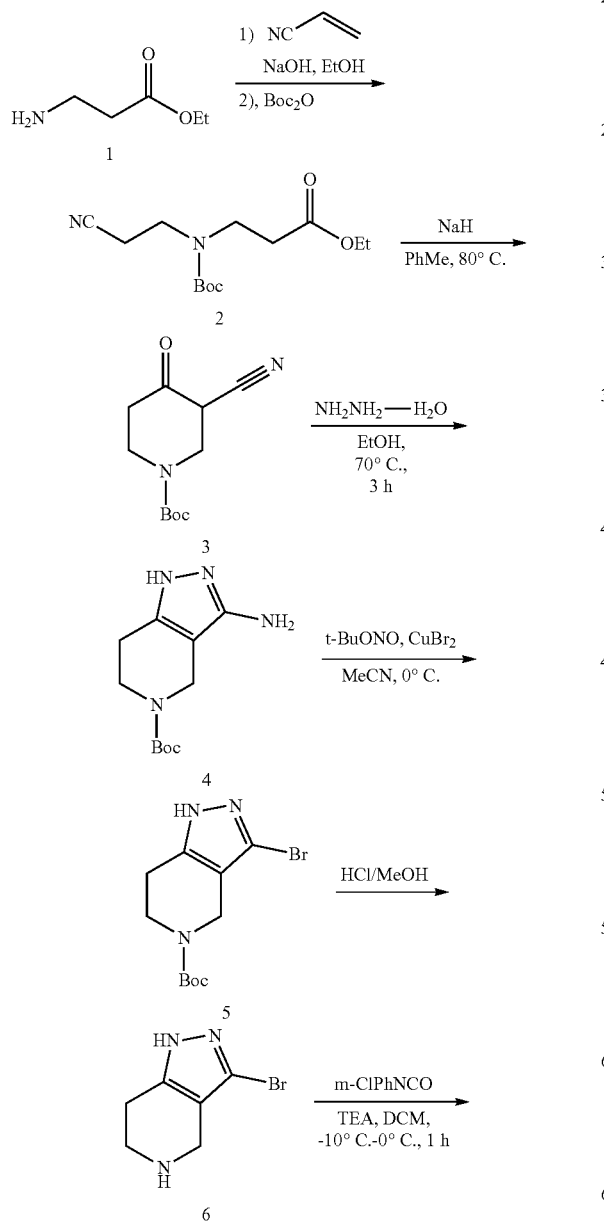

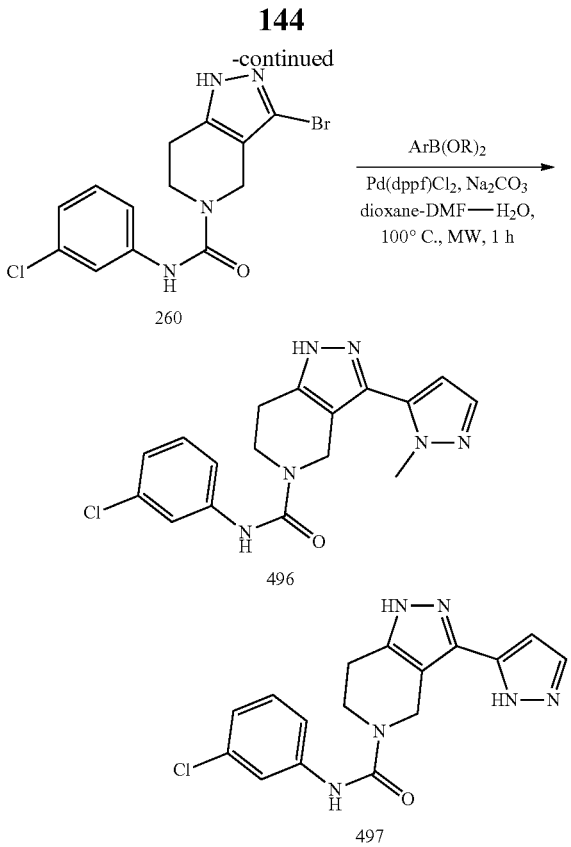

Step 1: Preparation of Compound 2

To a mixture of ethyl 3-aminopropanoate (50.00 g, 320.55 mmol, 1.00 eq, HCl salt) in MeOH (150.00 mL) was added NaOH (13 g, 320.55 mmol, 1.00 eq). The mixture was heated to 70° C. Acrylonitrile (21.8 g, 410.1 mmol, 1.26 eq) was added dropwise into the above mixture. And the mixture was stirred at 70° C. for 4 h. It was cooled 25° C., $Boc_2O$ (6.39 g, 29.30 mmol, 0.90 eq) was added. Then the mixture was stirred at 25° C. for 16 h. TLC showed the reaction completed. The mixture was filtered, the filtrate was wahsed with water (500 mL), extracted with EtOAc (500 mL*3), the filtrate was dried over $Na_2SO_4$ and concentrated to give Compound 2A (6.70 g, 24.79 mmol, 76.15% yield), which was used directly. $^1$H NMR (400 MHz, CHLOROFORM-d) 6=3.71 (s, 3H), 3.50-3.63 (m, 4H), 2.56-2.70 (m, 4H), 1.49 (s, 9H).

Step 2: Preparation of Compound 3

To a mixture of ethyl 3-[tert-butoxycarbonyl(2-cyano-ethyl)amino]propanoate (70.00 g, 258.95 mmol, 1.00 eq) in PhMe (150.00 mL) was added NaH (10.46 g, 261.54 mmol, 1.01 eq) in three portions. The mixture was stirred at 110° C. for 4 h. TLC showed the reaction completed. The reaction was quenched with aqueous saturate $NH_4Cl$ (200 mL), the aqueous was acidified with HCl (2N) to pH=6, then the mixture was extracted with EtOAc (150 mL*3), the organic layer was washed with brine (100 mL), dried over $Na_2SO_4$ and concentrated to give Compound 3 which was used directly. $^1$H NMR (400 MHz, CHLOROFORM-d) 6=4.40 (br. s., 1H), 4.16-4.26 (m, 1H), 3.58 (brs., 2H), 3.41 (d, J=7.28 Hz, 1H), 2.67 (d, J=14.31 Hz, 1H), 2.53 (dd, J=5.77, 9.54 Hz, 1H), 1.52 (s, 9H).

Step 3: Preparation of Compound 4

To a mixture of tert-butyl 3-cyano-4-oxo-piperidine-1-carboxylate (20.00 g, 89.18 mmol, 1.00 eq) in EtOH (200.00 mL) was added $NH_2NH_2.H_2O$ (8.93 g, 178.36 mmol, 2.00 eq) in one portion. The mixture was stirred at 80° C. for 2 h. TLC showed the reaction worked well. The mixture was concentrated to give Compound 4 (19.70 g, 82.67 mmol, 92.70% yield).

Step 4: Preparation of Compound 5

To a suspension of Compound 4 (40.00 g, 0.47 mol, 1.00 eq) and CuBr$_2$ (44 g, 0.58 mol, 1.20 eq) in 500 mL of acetonitrile was added t-BuONO (20.2 g, 0.58 mol, 1.20 eq) dropwise at 0° C. The contents were allowed to stir at 50° C. for 4 h. TLC showed the reaction completed. Then it was quenched with HCl (IM, 300 mL), extracted with EtOAc (200 mL*3), the organic layer was washed with brine (300 mL), dried over Na$_2$SO$_4$ and concentrated to give Compound 5 (11.00 g, 36.40 mmol, 21.69% yield). $^1$H NMR (400 MHz, CHLOROFORM-d) δ=4.33 (brs, 2H), 3.72 (brs, 2H), 2.83 (t, J=5.27 Hz, 2H), 1.50 (s, 9H).

Step 5: Preparation of Compound 6

To a mixture of Compound 5 (11.00 g, 36.40 mmol, 1.00 eq) in DCM (10.00 mL) was added HCl/dioxane (4 M, 20.02 mL) in one portion at 0° C. The mixture was stirred at 0° C. for 1 h. The mixture was concentrated to give Compound 5 (HCl).

Preparation of Compound 260

To a mixture of 3-bromo-4,5,6,7-tetrahydro-1H-pyrazolo [4,3-c]pyridine (10.50 g, 38.19 mmol, 1.00 eq, 2 HCl) in MeOH (350.00 mL) was added K$_2$CO$_3$ (13.20 g, 95.48 mmol, 2.50 eq). Then the mixture was filtered, the filtrate was used directly. And 1-chloro-3-isocyanato-benzene (5.86 g, 38.19 mmol, 1.00 eq) was added slowly into above filtrate at 25° C. The reaction was stirred at 25° C. for 1 h. LCMS showed the reaction worked well. The mixture was concentrated. The residue was rinsed with a mixed solution of PE/EA (10/1, 20 mL). The mixture was filtered and the cake was collected to give Compound 260 (11.00 g, 30.93 mmol, 80.99% yield). $^1$H NMR (400 MHz, DMSO-d6) δ=12.95 (brs, 1H), 8.88 (s, 1H), 7.64 (s, 1H), 7.41 (d, J=8.03 Hz, 1H), 7.26 (t, J=8.16 Hz, 1H), 6.99 (d, J=7.78 Hz, 1H), 4.34 (s, 2H), 3.72 (brs, 2H), 2.72 (brs, 2H). LCMS: 355 [M+1].

Preparation of Compound 496

To a mixture Compound 260 (100.00 mg, 281.20 umol, 1.00 eq) 1-methyl-5-(4,4,5,5-tetramethyl-1,3,2-dioxaborolan-2-yl)pyrazole (70.21 mg, 337.44 umol, 1.20 eq) in dioxane (1.50 mL) was added Pd(dppf)Cl$_2$ (20.58 mg, 28.12 umol, 0.10 eq) and Na$_2$CO$_3$ (65.57 mg, 618.64 umol, 2.20 eq) in one portion. The mixture was stirred at 100° C. for 1 h via microwave. LCMS showed major was desired product. The mixture was filtered and the filtrate was concentrated. The residue was purified by pre-HPLC (FA) to give Compound 496 (22.00 mg, 59.19 umol, 21.05% yield). $^1$H NMR (400 MHz, METHANOL-d4) δ=7.47-7.56 (m, 2H), 7.26-7.33 (m, 1H), 7.18-7.26 (m, 1H), 7.00 (d, J=7.53 Hz, 1H), 6.51 (d, J=1.76 Hz, 1H), 4.60 (s, 2H), 4.04 (brs, 3H), 3.87 (t, J=5.65 Hz, 2H), 2.89 (t, J=5.65 Hz, 2H). LCMS: 357 [M+1].

Preparation of Compound 497

To a mixture of Compound 260 (80.00 mg, 224.96 umol, 1.00 eq) 1H-pyrazol-5-ylboronic acid (30.20 mg, 269.95 umol, 1.20 eq) in dioxane (1.50 mL) was added Pd(dppf)Cl$_2$ (16.46 mg, 22.50 umol, 0.10 eq), Na$_2$CO$_3$ (65.57 mg, 618.64 umol, 2.20 eq) in one portion. The mixture was stirred at 100° C. for 1 h via microwave. LCMS showed DP:SM=1:1. The mixture was filtered and the filtrate was concentrated. The residue was purified by pre-HPLC (FA) to give Compound 497 (3.50 mg, 10.01 umol, 4.45% yield, 98.00% purity)$^1$H NMR (400 MHz, METHANOL-d4) δ=7.71 (s, 1H), 7.55 (s, 1H), 7.29-7.35 (m, 1H), 7.23 (t, J=8.03 Hz, 1H), 7.00 (d, J=7.78 Hz, 1H), 6.66 (d, J=1.76 Hz, 1H), 4.77 (s, 2H), 3.87 (t, J=5.65 Hz, 2H), 2.86 (t, J=5.52 Hz, 2H). LCMS: 343 [M+1].

Example 32: Preparation of Compound 555

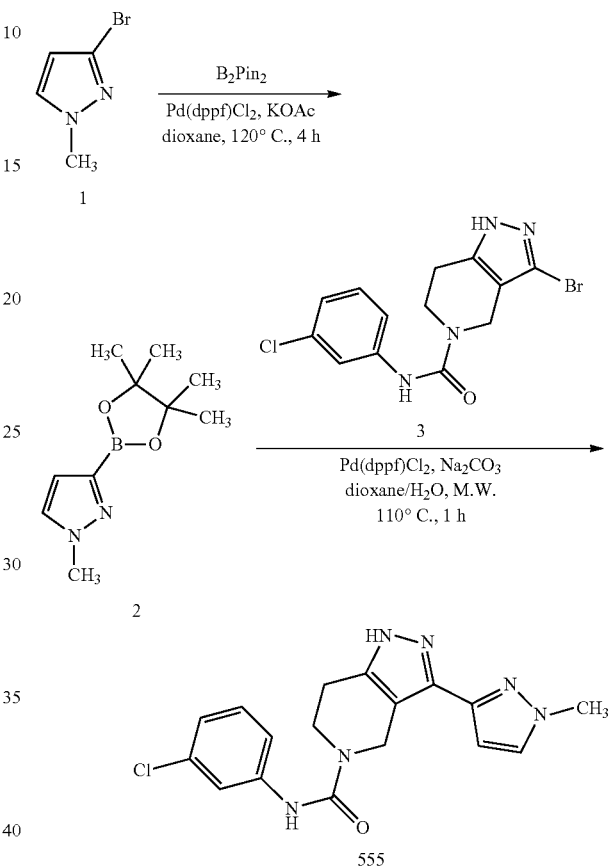

Step 1: Preparation of Compound 2

A mixture of 3-bromo-1-methyl-pyrazole (100.00 mg, 621.12 umol, 1.00 eq), 4,4,4',4',5,5,5',5'-octamethyl-2,2'-bi(1,3,2-dioxaborolane) (236.59 mg, 931.68 umol, 1.50 eq), AcOK (152.39 mg, 1.55 mmol, 2.50 eq) and Pd(dppf)Cl$_2$ (22.72 mg, 31.06 umol, 0.05 eq) in dioxane (3.00 mL) was heated to 120° C. for 4 hrs. The mixture was filtered and the filtrate was used directly for the next step.

Step 2: Preparation of Compound 555

A mixture of Compound 3 (60.00 mg, 168.72 umol, 1.00 eq), Compound 2 (70.21 mg, 337.44 umol, 2.00 eq), Na$_2$CO$_3$ (35.77 mg, 337.44 umol, 2.00 eq) and Pd(dppf)Cl$_2$ (6.17 mg, 8.44 umol, 0.05 eq) in dioxane (2.00 mL)/H$_2$O (400.00 uL) was heated to 110° C. in microwave for 1 hr. The reaction mixture was diluted with brine (60 mL) and extracted with EA (80 mL). The organic layer was concentrated under reduced pressure to give a yellow residue. The residue was purified by prep-TLC to give impure product (20 mg). The impure product was purified by prep-HPLC (FA) to afford the desired product, Compound 555, (6.00 mg, 16.65 umol, 9.87% yield, 99.00% purity) as white solid. LCMS: 357/359 [M+1]. $^1$H NMR (400 MHz, METHANOL-d$_4$) δ=7.65 (s, 1H), 7.55 (t, J=1.94 Hz, 1H), 7.30-7.38 (m, 1H), 7.18-7.29 (m, 1H), 6.92-7.08 (m, 1H), 6.62 (d, J=2.26 Hz, 1H), 4.78 (s, 2H), 3.97 (s, 3H), 3.87 (t, J=5.71 Hz, 2H), 2.81-2.92 (m, 2H).

Example 33: Preparation of Compound 287

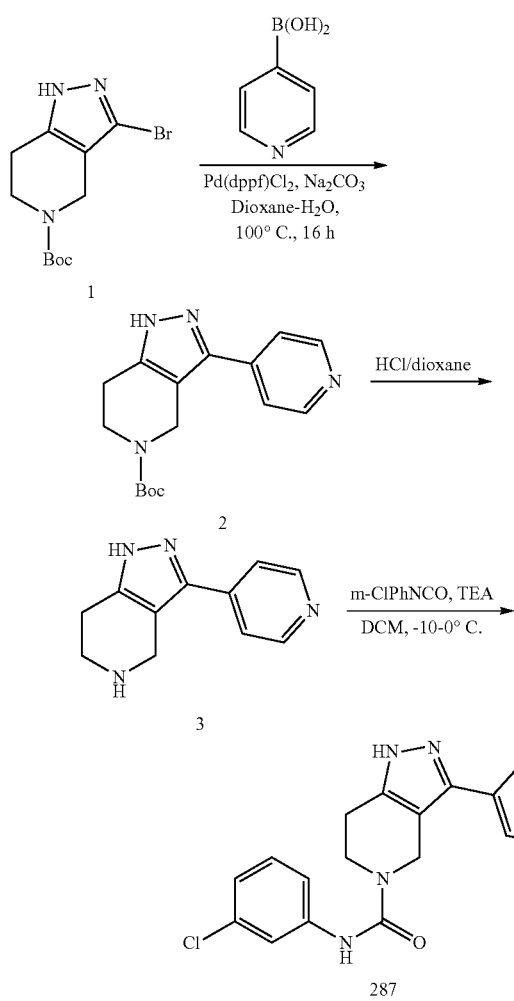

Step 1: Preparation of Compound 2
To a mixture of Compound 1 (100.00 mg, 330.94 umol, 1.00 eq) in dioxane (2.00 mL) was added Pd(dppf)Cl$_2$ (24.21 mg, 33.09 umol, 0.10 eq) and Na$_2$CO$_3$ (70.15 mg, 661.88 umol, 2.00 eq) in one portion. The mixture was stirred at 100° C. for 1 h via mircrowave. LCMS showed major was desire product. The mixture was filtered and concentrated. The residue was purified with column chromatography on silica gel (PE:EA=1:1) to give Compound 2 (70.00 mg, 233.06 umol, 70.42% yield). LCMS: 301[M+1].

Step 2: Preparation of Compound 3
To a mixture of Compound 2 (70.00 mg, 233.06 umol, 1.00 eq) in DCM (5.00 mL) was added HCl/MeOH (4 M, 6.21 mL, 106.65 eq) in one portion. The mixture was stirred at 0° C. for 0.5 h. TLC showed the reaction completed. The mixture was concentrated to give Compound 3 (65.00 mg, crude).

Step 3: Preparation of Compound 287
To a mixture of Compound 3 (50.00 mg, crude) in DCM (5.00 mL) was added TEA (64.83 mg, 640.64 umol, 3.50 eq) and 1-chloro-3-isocyanato-benzene (28.11 mg, 183.04 umol, 1.00 eq) in one portion. The mixture was stirred at 0° C. for 0.5 h. LCMS showed product was major. The mixture was concentrated. The residue was purified by pre-HPLC (FA) to give Compound 287 (32.00 mg, 88.64 umol, 48.43% yield, 98% purity). $^1$H NMR (400 MHz, METHANOL-d4) δ=8.59 (d, J=5.52 Hz, 2H), 7.72 (d, J=5.27 Hz, 2H), 7.53 (s, 1H), 7.27-7.34 (m, 1H), 7.19-7.26 (m, 1H), 7.01 (d, J=8.03 Hz, 1H), 4.84 (s, 2H), 3.88 (t, J=5.65 Hz, 2H), 2.89 (t, J=5.52 Hz, 2H). LCMS: 354[M+1].

Example 34: Preparation of Compound 436

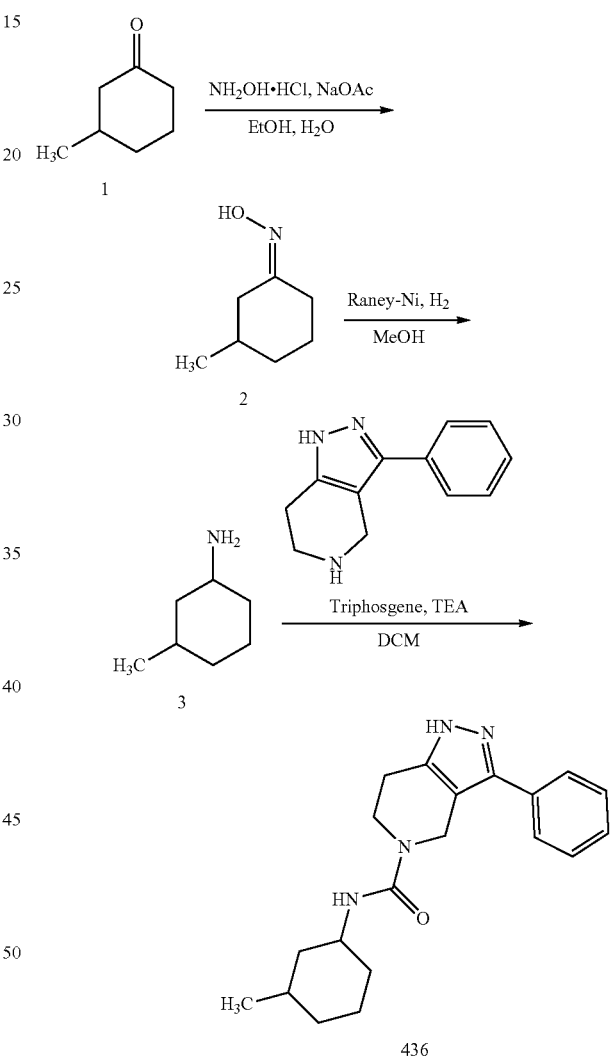

Step 1: Preparation of Compound 2
To a solution of 3-methylcyclohexanone (2.00 g, 17.83 mmol, 1.00 eq) in EtOH (15.00 mL) and H$_2$O (15.00 mL) was added NaOAc (4.39 g, 53.49 mmol, 3.00 eq) and NH$_2$OH.HCl (6.20 g, 89.15 mmol, 5.00 eq) in sequence, then the mixture was stirred at 20° C. for 16 hr. TLC indicated the reaction was completed and one new spot formed. The mixture was concentrated to remove the EtOH and then added into water (30 mL), extracted with EA (30 mL*3), the organic layers were dried over Na$_2$SO$_4$, filtered and concentrated to give the Compound 2 (2.00 g, 15.73 mmol, 88.20% yield).

Step 2: Preparation of Compound 3

To a solution of 3-methylcyclohexanone oxime (1.00 g, 7.86 mmol, 1.00 eq) in MeOH (10.00 mL) was added Raney-Ni (67.34 mg, 786.00 umol, 0.10 eq) under argon, and then stirred at 30° C. for 16 hr under H₂ (45 Psi). TLC indicated the reaction was completed and one new spot formed. The mixture was filtered by diatomite, then the filtrate was added into HCl/MeOH (4M, 30 mL), the mixture was stirred at 10° C. for 5 min, and concentrated to give the Compound 3 (800.00 mg, 5.35 mmol, 68.01% yield, HCl) as white solid.

Step 3: Preparation of Compound 436

To a mixture of 3-methylcyclohexanamine (63.49 mg, 424.25 umol, 1.00 eq, HCl) and TEA (429.30 mg, 4.24 mmol, 10.00 eq) in DCM (20.00 mL) was added triphosgene (50.36 mg, 169.70 umol, 0.40 eq) at 0° C. and stirred 10 min, 3-phenyl-4,5,6,7-tetrahydro-1H-pyrazolo[4,3-c]pyridine (100.00 mg, 424.25 umol, 1.00 eq, HCl) was added into the reaction and stirred at 0° C. for 2 hr. LC-MS showed the reaction was completed and one main peak with desired MS was detected. The reaction mixture was quenched by addition water 20 mL at 10° C., extracted with DCM (20 mL*3). The combined organic layers were dried over Na₂SO₄, filtered and concentrated under reduced pressure. The residue was purified by prep-TLC to obtained Compound 436 (40.00 mg, 118.19 umol, 27.86% yield) as light yellow solid.

LCMS: 339[M+H]. ¹H NMR (400 MHz, METHANOL-d4) δ ppm 7.30-7.77 (m, 5H) 4.65 (d, J=4.27 Hz, 2H) 3.88-3.97 (m, 1H) 3.72-3.82 (m, 2H) 3.55-3.65 (m, 1H) 2.75-2.87 (m, 2H) 1.62-1.96 (m, 4H) 1.13-1.61 (m, 5H) 0.92-1.00 (m, 3H).

Example 35: Preparation of Compound 559

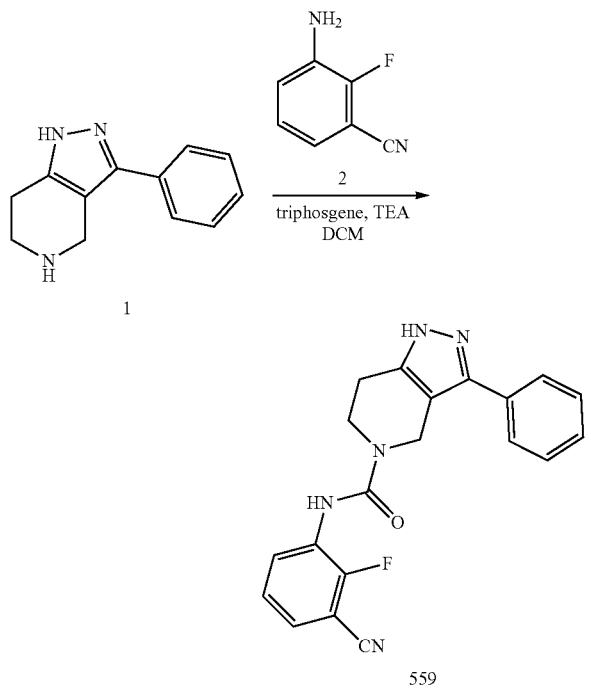

To a solution of 3-amino-2-fluoro-benzonitrile (57.75 mg, 424.25 umol, 1.00 eq) in DCM (3 mL) was added TEA (100 mg) and TRIPHOSGENE (50.36 mg, 169.70 umol, 0.40 eq) at 0° C. under N₂, the mixture stirred at this temperature for 10 min, then added into the solution of 3-phenyl-4,5,6,7-tetrahydro-1H-pyrazolo[4,3-c]pyridine (100.00 mg, 424.25 umol, 1.00 eq, HCl) which was freed by TEA (71 mg) in DCM (3 mL), stirred at 10° C. for 2 hr. LC-MS showed the reaction was completed and one main peak with desired MS was detected. The mixture was added into HCl (0.5 M, 10 mL), extracted with DCM (20 mL*3). The organic layers were concentrated. The residue was purified by prep-HPLC (FA condition) to give Compound 559 (45.00 mg, 119.55 umol, 28.18% yield, 96% purity) as white solid. LCMS: 262 [M+H]. 1H NMR (400 MHz, METHANOL-d4) δ ppm 7.72-7.80 (m, 1H) 7.57-7.70 (m, 2H) 7.43-7.53 (m, 3H) 7.33-7.40 (m, 1H) 7.29 (s, 1H) 4.81 (s, 2H) 3.91 (t, J=5.77 Hz, 2H) 2.90 (t, J=5.65 Hz, 2H).

Example 36: Preparation of Compound 560

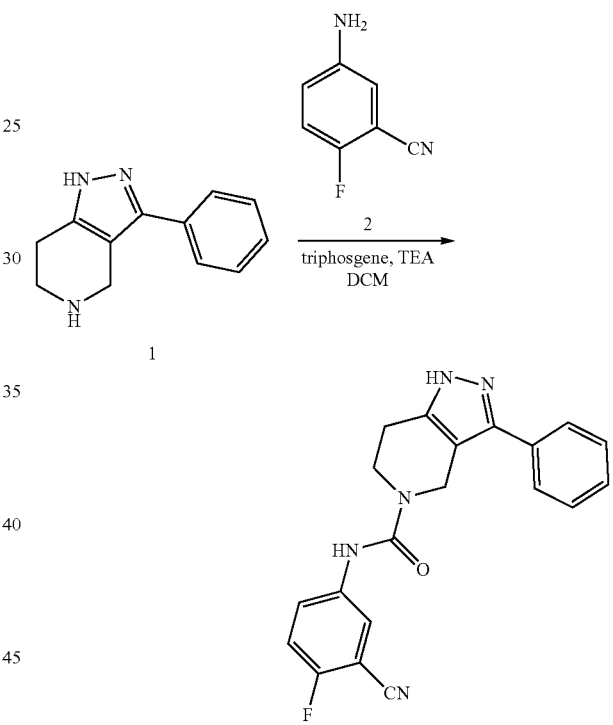

To a solution of 5-amino-2-fluoro-benzonitrile (57.75 mg, 424.25 umol, 1.00 eq) in DCM (3.00 mL) was added TRIPHOSGENE (125.90 mg, 424.25 umol, 1.00 eq) and TEA (42.93 mg, 424.25 umol, 1.00 eq) at 0° C., the mixture was stirred 10 min, then 3-phenyl-4,5,6,7-tetrahydro-1H-pyrazolo[4,3-c]pyridine (100.00 mg, 424.25 umol, 1.00 eq, HCl) was added into it, the reaction mixture was stirred at 10° C. for 2 hr. LC-MS showed the reaction was completed and one main peak with desired MS was detected. The mixture was concentrated and diluted with 10 mL HCl (0.5 M), then extracted with EA (20 mL*3), the organic layers were dried over Na₂SO₄, then filtered and concentrated. The residue was purified by prep-HPLC (FA condition) to give Compound 560 (50.00 mg, 135.60 umol, 31.96% yield, 98% purity) as white solid. LCMS: 362 [M+H]. ¹H NMR (400 MHz, METHANOL-d4) δ ppm 7.80 (dd, J=5.52, 2.76 Hz, 1H) 7.57-7.72 (m, 3H) 7.47 (t, J=7.40 Hz, 2H) 7.38 (d, J=7.28 Hz, 1H) 7.26 (t, J=9.03 Hz, 1H) 4.79 (s, 2H) 3.88 (t, J=5.77 Hz, 2H) 2.88 (t, J=5.65 Hz, 2H).

Example 37: Preparation of Compound 556

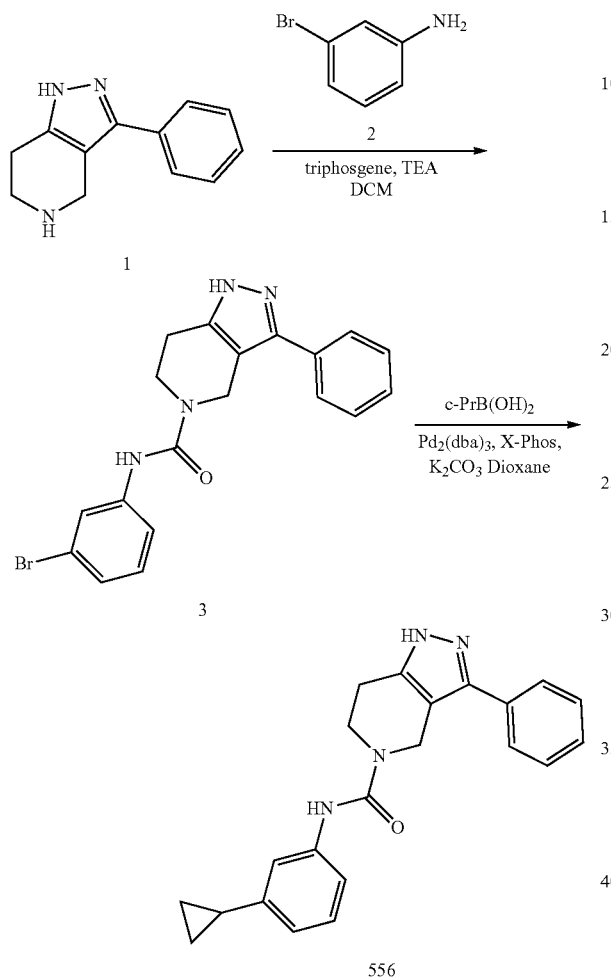

Step 1: Preparation of Compound 3

To a solution of 3-phenyl-4,5,6,7-tetrahydro-1H-pyrazolo[4,3-c]pyridine (500.00 mg, 2.12 mmol, 1.00 eq, HCl) in DCM (5.00 mL) was added TEA (1.07 g, 10.61 mmol, 5.00 eq), the mixture was stirred for 10 min, and 3-bromoaniline (2.12 mmol, 1.00 eq, HCl) was added into the reaction mixture and stirred at 10° C. for 16 hr. TLC indicated the reaction was completed and one new main spot formed. The mixture was added into HCl (0.5 M, 20 mL) and extracted with DCM (30 mL*3). The organic layers was dried over Na$_2$SO$_4$, filtered and concentrated. The residue was purified by column chromatography to give the Compound 3 (450.00 mg, 1.04 mmol, 49.16% yield, 92% purity) as white solid.

Step 2: Preparation of Compound 556

A mixture of N-(3-bromophenyl)-3-phenyl-1,4,6,7-tetrahydropyrazolo[4,3-c]pyridine-5-carboxamide (130.00 mg, 327.23 umol, 1.00 eq), cyclopropylboronic acid (140.55 mg, 1.64 mmol, 5.00 eq), K$_2$CO$_3$ (135.68 mg, 981.69 umol, 3.00 eq), Pd$_2$(dba)$_3$ (26.97 mg, 29.45 umol, 0.09 eq) and dicyclohexyl-[2-(2,4,6-triisopropylphenyl)phenyl] phosphane (12.48 mg, 26.18 umol, 0.08 eq) in dioxane (2.00 mL) was stirred at 110° C. for 16 hour under N$_2$ atmosphere. LC-MS showed the reaction was completed and one main peak with desired MS was detected. The mixture was added into the water (10 mL) and extracted with DCM (20 mL*3). The organic layers were dried over Na$_2$SO$_4$, filtered and concentrated. The residue was purified by prep-TLC to give desired compound as a light yellow solid, which was further purified by prep-HPLC (FA condition) to afford Compound 556 (20.00 mg, 55.24 umol, 16.88% yield, 99% purity) as white solid. LCMS: 359 [M+H]. $^1$H NMR (400 MHz, METHANOL-d4) δ ppm 7.60-7.67 (m, 1H) 7.43-7.51 (m, 1H) 7.33-7.40 (m, 1H) 7.05-7.16 (m, 3H) 6.74-6.80 (m, 1H) 4.77 (s, 2H) 3.84-3.91 (m, 2H) 2.84-2.91 (m, 2H) 1.80-1.91 (m, 1H) 0.88-0.96 (m, 2H) 0.63-0.70 (m, 2H).

Example 38: Preparation of Compounds 317 and 318

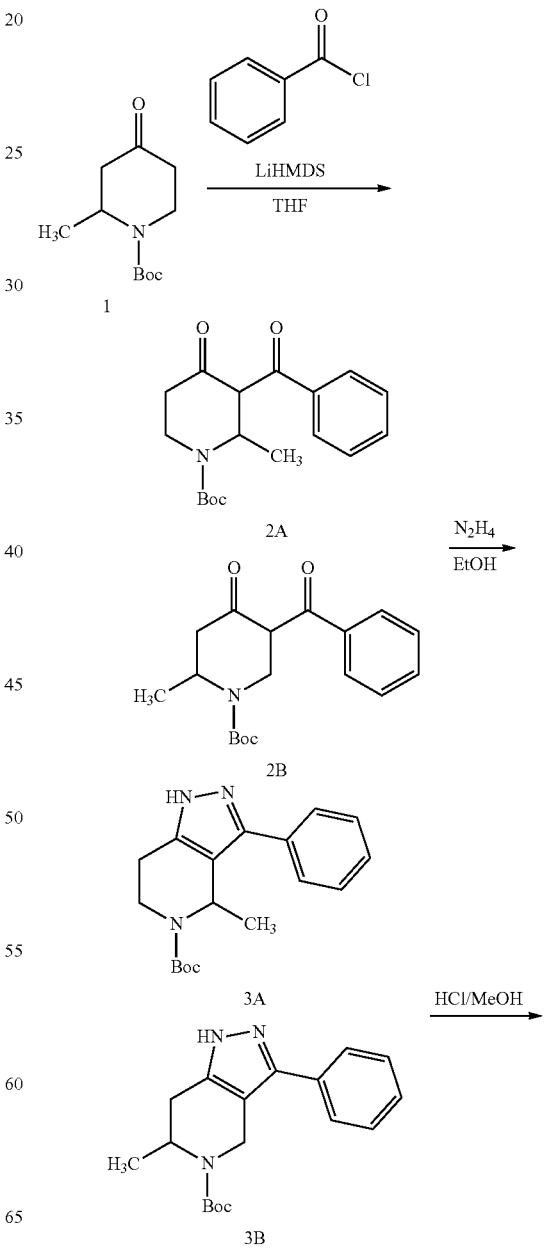

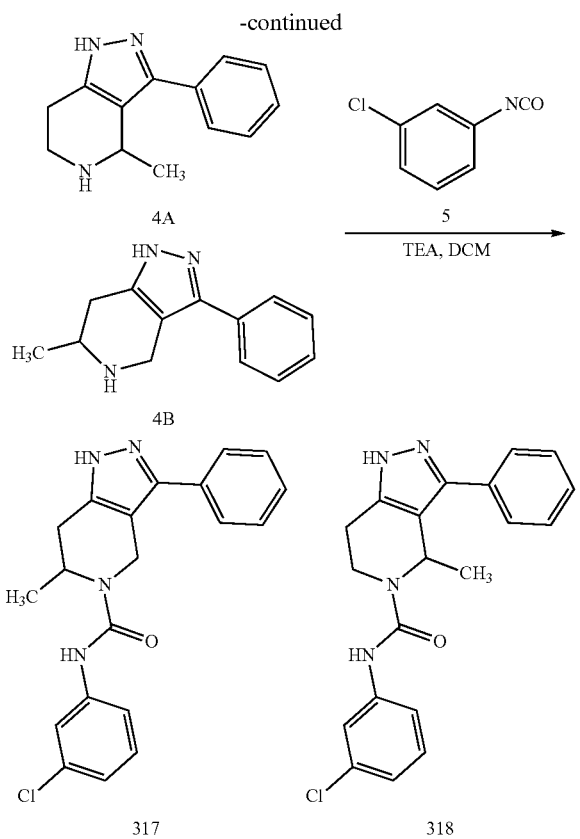

Step 1: Preparation of Compounds 2A and 2B

To a solution of LiHMDS (1 M, 15.47 mL, 2.20 eq) in THF (10.00 mL) was added tert-butyl-2-methyl-4-oxo-piperidine-1-carboxylate (1.50 g, 7.03 mmol, 1.00 eq) dropwise at −70° C. and stirred for 0.5 hr, then PhCOCl (988.68 mg, 7.03 mmol, 1.00 eq) in THF (2.00 mL) was added dropwise at −70° C. The reaction was stirred at −70° C. to 16° C. for 3 hr. The reaction was quenched with sat.NH₄Cl (20 mL) and then extracted with EA (20 mL*2). The combined organic phase was washed with brine (15 mL), dried over anhydrous Na₂SO₄, filtered and concentrated in vacuum. The residue was purified by flash silica gel chromatography (~5% Ethyl acetate/Petroleum ether gradient) to give a mixture of 2A and 2B (1.75 g) as yellow oil. LCMS: 218[M+1].

Step 2: Preparation of Compounds 3A and 3B

To a solution of 2A and 2B (1.75 g mixture of 2A and 2B, 5.51 mmol, 1.00 eq) in EtOH (15.00 mL) was added N₂H₄.H₂O (324.51 mg, 5.51 mmol, 1.00 eq), the solution was stirred at 90° C. for 3 hr. The solution was concentrated to give a mixture of 3A and 3B (1.75 g, 4.47 mmol, 81.08% yield, 80% purity) as light yellow solid. LCMS: 314[M+1].

Step 3: Preparation of Compounds 4A and 4B

To a mixture of 3A and 3B (330.00 mg, 842.40 umol, 1.00 eq) in dioxane (3.00 mL) was added HCl/dioxane (4 M, 10.00 mL, 47.48 eq). The mixture was stirred at 15° C. for 1 hr. Solid was formed, and the solvent was evaporated to afford a mixture of 4A and 4B (210.00 mg, crude, HCl salt) as light yellow solid.

Step 4: Preparation of Compound 317 and 318

A mixture of 6-methyl-3-phenyl-4,5,6,7-tetrahydro-1H-pyrazolo [4,3-c]pyridine and 4-methyl-3-phenyl-4,5,6,7-tetrahydro-1H-pyrazolo[4,3-c]pyridine (210.00 mg, 840.87 umol, 1.00 eq, HCl) in DCM (10.00 mL) was added TEA (170.18 mg, 1.68 mmol, 2.00 eq) and 1-chloro-3-isocyanatobenzene (129.13 mg, 840.87 umol, 1.00 eq). The mixture was stirred at 15° C. for 1 hr. LCMS showed the material was consumed completely, and a major peak with desired product detected. The mixture was washed with water (10 mL), the aqueous layer was extracted with DCM (15 mL*3). The combined organic layer was dried over anhydrous Na₂SO₄, and concentrated in vacuo. The residue was purified by prep-HPLC (FA) to afford a mixture of N-(3-chlorophenyl)-4-methyl-3-phenyl-1,4,6,7-tetrahydropyrazolo[4,3-c]pyridine-5-carboxamide and N-(3-chlorophenyl)-6-methyl-3-phenyl-1,4,6,7-tetrahydropyrazolo[4,3-c]pyridine-5-carboxamide (160.00 mg, 1:1 from H NMR, 436.16 umol, 51.87% yield, 4 isomers detected by SFC) as white solid. The mixture was separated by SFC (Instrument: SFC 80, Column: OD-10 um. Mobile phase: A for CO₂ and B for MeOH (0.1% NH₃H₂O), Gradient: B 35%, Flow rate: 65 mL/min, Back pressure: 100 bar, Column temperature: 35° C., Wavelength: 220 nm) to give Compound 318, Enantiomer 1 (peak 1, Rt=3.003 min, 22.76 mg, purity: 98.6%), Compound 317, Enantiomer 1 (peak 2, Rt=3.219 min, 26.27 mg, purity: 99.9%), Compound 318, Enantiomer 2 (peak 3, Rt=3.509 min, 24.3 mg, purity: 99.1%) and Compound 317, Enantiomer 2 (peak 4, Rt=3.930 min, 27.21 mg, purity: 99.0%), all as white solid.

Compound 318, Enantiomer 1: ¹H NMR (400 MHz, METHANOL-d4) δ ppm 7.68 (d, J=7.53 Hz, 2H), 7.56 (d, J=1.76 Hz, 1H), 7.50 (t, J=7.65 Hz, 2H), 7.42 (d, J=7.28 Hz, 1H), 7.32-7.38 (m, 1H), 7.27 (t, J=8.03 Hz, 1H), 7.05 (d, J=7.78 Hz, 1H), 5.77 (q, J=6.27 Hz, 1H), 4.40 (dd, J=13.80, 4.52 Hz, 1H), 3.37 (brs, 1H), 2.75-2.95 (m, 2H), 1.31 (d, J=6.53 Hz, 3H). LCMS: 367/369 [M+1].

Compound 317, Enantiomer 1: ¹H NMR (400 MHz, METHANOL-d4) δ ppm 7.69 (d, J=7.53 Hz, 2H), 7.46-7.59 (m, 3H), 7.39 (s, 1H), 7.29-7.34 (m, 1H), 7.22-7.28 (m, 1H), 7.03 (d, J=7.78 Hz, 1H), 5.07 (d, J=15.31 Hz, 1H), 4.99 (s, 1H), 4.48 (d, J=15.31 Hz, 1H), 3.09 (dd, J=15.81, 5.77 Hz, 1H), 2.73 (d, J=15.81 Hz, 1H), 1.28 (d, J=6.78 Hz, 3H). LCMS: 367/369 [M+1]. LCMS: 367/369 [M+1].

Compound 318, Enantiomer 2: ¹H NMR (400 MHz, METHANOL-d4) δ ppm 7.68 (d, J=7.53 Hz, 2H), 7.57 (s, 1H), 7.50 (t, J=7.65 Hz, 2H), 7.33-7.44 (m, 2H), 7.24-7.30 (m, 1H), 7.05 (d, J=7.53 Hz, 1H), 5.72-5.83 (m, 1H), 4.35-4.47 (m, 1H), 3.37 (brs, 1H), 2.76-2.94 (m, 2H), 1.31 (d, J=6.53 Hz, 3H). LCMS: 367/369 [M+1].

Compound 317, Enantiomer 2: ¹H NMR (400 MHz, METHANOL-d4) δ ppm 7.69 (d, J=7.78 Hz, 2H), 7.47-7.58 (m, 3H), 7.37-7.44 (m, 1H), 7.30-7.34 (m, 1H), 7.21-7.28 (m, 1H), 7.04 (s, 1H), 5.08 (d, J=15.31 Hz, 1H), 4.99-5.01 (m, 1H), 4.48 (d, J=15.31 Hz, 1H), 3.10 (dd, J=15.81, 5.77 Hz, 1H), 2.73 (d, J=15.81 Hz, 1H), 1.28 (d, J=6.78 Hz, 3H). LCMS: 367/369 [M+1].

Example 39: Preparation of Compounds 542 and 583

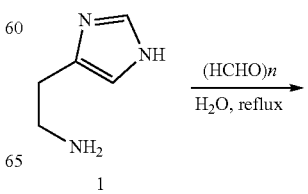

-continued

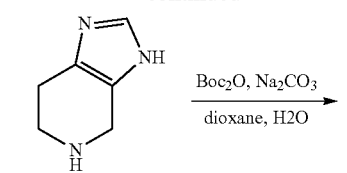

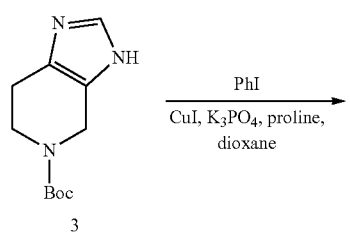

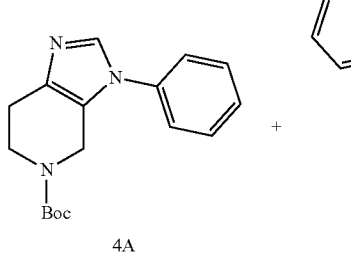

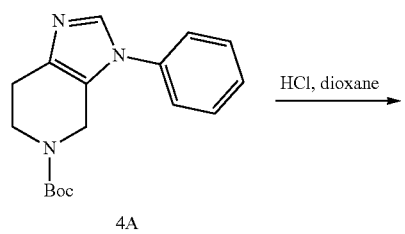

-continued

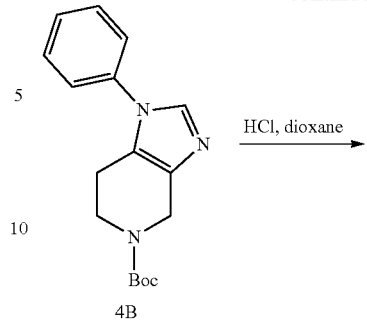

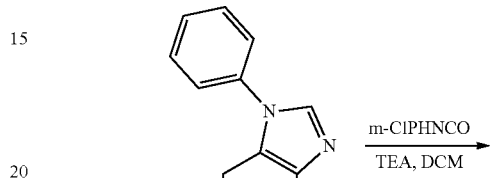

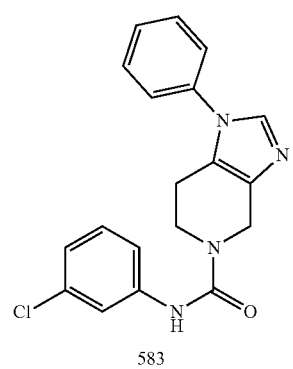

Step 1: Preparation of Compound 2

To a mixture of 2-(1H-imidazol-4-yl)ethanamine (1.00 g, 5.43 mmol, 1.00 eq, 2 HCl) in H2O (8.00 mL) was added HCHO (244.59 mg, 8.15 mmol, 1.50 eq) in one portion under N$_2$. The mixture was stirred at 100° C. for 10 hours. LCMS showed the reaction was completed. The mixture was concentrated in cacuum to afford 4,5,6,7-tetrahydro-3H-imadazo[4,5-c]pyridine (1.25 g, crude, 2 HCl) as yellow solid.

Step 2: Preparation of Compound 3

To a mixture of 4,5,6,7-tetrahydro-3H-imidazo[4,5-c]pyridine (669.00 mg, 3.41 mmol, 1.00 eq, 2 HCl) in dioxane (5.00 mL) and H$_2$O (3.00 mL) was added Na$_2$CO$_3$ (904.06 mg, 8.53 mmol, 2.50 eq) and Boc$_2$O (819.11 mg, 3.75 mmol, 1.10 eq) in one portion at 15° C. under N$_2$. The mixture was stirred at 15° C. for 10 hours. LCMS showed the reaction was completed. The residue was extracted with ethyl acetate (40 mL*2). The combined organic phase was washed with brine (40 mL*2), dried with anhydrous Na$_2$SO$_4$, filtered and concentrated in vacuum. The residue was purified by silica gel chromatography (Ethyl acetate) to afford tert-butyl 3,4,6,7-tetrahydroimidazo[4,5-c] pyridine-5-carboxylate (740.00 mg, 2.85 mmol, 83.58% yield, 86% purity) as yellow solid. $^1$H NMR (400 MHz, CHLOROFORM-D) 9.08-9.41 (M, 1 h), 7351 (S, 1H), 4.48 (s, 2H), 3.63-3.83 (m, 2H), 2.59-2.76 (m, 2H), 1.47 (s, 9H). LCMS: 224 [M+1].

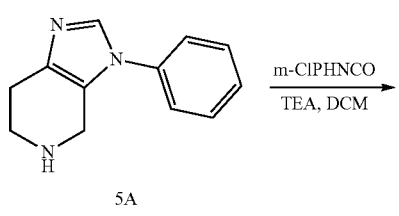

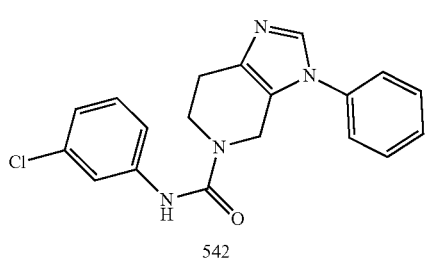

Step 3: Preparation of Compounds 4A and 4B

To a mixture of tert-butyl 3,4,6,7-tetrahydroimidazo[4,5-c]pyridine-5-carboxylate (300.00 mg, 1.34 mmol, 1.00 eq) and iodobenzene (356.36 mg, 1.75 mmol, 1.30 eq) in dioxane (3.00 mL) was added $K_3PO_4$ (570.44 mg, 2.69 mmol, 2.00 eq), CuI (51.18 mg, 268.73 umol, 0.20 eq) and N,N'-dimethylethane-1,2-diamine (236.89 mg, 2.69 mmol, 2.00 eq) in one portion under $N_2$. The mixture was stirred at 110° C. for 16 hours. LCMS showed the reaction was completed. The mixture was poured into water (20 mL) and stirred for 2 min. The aqueous phase was extracted with ethyl acetate (20 mL*2). The combined organic phase was washed with brine (20 mL*2), dried with anhydrous $Na_2SO_4$, filtered and concentrated in vacuum. The residue was purified by silica gel chromatography (Petroleum ether/ Ethyl acetate=4/1) to afford tert-butyl 3-phenyl-6,7-dihydro-4H-imidazo[4,5-c]pyridine-5-carboxylate (32.00 mg, 106.89 umol, 7.98% yield) as yellow oil and tert-butyl 1-phenyl-6,7-dihydro-4H-imidazo[4,5-c]pyridine-5-carboxylate (46.00 mg, 153.66 umol, 11.47% yield) as yellow oil.

Compound 4A: $^1$H NMR (400 MHz, METHANOL-$d_4$) 7.80 (s, 1H), 7.57 (s, 2H), 7.48-7.52 (m, 1H), 7.44 (d, J=1.25 Hz, 2H), 4.47 (s, 2H), 3.74-3.80 (m, 2H), 2.66-2.74 (m, 2H), 1.39-1.49 (m, 9H). LCMS: 300 [M+1].

Compound 4B: $^1$H NMR (400 MHz, METHANOL-$d_4$) 7.82 (s, 1H), 7.55 (s, 2H), 7.43 (s, 3H), 4.44-4.53 (m, 2H), 3.69-3.77 (m, 2H), 2.62-2.73 (m, 2H), 1.50 (s, 9H). LCMS: 300 [M+1].

Step 4a: Preparation of Compound 5A

To a mixture of tert-butyl 3-phenyl-6,7-dihydro-4H-imidazo[4,5-c]pyridine-5-carboxylate (30.00 mg, 100.21 umol, 1.00 eq) in dioxane (2.00 mL) was added HCl/dioxane (4 M, 4.00 mL, 159.66 eq) in one portion under $N_2$. The mixture was stirred at 15° C. for 1 hour. TLC (Ethyl acetate: Petroleum ether=1:1) showed the reaction was completed. The mixture was concentrated in vacuum to afford 3-phenyl-4,5,6,7-tetrahydroimidazo[4,5-c]pyridine (23.62 mg, 100.21 umol, 100.00% yield, HCl) as yellow solid.

Step 5a: Preparation of Compound 542

To a mixture of 3-phenyl-4,5,6,7-tetrahydroimidazo[4,5-c]pyridine (23.62 mg, 100.21 umol, 1.00 eq, HCl) and TEA (30.42 mg, 300.62 umol, 3.00 eq) in DCM (4.00 mL) was added 1-chloro-3-isocyanato-benzene (15.39 mg, 100.21 umol, 1.00 eq) in one portion at 15° C. under $N_2$. The mixture was stirred at 15° C. for 1 hours. LCMS showed the reaction was completed. The mixture was poured into water (10 mL) and stirred for 2 min. The aqueous phase was extracted with DCM (10 mL*2). The combined organic phase was washed with brine (10 mL*2), dried with anhydrous $Na_2SO_4$, filtered and concentrated in vacuum. The residue was purified by prep-HPLC(FA) to afford N-(3-chlorophenyl)-3-phenyl-6,7-dihydro-4H-imidazo [4,5-c] pyridine-5-carboxamide (17.00 mg, 47.36 umol, 47.26% yield, 98.3% purity) as white solid. $^1$H NMR (400 MHz, METHANOL-$d_4$) δ 7.82-7.91 (m, 1H), 7.55-7.62 (m, 3H), 7.49 (d, J=1.63 Hz, 6H), 7.18-7.29 (m, 3H), 6.96-7.03 (m, 1H), 4.61 (s, 2H), 3.89 (s, 2H), 2.81 (br. s., 2H). LCMS: 353 [M+1].

Step 4b: Preparation of Compound 5B

To a mixture of tert-butyl 1-phenyl-6,7-dihydro-4H-imidazo[4,5-c]pyridine-5-carboxylate (36.00 mg, 120.25 umol, 1.00 eq) in dioxane (2.00 mL) was added HCl/dioxane (4 M, 2.00 mL, 66.53 eq) in one portion under $N_2$. The mixture was stirred at 15° C. for 30 min. TLC (Ethyl acetate: Petroleum ether=2:1) showed the reaction was completed. The mixture was concentrated in vacuum to afford 1-phenyl-4,5,6,7-tetrahydroimidazo[4,5-c]pyridine (28.34 mg, 120.23 umol, 100.00% yield, HCl) as yellow solid.

Step 5b: Preparation of Compound 583

To a mixture of 1-phenyl-4,5,6,7-tetrahydroimidazo[4,5-c]pyridine (28.34 mg, 120.23 umol, 1.00 eq, HCl) and TEA (36.50 mg, 360.69 umol, 3.00 eq) in DCM (2.00 mL) was added 1-chloro-3-isocyanato-benzene (18.46 mg, 120.23 umol, 1.00 eq) in one portion at 15° C. under $N_2$. The mixture was stirred at 15° C. for 30 min. LCMS showed the reaction was completed. The mixture was poured into water (10 mL) and stirred for 2 min. The aqueous phase was extracted with DCM (10 mL*2). The combined organic phase was washed with brine (10 mL*2), dried with anhydrous $Na_2SO_4$, filtered and concentrated in vacuum. The residue was purified by prep-HPLC (FA) to afford N-(3-chlorophenyl)-1-phenyl-6,7-dihydro-4H-imidazo [4,5-c] pyridine-5-carboxamide (24.00 mg, 64.35 umol, 53.52% yield, 94.6% purity) as white solid. $^1$H NMR (400 MHz, METHANOL-$d_4$) 8.34-8.38 (m, 1H), 7.60 (d, J=7.65 Hz, 1H), 7.48-7.57 (m, 4H), 7.25 (s, 1H), 7.00-7.05 (m, 1H), 4.68 (s, 2H), 3.87 (t, J=5.52 Hz, 2H), 2.80 (t, J=5.21 Hz, 2H). LCMS: 353 [M+1].

Example 40: Preparation of Compound 576

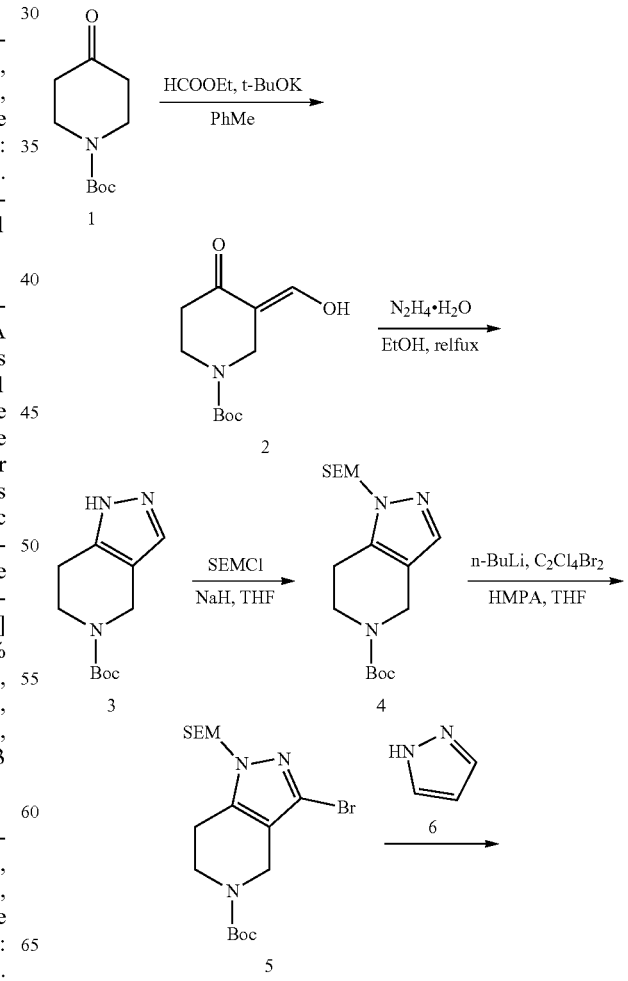

-continued

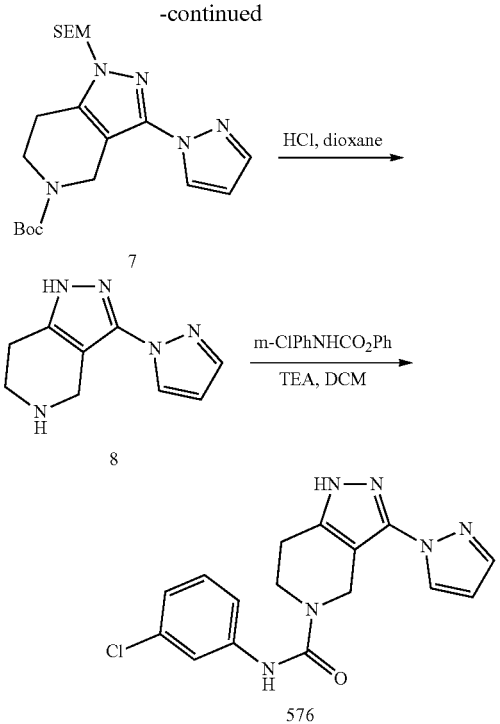

Step 1: Preparation of Compound 2

A mixture of tert-butyl 4-oxopiperidine-1-carboxylate (60.00 g, 301.13 mmol, 1.00 eq) in toluene (600.00 mL) was added t-BuOK (50.68 g, 451.70 mmol, 1.50 eq) at 0° C. under $N_2$. The mixture was stirred at 0° C. for 30 min. Then ethyl formate (33.46 g, 451.70 mmol, 1.50 eq) was added at 0° C., and the mixture was stirred at 15° C. for 16 hr under $N_2$ atmosphere. TLC showed the reaction was completed. The mixture was poured into ice-water (600 mL), extracted with EA (300 mL*2), the combined organic layer was washed with 10% NaOH (300 mL), the combined aqueous layer was adjust pH to 4 by 1N HCl, then the aqueous layer was extracted with EA (600*3), the combined organic layer was dried with anhydrous $Na_2SO_4$, filtered and concentrated in vacuum to give tert-butyl (3E)-3-(hydroxymethylene)-4-oxo-piperidine-1-carboxylate (70.60 g, crude) as a yellow oil and used directly in the next step.

Step 2: Preparation of Compound 3

A mixture of tert-butyl (3E)-3-(hydroxymethylene)-4-oxo-piperidine-1-carboxylate (70.00 g, 308.02 mmol, 1.00 eq), $NH_2NH_2\cdot H_2O$ (36.28 g, 616.04 mmol, 2.00 eq) in EtOH (700.00 mL) was degassed and purged with $N_2$ for 3 times, and then the mixture was stirred at 90° C. for 5 hour under $N_2$ atmosphere. LCMS showed the reaction was completed. The mixture was poured into HCl (0.5 N, 700 mL) and stirred at 5 min. The aqueous phase was extracted with ethyl acetate (300 mL*3). The combined organic phase was washed with brine (700 mL*2), dried with anhydrous $Na_2SO_4$, filtered and concentrated in vacuum to give tert-butyl 1,4,6,7-tetrahydropyrazolo[4,3-c]pyridine-5-carboxylate (65.00 g, 291.13 mmol, 94.52% yield) as a yellow oil, which was used directly for next step. LCMS: 224 [M+1].

Step 3: Preparation of Compound 4

To a mixture of NaH (16.12 g, 403.10 mmol, 60% purity, 1.50 eq) in THF (750 mL) was added a solution of tert-butyl 1,4,6,7-tetrahydropyrazolo[4,3-c]pyridine-5-carboxylate (60.00 g, 268.73 mmol, 1.00 eq) in THF (50 mL) dropwise at 0° C. under $N_2$. The mixture was stirred at 0° C. for 30 min. Then SEM-Cl (58.24 g, 349.35 mmol, 61.96 mL, 1.30 eq) was added to the mixture dropwise at 0° C. under $N_2$. The mixture was stirred at 15° C. for 2.5 hr under $N_2$ atmosphere. TLC showed the reaction was completed. The mixture was poured into ice-water (800 mL) and stirred at 5 min. The aqueous phase was extracted with ethyl acetate (500 mL*3). The combined organic phase was washed with brine (800 mL*2), dried with anhydrous $Na_2SO_4$, filtered and concentrated in vacuum. The residue was purified by column chromatography ($SiO_2$, Petroleum ether/Ethyl acetate=100/1 to 20/1) to give tert-butyl 1-(2-trimethylsilylethoxymethyl)-6,7-dihydro-4H-pyrazolo[4,3-c]pyri dine-5-carboxylate (72.00 g, 203.66 mmol, 75.79% yield) as a white oil. $^1$H NMR (400 MHz, CHLOROFORM-d) ppm 7.32 (s, 1H), 5.32-5.41 (m, 2H), 4.40-4.53 (m, 2H), 3.67-3.78 (m, 2H), 3.52-3.65 (m, 2H), 2.72-2.81 (m, 2H), 1.48 (s, 9H), 0.87-0.92 (m, 2H), −0.02 (d, J=5.52 Hz, 9H).

Step 4: Preparation of Compound 5

A mixture of tert-butyl 1-(2-trimethylsilylethoxymethyl)-6,7-dihydro-4H-pyrazolo [4,3-c]pyridine-5-carboxylate (20.00 g, 56.57 mmol, 1.00 eq) and HMPA (25.34 g, 141.42 mmol, 24.84 mL, 2.50 eq) in THF (200.00 mL) at −78° C., then n-BuLi (2.5 M, 33.94 mL, 1.50 eq) was added in one portion at −78° C. under $N_2$. The mixture was stirred at −78° C. for 0.5 hr under $N_2$. Then 1,2-dibromo-1,1,2,2-tetrachloro-ethane (36.84 g, 113.14 mmol, 13.59 mL, 2.00 eq) was added in one portion at −78° C. under $N_2$. The mixture was stirred at 15° C. for 2.5 hr under $N_2$ atmosphere. TLC showed the reaction was completed. The mixture was poured into ice-water (300 mL) and stirred at 5 min. The aqueous phase was extracted with ethyl acetate (100 mL*3). The combined organic phase was washed with brine (300 mL*2), dried with anhydrous $Na_2SO_4$, filtered and concentrated in vacuum. The residue was purified by column chromatography ($SiO_2$, Petroleum ether/Ethyl acetate=100/1 to 30/1) to give tert-butyl 3-bromo-1-(2-trimethylsilylethoxymethyl)-6,7-dihydro-4H-pyrazolo [4,3-c]pyridine-5-carboxylate (8.30 g, 19.19 mmol, 33.93% yield) as a yellow oil. $^1$H NMR (300 MHz, CHLOROFORM-d) ppm 5.40-5.42 (m, 1H), 5.38 (s, 1H), 4.27-4.42 (m, 2H), 3.55-3.71 (m, 4H), 2.66-2.78 (m, 2H), 1.47 (s, 9H), 0.91 (s, 2H), −0.03 (s, 9H).

Step 5: Preparation of Compound 7

To a mixture of tert-butyl 3-bromo-1-(2-trimethylsilylethoxymethyl)-6,7-dihydro-4H-pyrazolo[4,3-c]pyridine-5-carboxylate (100.00 mg, 231.25 umol, 1.00 eq) and 1H-pyrazole (23.62 mg, 346.88 umol, 1.50 eq) in DMF (2.00 mL) was added $Bu_4NCuI_2$ (25.89 mg, 46.25 umol, 0.20 eq), (1S,2S)—N1,N2-dimethylcyclohexane-1,2-diamine (6.58 mg, 46.25 umol, 0.20 eq) and t-BuOK (77.85 mg, 693.75 umol, 3.00 eq) in one portion under $N_2$. The mixture was stirred at 100° C. for 16 hours. TLC (Petroleum ether:Ethyl acetate=3:1) showed the desired product was detected. The mixture was poured into water (10 mL) and stirred for 2 min. The aqueous phase was extracted with ethyl acetate (15 mL*2). The combined organic phase was washed with brine (10 mL*2), dried with anhydrous $Na_2SO_4$, filtered and concentrated in vacuum to afford tert-butyl 3-pyrazol-1-yl-1-(2-trimethylsilylethoxymethyl)-6,7-dihydro-4H-pyrazolo[4,3-c]pyridine-5-carboxylate (60.00 mg, crude) as yellow oil. LCMS: 420 [M+1].

Step 6: Preparation of Compound 8

To a mixture of tert-butyl 3-pyrazol-1-yl-1-(2-trimethylsilylethoxymethyl)-6,7-dihydro-4H-pyrazolo[4,3-c]pyridine-5-carboxylate (20.00 mg, 47.67 umol, 1.00 eq) in dioxane (1.00 mL) was added HCl/dioxane (4 M, 4.00 mL, 335.64 eq). The mixture was stirred at 20° C. for 2 hours. TLC (Petroleum ether:Ethyl acetate=3:1) showed the reaction was completed. The mixture was concentrated in vacuum to afford 3-pyrazol-1-yl-4,5,6,7-tetrahydro-1H-pyrazolo[4,3-c]pyridine (10.76 mg, 47.68 umol, 100.00% yield, HCl) as yellow solid.

Preparation of Compound 576

To a mixture of 3-(1-bicyclo[3.1.0]hexanyl)-4,5,6,7-tetrahydro-H-pyrazolo[4,3-c] pyridine (15.80 mg, 65.90 umol, 1.00 eq, HCl) and TEA (20.01 mg, 197.70 umol, 3.00 eq) in DCM (2.00 mL) was added 1-chloro-3-isocyanato-benzene (9.11 mg, 59.31 umol, 0.90 eq) in one portion at 15° C. under $N_2$. The mixture was stirred at 15° C. for 30 min. LCMS showed the reaction was completed. The mixture was poured into water (10 mL) and stirred for 2 min. The aqueous phase was extracted with DCM (10 mL*2). The combined organic phase was washed with brine (10 mL*2), dried with anhydrous $Na_2SO_4$, filtered and concentrated in vacuum. The residue was purified by prep-HPLC (FA) to afford 3-(1-bicyclo[3.1.0]hexanyl)-N-(3-chlorophenyl)-1,4,6,7-tetrahydropyrazolo [4,3-c]pyridine-5-carboxamide (10.00 mg, 26.90 umol, 40.82% yield, 96.0% purity) as white solid. $^1$H NMR (400 MHz, METHANOL-d4) ppm 8.08-8.18 (m, 1H), 7.70-7.75 (m, 1H), 7.50-7.56 (m, 1H), 7.18-7.34 (m, 2H), 6.96-7.04 (m, 1H), 6.44-6.52 (m, 1H), 4.77 (s, 2H), 3.86 (t, J=5.71 Hz, 2H), 2.86 (t, J=5.65 Hz, 2H). LCMS: 343/345[M+1].

Example 41: Preparation of Compound 751

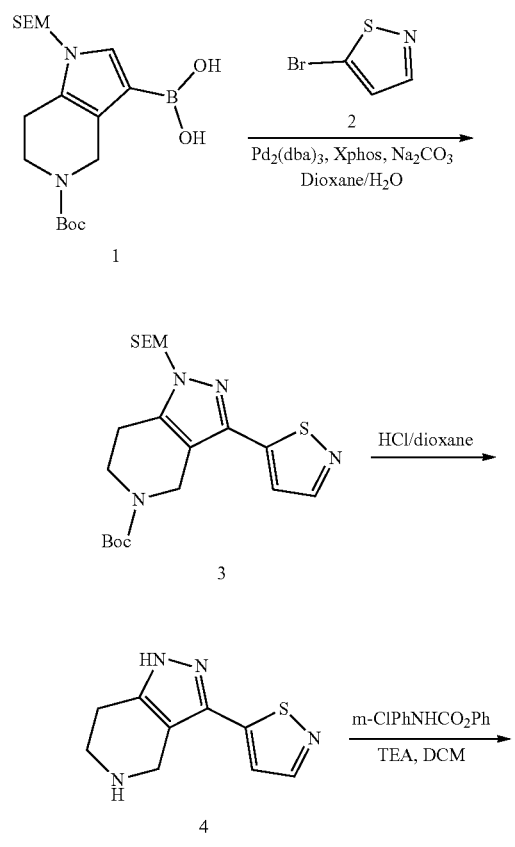

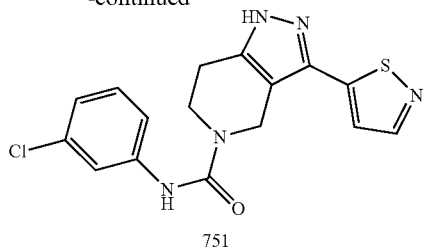

751

Step 1: Preparation of Compound 3

A mixture of [5-tert-butoxycarbonyl-1-(2-trimethylsilylethoxymethyl)-6,7-dihydro-4H-pyrazolo[4,3-c]pyridin-3-yl]boronic acid (120.00 mg, 302.00 umol, 1.00 eq), 5-bromoisothiazole (59.44 mg, 362.40 umol, 1.20 eq), XPhos (14.40 mg, 30.20 umol, 0.10 eq), $Pd_2(dba)_3$ (13.83 mg, 15.10 umol, 0.05 eq) and $Na_2CO_3$ (80.02 mg, 755.00 umol, 2.50 eq) in dioxane (4.00 mL) and $H_2O$ (500.00 uL) was degassed and purged with $N_2$ for 3 times, and then the mixture was stirred at 105° C. for 1 hour under $N_2$ atmosphere. LCMS showed the reaction was completed. The mixture was poured into water (10 mL) and stirred at 5 min. The aqueous phase was extracted with ethyl acetate (5 mL*3). The combined organic phase was washed with brine (10 mL*2), dried with anhydrous $Na_2SO_4$, filtered and concentrated in vacuum. The residue was purified by Prep-TLC (PE/EA=5/1) to give tert-butyl 3-isothiazol-5-yl-1-(2-trimethylsilylethoxymethyl)-6,7-dihydro-4H-pyrazolo [4,3-c]pyridine-5-carboxylate (29.00 mg, 46.49 umol, 15.39% yield, 70% purity) as a white solid. LCMS: 437[M+1].

Step 2: Preparation of Compound 4

A mixture of tert-butyl3-isothiazol-5-yl-1-(2-trimethylsilylethoxymethyl)-6,7-dihydro-4H-pyrazolo[4,3-c]pyridine-5-carboxylate (29.00 mg, 66.42 umol, 1.00 eq) in HCl/dioxane (4 M, 5.00 mL, 301.11 eq), and then the mixture was stirred at 15° C. for 0.5 hour. TLC showed the reaction was completed. The mixture was concentrated in vacuum to give 5-(4,5,6,7-tetrahydro-1H-pyrazolo[4,3-c]pyridin-3-yl)isothiazole (14.00 mg, 57.68 umol, 86.84% yield, HCl) as a white solid, which was used directly for next step.

Preparation of Compound 751

A mixture of 5-(4,5,6,7-tetrahydro-1H-pyrazolo[4,3-c]pyridin-3-yl)isothiazole (14.00 mg, 57.68 umol, 1.00 eq, HCl), phenyl N-(3-chlorophenyl)carbamate (12.86 mg, 51.91 umol, 0.90 eq), TEA (8.75 mg, 86.52 umol, 11.99 uL, 1.50 eq) in DCM (3.00 mL) was degassed and purged with $N_2$ for 3 times, and then the mixture was stirred at 15° C. for 16 hour under $N_2$ atmosphere. LCMS showed the reaction was completed. The mixture was poured into water (10 mL) and stirred at 5 min. The aqueous phase was extracted with DCM (5 mL*3). The combined organic phase was washed with brine (10 mL*2), dried with anhydrous $Na_2SO_4$, filtered and concentrated in vacuum. The residue was purified by Prep-HPLC (FA) to give N-(3-chlorophenyl)-3-isothiazol-5-yl-1,4,6,7-tetrahydropyrazolo[4,3-c]pyridine-5-carboxamide (11.10 mg, 30.85 umol, 53.48% yield) as a white solid. $^1$H NMR (400 MHz, METHANOL-d4) ppm 8.50-8.54 (m, 1H), 7.51-7.57 (m, 2H), 7.30 (dd, J=1.00, 2.01 Hz, 1H), 7.21-7.27 (m, 1H), 7.03 (s, 1H), 4.74 (s, 2H), 3.87 (t, J=5.71 Hz, 2H), 2.89 (t, J=5.71 Hz, 2H). LCMS: 360/362 [M+1].

Example 42: Preparation of Compound 569

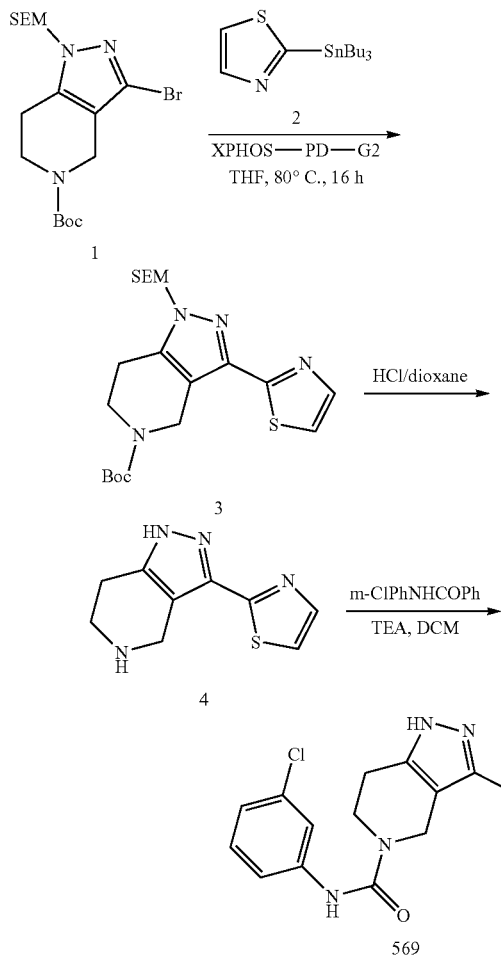

Step 1: Preparation of Compound 3

A solution of tert-butyl3-bromo-1-(2-trimethylsilylethoxymethyl)-6,7-dihydro-4H-pyrazolo[4,3-c]pyridine-5-carboxylate (200.00 mg, 462.50 umol, 1.00 eq) and tributyl (thiazol-2-yl)stannane (259.58 mg, 693.75 umol, 1.50 eq) in THF (10.00 mL) was added XPHOS-PD-G2 (36.39 mg, 46.25 umol, 0.10 eq). The mixture was stirred at 80° C. for 16 hr under $N_2$ protection. TLC (Peteoleum ether/ethyl acetate=5:1) showed material remained, and a new spot detected. The solvent was evaporated. The residue was purified by prep-TLC (Peteoleum ether/ethyl acetate=5:1) to afford a crude product. The crude product re-purified by prep-HPLC (FA) to afford tert-butyl 3-thiazol-2-yl-1-(2-trimethylsilylethoxymethyl)-6,7-dihydro-4H-pyrazolo [4,3-c]pyridine-5-carboxylate (40.00 mg, 43.97 umol, 9.51% yield, 48% purity) as colorless oil. $^1$H NMR (400 MHz, CDCl$_3$) δ 7.90-8.00 (m, 1H), 7.48 (d, J=3.01 Hz, 1H), 5.95 (s, 1H), 4.70 (brs, 2H), 3.77 (brs, 2H), 3.63-3.68 (m, 2H), 2.83 (d, J=5.27 Hz, 2H), 1.51 (s, 9H), 0.93 (d, J=8.28 Hz, 2H), −0.05 (s, 9H). LCMS: 437 [M+1].

Step 2: Preparation of Compound 4

A mixture of tert-butyl-3-thiazol-2-yl-1-(2-trimethylsilylethoxymethyl)-6,7-dihydro-4H-pyrazolo[4,3-c]pyridine-5-carboxylate (40.00 mg, 91.61 umol, 1.00 eq) and HCl/dioxane (4 M, 5.00 mL, 218.32 eq) was stirred at 25° C. for 2 hr. The solvent was evaporated to afford 2-(4,5,6,7-tetrahydro-1H-pyrazolo[4,3-c]pyridin-3-yl)thiazole (22.00 mg, 90.64 umol, 98.94% yield, HCl) as white solid, which was not purified and used directly in the next step.

Preparation of Compound 569

To a mixture of 2-(4,5,6,7-tetrahydro-1H-pyrazolo[4,3-c] pyridin-3-yl)thiazole (22.00 mg, 90.64 umol, 1.00 eq, HCl) and phenyl N-(3-chlorophenyl)carbamate (22.45 mg, 90.64 umol, 1.00 eq) in DCM (3.00 mL) was added TEA (18.34 mg, 181.28 umol, 25.12 uL, 2.00 eq). The mixture was stirred at 25° C. for 16 hr. LCMS showed the material was consumed completely, and major desired MS detected. The solvent was evaporated. The residue was purified by prep-HPLC (FA) to afford N-(3-chlorophenyl)-3-thiazol-2-yl-1,4,6,7-tetrahydropyrazolo[4,3-c] pyridine-5-carboxamide (14.41 mg, 40.05 umol, 44.18% yield, 100% purity) as white solid. $^1$H NMR (400 MHz, MeOD) δ 7.90 (d, J=2.51 Hz, 1H), 7.52-7.60 (m, 2H), 7.31-7.36 (m, 1H), 7.21-7.29 (m, 1H), 7.02 (d, J=8.03 Hz, 1H), 4.89-4.97 (m, 2H), 3.89 (t, J=5.65 Hz, 2H), 2.91 (t, J=5.65 Hz, 2H). LCMS: 360/362 [M+1].

Example 43: Preparation of Compound 726

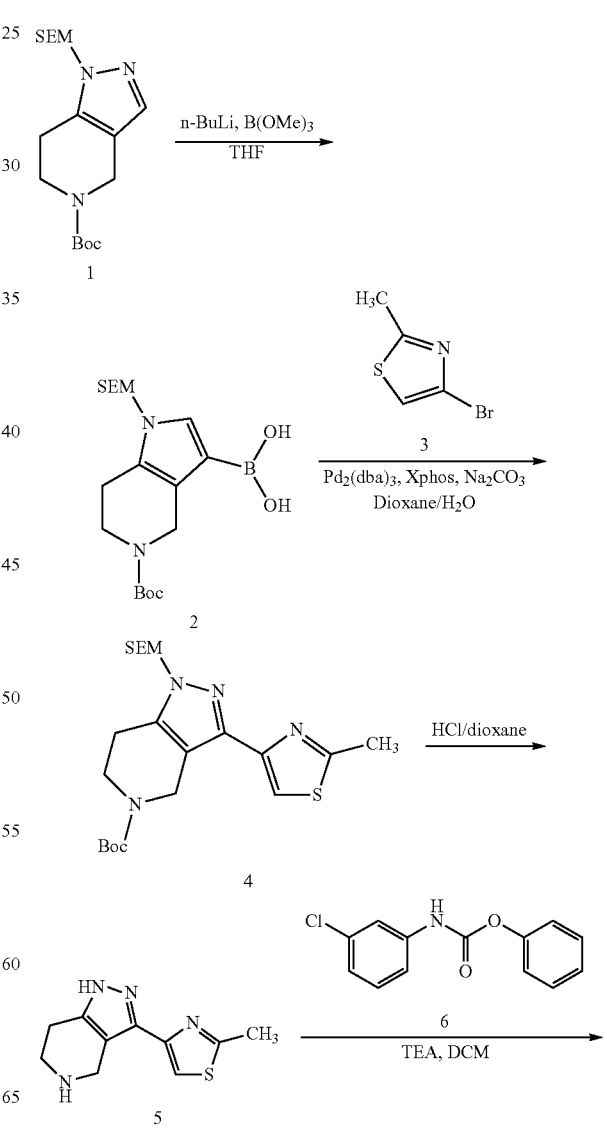

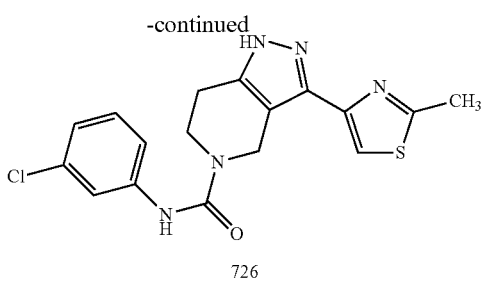

726

Step 1: Preparation of Compound 2

A mixture of tert-butyl 1-(2-trimethylsilylethoxymethyl)-6,7-dihydro-4H-pyrazolo [4,3-c]pyridine-5-carboxylate (5.70 g, 16.12 mmol, 1.00 eq) in THF (60.00 mL) at −78° C. under $N_2$. N-BuLi (2.5 M, 7.74 mL, 1.20 eq) was added in one portion at −78° C. under $N_2$. The mixture was stirred at −78° C. for 30 min. Then B(OMe)$_3$ (5.03 g, 48.36 mmol, 5.47 mL, 3.00 eq) was added in one portion at −78° C. under $N_2$. The mixture was stirred at 15° C. for 1.5 hr under $N_2$ atmosphere. LCMS showed the starting material/desired product=1/3. The mixture was poured into ice-NH$_4$Cl (aq. 80 mL) and stirred at 5 min. The aqueous phase was extracted with ethyl acetate (50 mL*3). The combined organic phase was washed with brine (80 mL*2), dried with anhydrous Na$_2$SO$_4$, filtered and concentrated in vacuum to give [5-tert-butoxycarbonyl-1-(2-trimethylsilylethoxymethyl)-6,7-dihydro-4H-pyrazolo[4,3-c]pyridin-3-yl]boronic acid (6.80 g, crude) was obtained as a yellow solid, which was used directly for next step. LCMS: 398[M+1].

Step 2: Preparation of Compound 4

[5-tert-butoxycarbonyl-1-(2-trimethylsilylethoxymethyl)-6,7-dihydro-4H-pyrazolo[4,3-c]pyridin-3-yl]boronic acid (120.00 mg, 302.00 umol, 1.00 eq), 4-bromo-2-methyl-thiazole (64.53 mg, 362.40 umol, 1.20 eq), Pd$_2$(dba)$_3$ (13.83 mg, 15.10 umol, 0.05 eq), XPhos (14.40 mg, 30.20 umol, 0.10 eq) and Na$_2$CO$_3$ (80.02 mg, 755.00 umol, 2.50 eq) were taken up into a microwave tube in dioxane (4.00 mL) and H$_2$O (500.00 uL) was degassed and purged with N$_2$ for 3 times. The sealed tube was heated at 105° C. for 1 hr under microwave. LCMS showed the reaction was completed. The mixture was poured into water (10 mL) and stirred at 5 min. The aqueous phase was extracted with ethyl acetate (5 mL*3). The combined organic phase was washed with brine (10 mL*2), dried with anhydrous Na$_2$SO$_4$, filtered and concentrated in vacuum. The residue was purified by Prep-TLC (PE/EA=5/1) to give tert-butyl3-(2-methylthiazol-4-yl)-1-(2-trimethylsilylethoxymethyl)-6,7-dihydro-4H-pyrazolo[4,3-c]pyridine-5-carboxylate (34.00 mg, 75.44 umol, 24.98% yield) as a light yellow solid. LCMS: 451[M+1].

Step 3: Preparation of Compound 5

A mixture of tert-butyl3-(2-methylthiazol-4-yl)-1-(2-trimethylsilylethoxy methyl)-6,7-dihydro-4H-pyrazolo[4,3-c]pyridine-5-carboxylate (34.00 mg, 75.44 umol, 1.00 eq) in HCl/dioxane (4 M, 2.00 mL, 106.04 eq), and then the mixture was stirred at 20° C. for 15 min. TLC showed the reaction was completed. The mixture was concentrated in vacuum to give 2-methyl-4-(4,5,6,7-tetrahydro-1H-pyrazolo[4,3-c]pyridin-3-yl)thiazole (15.00 mg, 58.42 umol, 77.44% yield, HCl) as a white solid, which was used directly for next step.

Preparation of Compound 726

A mixture of 2-methyl-4-(4,5,6,7-tetrahydro-1H-pyrazolo[4,3-c]pyridin-3-yl)thiazole (15.00 mg, 58.42 umol, 1.00 eq, HCl), phenyl N-(3-chlorophenyl)carbamate (13.02 mg, 52.58 umol, 0.90 eq), TEA (8.87 mg, 87.63 umol, 12.15 uL, 1.50 eq) in DCM (3.00 mL) was degassed and purged with N$_2$ for 3 times, and then the mixture was stirred at 20° C. for 16 hour under N$_2$ atmosphere. LCMS showed the reaction was completed. The mixture was poured into water (10 mL) and stirred at 5 min. The aqueous phase was extracted with DCM (5 mL*3). The combined organic phase was washed with brine (10 mL*2), dried with anhydrous Na$_2$SO$_4$, filtered and concentrated in vacuum. The residue was purified by prep-HPLC (FA) to give N-(3-chlorophenyl)-3-(2-methylthiazol-4-yl)-1,4,6,7-tetrahydropyrazolo[4,3-c]pyridine-5-carboxamide (12.00 mg, 31.84 umol, 54.50% yield, 99.2% purity) as a white solid. $^1$H NMR (400 MHz, METHANOL-d$_4$) ppm 7.54 (s, 1H), 7.28-7.33 (m, 1H), 7.20-7.26 (m, 1H), 6.98-7.03 (m, 1H), 4.80 (s, 2H), 3.83-3.88 (m, 2H), 2.84-2.89 (m, 2H), 2.76 (s, 3H). LCMS: 374/376[M+1].

Example 44: Preparation of Compound 730

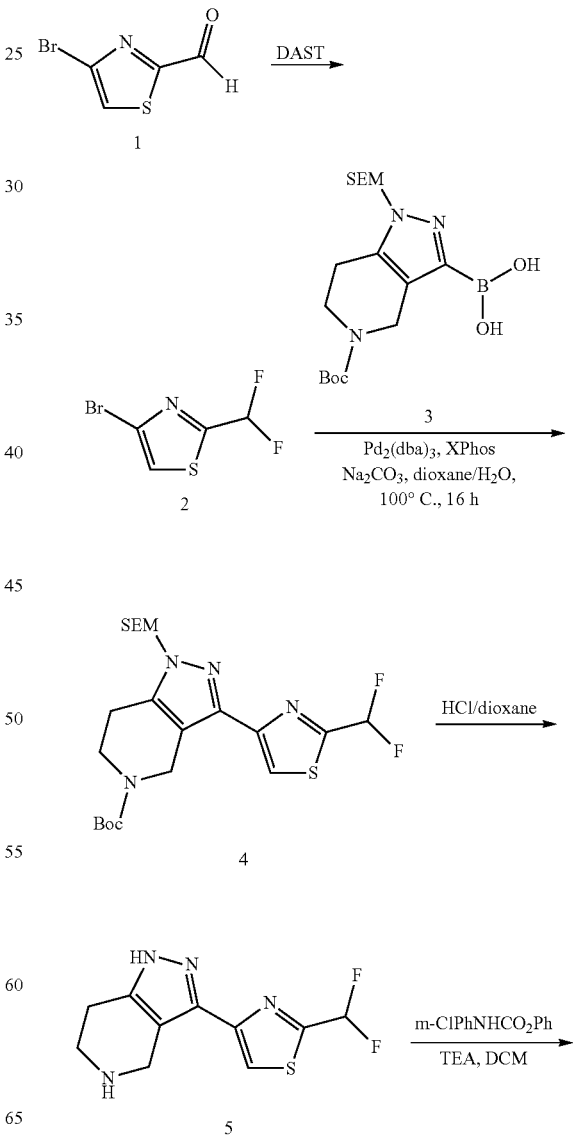

-continued

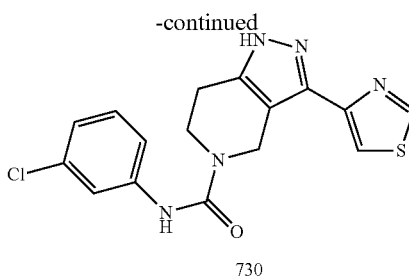

730

Step 1: Preparation of Compound 2

To a solution of 4-bromothiazole-2-carbaldehyde (500.00 mg, 2.60 mmol, 1.00 eq) in DCM (10.00 mL) was added DAST (838.19 mg, 5.20 mmol, 687.04 uL, 2.00 eq) at −78° C. dropwise under $N_2$ protection. The mixture was stirred at 25° C. for 16 hr. TLC (Petroleum ether/ethyl acetate=10:1) showed material was consumed completely, and a new spot detected. The mixture was poured into water (10 mL), extracted with ethyl acetate (10 mL*2), the combined organic layer was dried over anhydrous $Na_2SO_4$, concentrated. The residue was purified by chromatography (silica gel, eluting with Petroleum ether/ethyl acetate=100:1) to afford 4-bromo-2-(difluoromethyl)thiazole (300.00 mg, 1.40 mmol, 53.91% yield) as light yellow oil. $^1H$ NMR (400 MHz, $CDCl_3$) δ 7.38 (s, 1H), 6.75 (t, J=52.00 Hz, 1H).

Step 2: Preparation of Compound 4

To a solution of 4-bromo-2-(difluoromethyl)thiazole (300.00 mg, 1.40 mmol, 1.00 eq) and [5-tert-butoxycarbonyl-1-(2-trimethylsilylethoxymethyl)-6,7-dihydro-H-pyrazolo[4,3-c]pyridin-3-yl]boronic acid (556.29 mg, 1.40 mmol, 1.00 eq) in dioxane (10.00 mL) were added $Pd_2(dba)_3$ (64.10 mg, 70.00 umol, 0.05 eq), XPhos (66.74 mg, 140.00 umol, 0.10 eq) and $Na_2CO_3$ (296.77 mg, 2.80 mmol, 2.00 eq). The mixture was stirred at 100° C. for 16 hr under $N_2$ protection. LCMS showed material was consumed completely, and desired MS detected. TLC (Petroleum ether/ ethyl acetate=10:1) showed a major product. The solvent was evaporated. The residue was purified by chromatography (silica gel, eluting with Petroleum ether/ethyl acetate=10:1) to afford tert-butyl3-[2-(difluoromethyl)thiazol-4-yl]-1-(2-trimethylsilyl ethoxymethyl)-6,7-dihydro-4H-pyrazolo [4,3-c]pyridine-5-carboxylate (196.00 mg, 237.62 umol, 16.97% yield, 59% purity) as light yellow oil. $^1H$ NMR (400 MHz, $CDCl_3$) δ 7.98 (s, 1H), 7.34 (s, 1H), 6.74-7.06 (m, 1H), 5.62 (s, 1H), 5.38 (s, 1H), 4.70 (brs, 1H), 4.45 (brs, 1H), 3.66-3.78 (m, 3H), 3.52-3.61 (m, 1H), 2.80 (d, J=17.07 Hz, 2H), 1.45-1.56 (m, 9H), 0.86-1.00 (m, 2H), −0.04-0.06 (m, 9H). LCMS: 487 [M+1].

Step 3: Preparation of Compound 5

A mixture of tert-butyl 3-[2-(difluoromethyl)thiazol-4-yl]-1-(2-trimethylsilyl ethoxy methyl)-6,7-dihydro-4H-pyrazolo [4,3-c]pyridine-5-carboxylate (190.00 mg, 390.42 umol, 1.00 eq) and HCl/dioxane (4 M, 5.00 mL, 51.23 eq) was stirred at 25° C. for 1 hr. The solvent was evaporated to afford 2-(difluoromethyl)-4-(4,5,6,7-tetrahydro-1H-pyrazolo[4,3-c]pyridine-3-yl)thiazole (114.00 mg, 389.42 umol, 99.74% yield, HCl) as white solid, which was not purified and used directly in the next step.

Preparation of Compound 730

To a solution of 2-(difluoromethyl)-4-(4,5,6,7-tetrahydro-1H-pyrazolo[4,3-c]pyridine-3-yl)thiazole (114.00 mg, 389.42 umol, 1.00 eq, HCl) in DCM (4.00 mL) were added TEA (78.81 mg, 778.84 umol, 107.96 uL, 2.00 eq) and phenyl N-(3-chlorophenyl)carbamate (96.45 mg, 389.42 umol, 1.00 eq). The mixture was stirred at 25° C. for 16 hr. LCMS showed the material was consumed completely, and major desired MS detected. The solvent was evaporated. The residue was purified by prep-HPLC (FA) to afford N-(3-chlorophenyl)-3-[2-(difluoromethyl) thiazol-4-yl]-1,4,6,7-tetrahydropyrazolo[4,3-c]pyridine-5-carboxamide (29.83 mg, 72.09 umol, 18.51% yield, 99.04% purity) as white solid. $^1H$ NMR (400 MHz, MeOD) δ 7.94 (s, 1H), 7.49 (s, 1H), 7.26 (s, 1H), 6.92-7.23 (m, 3H), 4.74-4.81 (m, 2H), 3.83 (t, J=5.65 Hz, 2H), 2.85 (t, J=5.52 Hz, 2H). LCMS: 410/412 [M+1].

Example 45: Preparation of Compound 645

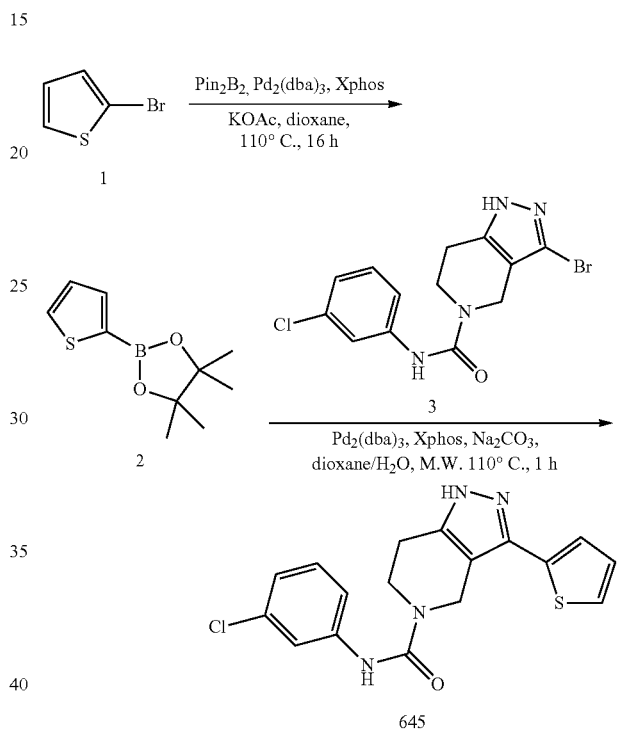

Step 1: Preparation of Compound 2

A mixture of 2-bromothiophene (400.00 mg, 2.45 mmol, 1.00 eq), 4,4,5,5-tetramethyl-2-(4,4,5,5-tetramethyl-1,3,2-dioxaborolan-2-yl)-1,3,2-dioxaborolane (933.23 mg, 3.68 mmol, 1.50 eq), AcOK (601.11 mg, 6.13 mmol, 2.50 eq), XPhos (116.80 mg, 245.00 umol, 0.10 eq) and $Pd_2(dba)_3$ (112.18 mg, 122.50 umol, 0.05 eq) in dioxane (10.00 mL) was heated to 110° C. under $N_2$ for 16 hrs. The reaction mixture was diluted with brine (60 mL) and extracted with EA (80 mL). The organic layer was dried over $Na_2SO_4$, filtered and concentrated under reduced pressure to give a brown residue. The residue was purified by silica gel column (PE/EA=100/1) to afford the desire product (420.00 mg, crude).

Preparation of Compound 645

A mixture of Compound 3 (60.00 mg, 168.72 umol, 1.00 eq), 4,4,5,5-tetramethyl-2-(2-thienyl)-1,3,2-dioxaborolane (120.00 mg, 571.16 umol, 3.39 eq), $Na_2CO_3$ (44.71 mg, 421.80 umol, 2.50 eq), XPhos (8.04 mg, 16.87 umol, 0.10 eq) and $Pd_2(dba)_3$ (7.72 mg, 8.44 umol, 0.05 eq) in dioxane (2.50 mL)/$H_2O$ (300.00 uL) was heated to 110° C. in microwave for 1 hr. The reaction mixture was diluted with brine (40 mL) and extracted with EA (40 mL). The organic layer was dried over $Na_2SO_4$, filtered and concentrated under reduced pressure to give a brown residue. The residue was purified by prep-HPLC (FA) to afford desire product (13.00 mg, 34.92 umol, 20.70% yield, 96.4% purity) as white solid. $^1$H NMR (400 MHz, METHANOL-$d_4$) δ 7.54-7.56 (m, 1H), 7.34-7.36 (m, 1H), 7.30-7.32 (m, 2H), 7.25-7.27 (m, 1H), 7.13-7.16 (m, 1H), 7.00-7.05 (m, 1H), 4.75 (s, 2H), 3.86-3.89 (m, 2H), 2.86-2.89 (m, 2H). LCMS: 359/361[M+1].

Example 46: Preparation of Compound 568

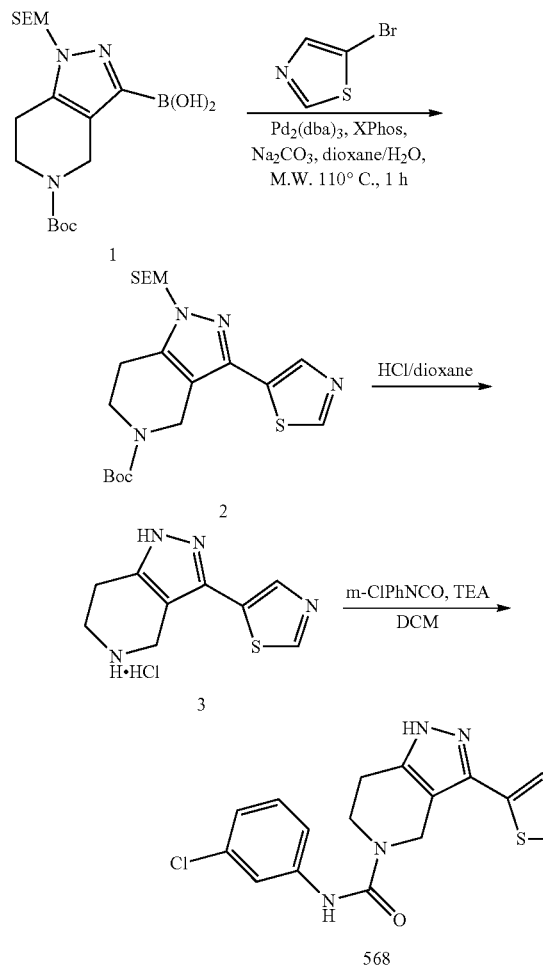

Step 1: Preparation of Compound 2

A mixture of Compound 1 (120.00 mg, 181.20 umol, 1.00 eq), 5-bromothiazole (35.66 mg, 217.44 umol, 1.20 eq), Na$_2$CO$_3$ (48.01 mg, 453.00 umol, 2.50 eq), XPhos (8.64 mg, 18.12 umol, 0.10 eq) and Pd$_2$(dba)$_3$ (8.30 mg, 9.06 umol, 0.05 eq) in dioxane (2.50 mL)/H$_2$O (500.00 uL) was heated to 110° C. in microwave for 1 hr. The mixture was diluted with EA (50 mL) and washed with brine (40 mL). The organic layer was dried over Na$_2$SO$_4$, filtered and concentrated under reduced pressure to give yellow oil. The yellow oil was purified by prep-TLC (EA/PE=2/3) to afford desire product (24.00 mg, 46.72 umol, 25.78% yield, 85% purity) as colorless oil. LCMS: 437 [M+1].

Step 2: Preparation of Compound 3

A mixture of Compound 2 (24.00 mg, 54.97 umol, 1.00 eq) in HCl/dioxane (4 M, 3.84 mL, 279.43 eq) was stirred at 18° C. for 0.5 hr. The mixture was concentrated under reduced pressure to give yellow residue to afford desire product (14.00 mg, crude, HCl) as yellow solid, which was used directly for the next step.

Preparation of Compound 568

To a solution of 5-(4,5,6,7-tetrahydro-1H-pyrazolo[4,3-c]pyridin-3-yl)thiazole (14.00 mg, 57.68 umol, 1.00 eq, HCl) and TEA (23.35 mg, 230.71 umol, 4.00 eq) in DCM (5.00 mL)/MeOH (500.00 uL) was added 1-chloro-3-isocyanatobenzene (7.97 mg, 51.91 umol, 0.90 eq) under N$_2$, and the mixture was stirred at 18° C. for 0.5 hr. The reaction mixture was diluted with DCM (30 mL) and washed with brine (30 mL). The organic layer was concentrated under reduced pressure to give yellow solid. The yellow solid was purified by prep-HPLC (FA) to afford desire product (8.00 mg, 21.57 umol, 37.39% yield, 97% purity) as white solid. $^1$H NMR (400 MHz, METHANOL-$d_4$) δ 9.00 (s, 1H), 8.12 (s, 1H), 7.55-7.56 (m, 1H), 7.23-7.34 (m, 2H), 7.02-7.04 (m, 1H), 4.76 (s, 2H), 3.88-3.90 (m, 2H), 2.88-2.91 (m, 2H). LCMS: 360/362 [M+1].

Example 47: Preparation of Compound 570

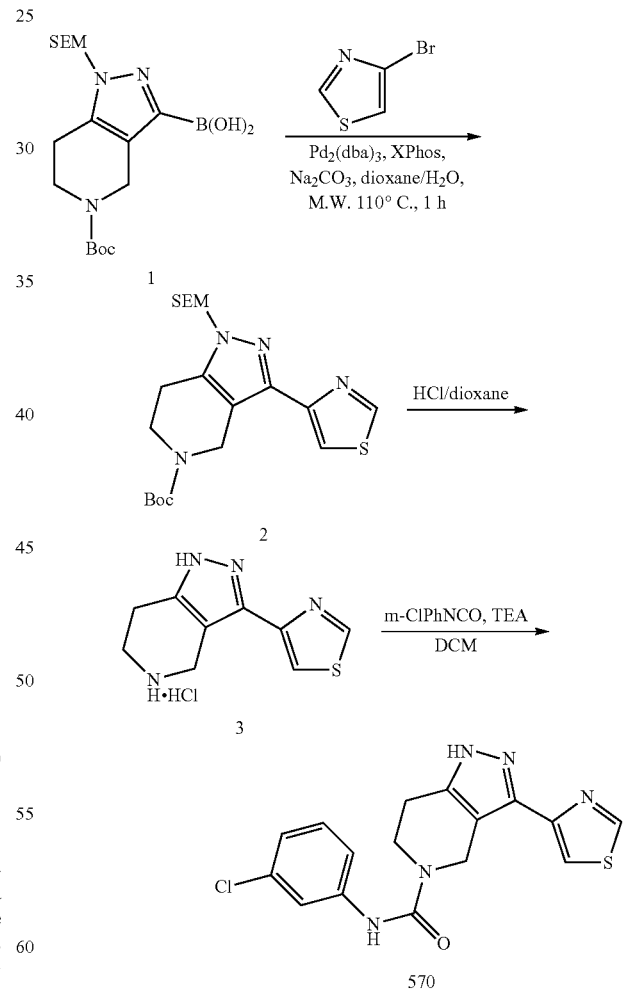

Step 1: Preparation of Compound 2

A mixture of Compound 1 (120.00 mg, 181.20 umol, 1.00 eq), 4-bromothiazole (35.66 mg, 217.44 umol, 1.20 eq), Na$_2$CO$_3$ (38.41 mg, 362.40 umol, 2.00 eq), XPhos (8.64 mg, 18.12 umol, 0.10 eq) and Pd₂(dba)₃ (8.30 mg, 9.06 umol, 0.05 eq) in dioxane (2.50 mL)/H₂O (500.00 uL) was heated to 110° C. in microwave for 1 hr. The mixture was diluted with EA (50 mL) and washed with brine (40 mL). The organic layer was dried over Na₂SO₄, filtered and concentrated under reduced pressure to give yellow oil. The yellow oil was purified by prep-TLC (EA/PE=2/3) to afford desire product (50.00 mg, 68.71 umol, 37.92% yield, 60% purity) as colorless oil. LCMS: 437[M+1].

Step 2: Preparation of Compound 3

A mixture of Compound 2 (50.00 mg, 114.51 umol, 1.00 eq) in HCl/dioxane (4 M, 6.67 mL, 232.86 eq) was stirred at 18° C. for 0.5 hr. The mixture was concentrated under reduced pressure to give yellow residue to afford desire product (28.00 mg, crude, HCl) as yellow solid, which was used directly for the next step.

Preparation of Compound 570

To a solution of 4-(4,5,6,7-tetrahydro-1H-pyrazolo[4,3-c]pyridin-3-yl)thiazole (28.00 mg, 115.35 umol, 1.00 eq, HCl) and TEA (46.69 mg, 461.42 umol, 4.00 eq) in DCM (5.00 mL) was added 1-chloro-3-isocyanato-benzene (15.94 mg, 103.82 umol, 0.90 eq) under N₂, and the mixture was stirred at 18° C. for 0.5 hr. The reaction mixture was diluted with DCM (30 mL) and washed with brine (30 mL). The organic layer was concentrated under reduced pressure to give yellow residue. The residue was purified by prep-HPLC (FA) to afford desire product (13.00 mg, 35.41 umol, 30.69% yield, 98% purity) as white solid. ¹H NMR (400 MHz, METHANOL-d₄) δ=9.09 (s, 1H), 7.82 (s, 1H), 7.55-7.56 (m, 1H), 7.32-7.33 (m, 1H), 7.23-7.27 (m, 1H), 7.03-7.04 (m, 1H), 4.86 (s, 2H), 3.87-3.90 (m, 2H), 2.88-2.91 (m, 2H). LCMS: 360/362[M+1].

Example 48: Preparation of Compound 729

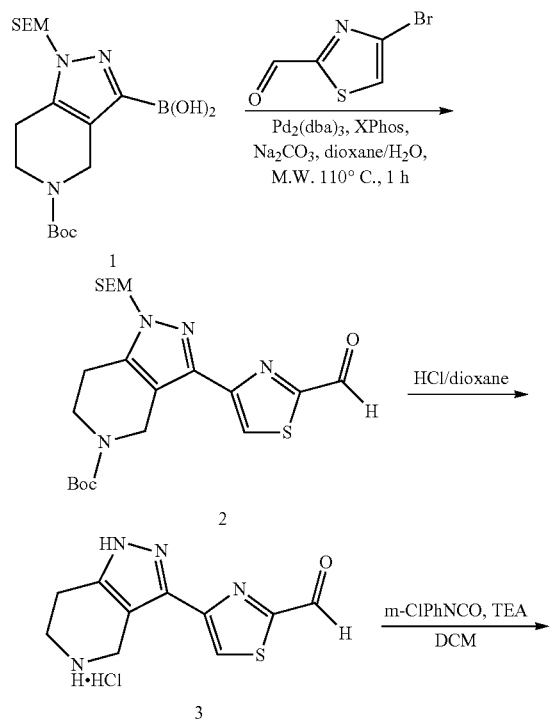

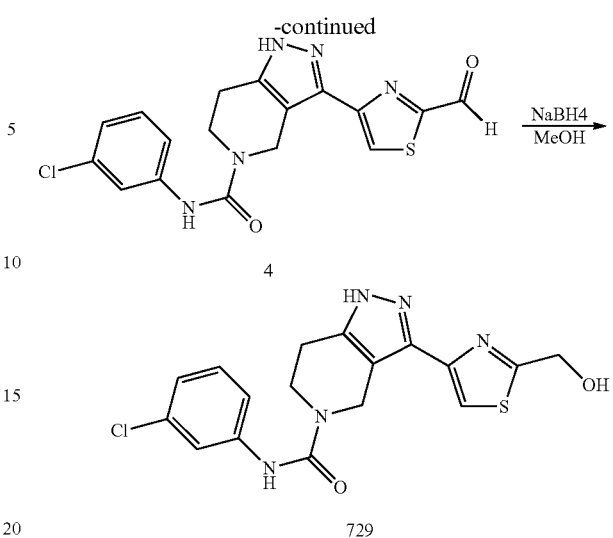

Step 1: Preparation of Compound 2

A mixture of Compound 1 (1.20 g, 1.81 mmol, 1.00 eq), 4-bromothiazole-2-carbaldehyde (347.57 mg, 1.81 mmol, 1.00 eq), Na₂CO₃ (479.60 mg, 4.52 mmol, 2.50 eq), XPhos (86.29 mg, 181.00 umol, 0.10 eq) and Pd₂(dba)₃ (82.87 mg, 90.50 umol, 0.05 eq) in dioxane (15.00 mL)/H₂O (2.00 mL) was heated to 110° C. in microwave for 1 hr. The mixture was filtered, the filtrated was diluted with EA (80 mL) and washed with brine (80 mL). The organic layer was dried over Na₂SO₄, filtered and concentrated under reduced pressure to give brown oil. The brown oil was purified by silica gel column (PE/EA=15/1) to afford desire product (724.00 mg, 856.99 umol, 47.35% yield, 55% purity) as colorless oil. LCMS: 465 [M+1].

Step 2: Preparation of Compound 3

A mixture of Compound 2 (100.00 mg, 118.37 umol, 1.00 eq) in HCl/dioxane (4 M, 4.00 mL, 135.17 eq) was stirred at 25° C. for 0.5 hr. The mixture was concentrated under reduced pressure to afford desire product (32.00 mg, 65.01 umol, 54.92% yield, 55% purity, HCl) as yellow solid, which was used directly for the next step.

Step 3: Preparation of Compound 4

To a solution of Compound 3 (32.00 mg, 65.01 umol, 1.00 eq, HCl) and TEA (19.73 mg, 195.03 umol, 27.03 uL, 3.00 eq) in DCM (5.00 mL)/MeOH (500.00 uL) was added 1-chloro-3-isocyanato-benzene (9.48 mg, 61.76 umol, 7.46 uL, 0.95 eq) under N₂, and the mixture was stirred at 25° C. for 0.5 hr. The reaction mixture was diluted with DCM (40 mL) and washed with brine (40 mL). The organic layer was concentrated under reduced pressure to give yellow residue. The residue was purified by prep-TLC (DCM/MeOH=12/1) to afford desire product (31.00 mg, 31.97 umol, 49.18% yield, 40% purity) as white solid. LCMS: 388/390[M+1].

Preparation of Compound 729

To a solution of Compound 4 (31.00 mg, 43.96 umol, 1.00 eq) in MeOH (2.00 mL) was added NaBH₄ (3.33 mg, 87.92 umol, 2.00 eq) and the mixture was stirred at 25° C. for 0.5 hr. The mixture was quenched with brine (30 mL) and extracted with EA (30 mL). The organic layer was dried over Na₂SO₄, filtered and the filtrate was concentrated under reduced pressure to give yellow residue. The residue was purified by prep-HPLC (FA) to afford desire product (10.00 mg, 25.14 umol, 57.19% yield, 98% purity) as white solid. ¹H NMR (400 MHz, METHANOL-d₄) δ 7.68 (s, 1H), 7.54-7.56 (m, 1H), 7.27-7.33 (m, 1H), 7.22-7.25 (m, 1H), 7.01-7.03 (m, 1H), 4.92 (s, 2H), 4.82 (s, 2H), 3.86-3.89 (m, 2H), 2.87-2.90 (m, 2H). LCMS: 390/392[M+1].

Example 49: Preparation of Compound 741

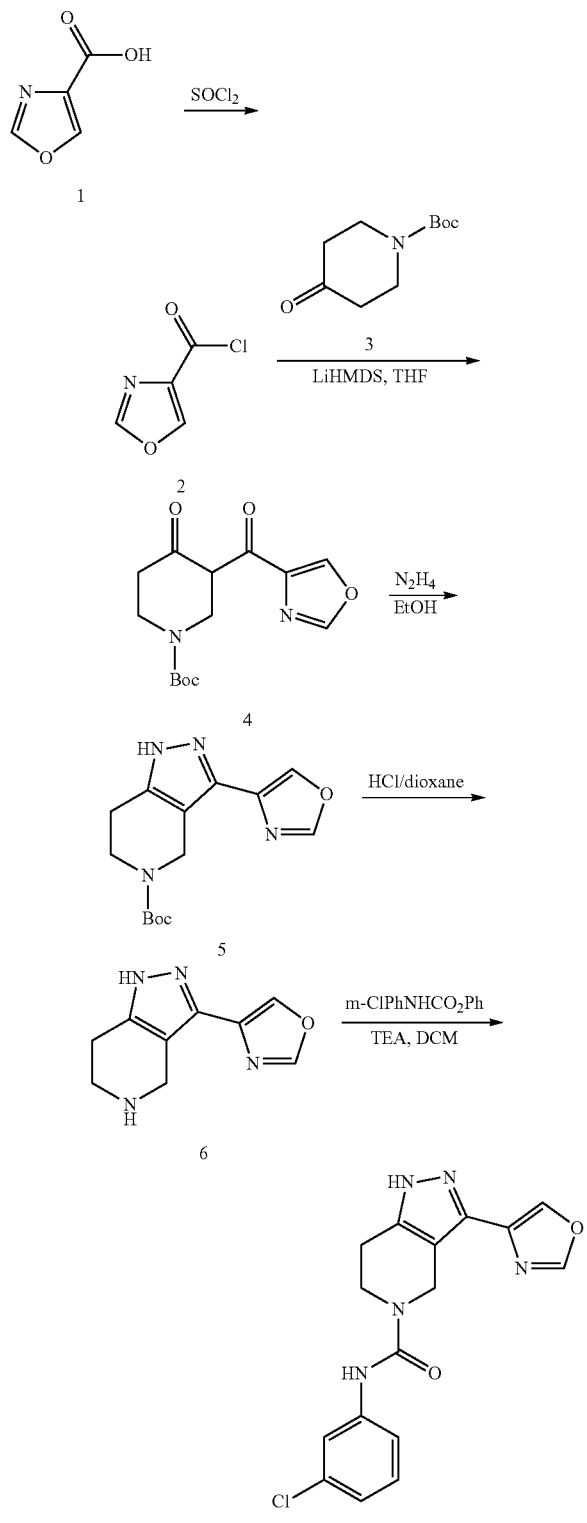

Step 1: Preparation of Compound 2

Oxazole-4-carboxylic acid (500.00 mg, 4.42 mmol, 1.00 eq) was added to $SOCl_2$ (10.00 mL), the reaction mixture was warmed to 70° C. and stirred at 70° C. for 2 hours. TLC indicated starting material was consumed completely. The solvent was evaporated. Compound oxazole-4-carbonyl chloride (570.00 mg, crude) was obtained as yellow oil. The crude product was used in the next step directly without purification.

Step 2: Preparation of Compound 4

Cooled the three-necked round bottom flask to −78° C., LiHMDS (1 M, 5.20 mL, 1.20 eq) was added under $N_2$, then a solution of tert-butyl 4-oxopiperidine-1-carboxylate (690.83 mg, 3.46 mmol, 0.80 eq) in THF (10.00 mL) was added dropwise. The reaction mixture was stirred at −78° C. for one hour under $N_2$. To the mixture was added a solution of oxazole-4-carbonyl chloride (570.00 mg, 4.33 mmol, 1.00 eq) in THF (10.00 mL). After addition, the reaction mixture was warmed to 30° C. and stirred at 30° C. for another 2 hours. Several new peaks were shown on LCMS and only 15% of desired compound was detected. The reaction mixture was added to aqueous solution of $NH_4Cl$ (30 mL) and extracted with EA (40 mL*3). The combined organic phase was dried over anhydrous $Na_2SO_4$, filtered and concentrated in vacuum to afford tert-butyl 3-(oxazole-4-carbonyl)-4-oxo-piperidine-1-carboxylate (930.00 mg, crude) as yellow oil. The crude product was used in the next step directly without purification. LCMS: 295 [M+1].

Step 3: Preparation of Compound 5

To a solution of tert-butyl 3-(oxazole-4-carbonyl)-4-oxo-piperidine-1-carboxylate (500.00 mg, 1.70 mmol, 1.00 eq) in EtOH (10.00 mL) was added $NH_2NH_2H_2O$ (120.14 mg, 2.04 mmol, 116.64 uL, 85% purity, 1.20 eq). The reaction mixture was warmed to 60° C. and stirred at 60° C. for one hour. LCMS showed starting material was consumed completely and one main peak with desired MS was detected. The mixture was extracted with EA (20 mL*3) and water (15 mL), the organic phase was dried with anhydrous $Na_2SO_4$, filtered and concentrated in vacuum. The residue was purified by silica gel chromatography to afford tert-butyl 3-oxazol-4-yl-1,4,6,7-tetrahydropyrazolo[4,3-c]pyridine-5-carboxylate (180.00 mg, 620.01 umol, 36.47% yield) as yellow oil. LCMS: 291 [M+1].

Step 4: Preparation of Compound 6

To a solution of tert-butyl 3-oxazol-4-yl-1,4,6,7-tetrahydropyrazolo [4,3-c]pyridine-5-carboxylate (150.00 mg, 516.67 umol, 1.00 eq) in dioxane (1.00 mL) was added HCl/dioxane (4 M, 3.00 mL, 23.23 eq), the reaction mixture was stirred at 30° C. for 30 minutes. TLC showed starting material was consumed completely. Evaporate the solution on a water bath under reduced pressure using a rotary evaporator to afford 4-(4,5,6,7-tetrahydro-1H-pyrazolo [4,3-c]pyridin-3-yl)oxazole (95.00 mg, 419.13 umol, 81.12% yield, HCl) as yellow solid. The crude product was used in the next step directly without purification.

Preparation of Compound 741

To a mixture of 4-(4,5,6,7-tetrahydro-1H-pyrazolo[4,3-c]pyridin-3-yl)oxazole (40.00 mg, 176.48 umol, 1.20 eq, HCl) in DCM (3.00 mL) was added TEA (44.64 mg, 441.19 umol, 61.16 uL, 3.00 eq), followed by phenyl N-(3-chlorophenyl)carbamate (36.42 mg, 147.06 umol, 1.00 eq), the reaction mixture was stirred at 30° C. for 16 hours. LCMS showed m-ClPhNHCO2Ph was consumed completely and one main peak with desired MS was detected. The mixture was extracted with DCM (15 mL*3) and water (15 mL), the organic phase was dried with anhydrous $Na_2SO_4$, filtered and concentrated in vacuum. Further purification by prep-HPLC (FA) to afford Compound 741 (39.00 mg, 112.77 umol, 76.68% yield, 99.4% purity) as white solid. $^1H$ NMR (400 MHz, METHANOL-d4) δ 8.26 (s, 1H), 8.21 (s, 1H), 7.53-7.54 (t, J=2.01 Hz, 1H), 7.30-7.32 (m, 1H), 7.21-7.25 (m, 1H), 7.00-7.01 (dd, J=7.91, 1.00 Hz, 1H), 4.75 (s, 2H), 3.84-3.87 (t, J=5.71 Hz, 2H), 2.84-2.87 (t, J=5.71 Hz, 2H). LCMS: 344/346 [M+1].

Example 50: Preparation of Compound 707

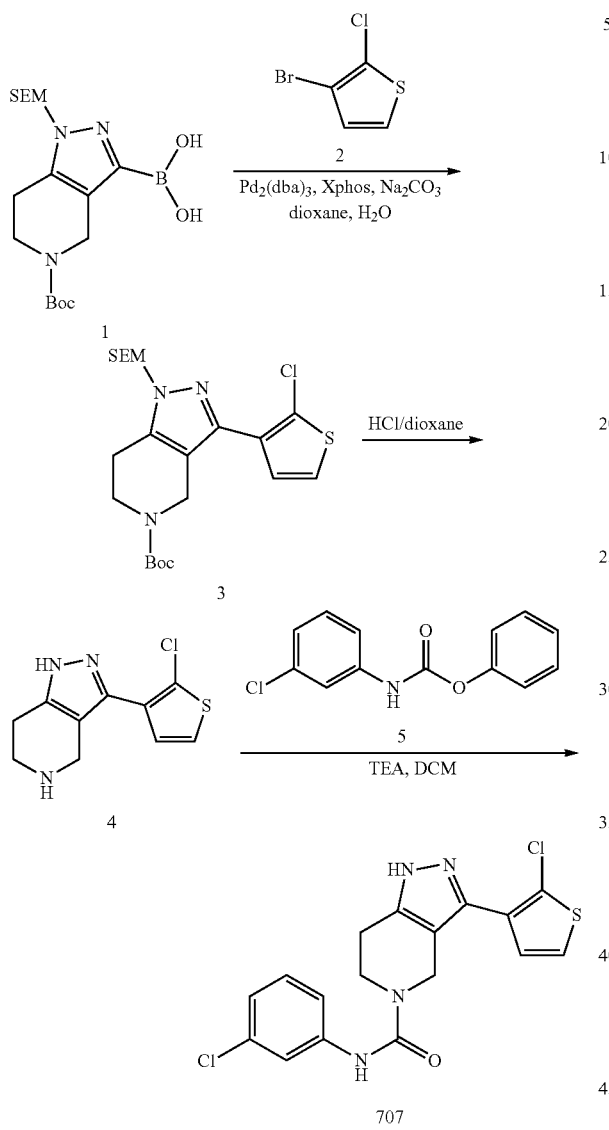

707

Step 1: Preparation of Compound 3

A mixture of compound 1 (200.00 mg, 503.33 umol, 1.00 eq), compound 2 (99.40 mg, 503.33 umol, 1.00 eq), Na$_2$CO$_3$ (133.37 mg, 1.26 mmol, 2.50 eq), XPhos (23.99 mg, 50.33 umol, 0.10 eq) and Pd$_2$(dba)$_3$ (23.05 mg, 25.17 umol, 0.05 eq) in dioxane (5.00 mL)/H$_2$O (500.00 uL) was heated to 100° C. and stirred for 16 h. TLC (Petroleum ether:Ethyl acetate=5:1) indicated desire product (R$_f$=0.7) was detected. Water (15 mL) was added to the mixture and extracted with EA (3*20 mL). The combined organic layers were dried over Na$_2$SO$_4$, filtered and concentrated under reduced pressure to give a residue. The residue was purified by prep-TLC (PE:EA 5:1) to afford compound 3 (45.00 mg, crude) as light yellow liquid.

Step 2: Preparation of Compound 4

A solution of compound 3 (45.00 mg, 95.72 umol, 1.00 eq) in HCl/dioxane (228.84 umol, 3.00 mL, 2.00 eq) was stirred at 30° C. for 20 min. Then the reaction mixture was concentrated to remove the solvent. Then another batch of HCl/dioxane (228.84 umol, 3.00 mL, 2.00 eq) was added to the residue. The resulting mixture was stirred at 30° C. for 20 min. LCMS showed about 72% of desired product was detected. The mixture was concentrated under reduced pressure to remove solvent to afford compound 4 (30.00 mg, crude, HCl) as yellow oil. The residue was not purified and used in the next step directly.

Preparation of Compound 707

A mixture of Compound 4 (30.00 mg, 125.15 umol, 1.00 eq) and TEA (75.98 mg, 750.90 umol, 104.08 uL, 6.00 eq) in DCM (3.00 mL) was degassed and purged with N$_2$ for 3 times, and then the mixture was stirred at 30° C. for 16 h under N$_2$ atmosphere. LCMS showed desired product was detected. The mixture was adjusted to pH=3 and concentrated under reduced pressure to remove solvent. The residue was purified by prep-HPLC(FA) to afford Compound 707 as white solid. LCMS: 393/395[M+1].

Example 51: Preparation of Compounds 708, 712, 715, and 769

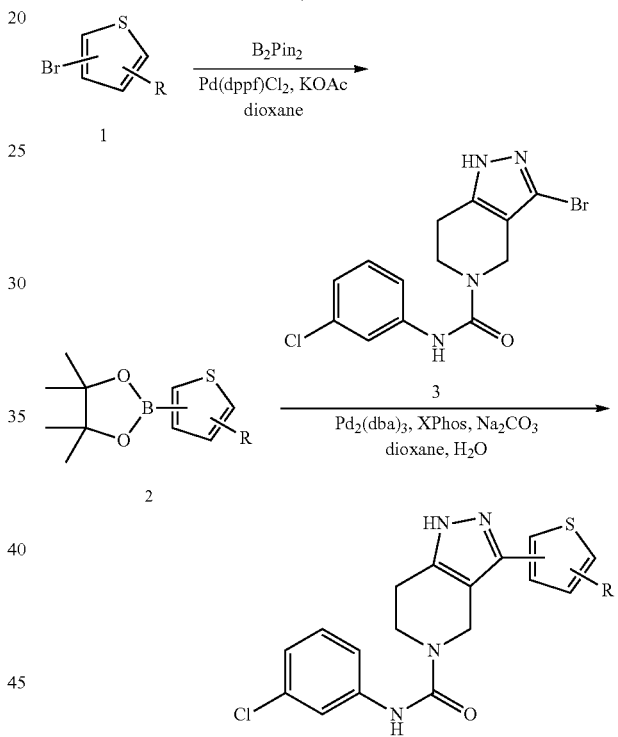

708, 712, 715, and 769

Step 1: Preparation of Compound 2

A mixture of compound 1 (1.00 eq), B$_2$Pin$_2$ (1.50 eq), KOAc (2.50 eq) and Pd(dppf)Cl$_2$ (0.05 eq) in dioxane (5.00 mL) were heated to 100 under N$_2$ for 16 hrs. TLC indicated starting material was consumed completely. The mixture was concentrated. The residue was purified by silica gel column to afford Compound 2.

Preparation of Compounds 708, 712, 715, or 769

A mixture of compound 2 (2.50 eq), compound 3 (1.00 eq), Na$_2$CO$_3$ (2.50 eq), XPhos (0.10 eq) and Pd$_2$(dba)$_3$ (0.05 eq) in dioxane/H$_2$O (10:1) were stirred at 100° C. under N$_2$ for 16 h. LCMS indicated the starting material was consumed completely and desired product was detected. The mixture was diluted with EA and washed with brine. The organic layer was dried over Na$_2$SO$_4$, filtered and concentrated. The residue was purified by silica gel and repurified by prep-HPLC(FA) to afford Compounds 708, 712, 715, or 769.

| Structure | Comp. ID | Analytical Data |
|---|---|---|
| (structure 708) | 708 | LCMS (M + 1): 373/375. |
| (structure 712) | 712 | LCMS (M + 1): 373/375. |
| (structure 715) | 715 | LCMS (M + 1): 384/386.<br>$^1$H NMR (400 MHz, METHANOL-$d_4$) ppm 7.94 (brs, 1 H), 7.51 (s, 1 H), 7.42 (d, J = 5.02 Hz, 1 H), 7.26-7.33 (m, 1 H), 7.19-7.25 (m, 1 H), 7.00 (d, J = 8.03 Hz, 1 H), 4.72 (s, 2 H), 3.89 (t, J = 5.77 Hz, 2 H), 2.91 (t, J = 5.77 Hz, 2 H). |
| (structure 769) | 769 | LCMS (M + 1): 389/391. |
Example 52: Preparation of Compounds 716 and 766
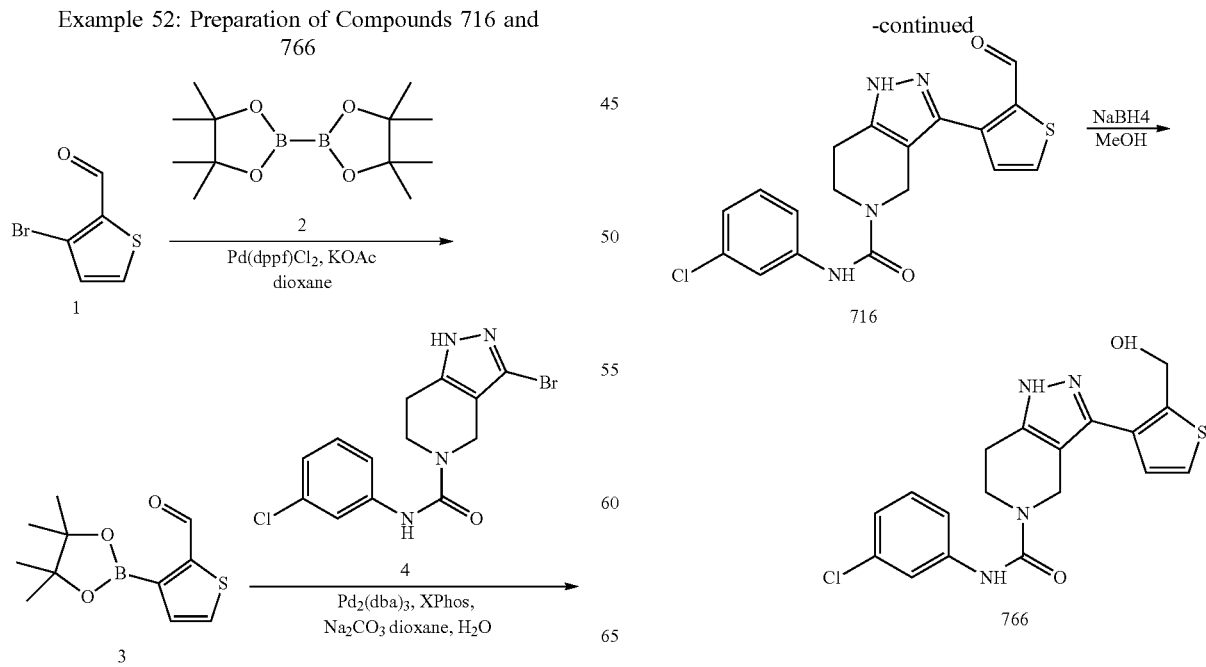

Step 1: Preparation of Compound 3

To a mixture of Compound 1 (500.00 mg, 2.62 mmol, 1.00 eq) and compound 2 (997.98 mg, 3.93 mmol, 1.50 eq) in dioxane (10.00 mL) was added Pd(dppf)Cl$_2$ (95.85 mg, 131.00 umol, 0.05 eq) and KOAc (514.25 mg, 5.24 mmol, 2.00 eq), the reaction mixture was warmed to 100° C. and stirred at 100° C. for 3 hours under N$_2$. TLC (Petroleum ether:Ethyl acetate=10:1) indicated compound 1 was consumed completely and one major new spot with larger polarity was detected. Evaporated the solution under reduced pressure using a rotary evaporator. The residue was purified by silica gel chromatography (200-300 mesh silica gel, Petroleum ether/Ethyl acetate=10/1 to 3/1) to afford Compound 3 (1.00 g, crude) as yellow oil.

Preparation of Compound 716

A mixture of compound 4 (150.00 mg, 421.80 umol, 1.00 eq), compound 3 (110.48 mg, 463.98 umol, 1.10 eq) and XPhos (20.11 mg, 42.18 umol, 0.10 eq) in dioxane (5.00 mL) and H$_2$O (750.00 uL) was degassed and purged with N$_2$ for 3 times. Pd$_2$(dba)$_3$ (19.31 mg, 21.09 umol, 0.05 eq) was added to the mixture. The resulting mixture was stirred at 80° C. for 15 h. LC-MS showed desired compound was detected, and the compound 4 was remained. Then another bacth of compound 3 (110.48 mg, 463.98 umol, 1.10 eq) was added to the reaction mixture. The resulting mixture was stirred at 80° C. for 5 h. TLC showed desired product was detected. The mixture was diluted with water (15 mL) and extracted by EtOAc (3*15 mL). The combined organic phases was dried over Na$_2$SO$_4$, filtered and concentrated. The residue was purified by prep-TLC (Dichloromethane:Methanol=20:1) to afford Compound 716 (113.00 mg, crude) as yellow solid. LCMS: 387/389 [M+1].

Preparation of Compound 766

A mixture of Compound 716 (113.00 mg, 292.10 umol, 1.00 eq) and NaBH$_4$ (22.10 mg, 584.20 umol, 2.00 eq) in MeOH (4.00 mL) was stirred at 30° C. for 1 h. LCMS indicated about 88% of desired compound was detected. The reaction mixture was added 10 drops of water and stirred for 10 min. The reaction mixture was filtered. The reaction mixture was purified by prep-HPLC(FA) and re-purified by prep-TLC (Dichloromethane:Methanol 20:1, Rf=0.2) to afford Compound 766 as white solid. LCMS: 411/413 [M+23].

Example 53: Preparation of Compound 747

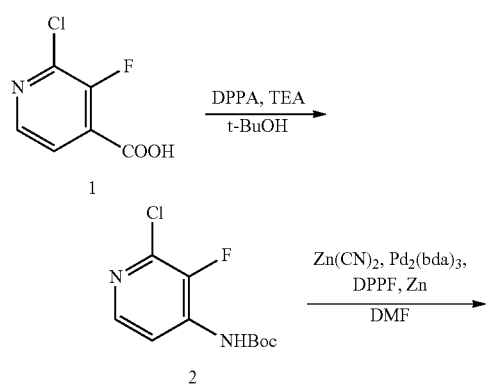

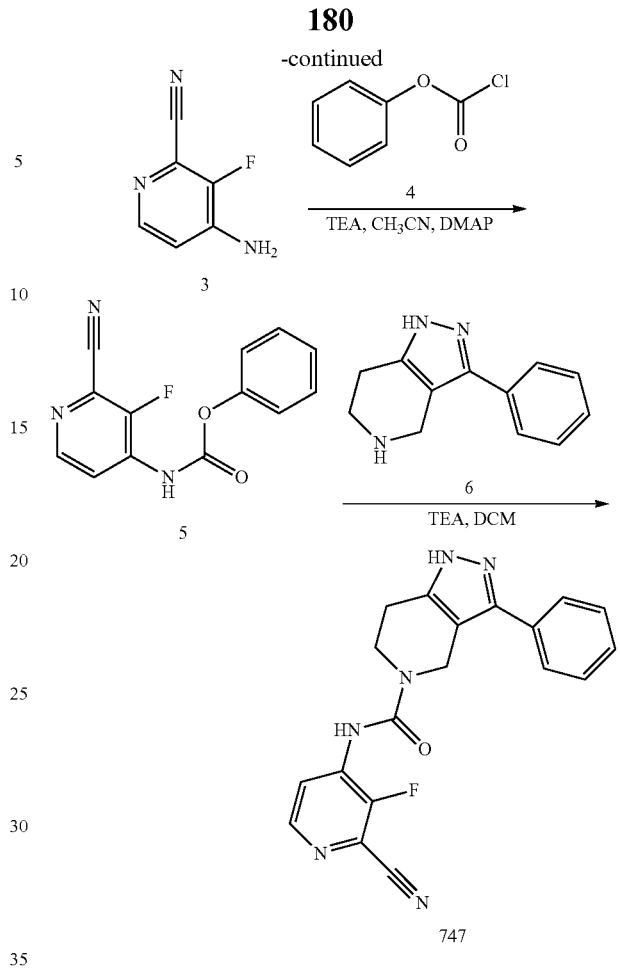

Step 1: Preparation of Compound 2

To a mixture of 2-chloro-3-fluoro-pyridine-4-carboxylic acid (3.00 g, 17.09 mmol, 1.00 eq) in t-BuOH (20.00 mL) was added DPPA (7.05 g, 25.64 mmol, 1.50 eq) and TEA (3.46 g, 34.18 mmol, 2.00 eq), the reaction mixture was warmed to 80° C. and stirred at 80° C. for 16 hours. Several new peaks were shown on LCMS and 20% of desired compound was detected. The mixture was extracted with EA (80 mL*3) and water (50 mL*2), the organic phase was dried with anhydrous Na$_2$SO$_4$, filtered and concentrated in vacuum. The residue was purified by silica gel chromatography (200-300 mesh silica gel, Petroleum ether/Ethyl acetate=20/1 to 5/1) to afford tert-butyl N-(2-chloro-3-fluoro-4-pyridyl)carbamate (1.70 g, 5.86 mmol, 34.28% yield, 85% purity) as yellow oil. LCMS: 247/249 [M+1].

Step 2: Preparation of Compound 3

To a mixture of tert-butyl N-(2-chloro-3-fluoro-4-pyridyl)carbamate (1.00 g, 4.05 mmol, 1.00 eq) in DMF (8.00 mL) was added Zn(CN)$_2$ (952.04 mg, 8.10 mmol, 514.62 uL, 2.00 eq), Zn (52.97 mg, 810.00 umol, 0.20 eq), DPPF (898.98 mg, 1.62 mmol, 0.40 eq) and Pd$_2$(dba)$_3$ (742.47 mg, 810.00 umol, 0.20 eq), and the reaction mixture was stirred at 120° C. for 16 hours under N$_2$. TLC indicated starting material was consumed completely and many new spots formed. The mixture was extracted with EA (20 mL*3) and water (10 mL*2), the organic phase was dried with anhydrous Na$_2$SO$_4$, filtered and concentrated in vacuum. The residue was purified by silica gel chromatography (200-300 mesh silica gel, Petroleum ether/Ethyl acetate=10/1 to 1/1) to afford 4-amino-3-fluoro-pyridine-2-carbonitrile (75.00 mg, 547.01 umol, 13.51% yield) as yellow solid. $^1$H NMR (400 MHz, DMSO-d$_6$) δ 7.96-7.97 (d, J=5.52 Hz, 1H), 6.91-6.94 (dd, J=7.53, 5.40 Hz, 1H), 6.86 (brs, 2H). LCMS: 138 [M+1].

Step 3: Preparation of Compound 5

To a mixture of 4-amino-3-fluoro-pyridine-2-carbonitrile (25.00 mg, 182.34 umol, 1.00 eq) in CH$_3$CN (2.00 mL) was added TEA (36.90 mg, 364.68 umol, 50.55 uL, 2.00 eq), compound 4(28.55 mg, 1.00 eq) and DMAP (2.23 mg, 18.23 umol, 0.10 eq), the reaction mixture was stirred at 30° C. for 16 hours. TLC indicated compound 3 was consumed completely, and one major new spot with lower polarity was detected. The mixture was extracted with EA (10 mL*3) and water (10 mL), the organic phase was dried with anhydrous Na$_2$SO$_4$, filtered and concentrated in vacuum. Further purification by prep-TLC to afford phenyl N-(2-cyano-3-fluoro-4-pyridyl)carbamate (23.00 mg, 74.22 umol, 40.70% yield, 83% purity) as white solid. LCMS: 258 [M+1].

Preparation of Compound 747

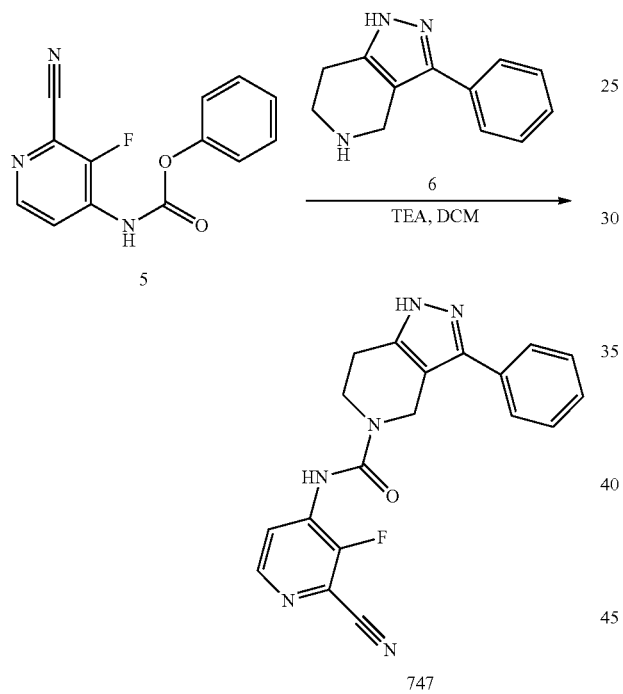

To a solution of phenyl N-(2-cyano-3-fluoro-4-pyridyl) carbamate (20.00 mg, 77.75 umol, 1.00 eq) in DCM (2.00 mL) was added TEA (23.60 mg, 233.25 umol, 32.33 uL, 3.00 eq) and 3-phenyl-4,5,6,7-tetrahydro-1H-pyrazolo[4,3-c]pyridine (18.33 mg, 77.75 umol, 1.00 eq, HCl), the reaction mixture was stirred at 25° C. for 2 hours. LCMS showed compound 5 was consumed completely and one main peak with desired MS was detected. The mixture was extracted with DCM (10 mL*3) and water (10 mL), the organic phase was dried with anhydrous Na$_2$SO$_4$, filtered and concentrated in vacuum. Further purification by prep-HPLC(FA) to afford Compound 747 (8.00 mg, 21.92 umol, 28.19% yield, 99.3% purity) as white solid. $^1$H NMR (400 MHz, DMSO-d6) δ 8.31-8.32 (d, J=5.40 Hz, 1H), 7.95-7.98 (t, J=6.02 Hz, 1H), 7.61-7.63 (d, J=7.28 Hz, 2H), 7.45-7.48 (t, J=6.90 Hz, 2H), 7.34-7.36 (d, J=7.03 Hz, 1H), 4.76 (s, 2H), 3.79-3.82 (t, J=5.65 Hz, 2H), 2.78 (brs, 2H). LCMS: 363 [M+1].

Example 54: Preparation of Compound 756

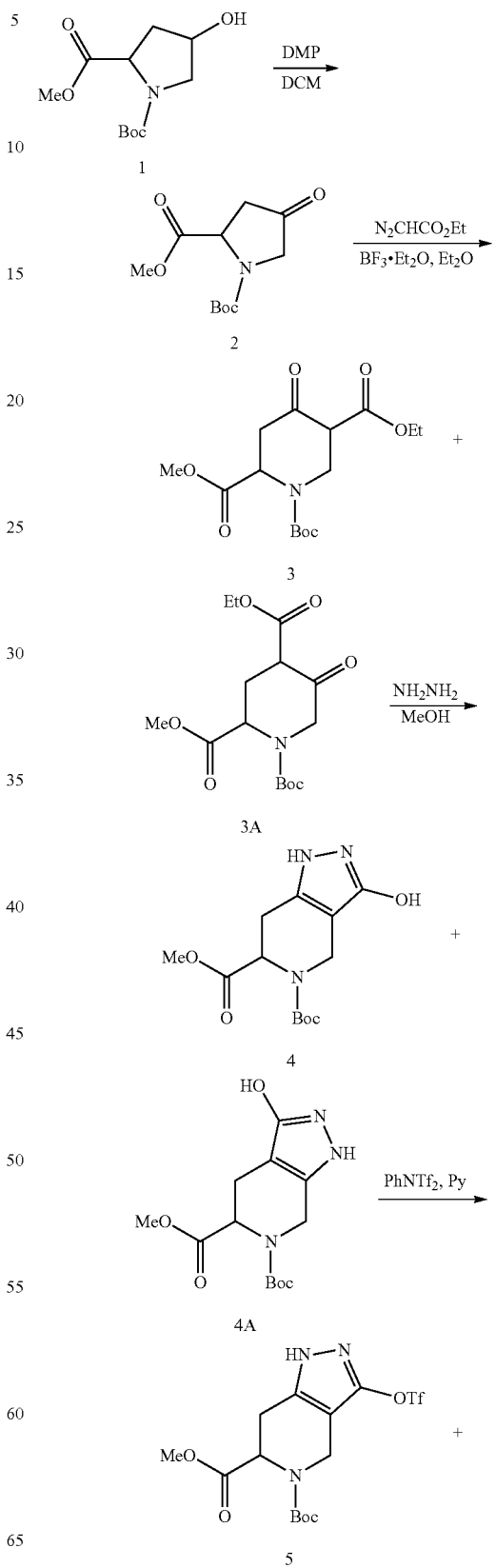

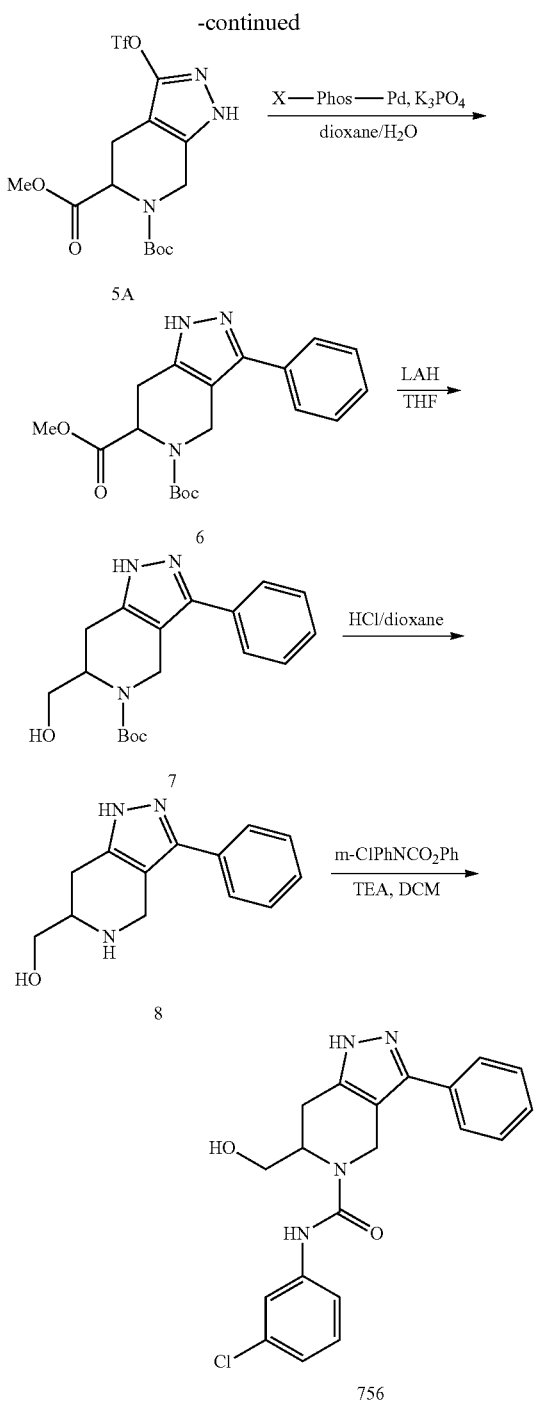

Step 1: Preparation of Compound 2

To a mixture of 1-tert-butyl 2-methyl 4-hydroxypyrrolidine-1,2-dicarboxylate (4.00 g, 16.31 mmol, 1.00 eq) in DCM (20.00 mL) was added Dess-Martin (8.30 g, 19.57 mmol, 1.20 eq) in one portion at 0° C. under $N_2$. The mixture was stirred at 20° C. for 5 hours. TLC (Petroleum ether: Ethyl acetate=3:1) showed the reaction was completed. The reaction was quenched by $Na_2S_2O_3$ slowly and then extracted with DCM (50 mL*2). The combined organic phase was washed with brine (40 mL*2), dried over anhydrous $Na_2SO_4$, filtered and concentrated in vacuo. The residue was purified by silica gel chromatography (Petroleum ether/Ethyl acetate=10/1) to afford 1-tert-butyl 2-methyl 4-oxopyrrolidine-1,2-dicarboxylate (3.70 g, 14.60 mmol, 89.53% yield, 96% purity) as yellow oil. $^1$H NMR (400 MHz, CHLOROFORM-d) δ 4.66-4.89 (m, 1H), 3.85-3.97 (m, 2H), 3.77 (s, 3H), 2.85-3.06 (m, 1H), 2.53-2.66 (m, 1H), 1.48 (d, J=7.78 Hz, 9H). LCMS: 244[M+1].

Step 2: Preparation of Compounds 3 and 3A

To a mixture of 1-tert-butyl 2-methyl 4-oxopyrrolidine-1,2-dicarboxylate (1.00 g, 4.11 mmol, 1.00 eq) and ethyl 2-diazoacetate (1.41 g, 12.33 mmol, 1.29 mL, 3.00 eq) in $Et_2O$ (10.00 mL) was added $BF_3.Et_2O$ (1.75 g, 12.33 mmol, 1.52 mL, 3.00 eq) dropwise at −45° C. under $N_2$. The mixture was stirred at −45° C. for 30 min, then warmed to 20° C. and stirred for 10 hours. TLC (Petroleum ether:Ethyl acetate=3:1) showed the desired product was detected. The mixture was poured into saturated $NaHCO_3$ (20 mL) and stirred for 3 min. The aqueous phase was extracted with ethyl acetate (20 mL*2). The combined organic phase was washed with brine (10 mL*2), dried with anhydrous $Na_2SO_4$, filtered and concentrated in vacuum. The residue was purified by silica gel chromatography (Petroleum ether/Ethyl acetate=15/1) to afford a mixture of 1-tert-butyl 4-ethyl 2-methyl 5-oxopiperidine-1,2,4-tricarboxylate and 1-tert-butyl 5-ethyl 2-methyl 4-oxopiperidine-1,2,5-tricarboxylate (400.00 mg, 1.21 mmol, 29.44% yield) as yellow oil. LCMS: 330[M+1].

Step 3: Preparation of Compounds 4 and 4A

To a mixture of 1-tert-butyl 4-ethyl 2-methyl 5-oxopiperidine-1,2,4-tricarboxy late and 1-tert-butyl 5-ethyl 2-methyl 4-oxopiperidine-1,2,5-tricarboxylate (670.00 mg, 2.03 mmol, 1.00 eq) in MeOH (10.00 mL) was added $N_2H_4.H_2O$ (131.79 mg, 2.24 mmol, 127.96 uL, 85% purity, 1.10 eq) in one portion under $N_2$. The mixture was stirred at 20° C. for 12 hours. LCMS showed the reaction was completed. The mixture was concentrated in vacuum to afford a mixture of 6-tert-butyl 5-methyl 3-hydroxy-1,4,5,7-tetrahydropyrazolo[3,4-c]pyridine-5,6-dicarboxylate and 5-tert-butyl 6-methyl 3-hydroxy-1,4,6,7-tetrahydropyrazolo[4,3-c]pyridine-5,6-dicarboxylate (600.00 mg, 2.02 mmol, 99.41% yield) as yellow solid. LCMS: 298[M+1].

Step 4: Preparation of Compounds 5 and 5A

To a mixture of 6-tert-butyl 5-methyl-3-hydroxy-1,4,5,7-tetrahydropyrazolo [3,4-c]pyridine-5,6-dicarboxylate and 5-tert-butyl 6-methyl-3-hydroxy-1,4,6,7-tetrahydro pyrazolo[4,3-c]pyridine-5,6-dicarboxylate (600.00 mg, 2.02 mmol, 1.00 eq) in Py (10.00 mL) was added 1,1,1-trifluoro-N-phenyl-N-(trifluoromethylsulfonyl)methane sulfonamide (1.08 g, 3.03 mmol, 1.50 eq) in one portion under $N_2$. The mixture was stirred at 20° C. for 12 hours. TLC (Petroleum ether:Ethyl acetate=3:1) showed the reaction was completed. The mixture was concentrated in vacuum. The residue was poured into 1 N HCl (30 mL) and stirred for 1 min. The aqueous phase was extracted with ethyl acetate (20 mL*2). The combined organic phase was washed with brine (20 mL*2), dried with anhydrous $Na_2SO_4$, filtered and concentrated in vacuum. The residue was purified by silica gel chromatography (Petroleum ether/Ethyl acetate=15/1, 10/1) to afford 5-tert-butyl 6-methyl-3-(trifluoromethylsulfonyloxy)-1,4,6,7-tetrahydropyrazolo[4,3-c]pyridine-5,6-dicarboxylate (120.00 mg, 279.48 umol, 13.84% yield) as yellow solid and 6-tert-butyl-5-methyl-3-(trifluoromethylsulfonyloxy)-1,4,5,7-tetrahydropyrazolo [3,4-c]pyridine-5,6-dicarboxylate (240.00 mg, 558.96 umol, 27.67% yield) as yellow solid. LCMS: 430[M+1].

Step 5: Preparation of Compound 6

To a mixture of 5-tert-butyl 6-methyl 3-(trifluoromethylsulfonyloxy)-1,4,6,7-tetrahydropyrazolo[4,3-c]pyridine-5,6-dicarboxylate (100.00 mg, 232.90 umol, 1.00 eq) and phenylboronic acid (42.60 mg, 349.35 umol, 1.50 eq) in dioxane (5.00 mL) and H₂O (500.00 uL) was added XPHOS-PD-G2 (18.32 mg, 23.29 umol, 0.10 eq), K₃PO₄ (98.88 mg, 465.80 umol, 2.00 eq) in one portion under N₂. The mixture was stirred at 110° C. for 10 hour. TLC (Ethyl acetate:Petroleum ether=2:1) showed the reaction was completed and the desired product was detected. The mixture was poured into water (30 mL) and stirred for 2 min. The aqueous phase was extracted with ethyl acetate (30 mL*2). The combined organic phase was washed with brine (30 mL*2), dried with anhydrous Na₂SO₄, filtered and concentrated in vacuum. The residue was purified by silica gel chromatography (Petroleum ether/Ethyl acetate=5/1) to afford 5-tert-butyl 6-methyl 3-phenyl-1,4,6,7-tetrahydropyrazolo[4,3-c]pyridine-5,6-dicarboxylate (40.00 mg, 105.20 umol, 45.17% yield, 94% purity) as yellow solid. ¹H NMR (400 MHz, METHANOL-d₄) δ 7.51-7.62 (m, 2H), 7.42-7.50 (m, 2H), 7.33-7.42 (m, 1H), 5.27-5.43 (m, 1H), 4.47-4.55 (m, 1H), 4.36-4.44 (m, 1H), 4.06-4.14 (m, 1H), 3.65-3.71 (m, 3H), 3.37 (d, J=4.39 Hz, 1H), 2.99-3.14 (m, 1H), 1.51 (d, J=6.15 Hz, 9H). LCMS: 358[M+1].

Step 6: Preparation of Compound 7

To a mixture of 5-tert-butyl 6-methyl 3-phenyl-1,4,6,7-tetrahydropyrazolo[4,3-c]pyridine-5,6-dicarboxylate (40.00 mg, 111.92 umol, 1.00 eq) in THF (5.00 mL) was added LiAlH₄ (21.24 mg, 559.60 umol, 5.00 eq) in one portion at 0° C. under N₂. The mixture was stirred at 0° C. for 5 hours. LCMS and TLC (Ethyl acetate:Petroleum ether=3:1) showed the reaction was completed. The mixture was poured into water (10 mL) and stirred for 5 min. The aqueous phase was extracted with ethyl acetate (10 mL*2). The combined organic phase was washed with brine (10 mL*2), dried with anhydrous Na₂SO₄, filtered and concentrated in vacuum. The residue was purified by prep-TLC (Petroleum ether/Ethyl acetate=1/4) to afford tert-butyl 6-(hydroxymethyl)-3-phenyl-1,4,6,7-tetrahydropyrazolo [4,3-c] pyridine-5-carboxylate (20.00 mg, 60.72 umol, 54.25% yield) as yellow solid. LCMS: 330[M+1].

Step 7: Preparation of Compound 8

To a mixture of tert-butyl 6-(hydroxymethyl)-3-phenyl-1,4,6,7-tetrahydropyrazolo [4,3-c]pyridine-5-carboxylate (10.00 mg, 30.36 umol, 1.00 eq) in dioxane (2.00 mL) was added HCl/dioxane (4 M, 4.00 mL, 527.01 eq) in one portion under N₂. The mixture was stirred at 20° C. for 2 hours. TLC (Ethyl acetate:Petroleum ether=3:1) showed the reaction was completed. The mixture was concentrated to afford (3-phenyl-4,5,6,7-tetrahydro-1H-pyrazolo[4,3-c] pyridin-6-yl)methanol (8.07 mg, 30.37 umol, 100.00% yield, HCl) as yellow solid.

Preparation of Compound 756

To a mixture of (3-phenyl-4,5,6,7-tetrahydro-1H-pyrazolo[4,3-c]pyridin-6-yl)methanol (8.07 mg, 30.37 umol, 1.00 eq, HCl) and phenyl N-(3-chlorophenyl)carbamate (7.52 mg, 30.37 umol, 1.00 eq) in DCM (5.00 mL) was added TEA (7.68 mg, 75.92 umol, 10.52 uL, 2.50 eq) in one portion under N₂. The mixture was stirred at 20° C. for 12 hours. LCMS showed the reaction was completed. The mixture was poured into water (10 mL) and stirred for 2 min. The aqueous phase was extracted with ethyl acetate (10 mL*2). The combined organic phase was washed with brine (10 mL*2), dried with anhydrous Na₂SO₄, filtered and concentrated in vacuum. The residue was purified by prep-HPLC (FA) to afford N-(3-chlorophenyl)-6-(hydroxyl methyl)-3-phenyl-1,4,6,7-tetrahydropyrazolo[4,3-c]pyridine-5-carboxamide (9.33 mg, 24.25 umol, 79.84% yield, 99.5% purity) as white solid. ¹H NMR (400 MHz, METHANOL-d₄) δ 7.62-7.70 (m, 1H), 7.42-7.56 (m, 2H), 7.27-7.41 (m, 2H), 7.19-7.26 (m, 1H), 6.98-7.03 (m, 1H), 5.05 (d, J=15.31 Hz, 2H), 4.47 (d, J=15.43 Hz, 1H), 3.54-3.69 (m, 2H), 2.99-3.08 (m, 1H), 2.86-2.94 (m, 1H). LCMS: 383/385[M+1].

Example 55: Preparation of Compound 754

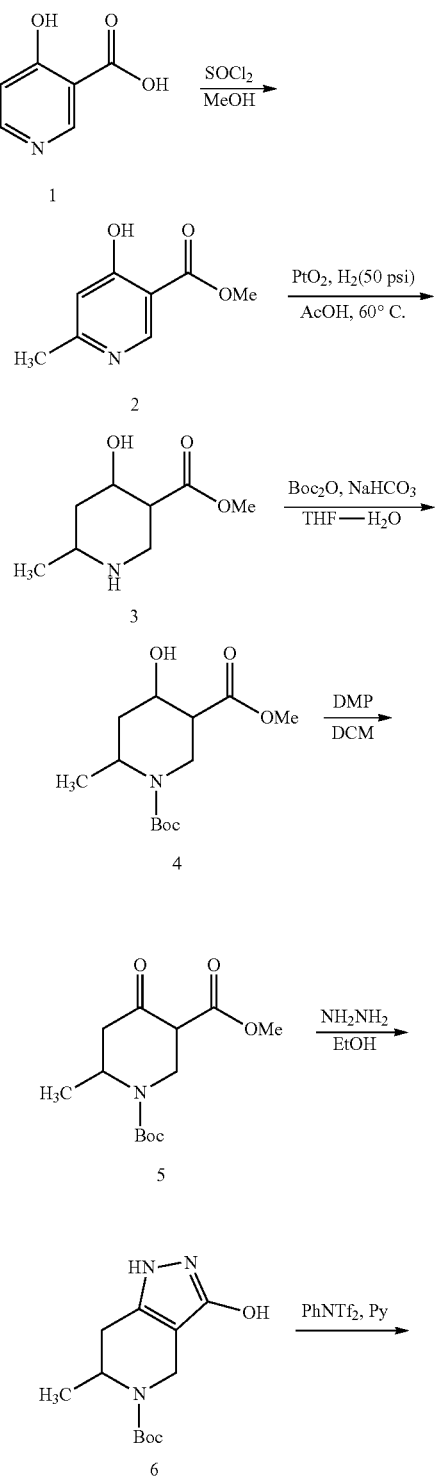

187
-continued

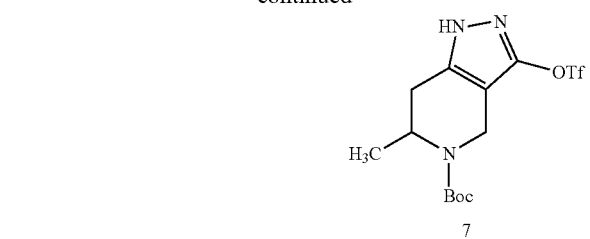
7

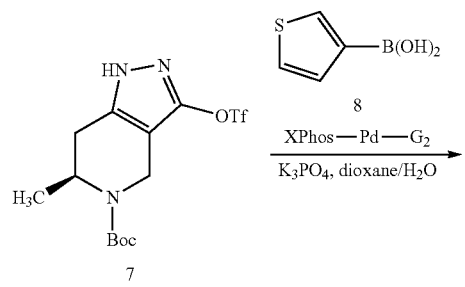
7

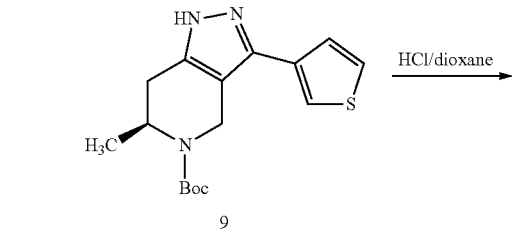
9

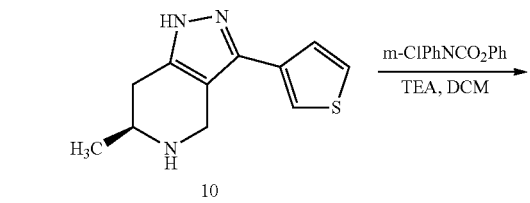
10

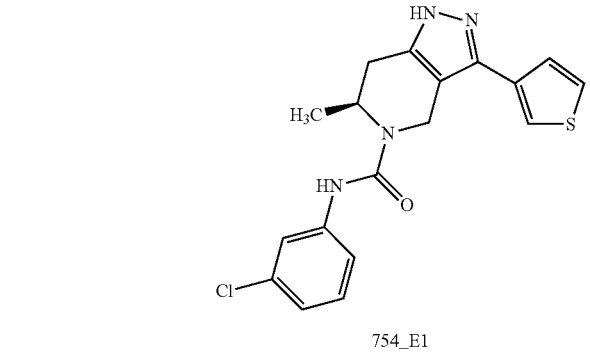
754_E1

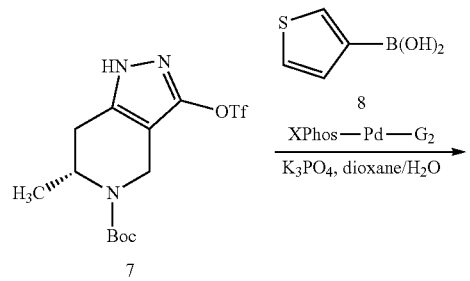
7

188
-continued

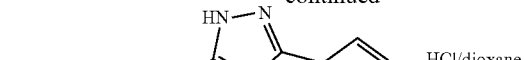
11

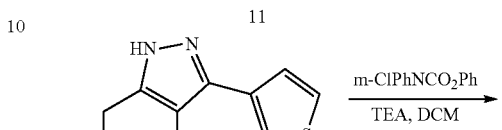
12

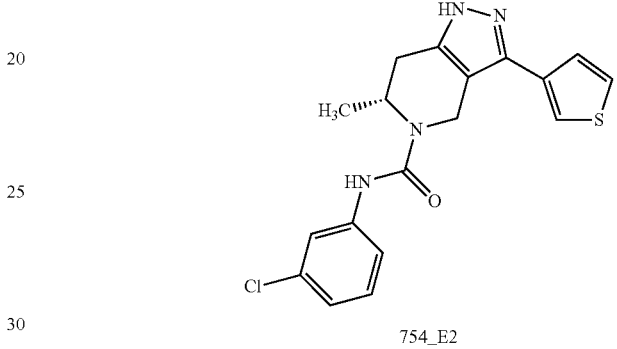
754_E2

Step 1: Preparation of Compound 2

To a mixture of 4-hydroxy-6-methyl-pyridine-3-carboxylic acid (5.00 g, 32.65 mmol, 1.00 eq) in MeOH (60.00 mL) was added $SOCl_2$ (23.31 g, 195.90 mmol, 6.00 eq) at 0° C. under $N_2$. The mixture was stirred at 0° C. for 30 min, then heated to 80° C. and stirred for 10 hours. TLC (Dichloromethane:Methanol=5:1) showed the reaction was completed. The mixture was cooled to 20° C. and concentrated in vacuum to afford methyl 4-hydroxy-6-methyl-pyridine-3-carboxylate (5.50 g, crude, HCl) as yellow solid. LCMS: 168[M+1].

Step 2: Preparation of Compound 3

To a solution of methyl 4-hydroxy-6-methyl-pyridine-3-carboxylate (8.00 g, 39.29 mmol, 1.00 eq, HCl) in AcOH (50.00 mL) was added $PtO_2$ (1.34 g, 5.89 mmol, 0.15 eq) under $N_2$. The suspension was degassed under vacuum and purged with $H_2$ several times. The mixture was stirred under $H_2$ (50 psi) at 60° C. for 24 hours. LCMS showed desired compound was detected. The reaction mixture was filtered and the filter was concentrated to afford methyl 4-hydroxy-6-methyl-piperidine-3-carboxylate (9.50 g, crude, AcOH salt) as yellow oil. LCMS: 174 [M+1].

Step 3: Preparation of Compound 4

To a mixture of methyl 4-hydroxy-6-methyl-piperidine-3-carboxylate (3.00 g, 12.86 mmol, 1.00 eq, HOAC) and $NaHCO_3$ (1.62 g, 19.29 mmol, 750.00 uL, 1.50 eq) in THF (10.00 mL) and $H_2O$ (10.00 mL) was added $Boc_2O$ (3.37 g, 15.43 mmol, 3.55 mL, 1.20 eq) at 0° C. under $N_2$. The mixture was stirred at 25° C. for 5 hours. LCMS and TLC (Petroleum ether:Ethyl acetate=3:1) showed the reaction was completed. The mixture was extracted with ethyl acetate (30 mL*2). The combined organic phase was washed with brine (20 mL*2), dried with anhydrous $Na_2SO_4$, filtered and concentrated in vacuum. The residue was purified by silica gel chromatography (Petroleum ether/Ethyl acetate=15/1) to afford 1-tert-butyl 3-methyl 4-hydroxy-6-methyl-piperidine-1,3-dicarboxylate (1.50 g, 5.49 mmol, 42.68% yield) as yellow oil. LCMS: 274[M+1].

Step 4: Preparation of Compound 5

To a mixture of 1-tert-butyl 3-methyl 4-hydroxy-6-methyl-piperidine-1,3-dicarboxylate (1.50 g, 5.49 mmol, 1.00 eq) in DCM (50.00 mL) was added Dess-Martin (2.79 g, 6.59 mmol, 2.04 mL, 1.20 eq) in one portion at 0° C. under $N_2$. The mixture was stirred at 0° C. for 5 hours. TLC (Petroleum ether:Ethyl acetate=5:1) showed the reaction was completed. The reaction was quenched by $Na_2S_2O_3$ slowly and then extracted with DCM (30 mL*2). The combined organic phase was washed with brine (30 mL*2), dried over anhydrous $Na_2SO_4$, filtered and concentrated in vacuo. The residue was purified by silica gel chromatography (Petroleum ether/Ethyl acetate=20/1) to afford 1-tert-butyl 3-methyl 6-methyl-4-oxo-piperidine-1,3-dicarboxylate (1.00 g, 3.69 mmol, 67.14% yield) as yellow oil. $^1$H NMR (300 MHz, CHLOROFORM-d) δ 11.99 (s, 1H), 4.53-4.69 (m, 1H), 4.46 (d, J=16.77 Hz, 1H), 3.80 (s, 3H), 3.54-3.72 (m, 1H), 2.60-2.78 (m, 1H), 2.26-2.46 (m, 1H), 1.44-1.52 (m, 11H), 1.15 (d, J=6.78 Hz, 3H). LCMS: 272[M+1].

Step 5: Preparation of Compound 6

To a mixture of 1-tert-butyl 3-methyl 6-methyl-4-oxo-piperidine-1,3-dicarboxylate (2.50 g, 9.21 mmol, 1.00 eq) in MeOH (10.00 mL) was added $N_2H_4$-$H_2O$ (705.14 mg, 11.97 mmol, 684.60 uL, 85% purity, 1.30 eq) in one portion under $N_2$. The mixture was stirred at 75° C. for 2 hours. TLC (Petroleum ether:Ethyl acetate=4:1) showed the reaction was completed. The mixture was concentrated in vacuum to afford tert-butyl 3-hydroxy-6-methyl-1,4,6,7-tetrahydropyrazolo[4,3-c]pyridine-5-carboxylate (2.40 g, crude) as yellow solid, which was separated by SFC (Column:IC (250 mm*30 mm,10 um), Condition: Base-MeOH) to afford two enantiomers (E1: 1.0 g; E2: 1.1 g). $^1$H NMR (300 MHz, METHANOL-$d_4$) δ 4.72-4.81 (m, 1H), 4.58-4.68 (m, 1H), 3.75-3.88 (m, 1H), 2.75-2.87 (m, 1H), 2.37-2.49 (m, 1H), 1.48 (d, J=1.13 Hz, 10H), 1.13 (d, J=6.78 Hz, 3H). LCMS: 254[M+1].

Preparation of Compound 7(S)

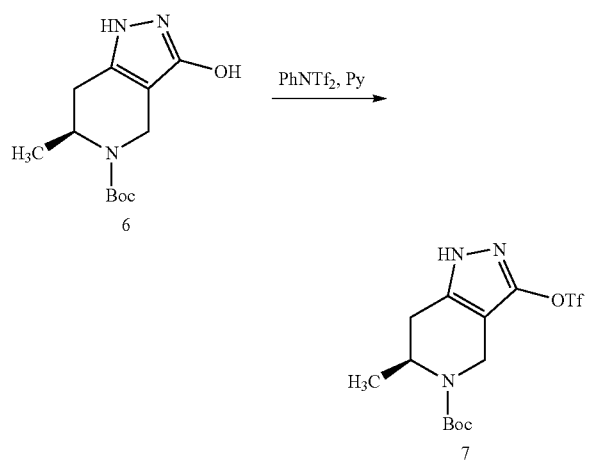

To a mixture of tert-butyl 3-hydroxy-6-methyl-1,4,6,7-tetrahydropyrazolo [4,3-c]pyridine-5-carboxylate (1.00 g, 3.95 mmol, 1.00 eq) in Py (15.00 mL) was added 1,1,1-trifluoro-N-phenyl-N-(trifluoromethylsulfonyl)methanesulfonamide (1.98 g, 5.53 mmol, 1.40 eq) in one portion under $N_2$. The mixture was stirred at 20° C. for 12 hours. TLC showed the reaction was completed. The mixture was concentrated in vacuum. The residue was diluted with ethyl acetate (50 mL) and poured into 0.5N HCl (20 mL) and stirred for 1 min. The aqueous phase was extracted with ethyl acetate (50 mL*2). The combined organic phase was washed with brine (40 mL*2), dried with anhydrous $Na_2SO_4$, filtered and concentrated in vacuum. The residue was purified by silica gel chromatography (Petroleum ether/Ethyl acetate=10/1) to afford tert-butyl 6-methyl-3-(trifluoromethylsulfonyloxy)-1,4,6,7-tetrahydropyrazolo[4,3-c]pyridine-5-carboxylate (850.00 mg, 2.21 mmol, 55.84% yield) as yellow solid. LCMS: 386[M+1].

Preparation of Compound 7(R)

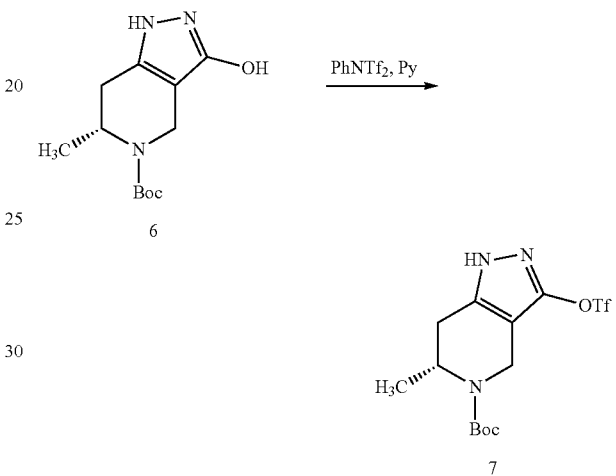

To a mixture of tert-butyl-3-hydroxy-6-methyl-1,4,6,7-tetrahydropyrazolo[4,3-c] pyridine-5-carboxylate (1.10 g, 4.34 mmol, 1.00 eq) in Py (15.00 mL) was added 1,1,1-trifluoro-N-phenyl-N-(trifluoromethylsulfonyl) methanesulfonamide (2.17 g, 6.08 mmol, 1.40 eq) in one portion under $N_2$. The mixture was stirred at 20° C. for 12 hours. TLC showed the reaction was completed. The mixture was concentrated in vacuum. The residue was diluted with ethyl acetate (60 mL) and poured into 0.5N HCl (20 mL) and stirred for 1 min. The aqueous phase was extracted with ethyl acetate (50 mL*2). The combined organic phase was washed with brine (50 mL*2), dried with anhydrous $Na_2SO_4$, filtered and concentrated in vacuum. The residue was purified by silica gel chromatography (Petroleum ether/Ethyl acetate=10/1) to afford tert-butyl6-methyl-3-(trifluoromethylsulfonyloxy)-1,4,6,7-tetrahydropyrazolo[4,3-c]pyridine-5-carboxylate (920.00 mg, 2.39 mmol, 55.01% yield) as yellow solid. LCMS: 386[M+1].

Preparation of Compound 9

To a mixture of tert-butyl 6-methyl-3-(trifluoromethylsulfonyloxy)-1,4,6,7-tetrahydropyrazolo[4,3-c]pyridine-5-carboxylate (60.00 mg, 155.70 umol, 1.00 eq) and 3-thienylboronic acid (29.88 mg, 233.55 umol, 1.50 eq) in dioxane (2.00 mL) and $H_2O$ (200.00 uL) was added [2-(2-aminophenyl)phenyl]-chloro-palladium; dicyclohexyl-[3-(2,4,6-triisopropylphenyl)phenyl]phosphane (12.25 mg, 15.57 umol, 0.10 eq) and $K_3PO_4$ (99.15 mg, 467.10 umol, 3.00 eq) in one portion under $N_2$. The mixture was stirred at 110° C. for 12 hours. TLC (Petroleum ether:Ethyl acetate=1:1) showed the reaction was completed. The mixture was poured into water (10 mL) and stirred for 2 min. The aqueous phase was extracted with ethyl acetate (10 mL*2). The combined organic phase was washed with brine (10 mL*2), dried with anhydrous Na₂SO₄, filtered and concentrated in vacuum. The residue was purified by prep-TLC (Petroleum ether/Ethyl acetate=1/1) to afford tert-butyl 6-methyl-3-(3-thienyl)-1,4,6,7-tetrahydropyrazolo [4,3-c] pyridine-5-carboxylate (43.80 mg, 137.12 umol, 88.07% yield, 100% purity) as yellow solid. LCMS: 320[M+1].

Preparation of Compound 10

To a mixture of tert-butyl 6-methyl-3-(3-thienyl)-1,4,6,7-tetrahydropyrazolo [4,3-c]pyridine-5-carboxylate (43.80 mg, 137.12 umol, 1.00 eq) in dioxane (3.00 mL) was added HCl/dioxane (4 M, 8.00 mL, 233.37 eq) in one portion under N₂. The mixture was stirred at 20° C. for 2 hours. TLC (Petroleum ether:Ethyl acetate=1:1) showed the reaction was completed. The mixture was concentrated in vacuum to afford 6-methyl-3-(3-thienyl)-4,5,6,7-tetrahydro-1H-pyrazolo [4,3-c]pyridine (35.07 mg, 137.12 umol, 100.00% yield, HCl) as yellow solid.

Preparation of Compound 754 (E1)

To a mixture of 6-methyl-3-(3-thienyl)-4,5,6,7-tetrahydro-1H-pyrazolo[4,3-c]pyridine (35.07 mg, 137.12 umol, 1.00 eq, HCl) and phenyl N-(3-chlorophenyl)carbamate (33.96 mg, 137.12 umol, 1.00 eq) in DCM (5.00 mL) was added TEA (41.62 mg, 411.35 umol, 57.02 uL, 3.00 eq) in one portion under N₂. The mixture was stirred at 20° C. for 12 hours. LCMS showed the reaction was completed. The mixture was poured into water (10 mL) and stirred for 2 min. The aqueous phase was extracted with DCM (10 mL*2). The combined organic phase was washed with brine (10 mL*2), dried with anhydrous Na₂SO₄, filtered and concentrated in vacuum. The residue was purified by prep-HPLC (FA) to afford N-(3-chlorophenyl)-6-methyl-3-(3-thienyl)-1,4,6,7-tetrahydropyrazolo[4,3-c]pyridine-5-carboxamide (23.00 mg, 60.39 umol, 44.04% yield, 97.9% purity) as white solid. ¹H NMR (400 MHz, METHANOL-d₄) δ 7.65-7.70 (m, 1H), 7.51-7.57 (m, 3H), 7.29-7.34 (m, 1H), 7.20-7.28 (m, 1H), 6.99-7.05 (m, 1H), 4.99-5.06 (m, 1H), 4.42 (d, J=15.18 Hz, 1H), 3.05 (s, 1H), 2.65-2.74 (m, 1H), 1.23 (d, J=6.90 Hz, 3H). LCMS: 373/375[M+1].

Preparation of Compound 11

To a mixture of tert-butyl 6-methyl-3-(trifluoromethylsulfonyloxy)-1,4,6,7-tetrahydro pyrazolo[4,3-c]pyridine-5-carboxylate (60.00 mg, 155.70 umol, 1.00 eq) and 3-thienylboronic acid (29.88 mg, 233.55 umol, 1.50 eq) in dioxane (2.00 mL) and H₂O (200.00 uL) was added [2-(2-aminophenyl)phenyl]-chloro-palladium; dicyclohexyl-[3-(2,4,6-triisopropylphenyl)phenyl]phosphane (12.25 mg, 15.57 umol, 0.10 eq) and K₃PO₄ (99.15 mg, 467.10 umol, 3.00 eq) in one portion under N₂. The mixture was stirred at 110° C. for 12 hours. TLC (Petroleum ether:Ethyl acetate=1:1) showed the reaction was completed. The mixture was poured into water (10 mL) and stirred for 2 min. The aqueous phase was extracted with ethyl acetate (10 mL*2). The combined organic phase was washed with brine (10 mL*2), dried with anhydrous Na₂SO₄, filtered and concentrated in vacuum. The residue was purified by prep-TLC (Petroleum ether/Ethyl acetate=1/1) to afford tert-butyl 6-methyl-3-(3-thienyl)-1,4,6,7-tetrahydropyrazolo [4,3-c] pyridine-5-carboxylate (42.20 mg, 132.11 umol, 84.85% yield, 100% purity) as yellow solid. LCMS: 320[M+1].

Preparation of Compound 12

To a mixture of tert-butyl 6-methyl-3-(3-thienyl)-1,4,6,7-tetrahydropyrazolo [4,3-c]pyridine-5-carboxylate (42.00 mg, 131.49 umol, 1.00 eq) in dioxane (3.00 mL) was added HCl/dioxane (4 M, 8.00 mL, 243.36 eq) in one portion under N₂. The mixture was stirred at 20° C. for 2 hours. TLC (Petroleum ether:Ethyl acetate=1:1) showed the reaction was completed. The mixture was concentrated in vacuum to afford 6-methyl-3-(3-thienyl)-4,5,6,7-tetrahydro-1H-pyrazolo [4,3-c]pyridine (33.63 mg, 131.49 umol, 100.00% yield, HCl) as yellow solid.

Preparation of Compound 754 (E2)

To a mixture of 6-methyl-3-(3-thienyl)-4,5,6,7-tetrahydro-1H-pyrazolo[4,3-c]pyridine (33.63 mg, 131.49 umol, 1.00 eq, HCl) and phenyl N-(3-chlorophenyl)carbamate (32.57 mg, 131.49 umol, 1.00 eq) in DCM (5.00 mL) was added TEA (39.91 mg, 394.46 umol, 54.68 uL, 3.00 eq) in one portion under N₂. The mixture was stirred at 20° C. for 12 hours. LCMS showed the reaction was completed. The mixture was poured into water (10 mL) and stirred for 2 min. The aqueous layer was extracted with DCM (10 mL*2). The combined organic phase was washed with brine (10 mL*2), dried with anhydrous Na₂SO₄, filtered and concentrated in vacuum. The residue was purified by prep-HPLC (FA) to afford N-(3-chlorophenyl)-6-methyl-3-(3-thienyl)-1,4,6,7-tetrahydropyrazolo[4,3-c]pyridine-5-carboxamide (25.00 mg, 66.58 umol, 50.63% yield, 99.3% purity) as white solid. ¹H NMR (400 MHz, METHANOL-d₄) δ 7.65-7.70 (m, 1H), 7.51-7.57 (m, 3H), 7.29-7.34 (m, 1H), 7.20-7.28 (m, 1H), 6.99-7.05 (m, 1H), 4.99-5.06 (m, 1H), 4.42 (d, J=15.18 Hz, 1H), 3.05 (s, 1H), 2.65-2.74 (m, 1H), 1.23 (d, J=6.90 Hz, 3H). LCMS: 373/375 [M+1].

Example 56: Preparation of Compounds 753, 819, 820, 821, 822, 823, 824, 825, 826, 851, 852, 853, 854, 856, and 857

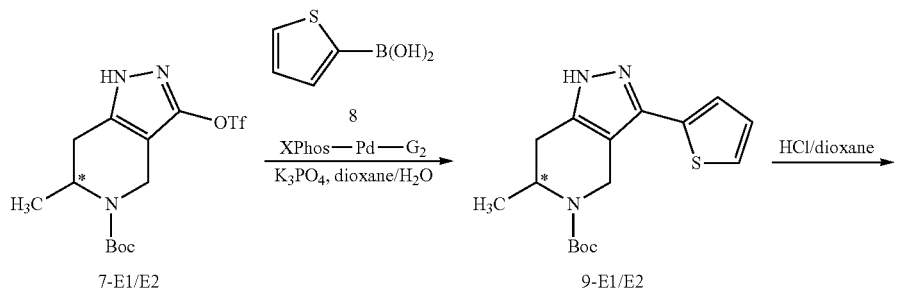

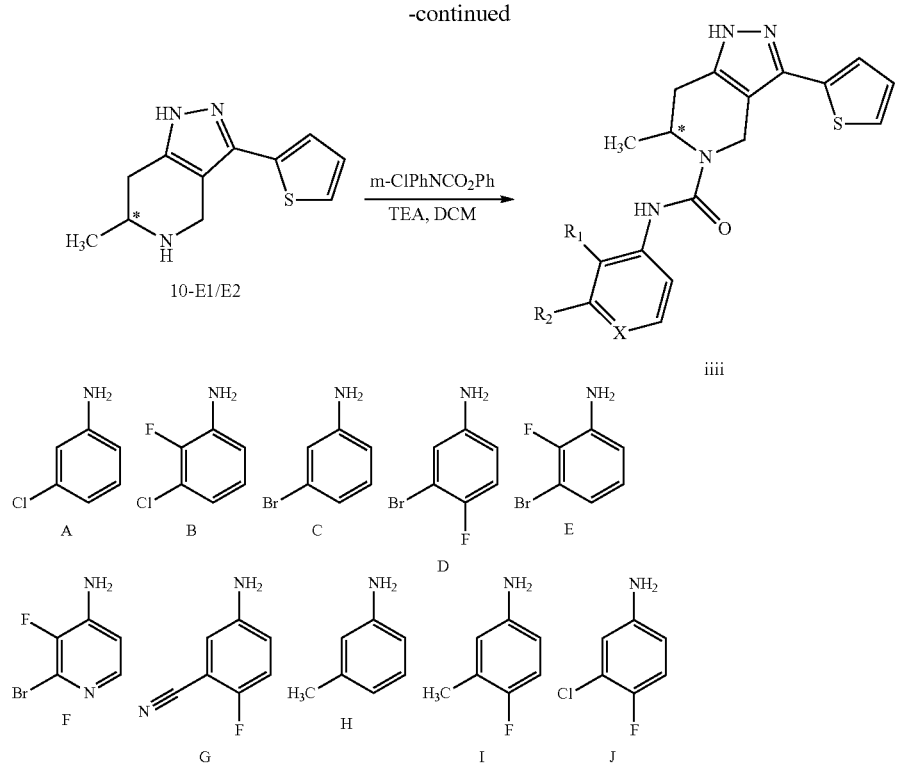

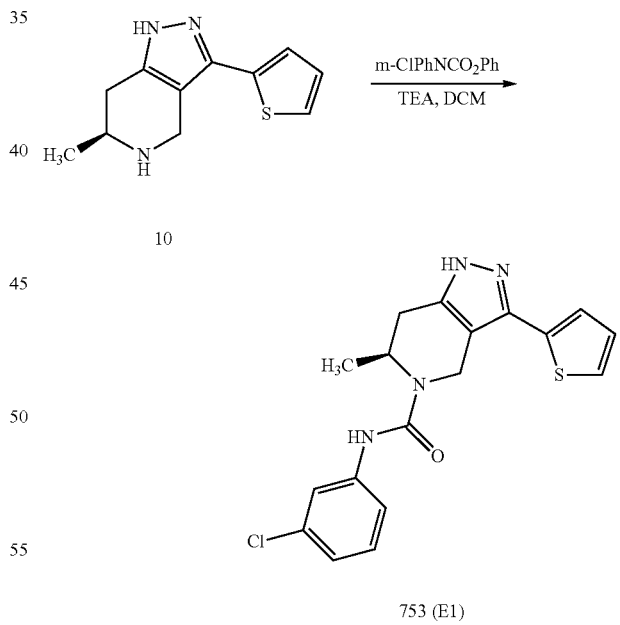

753 (E1)

Step 1: Preparation of Compound 9

To a mixture of tert-butyl 6-methyl-3-(trifluoromethylsulfonyloxy)-1,4,6,7-tetrahydro pyrazolo[4,3-c]pyridine-5-carboxylate (70.00 mg, 181.65 umol, 1.00 eq) and 2-thienylboronic acid (34.87 mg, 272.47 umol, 1.50 eq) in dioxane (1.00 mL) and H₂O (100.00 uL) was added [2-(2-aminophenyl)phenyl]-chloro-palladium; dicyclohexyl-[3-(2,4,6-triisopropylphenyl)phenyl]phosphane (14.29 mg, 18.16 umol, 0.10 eq) and K₃PO₄ (115.68 mg, 544.94 umol, 3.00 eq) in one portion under N₂. The mixture was stirred at 110° C. for 12 hours. TLC (Petroleum ether:Ethyl acetate=1:1) showed the reaction was completed. The mixture was poured into water (10 mL) and stirred for 2 min. The aqueous phase was extracted with ethyl acetate (10 mL*2). The combined organic phase was washed with brine (10 mL*2), dried with anhydrous Na₂SO₄, filtered and concentrated in vacuum. The residue was purified by prep-TLC (Petroleum ether/Ethyl acetate=1/1) to afford tert-butyl 6-methyl-3-(2-thienyl)-1,4,6,7-tetrahydropyrazolo[4,3-c]pyridine-5-carboxylate (10.00 mg, 31.31 umol, 17.23% yield, 100% purity) as yellow solid. LCMS: 320[M+1].

Step 2: Preparation of Compound 10

To a mixture of tert-butyl 6-methyl-3-(2-thienyl)-1,4,6,7-tetrahydropyrazolo [4,3-c]pyridine-5-carboxylate (10.00 mg, 31.31 umol, 1.00 eq) in dioxane (2.00 mL) was added HCl/dioxane (4 M, 5.00 mL, 638.77 eq) in one portion under N₂. The mixture was stirred at 20° C. 2 hours. TLC (Petroleum ether:Ethyl acetate=1:1) showed the reaction was completed. The mixture was concentrated in vacuum to afford 6-methyl-3-(2-thienyl)-4,5,6,7-tetrahydro-1H-pyrazolo [4,3-c]pyridine (8.00 mg, 31.28 umol, 99.90% yield, HCl) as white solid.

Preparation of Compound 753 (E1)

To a mixture of 6-methyl-3-(2-thienyl)-4,5,6,7-tetrahydro-1H-pyrazolo [4,3-c]pyridine (8.01 mg, 31.32 umol, 1.00 eq, HCl) and phenyl N-(3-chlorophenyl)carbamate (7.76 mg, 31.32 umol, 1.00 eq) in DCM (5.00 mL) was added TEA (12.68 mg, 125.28 umol, 17.37 uL, 4.00 eq) in one portion under N₂. The mixture was stirred at 20° C. for 12 hours. LCMS showed the reaction was completed. The mixture was poured into water (10 mL) and stirred for 2 min.

The aqueous phase was extracted with DCM (10 mL*2). The combined organic phase was washed with brine (10 mL*1), dried with anhydrous $Na_2SO_4$, filtered and concentrated in vacuum. The residue was purified by prep-HPLC (FA) to afford N-(3-chlorophenyl)-6-methyl-3-(2-thienyl)-1,4,6,7-tetrahydropyrazolo[4,3-c]pyridine-5-carboxamide (7.65 mg, 19.84 umol, 63.34% yield, 96.7% purity) as white solid. $^1$H NMR (400 MHz, METHANOL-$d_4$) δ 7.53 (s, 1H), 7.29-7.46 (m, 3H), 7.21-7.27 (m, 1H), 7.12-7.17 (m, 1H), 7.02 (d, J=8.41 Hz, 1H), 4.99-5.06 (m, 2H), 4.33-4.44 (m, 1H), 3.02-3.13 (m, 1H), 2.65-2.75 (m, 1H), 1.22-1.26 (m, 1H). LCMS: 373/375 [M+1].

Compounds 753 (E2), 819, 820, 821 through 826, and 851 through 857 were prepared by the same method.

| Structure | Comp. ID | $^1$H NMR | MS (M + H)$^+$ |
|---|---|---|---|
| 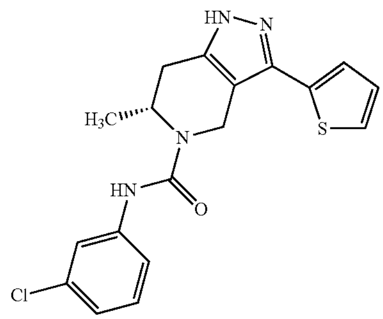 [SMILES: C[C@@H]1Cc2[nH]nc(-c3cccs3)c2CN1C(=O)Nc1cccc(Cl)c1] | 753 (E2) | $^1$H NMR (400 MHz, METHANOL-$d_4$) δ 7.53 (s, 1 H), 7.29-7.46 (m, 3 H), 7.21-7.27 (m, 1 H), 7.12-7.17 (m, 1 H), 7.02 (d, J = 8.41 Hz, 1 H), 4.99-5.06 (m, 2 H), 4.33-4.44 (m, 1 H), 3.02-3.13 (m, 1 H), 2.65-2.75 (m, 1 H), 1.22-1.26 (m, 1 H). | 373/375 |
| 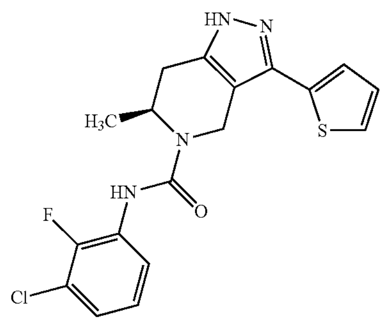 [SMILES: C[C@H]1Cc2[nH]nc(-c3cccs3)c2CN1C(=O)Nc1cccc(Cl)c1F] | 819 | | 391/393 |
| 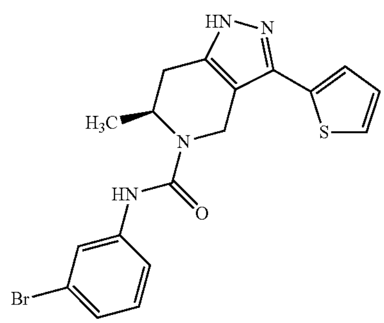 [SMILES: C[C@H]1Cc2[nH]nc(-c3cccs3)c2CN1C(=O)Nc1cccc(Br)c1] | 820 | | 417/419 |
| 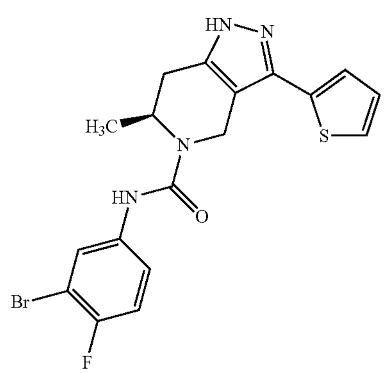 | 821 | | 435/437 |

| Structure | Comp. ID | ¹H NMR | MS (M + H)⁺ |
|---|---|---|---|
| 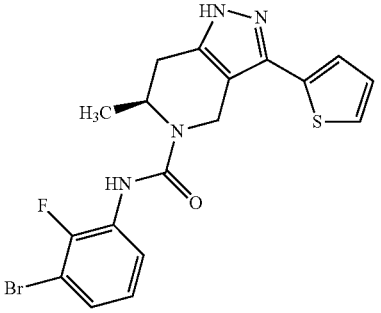 [SMILES: C[C@H]1Cc2[nH]nc(-c3cccs3)c2CN1C(=O)Nc1cccc(Br)c1F] | 822 | | 435/437 |
| 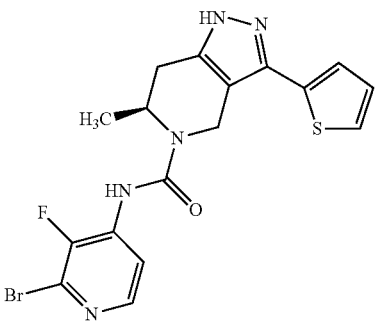 [SMILES: C[C@H]1Cc2[nH]nc(-c3cccs3)c2CN1C(=O)Nc1ccnc(Br)c1F] | 823 | ¹H NMR (400 MHz, METHANOL-d₄) δ 7.99-8.05 (m, 1 H), 7.77-7.84 (m, 1 H), 7.40-7.49 (m, 1 H), 7.30-7.37 (m, 1 H), 7.11-7.18 (m, 1 H), 5.04 (d, J = 15.56 Hz, 2 H), 4.45 (d, J = 15.43 Hz, 1 H), 3.06-3.16 (m, 1 H), 2.71 (d, J = 16.06 Hz, 1 H), 1.27 (d, J = 6.90 Hz, 3 H) | 436/438 |
| 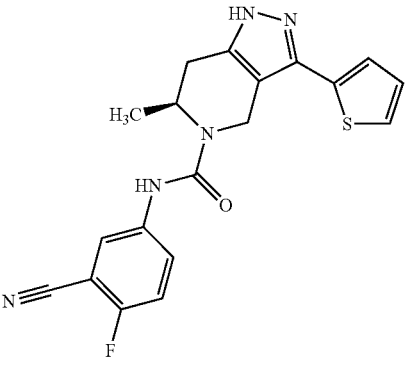 [SMILES: C[C@H]1Cc2[nH]nc(-c3cccs3)c2CN1C(=O)Nc1ccc(F)c(C#N)c1] | 824 | ¹H NMR (400 MHz, METHANOL-d₄) δ 7.81 (dd, J = 2.76, 5.65 Hz, 1 H), 7.67-7.75 (m, 1 H), 7.36 (brs, 2 H), 7.28 (t, J = 8.97 Hz, 1 H), 7.14 (brs, 1 H), 4.96-5.07 (m, 2 H), 4.38 (d, J = 15.56 Hz, 1 H), 3.02-3.11 (m, 1 H), 2.70 (d, J = 15.81 Hz, 1 H), 1.25 (d, J = 6.90 Hz, 3 H). | 382 |
| 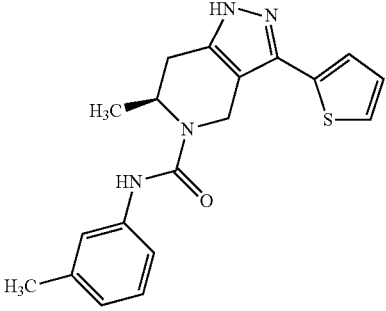 [SMILES: Cc1cccc(NC(=O)N2Cc3c(-c4cccs4)n[nH]c3C[C@@H]2C)c1] | 825 | ¹H NMR (400 MHz, METHANOL-d₄) δ 7.31-7.45 (m, 2 H), 7.17 (s, 4 H), 6.83-6.90 (m, 1 H), 4.96-5.06 (m, 2 H), 4.31-4.43 (m, 1 H), 3.01-3.12 (m, 1 H), 2.64-2.73 (m, 1 H), 2.31 (s, 3 H), 1.24 (d, J = 6.78 Hz, 3H). | 353 |

-continued

| Structure | Comp. ID | ¹H NMR | MS (M + H)⁺ |
|---|---|---|---|
| 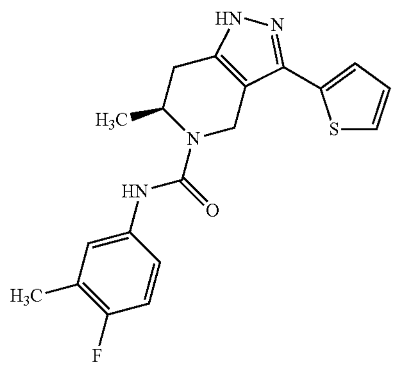 [SMILES: Cc1cc(NC(=O)N2Cc3c(-c4cccs4)n[nH]c3C[C@@H]2C)ccc1F] | 826 | ¹H NMR (400 MHz, METHANOL-d₄) δ 7.32-7.49 (m, 2 H), 7.21-7.26 (m, 1 H), 7.10-7.19 (m, 2 H), 6.94 (t, J = 9.10 Hz, 1 H), 5.01 (d, J = 15.43 Hz, 2 H), 4.31-4.39 (m, 1 H), 3.01-3.11 (m, 1 H), 2.65-2.72 (m, 1 H), 2.24 (d, J = 1.51 Hz, 3 H), 1.23 (d, J = 6.90 Hz, 3 H). | 371 |
| 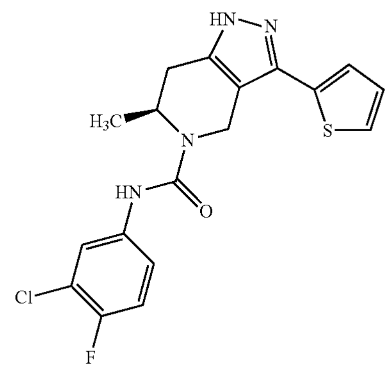 [SMILES: C[C@H]1Cc2[nH]nc(-c3cccs3)c2CN1C(=O)Nc1ccc(F)c(Cl)c1] | 857 | ¹H NMR (400 MHz, METHANOL-d₄) δ 7.57-7.62 (m, 1 H), 7.28-7.48 (m, 3 H), 7.11-7.19 (m, 2 H), 5.00-5.07 (m, 2 H), 4.37 (d, J = 15.18 Hz, 1 H), 3.00-3.10 (m, 1 H), 2.64-2.74 (m, 1 H), 1.24 (d, J = 6.78 Hz, 3 H). | 391/393 |
| 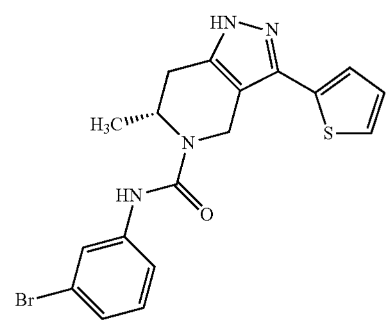 [SMILES: C[C@@H]1Cc2[nH]nc(-c3cccs3)c2CN1C(=O)Nc1cccc(Br)c1] | 851 | | 417/419 |
| 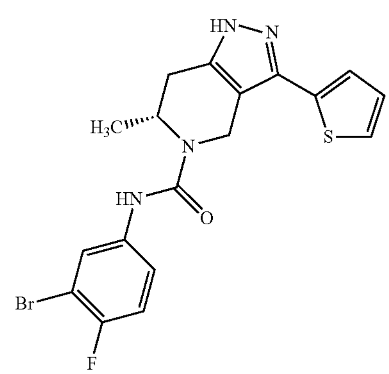 [SMILES: C[C@@H]1Cc2[nH]nc(-c3cccs3)c2CN1C(=O)Nc1ccc(F)c(Br)c1] | 852 | ¹H NMR (400 MHz, METHANOL-d₄) δ 7.69-7.78 (m, 1 H), 7.31-7.50 (m, 3 H), 7.06-7.20 (m, 2 H), 4.99-5.04 (m, 2 H), 4.31-4.43 (m, 1 H), 3.01-3.11 (m, 1 H), 2.65-2.74 (m, 1 H), 1.24 (d, J = 6.90 Hz, 3 H). | 435/437 |

| Structure | Comp. ID | ¹H NMR | MS (M + H)⁺ |
|---|---|---|---|
| (structure) | 853 | | 436/438 |
| (structure) | 854 | ¹H NMR (400 MHz, METHANOL-d4) δ 7.76-7.81 (m, 1 H), 7.65-7.69 (m, 1 H), 7.30-7.40 (m, 2 H), 7.09-7.23 (m, 2 H), 4.92-5.05 (m, 2 H), 4.36-4.39 (m, 1 H), 3.00-3.13 (m, 1 H), 2.57-2.77 (m, 1 H), 1.18-1.31 (m, 3 H). | 382 |
| (structure) | 855 | ¹H NMR (400 MHz, METHANOL-d4) δ 7.34-7.47 (m, 1 H), 7.11-7.27 (m, 2 H), 6.89-6.98 (m, 1 H), 5.01 (d, J = 15.18 Hz, 2 H), 4.32-4.40 (m, 1 H), 3.01-3.10 (m, 1 H), 2.65-2.72 (m, 1 H), 2.24 (d, J = 1.51 Hz, 3 H), 1.23 (d, J = 6.78 Hz, 3 H). | 371 |
| (structure) | 856 | | 391/393 |

Example 57: Preparation of Compound 830

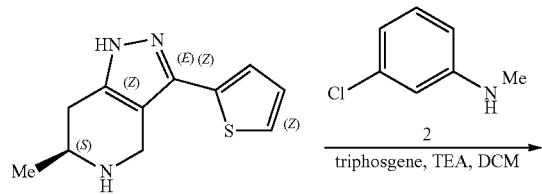

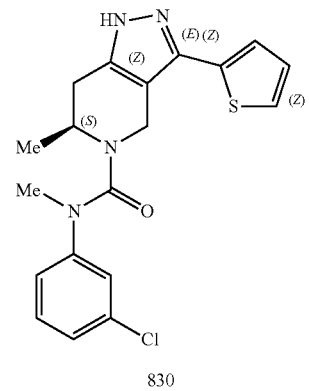

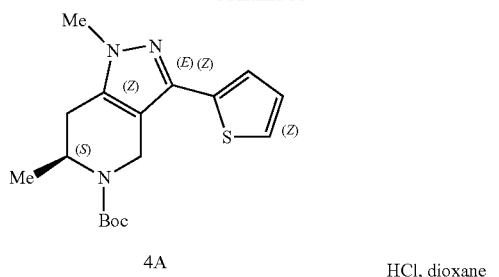

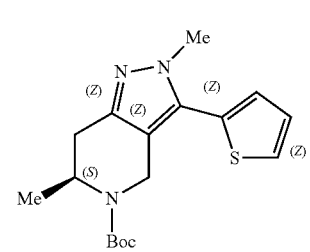

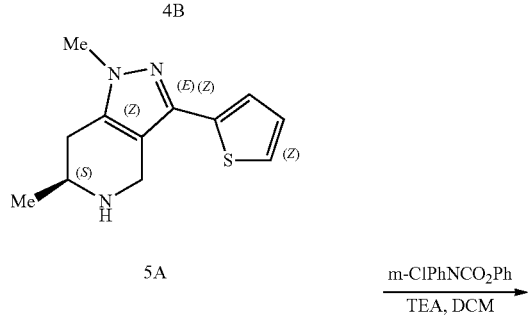

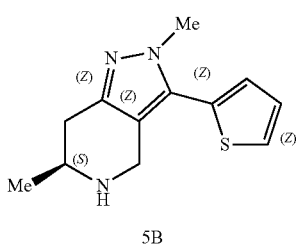

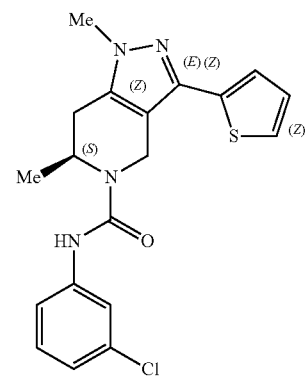

To a mixture of 3-chloro-N-methyl-aniline (18.27 mg, 129.02 umol, 15.75 uL, 1.10 eq) and TEA (35.61 mg, 351.87 umol, 48.78 uL, 3.00 eq) in DCM (2.00 mL) was added TRIPHOSGENE (27.85 mg, 93.83 umol, 0.80 eq) in one portion at 0° C. under $N_2$. The mixture was stirred at 0° C. for 5 min. Then (6S)-6-methyl-3-(2-thienyl)-4,5,6,7-tetrahydro-1H-pyrazolo[4,3-c]pyridine (30.00 mg, 117.29 umol, 1.00 eq, HCl) was added to the mixture, the mixture was stirred at 0° C. for 30 min. LCMS showed the reaction was completed. The mixture was poured into water (10 mL) and stirred for 2 min. The aqueous phase was extracted with DCM (10 mL*2). The combined organic phase was washed with brine (10 mL*2), dried with anhydrous $Na_2SO_4$, filtered and concentrated in vacuum. The residue was purified by prep-HPLC (FA) to afford (6S)—N-(3-chlorophenyl)-N,6-dimethyl-3-(2-thienyl)-1,4,6,7-tetrahydropyrazolo[4,3-c]pyridine-5-carboxamide (10.55 mg, 26.99 umol, 23.01% yield, 98.99% purity) as white solid. $^1$H NMR (400 MHz, METHANOL-$d_4$) δ 7.32-7.45 (m, 2H), 7.27-7.31 (m, 1H), 7.02-7.24 (m, 4H), 4.67-4.74 (m, 1H), 4.50-4.57 (m, 1H), 3.77-3.85 (m, 1H), 3.23 (s, 3H), 2.78 (d, J=5.27 Hz, 1H), 2.45-2.55 (m, 1H), 1.07-1.17 (m, 3H). LCMS: 387/389[M+1].

Example 58: Preparation of Compounds 831 and 832

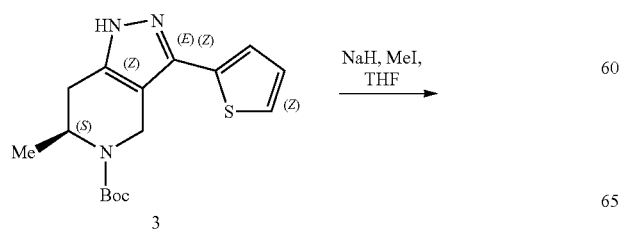

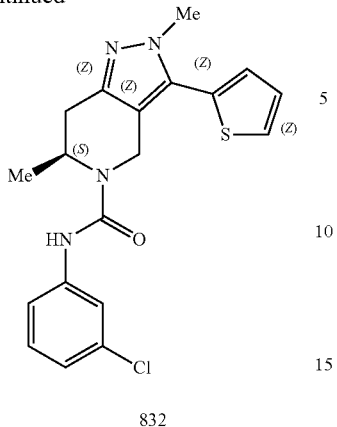

832

Step 1: Preparation of Compounds 4A and 4B

To a mixture of tert-butyl (6S)-6-methyl-3-(2-thienyl)-1,4,6,7-tetrahydro pyrazolo[4,3-c]pyridine-5-caboxylate (50.00 mg, 156.53 umol, 1.00 eq) in TH (2.00 mL) was added NaH (9.39 mg, 234.80 umol, 60% purity, 1.50 eq) in one portion at 0° C. under $N_2$. The mixture was stirred at 0° C. for 30 min, then MeMe (66.66 mg, 469.60 umol, 29.23 uL, 3.00 eq) was added to the mixture, The mixture was stirred at 0° C. for 1 hours. TLC (Petroleum ether:Ethyl acetate=2:1) showed the reaction was completed. The mixture was poured into water (10 mL) and stirred for 2 min. The aqueous phase was extracted with ethyl acetate (10 mL*2). The combined organic phase was washed with brine (10 mL*2), dried with anhydrous $Na_2SO_4$, filtered and concentrated in vacuum. The residue was purified by prep-TLC (Petroleum ether/Ethyl acetate=5/1, 10 times) to afford tert-butyl (6S)-1,6-dimethyl-3-(2-thienyl)-6,7-dihydro-4H-pyrazolo[4,3-c]pyridine-5-carboxylate (20.00 mg, 59.98 umol, 38.32% yield) as yellow solid and tert-butyl(6S)-2,6-dimethyl-3-(2-thienyl)-6,7-dihydro-4H-pyrazolo[4,3-c]pyridine-5-carboxylate (15.00 mg, 44.98 umol, 28.74% yield) as yellow solid.

Compound 4A: $^1$H NMR (400 MHz, CHLOROFORM-d) 807.26-7.29 (m, 1H), 7.16-7.21 (m, 1H), 7.06-7.11 (m, 1H), 4.76-5.12 (m, 2H), 4.08-4.22 (m, 1H), 3.78 (s, 3H), 2.88-3.01 (m, 1H), 2.39-2.53 (m, 1H), 1.51 (s, 9H), 1.18 (d, J=6.90 Hz, 3H). LCMS: 334[M+1].

Compound 4B: $^1$H NMR (400 MHz, CHLOROFORM-d) 807.43-7.48 (m, 1H), 7.14-7.18 (m, 1H), 7.13 (s, 1H), 4.72-4.99 (m, 2H), 3.99-4.09 (m, 1H), 3.93 (s, 3H), 2.91-3.03 (m, 1H), 2.52-2.65 (m, 1H), 1.48 (s, 9H), 1.16 (d, J=7.03 Hz, 3H). LCMS: 334[M+1].

Step 2A: Preparation of Compound 5A

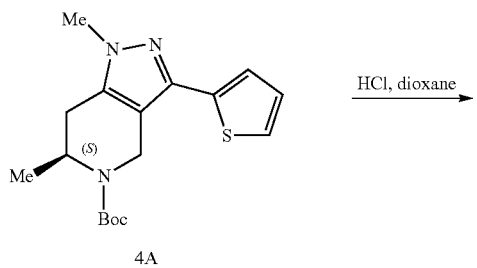

4A

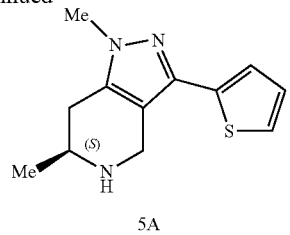

5A

To a mixture of tert-butyl (6S)-1,6-dimethyl-3-(2-thienyl)-6,7-dihydro-4H-pyrazolo [4,3-c]pyridine-5-carboxylate (20.00 mg, 59.98 umol, 1.00 eq) in dioxane (2.00 mL) was added HCl/dioxane (4 M, 729.81 uL, 48.67 eq) in one portion under $N_2$. The mixture was stirred at 30° C. for 2 hours. TLC (Petroleum ether:Ethyl acetate=3:1) showed the reaction was completed. The mixture was concentrated in vacuum to afford (6S)-1,6-dimethyl-3-(2-thienyl)-4,5,6,7-tetrahydropyrazolo [4,3-c] pyridine (16.18 mg, 59.97 umol, 100.00% yield, HCl) as white solid.

Preparation of Compound 831

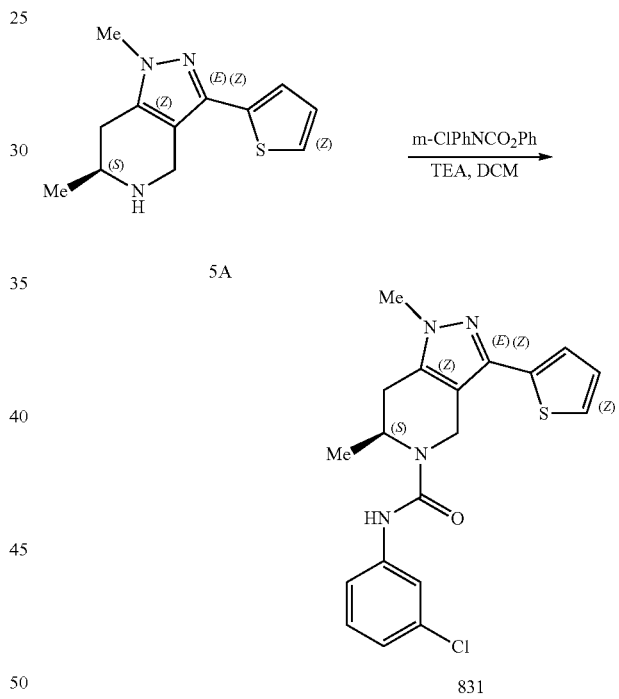

831

To a mixture of (6S)-1,6-dimethyl-3-(2-thienyl)-4,5,6,7-tetrahydropyrazolo [4,3-c] pyridine (16.18 mg, 59.97 umol, 1.00 eq, HCl) and phenyl N-(3-chlorophenyl)carbamate (14.85 mg, 59.97 umol, 1.00 eq) in DCM (5.00 mL) was added TEA (18.21 mg, 179.92 umol, 24.94 uL, 3.00 eq) in one portion under $N_2$. The mixture was stirred at 30° C. for 12 hours. LCMS showed the reaction was completed. The mixture was poured into water (10 mL) and stirred for 2 min. The aqueous phase was extracted with DCM (10 mL*2). The combined organic phase was washed with brine (10 mL*2), dried with anhydrous $Na_2SO_4$, filtered and concentrated in vacuum. The residue was purified by prep-HPLC (FA) to afford (6S)—N-(3-chlorophenyl)-1,6-dimethyl-3-(2-thienyl)-6,7-dihydro-4H-pyrazolo[4,3-c]pyridine-5-carboxamide (10.00 mg, 25.56 umol, 42.62% yield, 98.9% purity)

as white solid. $^1$H NMR (400 MHz, METHANOL-d$_4$) δ 7.51-7.54 (m, 1H), 7.36-7.39 (m, 1H), 7.27-7.34 (m, 2H), 7.20-7.27 (m, 1H), 7.09-7.14 (m, 1H), 6.99-7.04 (m, 1H), 4.98 (s, 2H), 4.31-4.38 (m, 1H), 3.78 (s, 3H), 2.97-3.06 (m, 1H), 2.67-2.76 (m, 1H), 1.25 (d, J=6.90 Hz, 3H). LCMS: 387/389[M+1].

Step 2B: Preparation of Compound 5B

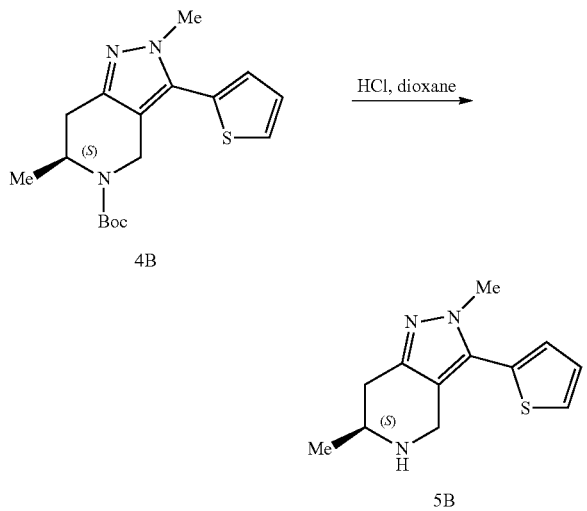

To a mixture of tert-butyl (6S)-2,6-dimethyl-3-(2-thienyl)-6,7-dihydro-4H-pyrazolo [4,3-c]pyridine-5-carboxylate (15.00 mg, 44.98 umol, 1.00 eq) in dioxane (1.00 mL) was added HCl/dioxane (4 M, 4.00 mL, 355.71 eq) in one portion at 30° C. under N$_2$. The mixture was stirred at 30° C. for 2 hours. TLC (Petroleum ether:Ethyl acetate=3:1) showed the reaction was completed. The mixture was concentrated in vacuum to afford (6S)-2,6-dimethyl-3-(2-thienyl)-4,5,6,7-tetrahydropyrazolo[4,3-c] pyridine (12.14 mg, 45.00 umol, 100.00% yield, HCl) as yellow solid.

Preparation of Compound 832

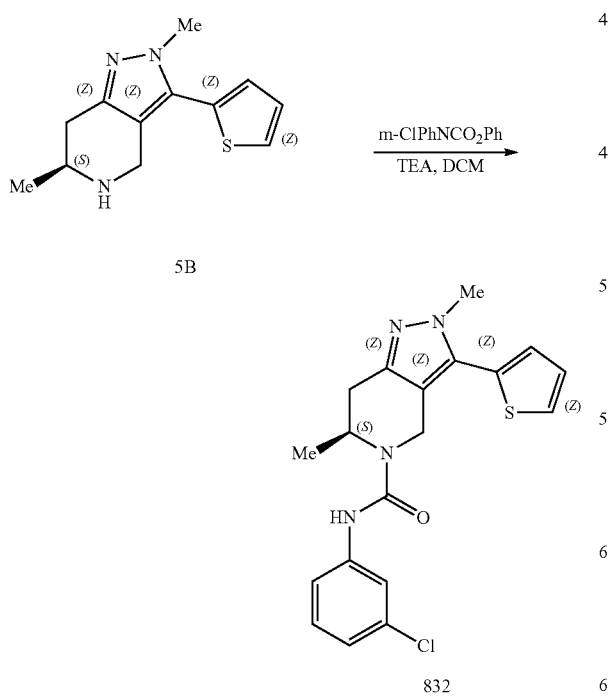

To a mixture of (6S)-2,6-dimethyl-3-(2-thienyl)-4,5,6,7-tetrahydropyrazolo [4,3-c] pyridine (12.14 mg, 45.00 umol, 1.00 eq, HCl) and phenyl N-(3-chlorophenyl)carbamate (11.15 mg, 45.00 umol, 1.00 eq) in DCM (3.00 mL) was added TEA (13.66 mg, 134.99 umol, 18.71 uL, 3.00 eq) in one portion at 30° C. under N$_2$. The mixture was stirred at 30° C. for 12 hours. LCMS showed the reaction was completed. The mixture was poured into water (10 mL) and stirred for 3 min. The aqueous phase was extracted with ethyl acetate (10 mL*2). The combined organic phase was washed with brine (10 mL*2), dried with anhydrous Na$_2$SO$_4$, filtered and concentrated in vacuum. The residue was purified by prep-HPLC (FA) to afford (6S)—N-(3-chlorophenyl)-2,6-dimethyl-3-(2-thienyl)-6,7-dihydro-4H-pyrazolo[4,3-c]pyridine-5-carboxamide (16.38 mg, 42.34 umol, 94.08% yield, 100% purity) as white solid. $^1$H NMR (400 MHz, METHANOL-d$_4$) δ 7.64-7.69 (m, 1H), 7.48-7.51 (m, 1H), 7.30-7.34 (m, 1H), 7.18-7.29 (m, 1H), 6.97-7.03 (m, 1H), 4.93 (d, J=6.15 Hz, 2H), 4.22-4.30 (m, 1H), 3.91 (s, 3H), 2.98-3.07 (m, 1H), 2.60-2.69 (m, 1H), 1.23 (d, J=6.78 Hz, 3H). LCMS: 387/389[M+1].

Example 59: Preparation of Compound 753 (S)

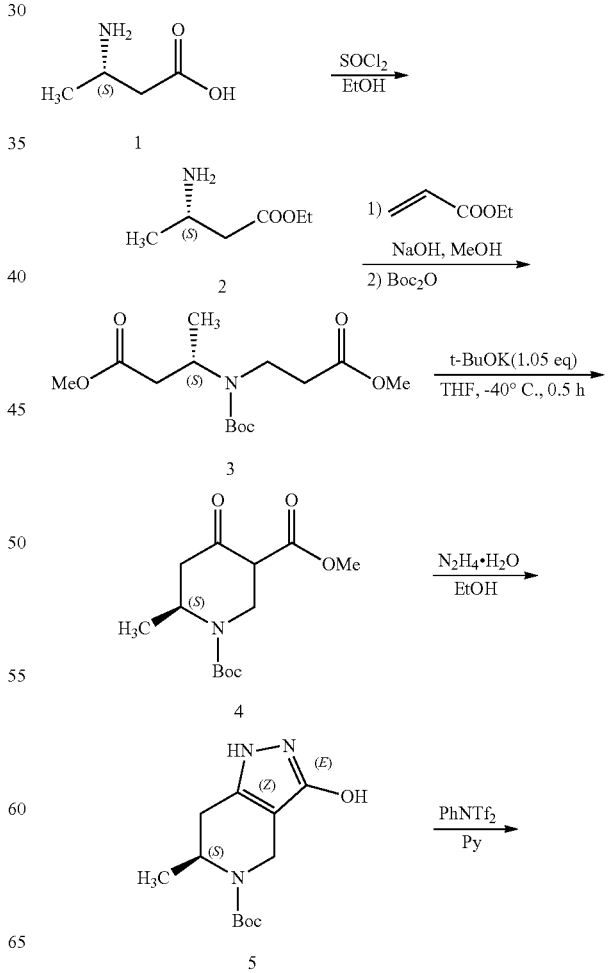

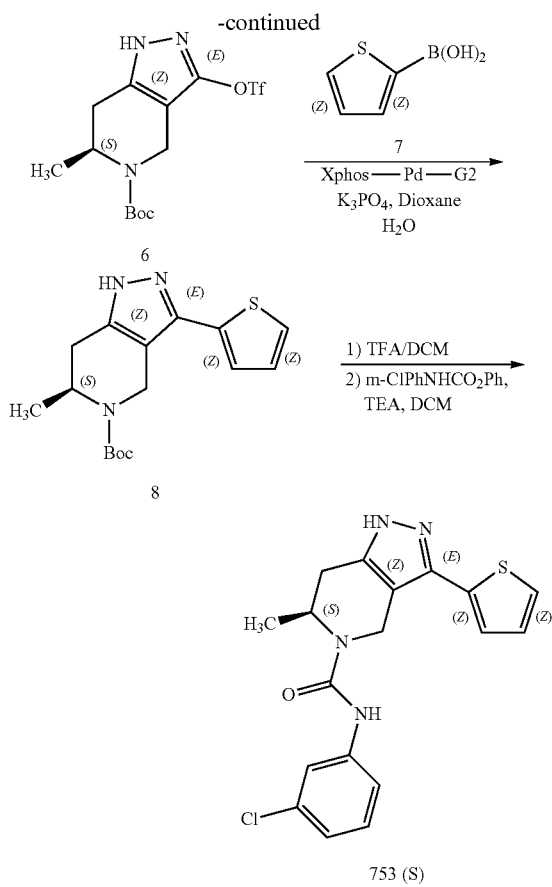

Step 1: Preparation of Compound 2

To a solution of (3S)-3-aminobutanoic acid (13.00 g, 93.14 mmol, 1.00 eq, HCl) in EtOH (130.00 mL) was added SOCl$_2$ (16.62 g, 139.70 mmol, 10.13 mL, 1.50 eq). The mixture was heated to 80° C. for 3 hr. The mixture was concentrated in vacuum to afford ethyl (3S)-3-aminobutanoate (15.60 g, 93.06 mmol, 99.92% yield, HCl) as brown oil.

Step 2: Preparation of Compound 3

To a solution of ethyl (3S)-3-aminobutanoate (15.60 g, 93.06 mmol, 1.00 eq, HCl) in MeOH (150.00 mL) was added NaOH (4.47 g, 111.67 mmol, 1.20 eq) followed by ethyl prop-2-enoate (10.25 g, 102.37 mmol, 11.14 mL, 1.10 eq). The mixture was heated to 80° C. for 16 hr. The mixture was cooled to 0° C. and added Boc$_2$O (20.31 g, 93.06 mmol, 21.38 mL, 1.00 eq) followed by TEA (9.42 g, 93.06 mmol, 12.90 mL, 1.00 eq). The mixture was stirred at 25° C. for 2 hr. The mixture was concentrated in vacuum. The residue was extracted with DCM (100 mL*2) and H$_2$O (100 mL). The combined organic layer was washed with 1N HCl (100 mL), dried over Na$_2$SO$_4$, filtrated. The filtrate was concentrated in vacuum. The residue was purified by flash chromatography (PE:EA=0%-15%) to afford methyl (3S)-3-[tert-butoxycarbonyl-(3-methoxy-3-oxo-propyl)amino] butanoate (13.00 g, 42.85 mmol, 46.05% yield) as colorless oil. $^1$H NMR (400 MHz, CHLOROFORM-d) δ 4.13 (q, J=7.2 Hz, 2H), 3.65-3.72 (m, 5H), 3.29-3.54 (m, 2H), 2.51-2.73 (m, 3H), 2.47 (dd, J=6.8, 14.9 Hz, 1H), 1.43-1.49 (m, 9H), 1.22-1.29 (m, 5H).

Step 3: Preparation of Compound 4

To a solution of methyl 3S)-3-[tert-butoxycarbonyl-(3-methoxy-3-oxo-propyl)amino] butanoate (7.00 g, 23.08 mmol, 1.00 eq) in THF (200.00 mL) was added t-BuOK (2.85 g, 25.38 mmol, 1.10 eq) at −40° C. The mixture was stirred at −40° C. for 0.5 hr. The mixture was quenched with NH$_4$Cl (100 mL) and extracted with EA (200 mL). The organic layer was dried over Na$_2$SO$_4$, filtered. The filtrate was concentrated to afford 01-tert-butyl-O3-methyl (6S)-6-methyl-4-oxo-piperidine-1,3-dicarboxylate (5.80 g, 21.38 mmol, 92.62% yield) as brown oil.

Step 4: Preparation of Compound 5

To a solution of O1-tert-butyl O3-methyl (6S)-6-methyl-4-oxo-piperidine-1,3-dicarboxylate (5.80 g, 21.38 mmol, 1.00 eq) in EtOH (60.00 mL) was added NH$_2$NH$_2$.H$_2$O (2.52 g, 42.76 mmol, 2.44 mL, 85% purity, 2.00 eq). The mixture was heated to 80° C. for 2 hr. The mixture was concentrated in vacuum. The residue was extracted with EA (100 mL*2) and H$_2$O (80 mL). The combined organic layer was dried over Na$_2$SO$_4$, filtrated. The filtrate was concentrated in vacuum. The residue was purified by prep-HPLC (FA) to afford tert-butyl-(6S)-3-hydroxy-6-methyl-1,4,6,7-tetrahydropyrazolo[4,3-c]pyridine-5-carboxylate (1.50 g, 5.80 mmol, 27.14% yield, 98% purity) as white solid.

Step 5: Preparation of Compound 6

To a solution of tert-butyl-(6S)-3-hydroxy-6-methyl-1,4,6,7-tetrahydropyrazolo[4,3-c]pyridine-5-carboxylate (1.00 g, 3.95 mmol, 1.00 eq) in Py (10.00 mL) was added 1,1,1-trifluoro-N-phenyl-N-(trifluoromethylsulfonyl) methanesulfonamide (1.48 g, 4.15 mmol, 1.05 eq). The mixture was stirred at 25° C. for 16 hr. The mixture was concentrated in vacuum and extracted with EA (100 mL*2) and 1N HCl (50 mL). The combined organic layer was dried over Na$_2$SO$_4$, filtrated. The filtrate was concentrated in vacuum. The residue was purified by column chromatography PE:EA=10%-50% to afford tert-butyl (6S)-6-methyl-3-(triFluoromethylsulfonyloxy)-1,4,6,7-tetrahydropyrazolo[4,3-c] pyridine-5-carboxylate (700.00 mg, 1.82 mmol, 45.99% yield) as white solid.

Step 6: Preparation of Compound 8

To a solution of tert-butyl (6S)-6-methyl-3-(trifluoromethylsulfonyloxy)-1,4,6,7-tetrahydropyrazolo[4,3-c]pyridine-5-carboxylate (50.00 mg, 129.75 umol, 1.00 eq) and 2-thienylboronic acid (24.90 mg, 194.63 umol, 1.50 eq) in dioxane (2.00 mL) and H$_2$O (200.00 uL) was added XPHOS-PD-G2 (10.21 mg, 12.98 umol, 0.10 eq) and K$_3$PO$_4$ (82.63 mg, 389.25 umol, 3.00 eq). The mixture was heated to 100° C. for 16 hr. The mixture was extracted with EA (30 mL*2) and H$_2$O (30 mL). The combined organic layer was dried over Na$_2$SO$_4$, filtrated. The filtrate was concentrated in vacuum. The residue was purified by prep-TLC (PE:EA=3:1) to afford tert-butyl (6S)-6-methyl-3-(2-thienyl)-1,4,6,7-tetrahydropyrazolo[4,3-c] pyridine-5-carboxylate (30.00 mg, 93.92 umol, 72.39% yield) as white solid.

Step 7: Preparation of Compound 9

Tert-butyl (6S)-6-methyl-3-(2-thienyl)-1,4,6,7-tetrahydropyrazolo [4,3-c]pyridine-5-carboxylate (30.00 mg, 93.92 umol, 1.00 eq) in DCM (2.00 mL) was added TFA (27.01 mmol, 2.00 mL, 287.62 eq). The mixture was stirred at 25° C. for 1 hr. The mixture was concentrated in vacuum to afford (6S)-6-methyl-3-(2-thienyl)-4,5,6,7-tetrahydro-1H-pyrazolo[4,3-c]pyridine (45.00 mg, crude, 2TFA) as brown oil.

Preparation of Compound 753(S)

To a solution of (6S)-6-methyl-3-(2-thienyl)-4,5,6,7-tetrahydro-1H-pyrazolo[4,3-c] pyridine (42.00 mg, 93.89 umol, 1.00 eq, 2TFA) in DCM (5.00 mL) was added TEA (38.00 mg, 375.56 umol, 52.05 uL, 4.00 eq) followed by phenyl N-(3-chlorophenyl)carbamate (23.35 mg, 93.89 umol, 1.00 eq). The mixture was stirred at 25° C. for 16 hr. The mixture was concentrated in vacuum. The residue was purified by prep-HPLC (FA) to afford (6S)—N-(3-chlorophenyl)-6-methyl-3-(2-thienyl)-1,4,6,7-tetrahydropyrazolo [4,3-c]pyridine-5-carboxamide (16.00 mg, 42.65 umol, 45.43% yield, 99.4% purity) as white solid. $^1$H NMR (400 MHz, METHANOL-d4) δ 7.55 (t, J=2.0 Hz, 1H), 7.36-7.50 (m, 2H), 7.30-7.36 (m, 1H), 7.22-7.29 (m, 1H), 7.16 (t, J=4.1 Hz, 1H), 7.01-7.07 (m, 1H), 4.95-5.11 (m, 2H), 4.39 (d, J=15.4 Hz, 1H), 3.09 (dd, J=5.8, 16.3 Hz, 1H), 2.71 (d, J=15.9 Hz, 1H), 1.26 (d, J=6.9 Hz, 3H). LCMS: 373/375 [M+1].

Example 60: Preparation of Compounds 917, 918, 919, 920, 921, 922, 923, and 924 (E1 &E2)

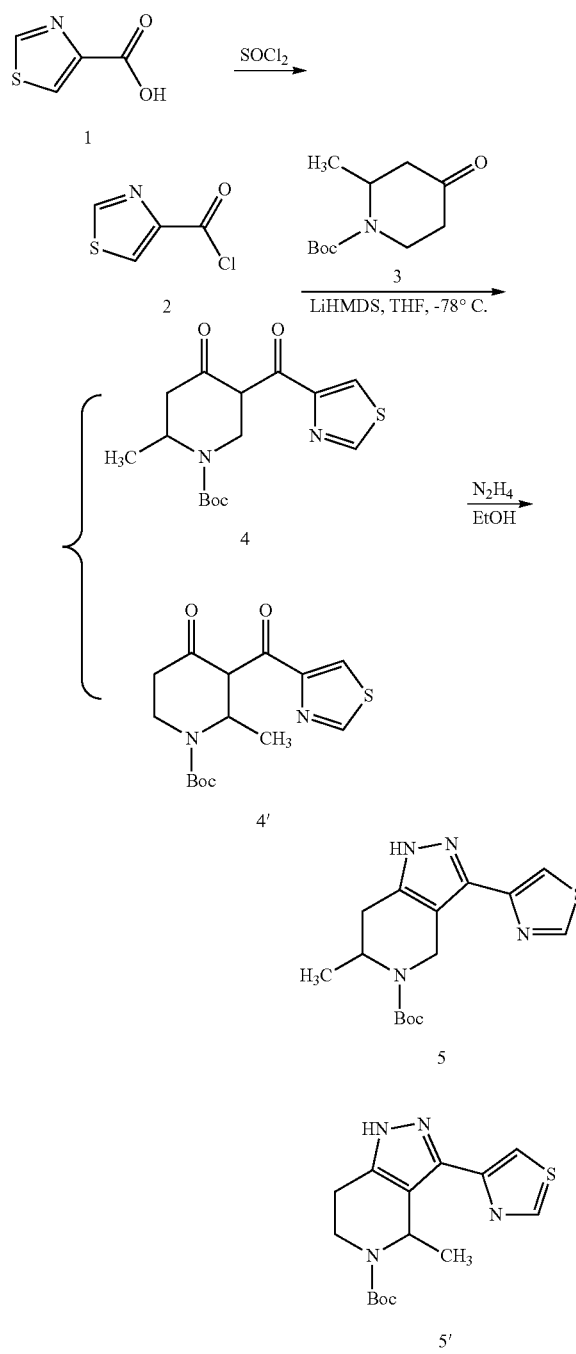

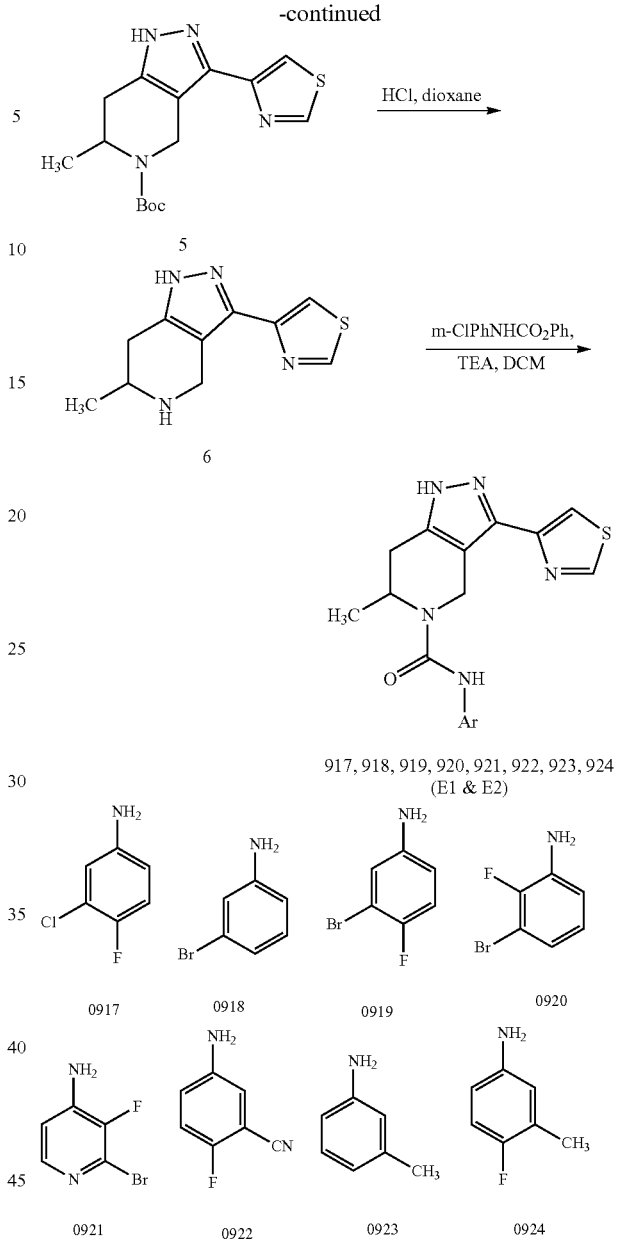

Step 1: Preparation of Compound 2
Thiazole-4-carboxylic acid (6.00 g, 46.46 mmol, 1.00 eq) was dissolved in SOCl$_2$ (100.00 mL) and heated to 80° C. for 2 hr. The mixture was concentrated in vacuum to afford thiazole-4-carbonyl chloride (7.00 g, crude) as yellow solid.

Step 2: Preparation of Compound 4
To a solution of tert-butyl 2-methyl-4-oxo-piperidine-1-carboxylate (9.60 g, 45.01 mmol, 1.00 eq) in THF (100.00 mL) was added LiHMDS (1 M, 67.52 mL, 1.50 eq) dropwise at −70° C. The mixture was stirred at −70° C. for 0.5 hr. Thiazole-4-carbonyl chloride (6.64 g, 45.01 mmol, 1.00 eq) in THF (60.00 mL) was added dropwise at −70° C. The mixtre was stirred at −60° C. for 2 hr. The mixture was quenched by NH$_4$Cl (200 mL) and extracted with EA (500 mL*4). The combined organic layer was dried over Na$_2$SO$_4$ and filtrated. The filtrate was concentrated in vacuum to afford a mixture of tert-butyl 2-methyl-4-oxo-3-(thiazole-4-carbonyl)piperidine-1-carboxylate and tert-butyl 2-methyl-4-oxo-5-(thiazole-4-carbonyl)piperidine-1-carboxylate (13.00 g, crude) as black oil.

Step 3: Preparation of Compound 5

To a solution of a mixuture (13.00 g, 40.08 mmol, 1.00 eq) of tert-butyl 2-methyl-4-oxo-3-(thiazole-4-carbonyl)piperidine-1-carboxylate and tert-butyl 2-methyl-4-oxo-5-(thiazole-4-carbonyl)piperidine-1-carboxylate in EtOH (150.00 mL) was added NH2NH2.H2O (3.54 g, 60.12 mmol, 3.44 mL, 85% purity, 1.50 eq). The mixture was stirred at 25° C. for 8 hr. The mixture was concentrated in vacuum and extracted with EA (500 mL*5) and water (300 mL). The combined organic layer was dried over $Na_2SO_4$, and filtrated. The filtrate was concentrated in vacuum. The residue was purified by flash chromatography (PE:EA=30%-100%) to afford a mixture (5.00 g, 15.61 mmol, 38.93% yield) of tert-butyl 4-methyl-3-thiazol-4-yl-1,4,6,7-tetrahydropyrazolo[4,3-c] pyridine-5-carboxylate and tert-butyl 6-methyl-3-thiazol-4-yl-1,4,6,7-tetrahydropyrazolo[4,3-c]pyridine-5-carboxylate as yellow solid.

2.65 g of mixture were seperated by SFC (Column: AD-10 um; Mobile phase: A for CO2 and B for Isopropanol (0.1% NH3H2O); Isocratic: B 50%; Flow rate: 70 mL/min; Back pressure: 100 bar; Column temperature: 35° C.; Wavelength: 220 nm) to get a mixture (1.2 g) of peak one and peak two and peak three (683 mg); peak four (559 mg). The resulting mixture (1.2 g) of peak one and peak two was further separated by SFC (Instrument: SFC 80; Column: AD-10 um; Mobile phase: A for CO2 and B for Methanol (0.1% NH3H2O); Isocratic: B 35%; Flow rate: 65 mL/min.

Back pressure: 100 bar; Column temperature: 35° C.; Wavelength: 220 nm) to get peak one (500 mg) and peak two (650 mg).

Peak 1 and peak 4 were confirmed as both enantiomers of tert-butyl 4-methyl-3-thiazol-4-yl-1,4,6,7-tetrahydropyrazolo[4,3-c]pyridine-5-carboxylate 5' by H NMR, and peak 2 and peak 3 were both enantiomers of tert-butyl 4-methyl-3-thiazol-4-yl-1,4,6,7-tetrahydropyrazolo[4,3-c] pyridine-5-carboxylate 5.

5'_E1 (peak 1): 1H NMR (400 MHz, CHLOROFORM-d) δ ppm 8.91 (br. s., 1H), 7.50 (d, J=1.6 Hz, 1H), 5.76-5.43 (m, 1H), 4.55-4.24 (m, 1H), 3.34-3.09 (m, 1H), 2.94-2.70 (m, 2H), 1.63-1.36 (m, 12H)

5_E1 (peak 2): 1H NMR (400 MHz, CHLOROFORM-d) δ ppm 8.96 (d, J=1.8 Hz, 1H), 7.44 (d, J=1.9 Hz, 1H), 5.20-5.06 (m, 1H), 4.89 (br. s., 1H), 4.26 (d, J=15.8 Hz, 1H), 3.05 (dd, J=5.9, 15.7 Hz, 1H), 2.68 (d, J=15.7 Hz, 1H), 1.53 (s, 9H), 1.19 (d, J=6.9 Hz, 3H).

5_E2 (peak 3): 1H NMR (400 MHz, CHLOROFORM-d) δ ppm 8.96 (d, J=1.6 Hz, 1H), 7.44 (d, J=1.5 Hz, 1H), 5.13 (d, J=15.1 Hz, 1H), 4.90 (br. s, 1H), 4.26 (d, J=15.9 Hz, 1H), 3.05 (dd, J=5.9, 15.7 Hz, 1H), 2.68 (d, J=15.7 Hz, 1H), 1.53 (s, 9H), 1.19 (d, J=6.9 Hz, 3H).

5'_E2 (peak 4): 1H NMR (400 MHz, CHLOROFORM-d) δ ppm 8.93 (br. s, 1H), 7.51 (s, 1H), 5.75-5.49 (m, 1H), 4.54-4.24 (m, 1H), 3.31-3.10 (m, 1H), 2.91-2.73 (m, 2H), 1.53 (s, 9H), 1.43 (d, J=6.5 Hz, 3H).

Step 4: Preparation of Compound 6 (E1)

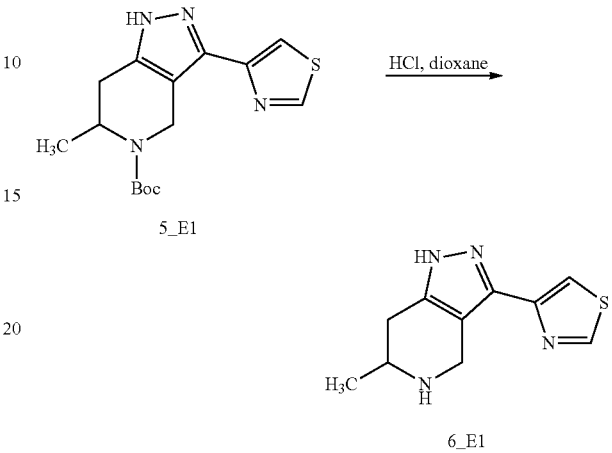

Tert-butyl 6-methyl-3-thiazol-4-yl-1,4,6,7-tetrahydropyrazolo [4,3-c]pyridine-5-carboxylate 5_E1 (650.00 mg, 2.03 mmol, 1.00 eq) was dissolved in HCl/dioxane (4 M, 15.00 mL, 29.56 eq) and stirred at 25° C. for 2 hr. The mixture was concentrated in vacuum to afford 4-(6-methyl-4,5,6,7-tetrahydro-1H-pyrazolo [4,3-c]pyridin-3-yl) thiazole (602.00 mg, crude, 2 HCl) as white solid.

General Preparation of Compounds 917 through 924 (E1&E2)

(Compound 917 (E1) as Example)

To a mixture of 4-(6-methyl-4,5,6,7-tetrahydro-1H-pyrazolo[4,3-c]pyridin-3-yl) thiazole (40.00 mg, 136.42 umol, 1.00 eq, 2 HCl) in DCM (2.00 mL) was added TEA (41.41 mg, 409.26 umol, 56.73 uL, 3.00 eq), followed by phenyl N-(3-chloro-4-fluoro-phenyl)carbamate (36.24 mg, 136.42 umol, 1.00 eq), the reaction mixture was stirred at 25° C. for 16 hours. LCMS showed the starting material consumed completely and the desired product was detected. The solvent was remoced on a rotary evaporator, and the residue was purified by prep-HPLC(FA) to give N-(3-chloro-4-fluoro-phenyl)-6-methyl-3-thiazol-4-yl-1,4,6,7-tetrahydropyrazolo[4,3-c]pyridine-5-carboxamide (43.00 mg, 109.30 umol, 80.12% yield, 99.6% purity) as white solid.

| Structure | Comp. ID | Analytical Data |
|---|---|---|
| 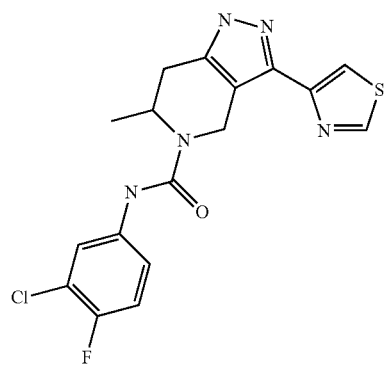 [SMILES: CC1Cc2[nH]nc(-c3cscn3)c2CN1C(=O)Nc1ccc(F)c(Cl)c1] | 0917 (E1) | LCMS (M + 1): 392 |

-continued

| Structure | Comp. ID | Analytical Data |
|---|---|---|
| | 917 (E2) | LCMS (M + 1): 392.0 |
| 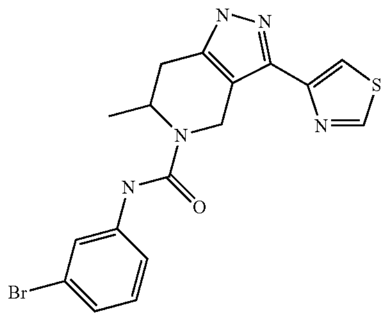 [SMILES: CC1Cc2[nH]nc(-c3cscn3)c2CN1C(=O)Nc1cccc(Br)c1] | 918 (E1) | LCMS (M + 1): 418,420 $^1$H NMR (400 MHz, METHANOL-d4) d ppm 9.10 (d, J = 2.01 Hz, 1 H) 7.84 (d, J = 1.88 Hz, 1 H) 7.67-7.71 (m, 1 H) 7.37 (dt, J = 7.12, 2.02 Hz, 1 H) 7.13-7.22 (m, 2 H) 5.15 (d, J = 15.81 Hz, 1 H) 4.99 (quin, J = 6.43 Hz, 1 H) 4.47 (d, J = 15.81 Hz, 1 H) 3.07 (dd, J = 15.87, 5.71 Hz, 1 H) 2.71 (d, J = 15.81 Hz, 1 H) 1.23 (d, J = 6.78 Hz, 3 H) |
| | 918 (E2) | LCMS (M + 1): 418.0 |
| 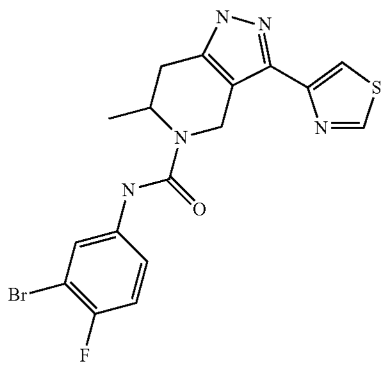 | 919 (E1) | LCMS (M + 1): 436,438 $^1$H NMR (400 MHz, METHANOL-d4) d ppm 9.09 (d, J = 1.88 Hz, 1 H) 7.83 (d, J = 1.88 Hz, 1 H) 7.74 (dd, J = 6.21, 2.57 Hz, 1 H) 7.37 (ddd, J = 8.94, 4.23, 2.64 Hz, 1 H) 7.13 (t, J = 8.72 Hz, 1 H) 5.14 (d, J = 15.81 Hz, 1 H) 4.95-5.01 (m, 1 H) 4.47 (d, J = 15.81 Hz, 1 H) 3.07 (dd, J = 15.81, 5.77 Hz, 1 H) 2.71 (d, J = 15.81 Hz, 1 H) 1.23 (d, J = 6.78 Hz, 3H) |
| | 919 (E2) | LCMS (M + 1): 436.1 |
| | 920 (E1) | LCMS (M + 1): 436,438 |
| 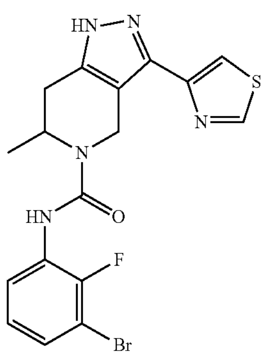 [SMILES: CC1Cc2[nH]nc(-c3cscn3)c2CN1C(=O)Nc1cccc(Br)c1F] | 920 (E2) | LCMS (M + 1): 436.0 $^1$H NMR (400 MHz, Methanol-d$_4$) ppm 9.08 (s, 1 H) 7.82 (d, J = 1.76 Hz, 1 H) 7.34-7.48 (m, 2 H) 7.02-7.09 (m, 1 H) 5.16 (d, J = 15.81 Hz, 1 H) 4.95-5.01 (m, 1 H) 4.50 (d, J = 15.81 Hz, 1 H) 3.04-3.15 (m, 1 H) 2.72 (d, J = 15.81 Hz, 1 H) 1.25 (d, J = 6.78 Hz, 3 H) |
| 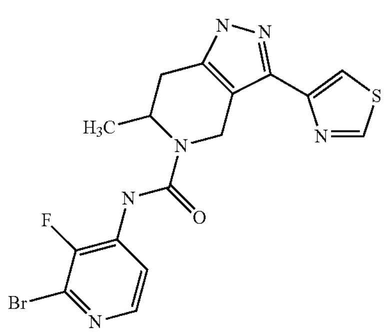 [SMILES: CC1Cc2[nH]nc(-c3cscn3)c2CN1C(=O)Nc1ccnc(Br)c1F] | 921 (E1) | LCMS: 437/439 [M + 1]. |
| | 921 (E2) | LCMS: 437/439 [M + 1]. |

| Structure | Comp. ID | Analytical Data |
|---|---|---|
| 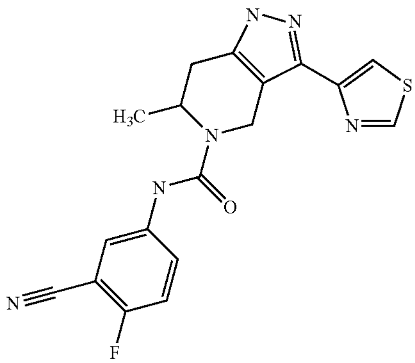 [SMILES: CC1Cc2[nH]nc(-c3cscn3)c2CN1C(=O)Nc1ccc(F)c(C#N)c1] | 922 (E1) | LCMS: 383 [M + 1]. |
| | 922 (E2) | LCMS: 383 [M + 1]. |
| 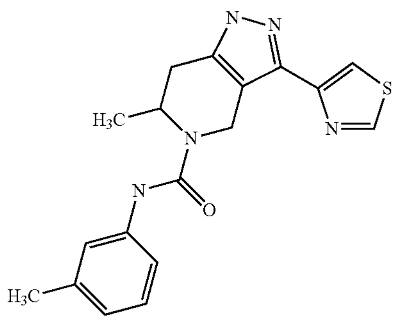 [SMILES: Cc1cccc(NC(=O)N2Cc3c(-c4cscn4)n[nH]c3CC2C)c1] | 923 (E1) | 1H NMR (400 MHz, METHANOL-d4) δ = 9.11 (d, J = 1.9 Hz, 1 H), 7.86 (d, J = 2.0 Hz, 1 H), 7.24 (s, 1 H), 7.14-7.22 (m, 2 H), 6.88 (d, J = 6.9 Hz, 1H), 5.16 (d, J = 15.7 Hz, 1 H), 4.98-5.06 (m, 1 H), 4.49 (d, J = 15.7 Hz, 1 H), 3.09 (dd, J = 5.7, 15.7 Hz, 1 H), 2.73 (d, J = 15.9 Hz, 1 H), 2.33 (s, 3 H), 1.25 (d, J = 6.8 Hz, 3 H). LCMS: 354 [M + 1]. |
| | 923 (E2) | LCMS: 354 [M + 1]. |
| 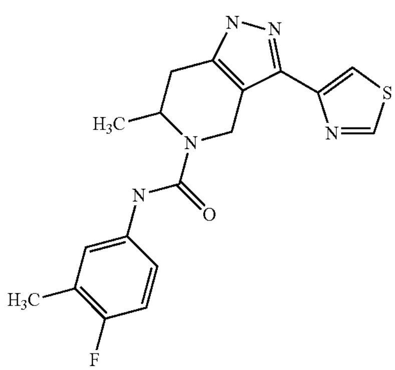 [SMILES: Cc1cc(NC(=O)N2Cc3c(-c4cscn4)n[nH]c3CC2C)ccc1F] | 924 (E1) | 1H NMR (400 MHz, METHANOL-d4) δ = 9.10 (d, J = 1.6 Hz, 1 H), 7.85 (d, J = 1.8 Hz, 1 H), 7.16-7.30 (m, 2 H), 6.95 (t, J = 9.2 Hz, 1 H), 5.15 (d, J = 15.7 Hz, 1 H), 5.00 (quin, J = 6.4 Hz, 1 H), 4.47 (d, J = 15.7 Hz, 1 H), 3.08 (dd, J = 5.8, 15.8 Hz, 1 H), 2.72 (d, J = 15.8 Hz, 1 H), 2.25 (d, J = 1.3 Hz, 3 H), 1.24 (d, J = 6.8 Hz, 3 H). LCMS: 372 [M + 1]. |
| | 924 (E2) | 1H NMR (400 MHz, METHANOL-d4) δ = 9.11 (d, J = 1.8 Hz, 1 H), 7.85 (d, J = 2.0 Hz, 1H), 7.26 (dd, J = 2.4, 6.9 Hz, 1 H), 7.16-7.22 (m, 1 H), 6.96 (t, J = 9.1 Hz, 1 H), 5.15 (d, J = 15.6 Hz, 1 H), 5.01 (quin, J = 6.4 Hz, 1 H), 4.48 (d, J = 15.7 Hz, 1 H), 3.08 (dd, J = 6.0, 15.7 Hz, 1 H), 2.72 (d, J = 15.8 Hz, 1 H), 2.26 (d, J = 1.9 Hz, 3 H), 1.25 (d, J = 6.9 Hz, 3 H). LCMS: 372 [M + 1]. |

Example 61: Preparation of Compound 289

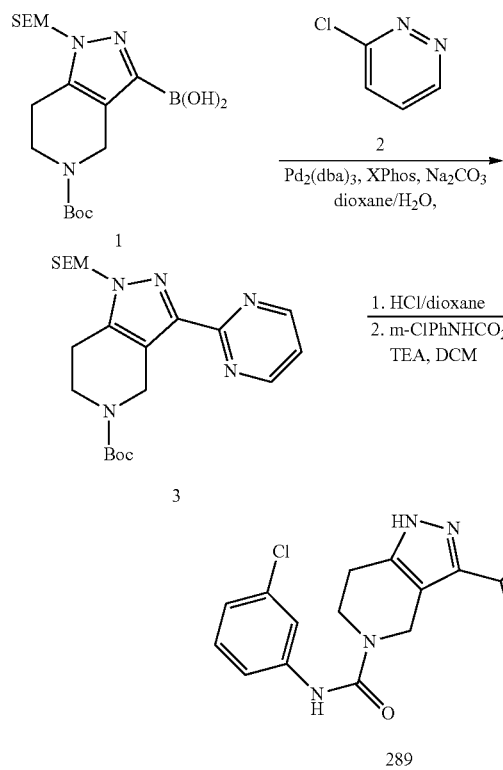

Step 1: Preparation of Compound 3

To a solution of [5-tert-butoxycarbonyl-1-(2-trimethylsilylethoxymethyl)-6,7-dihydro-4H-pyrazolo[4,3-c]pyridin-3-yl]boronic acid (300.00 mg, 755.00 umol, 1.00 eq) and 2-chloropyrimidine (129.71 mg, 1.13 mmol, 1.50 eq) in dioxane (2.00 mL) was added $Pd_2(dba)_3$ (69.14 mg, 75.50 umol, 0.10 eq), xphos (71.98 mg, 151.00 umol, 0.20 eq) followed by a solution of $Na_2CO_3$ (240.07 mg, 2.27 mmol, 3.00 eq) in H2O (400.00 uL). The mixture was heated to 90° C. for 16 h. The mixture was extratced with EA (50 mL*2) and $H_2O$ (10 mL). The combined organic layer was dried over $Na_2SO_4$, and filtrated. The filtrate was concentrated in vacuum. The residue was purified by falsh chromatography (PE:EA: 0%~30%) to get 220 mg product with 30% purity. The product was purified by prep-HPLC (FA) to afford tert-butyl 3-pyrimidin-2-yl-1-(2-trimethylsilylethoxymethyl)-6,7-dihydro-4H-pyrazolo[4,3-c]pyridine-5-carboxylate (46.50 mg, 107.74 umol, 14.27% yield) as colorless oil. LCMS (M+1): 432.

Preparation of Compound 289

Tert-butyl 3-pyrimidin-2-yl-1-(2-trimethylsilylethoxymethyl)-6,7-dihydro-4H-pyrazolo[4,3-c]pyridine-5-carboxylate (60.00 mg, 139.02 umol, 1.00 eq) was dissolved in TFA (54.03 mmol, 4.00 mL, 388.62 eq) and stirred at 20° C. for 16 hr. The mixture was conentrated in vacuum to afford 3-pyrimidin-2-yl-4,5,6,7-tetrahydro-1H-pyrazolo[4,3-c]pyridine (44.00 mg, crude, TFA) as yellow oil.

To a solution of 3-pyrimidin-2-yl-4,5,6,7-tetrahydro-1H-pyrazolo[4,3-c]pyridine (30.00 mg, 95.16 umol, 1.00 eq, TFA) and phenyl N-(3-chlorophenyl) carbamate (18.86 mg, 76.13 umol, 0.80 eq) in DCM (4.00 mL) was added TEA (48.15 mg, 475.80 umol, 65.96 uL, 5.00 eq). The mixture was stirred at 20° C. for 16 hr. The mixture was concentrated in vacuum. The residue was purified by prep-HPLC (FA) to afford N-(3-chlorophenyl)-3-pyrimidin-2-yl-1,4,6,7-tetrahydropyrazolo [4,3-c] pyridine-5-carboxamide (22.39 mg, 62.60 umol, 65.79% yield, 99.2% purity) as white solid. $^1$H NMR (400 MHz, DMSO-d6) δ ppm 8.86-8.97 (m, 3H), 7.64 (s, 1H), 7.41 (d, J=5.8 Hz, 2H), 7.26 (t, J=8.1 Hz, 1H), 6.94-7.02 (m, 1H), 4.83 (brs, 2H), 3.78 (brs, 2H), 2.79 (brs, 2H). LCMS: 355 [M+1].

Example 62: Preparation of Compound 290

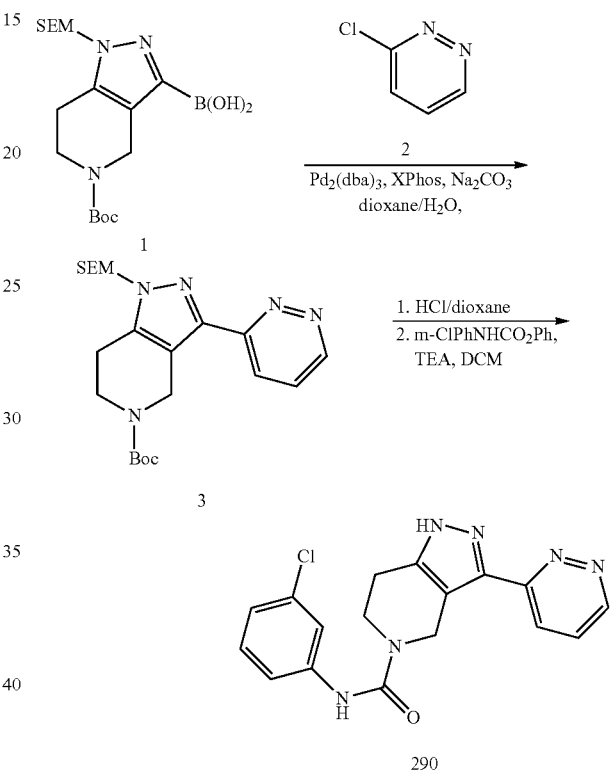

Step 1: Preparation of Compound 3

To a solution of [5-tert-butoxycarbonyl-1-(2-trimethylsilylethoxymethyl)-6,7-dihydro-4H-pyrazolo[4,3-c]pyridin-3-yl]boronic acid (300.00 mg, 755.00 umol, 1.00 eq and 3-chloropyridazine (129.71 mg, 1.13 mmol, 1.50 eq) in dioxane (8.00 mL) was added $Pd_2(dba)_3$ (69.14 mg, 75.50 umol, 0.10 eq), XPhos (71.98 mg, 151.00 umol, 0.20 eq) followed by a solution of $Na_2CO_3$ (240.07 mg, 2.27 mmol, 3.00 eq) in $H_2O$ (2.00 mL). The mixture was heated to 85° C. for 16 hr. The mixture was extracted with EA (50 mL*2) and $H_2O$ (20 mL). The combined organic layer was dried over $Na_2SO_4$, and filtrated. The filtrate was concentrated in vacuum. The residue was purified by column chromatography (PE:EA=20%-50%) to afford tert-butyl 3-pyridazin-3-yl-1-(2-trimethylsilylethoxymethyl)-6,7-dihydro-4H-pyrazolo[4,3-c]pyridine-5-carboxylate (75.00 mg, 147.71 umol, 19.56% yield, 85% purity) as yellow oil. LCMS (M+1): 432.

Preparation of Compound 290

Tert-butyl-3-pyridazin-3-yl-1-(2-trimethylsilylethoxymethyl)-6,7-dihydro-4H-pyrazolo[4,3-c]pyridine-5-carboxylate (75.00 mg, 137.46 umol, 1.00 eq, TFA) was dissolved in TFA (6.85 g, 60.09 mmol, 4.45 mL, 437.19 eq) and stirred at 20° C. for 16 hr. The mixture was concentrated in vacuum to afford 3-pyridazin-3-yl-4,5,6,7-tetrahydro-1H-pyrazolo[4,3-c]pyridine (59.00 mg, crude, TFA) as yellow oil.

To a solution of 3-pyridazin-3-yl-4,5,6,7-tetrahydro-1H-pyrazolo[4,3-c]pyridine (59.00 mg, 187.15 umol, 1.00 eq, TFA) in DCM (4.00 mL) was added phenyl N-(3-chlorophenyl)carbamate (46.35 mg, 187.15 umol, 1.00 eq) followed by TEA (94.69 mg, 935.75 umol, 129.71 uL, 5.00 eq). The mixture was stirred at 20° C. for 16 hr. LCMS showed that compound 3 remained. Another batch of phenyl N-(3-chlorophenyl)carbamate (30 mg) was added. The mixture was stirred at 20° C. for another 16 hr. The mixture was concentrated in vacuum. LCMS showed 30% desired product. The residue was purified by prep-HPLC (FA) to afford N-(3-chlorophenyl)-3-pyridazin-3-yl-1,4,6,7-tetrahydropyrazolo[4,3-c]pyridine-5-carboxamide (25.00 mg, 70.32 umol, 37.58% yield, 99.8% purity) as white solid.

$^1$H NMR (400 MHz, METHANOL-d4) δ ppm 2.93 (t, J=5.71 Hz, 2H) 3.90 (t, J=5.71 Hz, 2H) 5.00 (s, 2H) 6.99-7.04 (m, 1H) 7.21-7.29 (m, 1H) 7.31-7.37 (m, 1H) 7.56 (t, J=2.01 Hz, 1H) 7.77 (dd, J=8.41, 4.77 Hz, 1H) 8.28 (d, J=8.91 Hz, 1H) 9.11 (d, J=4.64 Hz, 1H). LCMS: 355 [M+1].

Example 63: HBV Assembly Assay

The interference of compounds from this invention with HBV capsid assembly could be measured using an in vitro assembly assay based on fluorescence quenching, which was developed according to a method described by Zlotnick and coworkers (Nature Biotechnology 2006, 24:358). In a typical assay, a mutant HBV $C_{150}$ protein (amino acids 1-150, C49A, C61A, C107A, 150C) is cloned into a T7 RNA-polymerase based expression vector, expressed in E. coli and purified to homogeneity as a dimer. The purified HBV core protein is desalted and labeled with BODIPY-FL Dye.

In a non-limiting embodiment, the assembly assay is conducted in 96-well plate format. The assembly reactions are carried out in 50 mM Hepes buffer, pH 7.5 and 150 mM NaCl. The compounds are pre-incubated with the HBV CA protein for 15 min, and the assembly reactions are initiated by addition of NaCl. The reaction is allowed to continue for 1 hour at room temperature. The changes in fluorescence between DMSO treated and compound treated samples are recorded and analyzed for assembly modulation.

Example 64: HBV Replication Inhibition Assay

HBV replication inhibition by the compounds of this invention could be determined in cells infected or transfected with HBV, or cells with stably integrated HBV, such as HepG2.2.15 cells (Sells et al. 1987). In this example, HepG2.2.15 cells were maintained in cell culture medium containing 10% fetal bovine serum (FBS), Geneticin, L-glutamine, penicillin and streptomycin. HepG2.2.15 cells could be seeded in 96-well plates at a density of 40,000 cells/well and be treated with serially diluted compounds at a final DMSO concentration of 0.5% either alone or in combination by adding drugs in a checker box format. Cells were incubated with compounds for three days, after which medium was removed and fresh medium containing compounds was added to cells and incubated for another three days. At day 6, supernatant was removed and treated with DNase at 37° C. for 60 minutes, followed by enzyme inactivation at 75° C. for 15 minutes. Encapsidated HBV DNA was released from the virions and covalently linked HBV polymerase by incubating in lysis buffer (Affymetrix QS0010) containing 2.5 ag proteinase K at 50° C. for 40 minutes. HBV DNA was denatured by addition of 0.2 M NaOH and detected using a branched DNA (BDNA) QuantiGene assay kit according to manufacturer recommendation (Affymetrix). HBV DNA levels could also be quantified using qPCR, based on amplification of encapsidated HBV DNA extraction with QuickExtraction Solution (Epicentre Biotechnologies) and amplification of HBV DNA using HBV specific PCR probes that can hybridize to HBV DNA and a fluorescently labeled probe for quantitation. In addition, cell viability of HepG2.2.15 cells incubated with test compounds alone or in combination was determined by using CellTitre-Glo reagent according to the manufacturer protocol (Promega). The mean background signal from wells containing only culture medium was subtracted from all other samples, and percent inhibition at each compound concentration was calculated by normalizing to signals from HepG2.2.15 cells treated with 0.5% DMSO using equation E1.

E1: % inhibition=(DMSOave−Xi)/DMSOave×100% where DMSOave is the mean signal calculated from the wells that were treated with DMSO control (0% inhibition control) and Xi is the signal measured from the individual wells. EC50 values, effective concentrations that achieved 50% inhibitory effect, were determined by non-linear fitting using Graphpad Prism software (San Diego, Calif.) and equation E2

E2: Y=Ymin+(Ymax−Ymin)/(1+10(Log EC50−X)×HillSlope)

where Y represents percent inhibition values and X represents the logarithm of compound concentrations.

Selected compounds of the invention were assayed in the HBV replication assay (BDNA assay), as described above and a representative group of these active compounds is shown in Table 3. In Table 3, "A" represents 0.01≤$EC_{50}$<0.10; "B" represents 0.10≤$EC_{50}$<0.50; "C" represents 0.50≤$EC_{50}$<1.0; "D" represents 1.0≤$EC_{50}$<1.5; and "E" represents 1.5≤$EC_{50}$<5.

TABLE 3

Activity in BDNA-assay: '+' indicates >50% activity at 10 μM, or numerical value indicates EC50 (μM).

| Compound | Activity | Compound | Activity |
|---|---|---|---|
| 001 | + | 318(E1) | B |
| 014 | D | 318(E2) | B |
| 017 | + | 325 | + |
| 016 | + | 326 | B |
| 021 | + | 327 | B |
| 022 | B | 436 | C |
| 024 | + | | |
| 027 | + | 472 | B |
| 030 | + | 473 | C |
| 057 | + | 495 | D |
| 112 | A | 496 | B |
| 114 | A | 497 | B |
| 113 | + | 542 | C |
| 142 | + | 555 | B |
| 143 | + | 556 | B |
| 144 | + | 559 | A |
| 145 | + | 560 | A |
| 147 | + | 562 | A |
| 148 | + | 583 | E |
| 149 | + | 917 E1 | A |
| 150 | + | 917 E2 | A |
| 154 | + | 918 E1 | A |
| 156 | + | 918 E2 | A |
| 163 | + | 919 E1 | A |
| 164 | + | 919 E2 | A |
| 165 | + | 920 E1 | A |

TABLE 3-continued

Activity in BDNA-assay: '+' indicates >50% activity at 10 μM, or numerical value indicates EC50 (μM).

| Compound | Activity | Compound | Activity |
|---|---|---|---|
| 171 | + | 920 E2 | A |
| 190 | C | 921 E1 | A |
| 191 | C | 921 E2 | A |
| 192 | B | 922 E1 | A |
| 201 | + | 922 E2 | A |
| 204 | + | 923 E1 | A |
| 205 | B | 923 E2 | A |
| 214 | + | 924 E1 | A |
| 226 | + | 924 E2 | A |
| 276 | B | 289 | A |
| 277 | + | 290 | A |
| 278 | B | | |
| 279 | B | | |
| 280 | B | | |
| 281 | + | | |
| 286 | C | | |
| 287 | B | | |
| 291 | B | | |
| 317 (E1) | A | | |
| 317(E2) | B | | |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A compound of Formula IIIa:

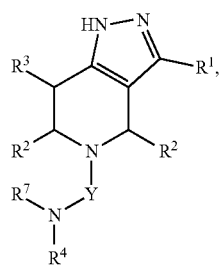

IIIa or a pharmaceutically acceptable salt thereof, wherein
Y is —C(O)— or —SO$_2$—;
R$^1$ is C$_1$-C$_9$-heteroaryl which is optionally substituted with 1 or 2 groups each independently selected from —OH, halo, C$_1$-C$_6$-alkyl, C$_1$-C$_6$-haloalkyl, —O—C$_1$-C$_6$-alkyl, C$_1$-C$_6$-alkyl-OH, CN, and C(O)H;
R$^2$ is, at each occurrence, independently selected from H, —OH, halo, C$_1$-C$_6$-alkyl, C$_1$-C$_6$-haloalkyl, —O—C$_1$-C$_6$-alkyl, and C$_1$-C$_6$-alkyl-OH;
R$^3$ is selected from H, —OH, halo, C$_1$-C$_6$-alkyl, C$_1$-C$_6$-haloalkyl, —O—C$_1$-C$_6$-alkyl, and C$_1$-C$_6$-alkyl-OH;
R$^4$ is (CR$^8$R$^9$)$_p$—C$_6$-C$_{12}$-aryl, optionally substituted with 1, 2, or 3 groups, each independently selected from —OH, halo, CN, C$_1$-C$_6$-alkyl, C$_1$-C$_6$-haloalkyl, —O—C$_1$-C$_6$-alkyl, and C$_1$-C$_6$-alkyl-OH;
R$^7$ is selected from H, C$_1$-C$_6$-alkyl, and C$_1$-C$_6$-alkyl-OH;
R$^8$ is, at each occurrence, independently selected from H, —OH, halo, C$_1$-C$_6$-alkyl, C$_1$-C$_6$-haloalkyl, —O—C$_1$-C$_6$-alkyl, and C$_1$-C$_6$-alkyl-OH;
R$^9$ is, at each occurrence, independently selected from H and C$_1$-C$_6$-alkyl; and
p is 0, 1, 2, 3, or 4.

2. The compound of claim 1, wherein Y is —C(O)—.

3. The compound of claim 1, wherein R$^1$ is pyrimidyl, pyridyl, pyrazolyl, thienyl, thiazolyl, isothiazolyl, oxazolyl, pyridazinyl, pyrazinyl, or pyrrolyl, any of which are optionally substituted by 1 or 2 groups independently selected from —OH, halo, C$_1$-C$_6$-alkyl, C$_1$-C$_6$-haloalkyl, —O—C$_1$-C$_6$-alkyl, C$_1$-C$_6$-alkyl-OH, CN, and C(O)H.

4. The compound of claim 1, wherein R$^2$ is H, C$_1$-C$_6$-alkyl, or C$_1$-C$_6$-alkyl-OH and R$^3$ is H or C$_1$-C$_6$-alkyl.

5. The compound of claim 1, wherein R$^4$ is (CR$^8$R$^9$)$_p$—C$_6$-aryl, which is optionally substituted with 1, 2, or 3 groups, each independently selected from —OH, halo, CN, and C$_1$-C$_6$-alkyl;
R$^8$ is H or C$_1$-C$_6$-alkyl;
R$^9$ is H or C$_1$-C$_6$-alkyl; and
p is 0 or 1.

6. The compound of claim 1, wherein R$^4$ is:

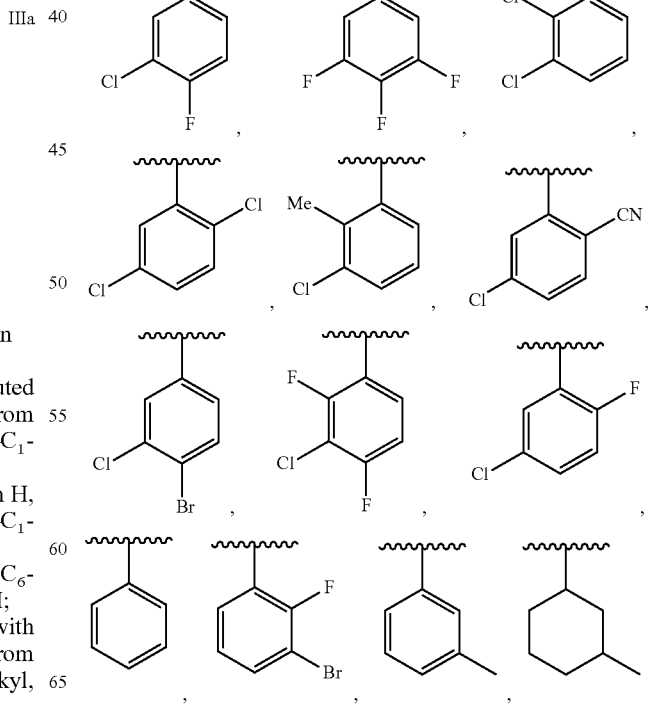

225
-continued
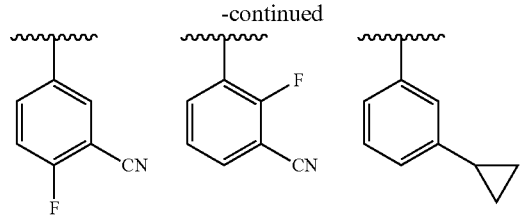
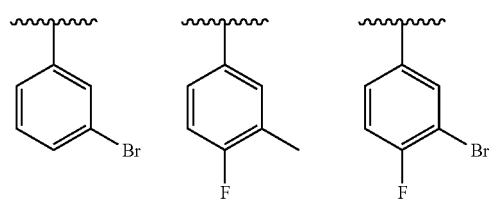
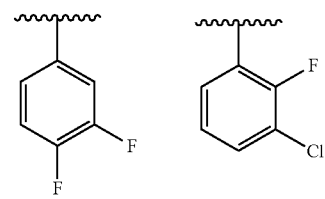
, or .
7. The compound of claim 1, wherein the compound of Formula IIIa is selected from the group consisting of:
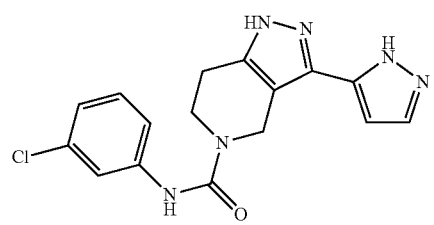
497
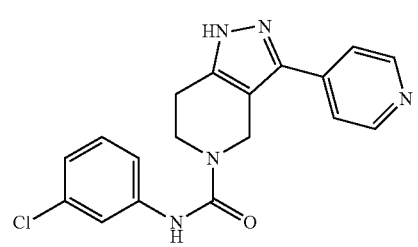
287
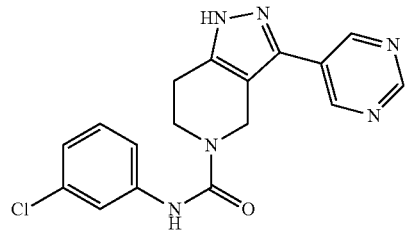
291
226
-continued
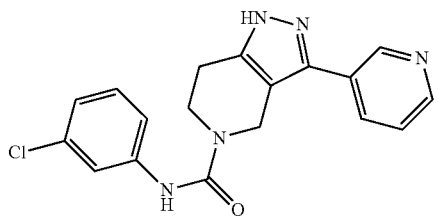
286
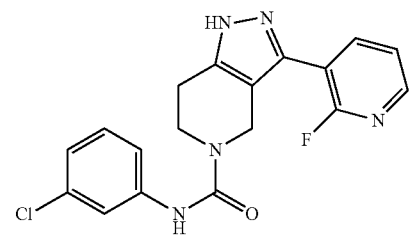
472
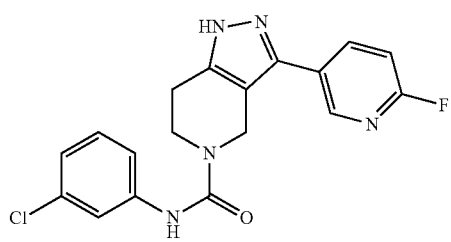
473
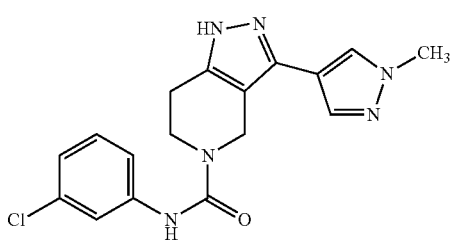
495
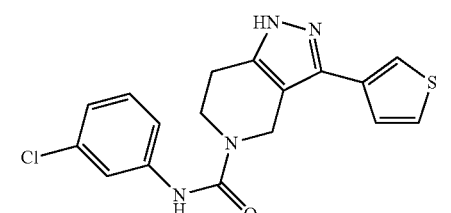
562
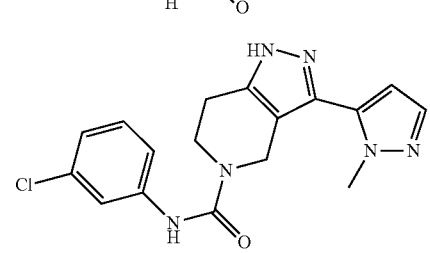
496
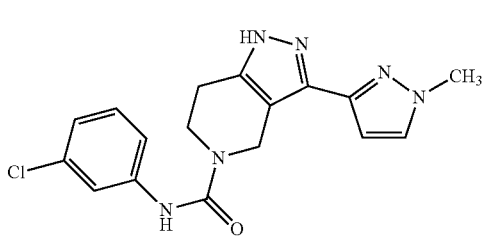
555

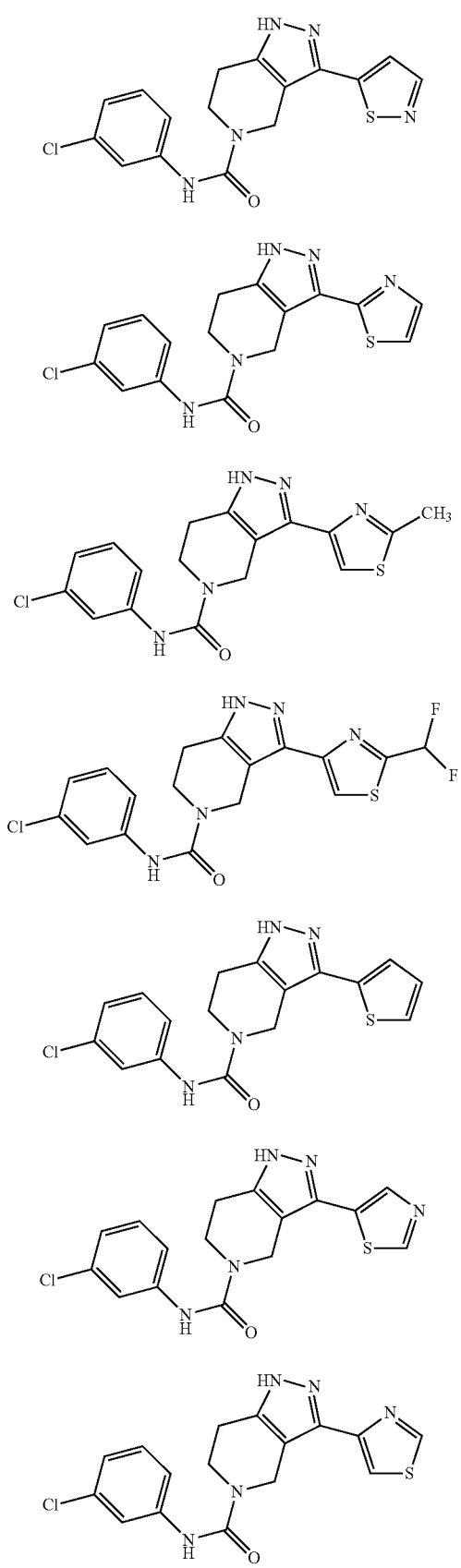
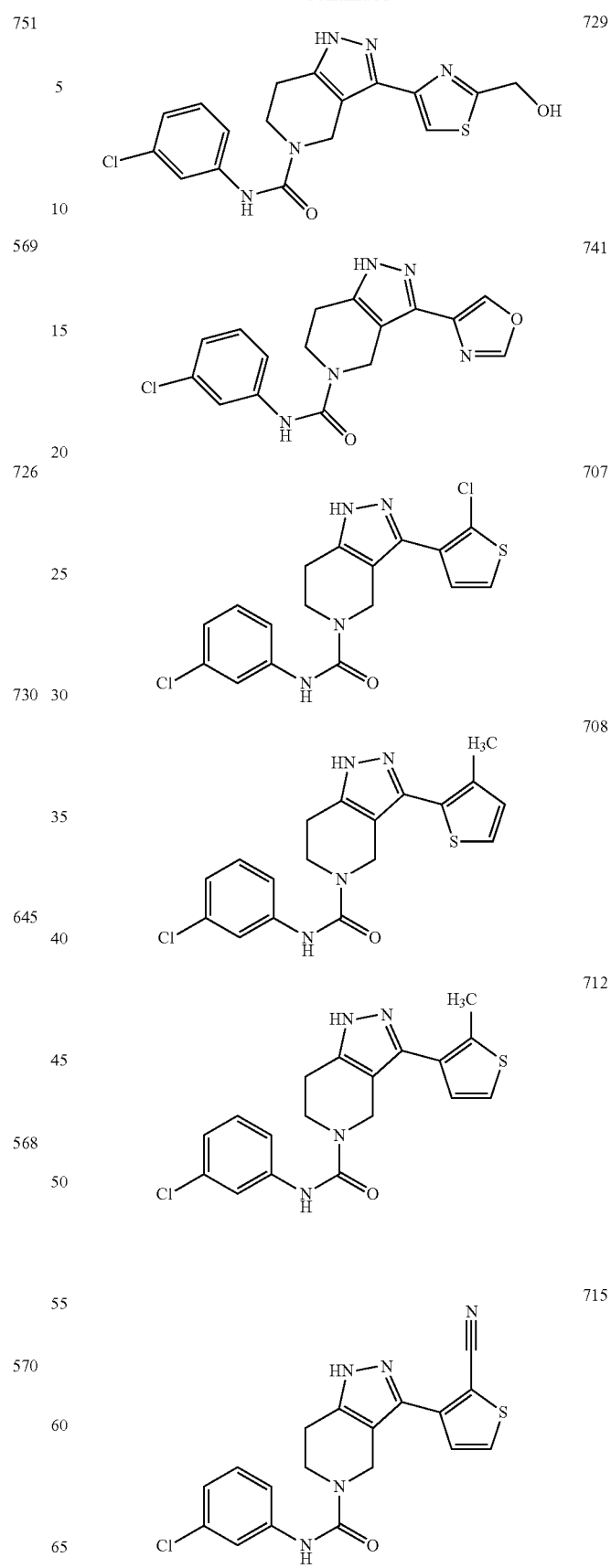

229
-continued

769
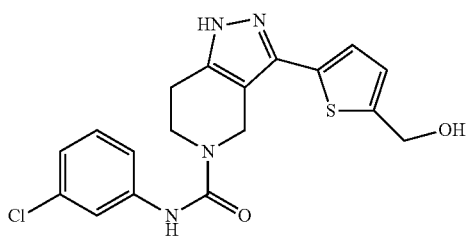

766
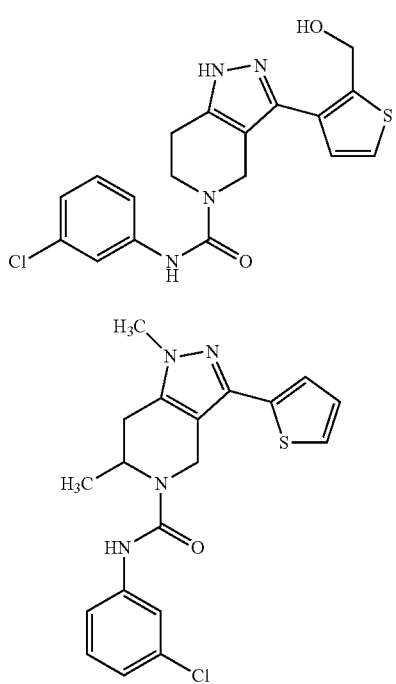

831

832
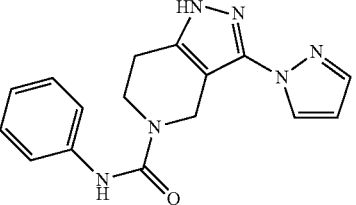

230
-continued

290
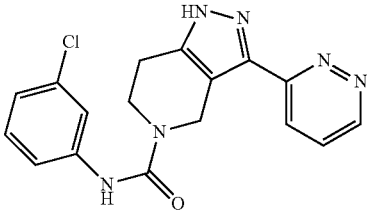

and pharmaceutically acceptable salts thereof.

8. The compound of claim 1, wherein:
Y is —C(O)—;
$R^2$ is, at each occurrence, H;
$R^3$ is H;
$R^4$ is phenyl substituted with 1, 2, or 3 substituents, each independently selected from the group consisting of —OH, halo, CN, $C_1$-$C_6$-alkyl, $C_1$-$C_6$-haloalkyl, —O—$C_1$-$C_6$-alkyl, and $C_1$-$C_6$-alkyl-OH; and
$R^7$ is H.

9. The compound of claim 8, wherein $R^1$ is thienyl optionally substituted with halo, $C_1$-$C_6$-alkyl, $C_1$-$C_6$-alkyl-OH or CN.

10. The compound of claim 8, wherein $R^4$ is substituted with 1, 2 or 3 substituents, each independently selected from the group consisting of halo, methyl and CN.

11. The compound of claim 8, wherein the compound of Formula IIIa is selected from the group consisting of:

562
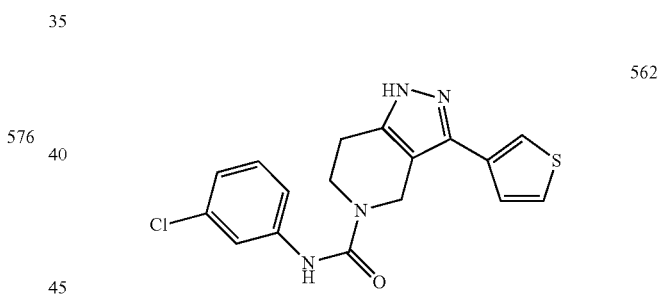

645
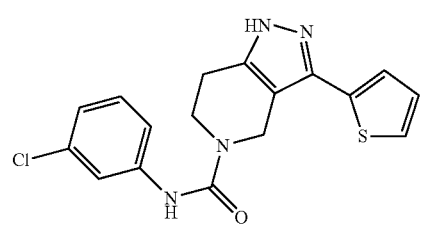

715
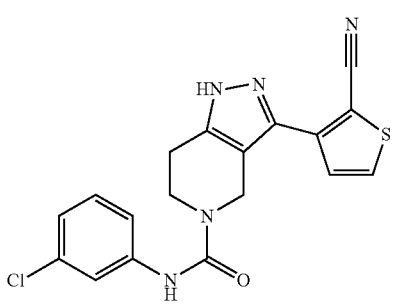

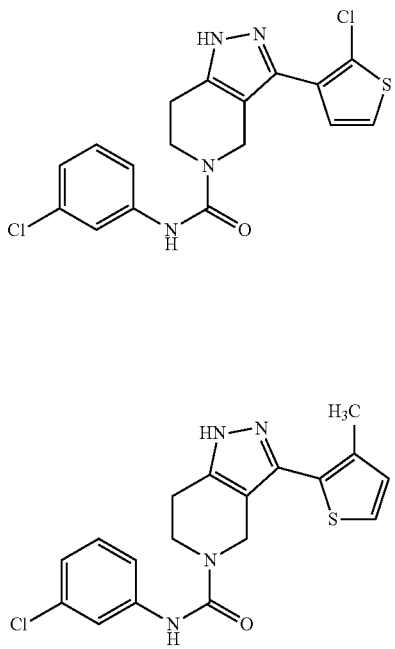
707
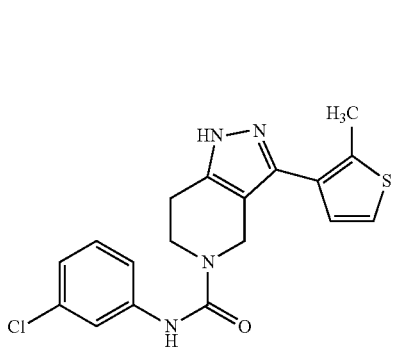
708
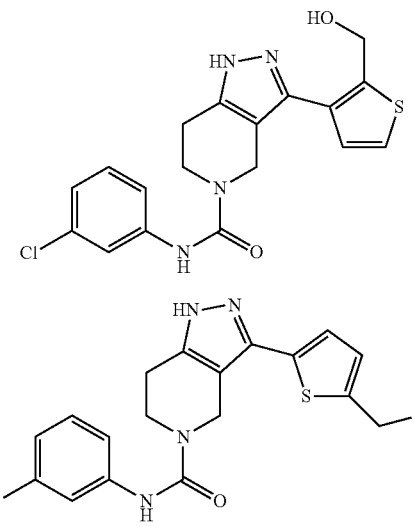
712
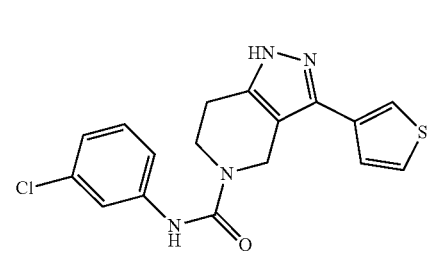
and pharmaceutically acceptable salts thereof.
12. A pharmaceutical composition comprising a compound of claim 1, or a pharmaceutically acceptable salt thereof, together with a pharmaceutically acceptable carrier.
13. The compound of claim 1, wherein the compound of Formula IIIa is:
766
769
562
or a pharmaceutically acceptable salt thereof.
* * * * *